United States Patent
Shimano et al.

(10) Patent No.: US 7,511,144 B2
(45) Date of Patent: Mar. 31, 2009

(54) REVERSE HYDROXAMIC ACID DERIVATIVES

(75) Inventors: Masanao Shimano, Kyoto (JP); Noriyuki Kamei, Kyoto (JP); Tomohiro Tanaka, Kyoto (JP); Tatsuhiro Harada, Kyoto (JP); Makoto Haino, Kyoto (JP); Akihiko Okuyama, Kyoto (JP); Yoshio Arakawa, Kyoto (JP); Yoshiko Murakami, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 805 days.

(21) Appl. No.: 10/488,530

(22) PCT Filed: Sep. 5, 2002

(86) PCT No.: PCT/JP02/09036

§ 371 (c)(1),
(2), (4) Date: Mar. 4, 2004

(87) PCT Pub. No.: WO03/022801

PCT Pub. Date: Mar. 20, 2003

(65) Prior Publication Data

US 2004/0242928 A1 Dec. 2, 2004

(30) Foreign Application Priority Data

Sep. 7, 2001 (JP) .............................. 2001-272527

(51) Int. Cl.
C07D 215/38 (2006.01)
C07D 215/44 (2006.01)

(52) U.S. Cl. ....................................... 546/157; 546/153

(58) Field of Classification Search ................. 546/157, 546/153
See application file for complete search history.

(56) References Cited

FOREIGN PATENT DOCUMENTS

| EP | 698814 | * | 2/1996 |
|----|--------|---|--------|
| WO | 99/06361 | * | 2/1999 |
| WO | WO 99/06361 A2 | | 2/1999 |
| WO | WO9906361 | * | 2/1999 |
| WO | WO 99/38843 A1 | | 8/1999 |
| WO | 00/12478 | * | 3/2000 |
| WO | WO 00/12478 A1 | | 3/2000 |
| WO | 00/44712 | * | 8/2000 |
| WO | 00/44713 A1 | | 8/2000 |
| WO | 00/44723 A1 | | 8/2000 |
| WO | 00/44739 | * | 8/2000 |
| WO | WO 00/44712 A1 | | 8/2000 |
| WO | WO 00/44739 A1 | | 8/2000 |
| WO | WO 00/75108 A1 | | 12/2000 |
| WO | WO 01/62742 A1 | | 8/2001 |
| WO | WO 03/040103 A1 | | 5/2003 |
| WO | WO 2004/006925 A1 | | 1/2004 |
| WO | WO 2004/006926 A1 | | 1/2004 |
| WO | WO 2004/006927 A2 | | 1/2004 |

* cited by examiner

*Primary Examiner*—D. Margaret Seaman
(74) *Attorney, Agent, or Firm*—Birch, Stewart, Kolasch & Birch, LLP

(57) ABSTRACT

Reverse hydroxamic acid derivatives having specific structure represented by a general formula (Ia):

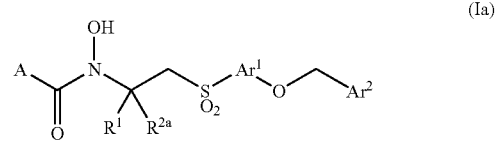

(Ia)

(wherein A is a hydrogen atom or the like; $Ar^1$ is an arylene or the like; $Ar^2$ is an optionally substituted aryl, a heteroaryl or the like; $R^1$ is a hydrogen atom, an alkyl or the like; $R^{2a}$ is a substituted cycloaryl, a heterocycloaryl or the like) and a general formula (I):

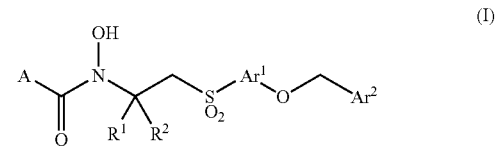

(I)

(wherein A, $Ar^1$, $Ar^2$, and $R^1$ are the same as defined above and $R^2$ is an hydrogen atom, $R^{2a}$ or the like) and salts thereof, which have TNF-α converting enzyme (TACE) inhibitory activity.

9 Claims, No Drawings

REVERSE HYDROXAMIC ACID DERIVATIVES

TECHNICAL FIELD

This invention relates to novel reverse hydroxamic acid derivatives, and a medicament and inhibitors of tumor necrosis factor alpha (TNF-α) converting enzyme (TACE) containing them as an effective component.

BACKGROUND ART

TNF-α was discovered in 1975 as an endogenous protein having a necrotic activity against tumor cells (Carswell, E. A. et al., Proc. Natl. Acad. Sci. U.S.A. 1975, 72, 3666-3670). At present, TNF-α is recognized as one of the cytokines secreted from macrophages, monocytes and the like activated by exogenous and endogenous factors and to be widely involved in regulation of various cytokines production and protection from infectious diseases. However, persistent and excessive production and secretion of TNF-α cause overproduction of pro-inflammatory cytokines, apoptosis of cells, interference of intracellular signal transduction and the like, resulting in the primary and secondary tissue injury, and eventually becomes a factor responsible for etiology and exacerbation of various diseases (Aggarwall B. B., Puri R. K., eds. 1995. Human Cytokines: Their Role in Disease and Therapy. Cambridge, Mass., USA: Blackwell Sci.). Accordingly, for the treatment of disease conditions likely to be caused by an excessive production and secretion of TNF-α, it seems important to suppress the production and secretion of TNF-α or the action of TNF-α. Examples of these diseases in which TNF-α participates include many diseases, for example, commencing with rheumatoid arthritis, systemic lupus erythematosus (SLE), Crohn's disease, Behchet's disease, multiple sclerosis, arteriosclerosis, myasthenia gravis, diabetes mellitus, sepsis, acute infectious disease, asthma, atopic dermatitis, fever, anemia and the like.

As examples of the above treatment, it has already been reported that a human anti-TNF-α chimeric antibody and a TNF-α receptor (p75)-Fc fusion protein, both of which are biologics, are effective for rheumatoid arthritis patients (Elliott, M. et al., Lancet 1994, 344, 1105-1110; Moreland L. W. et al., N. Engl. J. Med. 1997, 337, 141-147). However, these biologics are pointed out to have problems such as; (a) generally expensive, (b) there is no option for their administration routes except for injection, thereby putting a considerable burden on patients, and (c) their administration may trigger the immune response and their effect may be lowered at the second and subsequent administration (Feldmann, M., et al., Adv. Immunol., 1997, 64, 283-350).

Therefore, in order to overcome the above various problems associated with biologics, a number of studies have been carried out on low molecular weight compounds which inhibit the production and secretion of TNF-α or suppress its action (Newton, R. C. et al., J. Med. Chem. 1999, 42, 2295-2314).

On the other hand, TACE (otherwise known as ADAM 17) is a membrane-bound proteinase, having a zinc at the catalytic site thereof, classified in the ADAM (a disintegrin and metalloproteinase) family (Black, R. A. et al., Nature 1997, 385, 729-733; Moss, M. L. et al., Nature 1997, 385, 733-736). It has been reported that TACE cleaves membrane-bound TNF-α (pro-TNF-α) to generate soluble TNF-α and that 90% of soluble TNF-α is produced by the enzymatic action of TACE based on an experiment performed with TACE knock out mouse (Black, R. A. et al., Nature 1997, 385, 729-733).

On the other hand, it has been suggested from an in vitro experiment that ADAM-10 belonging to the same family as TACE also participates in the release of TNF-α, but the recent experimental results obtained using an antisense or an ADAM-10 inhibitor have suggested that ADAM-10 is not involved in the release of TNF-α (Condon, T. P., et al., Antisense & Nucleic Acid Drug Development 2001, 11, 107-116; Moss, M. L., et al., Drug Discovery Today 2001, 6, 417-426). In other words, this suggests that the only enzyme responsible for the release of TNF-α from pro-TNF-α is TACE. Thus, compounds which inhibit the enzymatic action of TACE are likely to suppress the production of soluble TNF-α, thereby serving as a therapeutic drug for the above various disease conditions caused by TNF-α. From the foregoing, studies on compounds which are likely to be associated with the action of inhibiting TACE have become active (Nelson, F. C. et al., Exp. Opin. Invest. Drugs 1999, 8, 383-392).

Matrix metalloproteinases (otherwise known as matrixin) (MMP) are proteinases having a zinc at the catalytic site thereof and degrade extracellular matrices. There are about 20 known MMPs which are suspected to participate in a variety of disease states. Although their in vivo actions have not been fully elucidated, studies on their inhibitors are being very actively developed (Whittaker, M. et al., Chem. Rev. 1999, 99, 2735-2776; Motoo Nakajima, TANPAKUSHITSU KAKUSAN KOUSO 2000, 45, 1083-1089; Connell, R. D. et al., Exp. Opin. Ther. Patents 2001, 11, 77-114).

Compounds which inhibit MMP had been reported to inhibit the production of TNF-α as well (Mohler, K. M. et al., Nature 1994, 370, 218-220; Gearing, A. J. H. et al., Nature, 1994, 370, 555-557; McGeehan, G. M. et al., Nature 1994, 370, 558-561), and thenafter, a similarity of the 3-dimensional structure of TACE (Maskos, K. et al., Proc. Natl. Acad. Sci. USA 1998, 95, 3408-3412) to that of MMP was also reported. Based on these, a number of patent applications of compounds having properties of inhibiting MMP and/or TACE have been filed (WO 97/18188, WO 97/20824, WO 97/22587, WO 98/16503, WO 98/16506, WO 98/16514, WO 98/16520, WO 98/24759, WO 98/32748, WO 98/37877, WO 98/38163, WO 98/38179, WO 98/43963, WO 98/50348, WO 98/51665, WO 99/37625, WO 99/38843, WO 99/41246, WO 99/42436, WO 99/52889, WO 99/52910, WO 99/58528, WO 99/58531, WO 99/61413, WO 99/65867, WO 00/09485, WO 00/12466, WO 00/12467, WO 00/12477, WO 00/12478, WO 00/50017, WO 00/51975, WO 00/59285, WO 00/69812, WO 00/71514, WO 00/75108, U.S. Pat. Nos. 5,985,900, 6,057, 297, 6,162,821, JP-A-11-504015, EP 1 041 072 A). However, it has been reported that rats continuously administered with an agent which inhibits many kinds of MMPs at the same time had a hypertrophic degeneration on the cartilage growth plates (Nakajima, M., The Bone 2001, 15, 161-166) and that MT1-MMP (MMP14) knock out mouse was observed to present a symptom of arthritis (Holmbeck, K., et al., Cell 1999, 99, 81-92). Because of these reports and the fact that many MMPs are involved in the maintenance and homeostasis of extracellular matrices which form the basic structure of a living body, inhibiting the catalytic activities of many MMPs nonselectively is likely to cause serious adverse effects. Therefore, it is preferred that the compounds with the aim of suppressing the TNF-α production based on the TACE inhibition have very low inhibitory activities for other MMPs.

However, there are few patent applications concerned with compounds inhibiting TACE selectively (WO 98/38179, WO 00/00465, WO 00/09492, WO 00/23443, WO 00/35885, WO 00/44710, WO 00/44713, WO 00/44716, WO 00/44723, WO 00/44730, WO 00/44740, JP-A-11-343279, GB 2 326 881 A, WO 02/18326), and in most cases, there is poor selectivity in the compounds or no description on the results of their evaluation, and examples having obtained a high selectivity have scarcely ever been reported.

The present invention has been accomplished with the aim of treatment and prevention of TNF-α -mediated diseases, and objects of the present invention are to provide novel compounds and salts thereof which exhibit a TACE-selective inhibitory action and do not inhibit other MMPs, and to provide a pharmaceutical containing these as an effective component.

DISCLOSURE OF INVENTION

As a result of intensive studies to solve the above problems, it has been found that reverse hydroxamic acid derivatives with specific structures have an excellent selective TACE-inhibitory action, and the present invention has been completed on the basis of this knowledge.

That is, the present invention relates to a reverse hydroxamic acid derivative represented by a general formula (Ia):

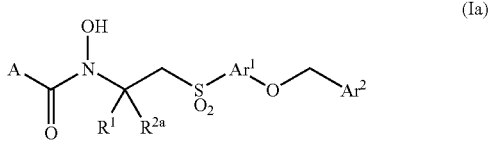

[wherein A is a hydrogen atom, a lower alkyl, a cycloalkyl or —$NR^3R^4$ (wherein $R^3$ and $R^4$ are independently a hydrogen atom, a lower alkyl or a cycloalkyl, or form a nitrogen-containing heterocycle together with the nitrogen to which $R^3$ and $R^4$ are attached); $Ar^1$ is an arylene or a heteroarylene; $Ar^2$ is an optionally substituted aryl, an optionally substituted aralkyl, an optionally substituted heteroaryl or an optionally substituted heteroarylalkyl; $R^1$ is a hydrogen atom, an optionally substituted lower alkyl, an optionally substituted lower alkenyl or an optionally substituted cycloalkyl; $R^{2a}$ is represented by a general formula (a):

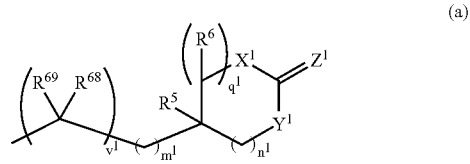

(wherein $R^5$ and $R^6$ are independently a hydrogen atom, a halogen atom, hydroxyl, cyano, trifluoromethyl, an optionally substituted lower alkyl or an optionally substituted lower alkoxy; $R^{68}$ and $R^{69}$ are independently a hydrogen atom or an optionally substituted lower alkyl; $X^1$ and $Y^1$ are independently a single bond, oxygen, sulfur, —$CR^7R^8$— (wherein $R^7$ and $R^8$ are independently the same as $R^5$) or —$NR^9$— (wherein $R^9$ is a hydrogen atom or an optionally substituted lower alkyl, an optionally substituted aryl or an optionally substituted heteroaryl); $Z^1$ is oxygen, sulfur, =$CR^{10}OR^{11}$ (wherein $R^{10}$ and $R^{11}$ are independently a hydrogen atom, a halogen atom, cyano, trifluoromethyl, an optionally substituted lower alkyl, carboxyl, —$CONR^{12}R^{13}$ (wherein $R^{12}$ and $R^{13}$ are independently a hydrogen atom, a lower alkyl or a cycloalkyl, or form a nitrogen-containing heterocycle together with the nitrogen to which $R^{12}$ and $R^{13}$ are attached), —$COR^{14}$ (wherein $R^{14}$ is a hydrogen atom, an optionally substituted lower alkyl, an optionally substituted lower alkoxy, an optionally substituted aryl, an optionally substituted aralkyl, an optionally substituted heteroaryl or an optionally substituted heteroarylalkyl)), =$NR^{15}$ (wherein $R^{15}$ is a hydrogen atom, hydroxyl, an optionally substituted lower alkyl, an optionally substituted lower alkoxy or an optionally substituted acyl), —$O(CH_2)_{p1}O$— (wherein $p^1$ is an integer from 2 to 4), —$S(CH_2)_{r1}S$— (wherein $r^1$ is an integer from 2 to 4) or —$O(CH_2)_{t1}S$— (wherein $t^1$ is an integer from 2 to 4); m1 is an integer from 0 to 6; $n^1$ and $q^1$ are independently an integer from 0 to 3; and $v^1$ is 0 or 1), by a general formula (b):

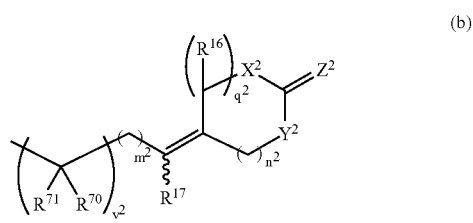

(wherein $R^{16}$ is a hydrogen atom, a halogen atom, hydroxyl, cyano, trifluoromethyl, an optionally substituted lower alkyl or an optionally substituted lower alkoxy; $R^{17}$ is a hydrogen atom, a halogen atom, or an optionally substituted lower alkyl; $R^{70}$ and $R^{71}$ are independently a hydrogen atom or an optionally substituted lower alkyl; $X^2$ and $Y^2$ are independently a single bond, oxygen, sulfur, —$CR^{18}R^{19}$— (wherein $R^{18}$ is a hydrogen atom, a halogen atom, an optionally substituted lower alkyl or an optionally substituted lower alkoxy, and $R^{19}$ is a hydrogen atom, a halogen atom, hydroxyl, cyano, trifluoromethyl, an optionally substituted lower alkyl, an optionally substituted lower alkoxy, an optionally substituted acyl, carboxyl, —$CONR^{20}R^{21}$ (wherein $R^{20}$ and $R^{21}$ are independently a hydrogen atom, a lower alkyl or a cycloalkyl, or form a nitrogen-containing heterocycle together with the nitrogen to which $R^{20}$ and $R^{21}$ are attached), —$SO_2R^{22}$ (wherein $R^{22}$ is a lower alkyl, a cycloalkyl, an optionally substituted aryl or an optionally substituted heteroaryl), —$NR^{23}R^{24}$ (wherein $R^{23}$ and $R^{24}$ are independently a hydrogen atom, an optionally substituted lower alkyl, formyl, an optionally substituted acyl, a lower alkylsulfonyl, an optionally substituted arylsulfonyl, an optionally substituted heteroarylsulfonyl, —$CONR^{25}R^{26}$ (wherein $R^{25}$ and $R^{26}$ are independently a hydrogen atom, an optionally substituted lower alkyl, an optionally substituted aryl or an optionally substituted heteroaryl, or form a nitrogen-containing heterocycle together with the nitrogen to which $R^{25}$ and $R^{26}$ are attached), or a cycloalkyl, or form a nitrogen-containing heterocycle together with the nitrogen to which $R^{23}$ and $R^{24}$ are attached), or —$OCOR^{27}$ (wherein $R^{27}$ is an optionally substituted lower alkyl, an optionally substituted aryl, an optionally substituted heteroaryl or —$NR^{28}R^{29}$ (wherein $R^{28}$ and $R^{29}$ are independently a hydrogen atom, an optionally substituted lower alkyl, an optionally substituted aryl or an optionally substituted heteroaryl, or form a nitrogen-containing heterocycle together with the nitrogen to which $R^{28}$ and $R^{29}$ are attached))), or —$NR^{30}$— (wherein $R^{30}$ is a hydrogen atom, an optionally substituted lower alkyl, an optionally substituted aryl, an optionally substituted heteroaryl, —$COR^{31}$ (wherein $R^{31}$ is a hydrogen atom, an optionally substituted lower alkyl or an optionally substituted lower alkoxy) or —$CONR^{32}R^{33}$ (wherein $R^{32}$ and $R^{33}$ are independently a hydrogen atom, a lower alkyl or a cycloalkyl, or form a nitrogen-containing heterocycle together with the nitrogen to which $R^{32}$ and $R^{33}$ are attached)); $Z^2$ is two hydrogen atoms, oxygen, sulfur, =$CR^{34}R^{35}$ (wherein $R^{34}$ and $R^{35}$ are independently a hydrogen atom, a halogen atom, cyano, trifluoromethyl or an optionally substituted lower alkyl, an optionally substituted acyl, carboxyl, —$CONR^{36}R^{37}$ (wherein $R^{36}$ and $R^{37}$ are independently a hydrogen atom, a lower alkyl or a cycloalkyl, or form a nitrogen-containing heterocycle together with the nitrogen to which $R^{36}$ and $R^{37}$ are attached)), =$NR^{38}$ (wherein $R^{38}$ is a hydrogen atom, hydroxyl, an optionally substituted lower alkyl, an optionally substituted lower alkoxy or an optionally substituted acyl), —$O(CH_2)_{p2}O$— (wherein $p^2$ is an integer from 2 to 4), —$S(CH_2)_{r2}S$— (wherein $r^2$ is an integer from 2 to 4) or —$O(CH_2)_{t2}S$— (wherein $t^2$ is an integer from 2 to 4); $m^2$ is an integer from 0 to 6; $n^2$ and $q^2$ are independently an integer from 0 to 3, and $v^2$ is 0 or 1), by a general formula (c):

(c)

(wherein $G^1$ is an unsaturated four to seven membered ring optionally substituted with 1 to 4 of independent $R^{39}$ at an optional position; $R^{39}$ is hydroxyl, a halogen atom, cyano, trifluoromethyl, an optionally substituted lower alkyl, an optionally substituted lower alkoxy, an optionally substituted acyl, carboxyl, —$CONR^{40}R^{41}$ (wherein $R^{40}$ and $R^{41}$ are independently a hydrogen atom, a lower alkyl or a cycloalkyl, or form a nitrogen-containing heterocycle together with the nitrogen to which $R^{40}$ and $R^{41}$ are attached), —$SO_2R^{42}$ (wherein $R^{42}$ is a lower alkyl, a cycloalkyl, an optionally substituted aryl or an optionally substituted heteroaryl), —$NR^{43}R^{44}$ (wherein $R^{43}$ and $R^{44}$ are independently a hydrogen atom, an optionally substituted lower alkyl, formyl, an optionally substituted acyl, a lower alkylsulfonyl, an optionally substituted arylsulfonyl, an optionally substituted heteroarylsufonyl, —$CONR^{45}R^{46}$ (wherein $R^{45}$ and $R^{46}$ are independently a hydrogen atom, an optionally substituted lower alkyl, an optionally substituted aryl or an optionally substituted heteroaryl, or form a nitrogen-containing heterocycle together with the nitrogen to which $R^{45}$ and $R^{46}$ are attached) or a cycloalkyl, or form a nitrogen-containing heterocycle together with the nitrogen to which $R^{43}$ and $R^{44}$ are attached), or —$OCOR^{47}$ (wherein $R^{47}$ is an optionally substituted lower alkyl, an optionally substituted aryl, an optionally substituted heteroaryl or —$NR^{48}R^{49}$ (wherein $R^{48}$ and $R^{49}$ are independently a hydrogen atom, an optionally substituted lower alkyl, an optionally substituted aryl or an optionally substituted heteroaryl, or form a nitrogen-containing heterocycle together with the nitrogen to which $R^{48}$ and $R^{49}$ are attached)); and $m^3$ is an integer from 0 to 6), by a general formula (da):

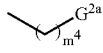

(da)

(wherein $G^{2a}$ is an optionally substituted aryl, an optionally substituted heteroaryl, an optionally substituted cycloalkyl or an optionally substituted heterocycloalkyl each of which are substituted with $R^{50}$ at an optional position ($R^{50}$ is an optionally substituted lower alkyl or an optionally substituted lower alkenyl); and $m^4$ is an integer from 0 to 6), by a general formula (e):

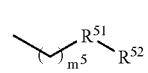

(e)

(wherein $R^{51}$ is —$CR^{72}$=$CR^{73}$—, —$C\equiv C$— or —$CR^{74}R^{75}$—$CR^{76}R^{77}$— (wherein $R^{72}$, $R^{73}$, $R^{74}$, $R^{75}$, $R^{76}$ and $R^{77}$ are independently a hydrogen atom or an optionally substituted lower alkyl); $R^{52}$ is an optionally substituted aryl, an optionally substituted aralkyl, an optionally substituted heteroaryl, an optionally substituted heteroarylalkyl, an optionally substituted cycloalkyl, an optionally substituted cycloalkylalkyl, an optionally substituted heterocycloalkyl, an optionally substituted heterocycloalkenyl, an optionally substituted heterocycloalkylalkyl or an optionally substituted heterocycloalkenylalkyl; and $m^5$ is an integer from 0 to 6), or by a general formula (f):

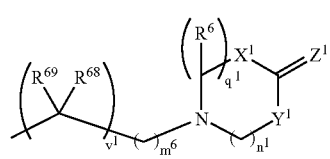

(f)

(wherein $R^6$, $R^{68}$, $R^{69}$, $X^1$, $Y^1$, $Z^1$, $n^1$, $q^1$ and $v^1$ are the same as defined above; and $m^6$ is an integer from 1 to 6) or a salt thereof (hereinafter, referred to as a reverse hydroxamic acid derivative Ia).

The present invention also relates to a medicament comprising the reverse hydroxamic acid derivative Ia as an active component.

The present invention relates to TNF-α converting enzyme (TACE) inhibitors comprising a reverse hydroxamic acid derivative represented by a general formula (I):

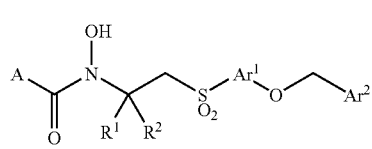

(I)

(wherein A, $Ar^1$, $Ar^2$ and $R^1$ are the same as defined above, and $R^2$ is the same as the above $R^{2a}$, or a hydrogen atom, an optionally substituted lower alkyl or $R^2$ is represented by a general formula (d), in which $G^2$ is not substituted with $R^{50}$ described in the above general formula (da):

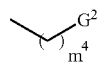

(d)

(wherein $G^2$ is an optionally substituted aryl, an optionally substituted heteroaryl, an optionally substituted cycloalkyl or an optionally substituted heterocycloalkyl; and $m^4$ is the same as defined above)) or a salt thereof (hereinafter referred to as a reverse hydroxamic acid derivative I) as an active component.

Furthermore, the present invention relates to a method for treating a disease condition caused by TNF-α, which comprises administering to a patient in need thereof an effective amount of the reverse hydroxamic acid derivative I or the salt thereof.

DETAILED DESCRIPTION OF THE INVENTION

The reverse hydroxamic acid derivative represented by the general formula (Ia) in the present invention refers to the reverse hydroxamic acid derivative represented by the general formula (I) in which $R^2$ is $R^{2a}$, thus it is included in the reverse hydroxamic acid derivative represented by the general formula (I) of the present invention. Therefore, the explanation for the general formula (I) herein is applicable to the general formula (Ia).

Next, each substituent in the above-mentioned general formula (I) is explained.

"A lower alkyl" means a straight or branched $C_1$ to $C_6$ alkyl. As specific examples thereof, there include methyl, ethyl, n-propyl, isopropyl, n-butyl, isobutyl, tert-butyl, sec-butyl, n-pentyl, tert-amyl, 3-methylbutyl, neopentyl, n-hexyl and the like.

"A cycloalkyl" includes, for example, cyclopropyl, cyclobutyl, cyclopentyl, cyclohexyl, cycloheptyl and the like.

"A halogen atom" is concretely fluorine atom, chlorine atom, bromine atom or iodine atom.

"A nitrogen-containing heterocycle" refers to a saturated or unsaturated heterocycle containing at least one N. Specific examples of the nitrogen-containing heterocycle include azetidine ring, pyrrolidine ring, piperidine ring, thiazolidine ring, morpholine ring, thiomorpholine ring, dihydropyrrole ring and the like, but are not limited thereto. Examples of the substituent include lower alkyl, lower alkoxy, hydroxyl, nitro, cyano, trifluoromethyl, hydroxymethyl and the like.

"A heterocycle" represents a 3- to 10-membered monocyclic ring or bicyclic ring composed of carbon atoms and 1 to 3 hetero atoms independently selected from N, O or S, in which N and S may be optionally oxidized, and N may be optionally quarternized, substituted, and may be condensed with a carbon ring or another heterocycle at any of the substitutable position(s). Specifically, examples of the heterocycle include dioxolole ring, oxathiol ring, dihydrooxathiin ring, dihydrodioxin ring, dihydrofuran ring, dihydrothiophene ring, dihydropyrrole ring, furan ring, thiophene ring, pyrrole ring, oxazole ring, thiazole ring, pyridine ring and the like, but are not limited thereto.

It should be noted that the heterocycle herein means the above-mentioned "a heterocycle".

"A carbon ring" refers to a 3- to 10-membered monocyclic ring or bicyclic ring and, as specific examples, there include cyclopentene ring, cyclohexene ring, benzene ring and the like; but it is not limited thereto.

It should be noted that the carbon ring herein means the above-mentioned "a_carbon ring".

"An arylene" means, for example, a phenylene, a naphthylene or the like, more specifically, including 1,2-phenylene, 1,3-phenylene, 1,4-phenylene, 1,4-naphthylene.

"A heteroarylene" means, for example, a pyridinediyl, a thiophenediyl, a furandiyl or the like, more specifically, including 2,5-pyridinediyl, 2,5-thiophenediyl, 2,5-furandiyl.

An "aryl" represents an aromatic carbon ring, and for example, phenyl, naphthyl and the like are included.

"An aralkyl" refers to the above-mentioned lower alkyl which is substituted with the above-mentioned aryl group. Such substitution may be carried out at any of the substitutable position(s). Examples of the aralkyl include, benzyl, phenethyl, 1-phenylethyl, 1-phenylpropyl, 3-phenylpropyl, α-naphthylmethyl, β-naphthylmethyl, 1-(α-naphthyl)ethyl, 2-(αnaphthyl)ethyl and the like. In the aryl moiety, an optional substituent may be provided.

"A heteroaryl" represents a 5- to 6-membered aromatic heterocycle. Examples of the heteroaryl include a pyrrolyl (e.g. 2-pyrrolyl), a furyl (e.g. 3-furyl), a thienyl (e.g. 2-thienyl), an imidazolyl (e.g. 4-imidazolyl), a pyrazolyl (e.g. 3-pyrazolyl), an oxazolyl (e.g. 2-oxazolyl), an isoxazolyl (e.g. 3-isoxazolyl), a thiazolyl (e.g. 2-thiazolyl), an isothiazolyl (e.g. 3-isothiazolyl), a pyridyl (e.g. 2-pyridyl, 3-pyridyl, 4-pyridyl), a pyridazinyl (e.g. 3-pyridazinyl), a pyrimidyl (e.g. 4-pyrimidyl), a pyrazinyl (e.g. 2-pyrazinyl), an indolyl (e.g. 2-indolyl, 3-indolyl, 4-indolyl), a benzofuryl (e.g. 3-benzofuryl, 4-benzofuryl), a benzothienyl (e.g. 3-benzothienyl, 4-benzothienyl), a benzoimidazolyl (e.g. 2-benzoimidazolyl), an indazolyl (e.g. 4-indazolyl), a benzoxazolyl (e.g. 4-benzoxazolyl), a benzothiazolyl (e.g. 4-benzothiazolyl), a benzoisoxazolyl (e.g. 4-benzoisoxazolyl), a benzoisothiazolyl (e.g. 4-benzoisothiazolyl), a quinolyl (e.g. 2-quinolyl, 4-quinolyl, 5-quinolyl, 8-quinolyl), an isoquinolyl (e.g. 1-isoquinolyl, 4-isoquinolyl, 5-isoquinolyl, 8-isoquinolyl), a cinnolinyl (e.g. 4-cinnolinyl, 5-cinnolinyl, 8-cinnolinyl), a quinazolinyl (e.g. 4-quinazolinyl, 5-quinazolinyl, 8-quinazolinyl), tetrazolyl and the like. Such heteroaryl may have an optional substituent.

"A heteroarylalkyl" refers to the above-mentioned lower alkyl which is substituted with the above-mentioned heteroaryl. Such substitution may be carried out at any of the substitutable position(s). Examples of the heteroarylalkyl include a pyridylmethyl (e.g. 2-pyridylmethyl), an oxazolylethyl (e.g. 2-oxazolyl-2-ethyl), a thiazolylmethyl (e.g. 4-thiazolylmethyl), an indolylmethyl (e.g. 2-indolylmethyl, 3-indolylmethyl, 4-indolylmethyl), a benzofurylmethyl (e.g. 3-benzofurylmethyl, 4-benzofurylmethyl), a benzothienylmethyl (e.g. 3-benzothienylmethyl, 4-benzothienylmethyl), a benzothiazolylmethyl (e.g. 2-benzothiazolylmethyl), a quinolylmethyl (e.g. 2-quinolylmethyl, 4-quinolylmethyl, 5-quinolylmethyl, 8-quinolylmethyl), an isoquinolylmethyl (e.g. 1-isoquinolylmethyl, 4-isoquinolylmethyl, 5-isoquinolylmethyl, 8-isoquinolylmethyl), a cinnolinylmethyl (e.g. 4-cinnolinylmethyl, 5-cinnolinylmethyl, 8-cinnolinylmethyl), a quinazolinylmethyl (e.g. 4-quinazolinylmethyl, 5-quinazolinylmethyl, 8-quinazolinylmethyl) and the like. Such heteroaryl may have an optional substituent.

"A lower alkenyl" means a straight or branched $C_1$ to $C_6$ alkenyl group having one or more double bond. As specific examples, there include vinyl, 1-propenyl, 2-propenyl, isopropenyl, 2-butenyl, 3-butenyl, isobutenyl, 2-methyl-1-propenyl, 1-methyl-1-propenyl, 1-pentenyl, 2-pentenyl, 4-pentenyl, prenyl, 1-hexenyl, 2-hexenyl, 5-hexenyl and the like.

"A lower alkoxy" refers to an alkoxy whose alkyl moiety is the same as defined in the above lower alkyl. Examples of the lower alkoxy include straight or branched alkoxy groups such as methoxy, ethoxy, n-propoxy, isopropoxy, n-butoxy, isobutoxy, tert-butoxy, sec-butoxy, n-pentyloxy, tert-amyloxy, 3-methylbutoxy, neopentyloxy and n-hexyloxy.

"An acyl" refers to an alkylcarbonyl whose alkyl moiety is the same as defined in the above lower alkyl. Examples of the acyl include straight or branched alkylcarbonyl groups such as acetyl, propionyl, butyryl, isobutyryl, valeryl, isovaleryl and pivaloyl.

"An unsaturated 4- to 7-membered ring" represents a 4- to 7-membered carbon ring or heterocyclic ring having one double bond at optional position within the ring. Examples thereof include cyclopentene, cyclohexene, cycloheptene, a dihydrofuran (e.g. 2,5-dihydrofuran), a dihydropyran (e.g. 5,6-dihydro-2H-pyran), a dihydropyrrole (e.g. 3-pyrroline), a tetrahydropyridine (e.g. 1,2,3,6-tetrahydropyridine), a dihydrothiophene (e.g. 2,5-dihydrothiophene), a dihydrothiopyran (e.g. 5,6-dihydro-2H-thiopyran), a dehydrohomopiperidine (e.g. 4,5-dehydrohomopiperidine) and the like, but are not limited thereto.

"A cycloalkylalkyl" refers to the above-mentioned lower alkyl which is substituted with the above-mentioned cycloalkyl. Such substitution may be carried out at any of the substitutable position(s). Examples thereof include cyclopropylmethyl, cyclobutylmethyl, cyclopentylmethyl, a cyclopentylethyl (e.g. 2-cyclopentylethyl), cyclohexylmethyl, a cyclohexylpropyl (e.g. 3-cyclohexylpropyl) and the like, each of which may have an optional substituent in cycloalkyl moiety.

"A heterocycloalkyl" represents a saturated monocyclic heterocycle. For example, a pyrrolidinyl (e.g. 1-pyrrolidinyl, 2-pyrrolidinyl, 3-pyrrolidinyl), a piperidinyl (e.g. 1-piperidinyl, 4-piperidinyl), a homopiperidinyl (e.g. 1-homopiperidinyl, 4-homopiperidinyl), a tetrahydrofuranyl (e.g. 2-tetrahydrofuranyl, 3-tetrahydrofuranyl), a tetrahydropyranyl (e.g. 4-tetrahydropyranyl), a piperazinyl (e.g. 1-piperazinyl), a homopiperazinyl (1-piperazinyl) and the like are included.

"A heterocycloalkenyl" represents a monocyclic heterocycle having one double bond at any position of the ring. For example, a dihydrofuryl (e.g. 2,5-dihydrofuran-3-yl), a dihydropyranyl (e.g. 5,6-dihydro-2H-pyran-4-yl), a dihydropyrrolyl (e.g. 3-pyrroline-3-yl), a tetrahydropyridyl (e.g. 1,2,3,6-tetrahydropyridin-4-yl), a dihydrothienyl (e.g. 2,5-dihydrothiophen-3-yl), a dihydrothiopyranyl (e.g. 5,6-dihydro-2H-thiopyran-4-yl), a dehydrohomopiperidinyl (e.g. 4,5-dehydrohomopiperidin-4-yl) and the like are included.

"A heterocycloalkylalkyl" refers to the above-mentioned lower alkyl which is substituted with the above-mentioned heterocycloalkyl. Such substitution may be carried out at any of the substitutable position(s). For example, there include a pyrrolidinylmethyl (e.g. 1-pyrrolidinylmethyl, 2-pyrrolidinylmethyl, 3-pyrrolidinylmethyl), a piperidinylmethyl (e.g. 1-piperidinylmethyl, 4-piperidinylmethyl), a piperidinylethyl (e.g. 1-piperidinyl-2-ethyl, 4-piperidinyl-2-ethyl), a homopiperidinylmethyl (e.g. 1-homopiperidinylmethyl, 4-homopiperidinylmethyl), a tetrahydrofuranylmethyl (e.g. 2-tetrahydrofuranylmethyl, 3-tetrahydrofuranylmethyl), a tetrahydropyranylmethyl (e.g. 4-tetrahydropyranylmethyl), a piperazinylmethyl (e.g. 1-piperazinylmethyl), a homopiperazinylmethyl (1-homopiperazinylmethyl) and the like.

"A heterocycloalkenylalkyl" refers to the above-mentioned lower alkyl which is substituted with the above-mentioned heterocycloalkenyl. Such substitution may be carried out at any of the substitutable position(s). For example, there include a dihydrofurylmethyl (e.g. 2,5-dihydrofuran-3-ylmethyl), a dihydropyranylmethyl (e.g. 5,6-dihydro-2H-pyran-4-ylmethyl), a dihydropyrrolylmethyl (e.g. 3-pyrroline-3-ylmethyl), a tetrahydropyridylmethyl (e.g. 1,2,3,6-tetrahydropyridin-4-ylmethyl), a tetrahydropyridylethyl (e.g. 1,2,3,6-tetrahydropyridin-4-yl-2-ethyl), a dihydrothienylmethyl (e.g. 2,5-dihydrothiophen-3-ylmethyl), a dihydrothiopyranylmethyl (e.g. 5,6-dihydro-2H-thiopyran-4-ylmethyl), a dehydrohomopiperidinylmethyl (e.g. 4,5-dehydrohomopiperidin-4-ylmethyl) and the like.

"An arylsulfonyl" represents a functional group in which the above aryl is attached via one sulfonyl. For example, phenylsulfonyl, 1-naphthylsulfonyl, 2-naphthylsulfonyl and the like are included.

"A heteroarylsufonyl" represents a functional group in which the above heteroaryl is attached via one sulfonyl. Examples of the heteroarylsufonyl include 2-pyridylsulfonyl, 4-pyridylsulfonyl, 2-thienylsulfonyl and the like, but are not limited thereto.

"A lower alkylsulfonyl" represents a straight or branched alkylsulfonyl having $C_1$ to $C_6$ alkylsulfonyl including, as specific examples, methanesulfonyl, ethanesulfonyl, n-propylsulfonyl, isopropylsulfonyl, n-butylsulfonyl, sec-butylsulfonyl, tert-butylsulfonyl and the like.

As a substituent on the aromatic ring in "an optionally substituted aryl", "an optionally substituted aralkyl", "an optionally substituted heteroaryl" or "an optionally substituted heteroarylalkyl", there include hydroxyl, a halogen atom, cyano, nitro, trifluoromethyl, an optionally substituted lower alkyl, an optionally substituted lower alkoxy, mercapto, an optionally substituted lower alkylthio, an optionally substituted lower alkylsulfonyl, a cycloalkyl, carboxyl, a lower alkoxycarbonyl, —$NR^{53}R^{54}$ (wherein $R^{53}$ and $R^{54}$ are independently a hydrogen atom, an optionally substituted lower alkyl, formyl, an optionally substituted acyl, a lower alkylsulfonyl, an optionally substituted arylsulfonyl, an optionally substituted heteroarylsulfonyl, —$CONR^{55}R^{56}$ (wherein $R^{55}$ and $R^{56}$ are independently a hydrogen atom, an optionally substituted lower alkyl, an aryl which is optionally substituted with $R^{57}$ ($R^{57}$ is a lower alkyl, a lower alkoxy or a halogen atom), a heteroaryl which is optionally substituted with $R^{57}$ ($R^{57}$ is the same as the above), or form a nitrogen-containing heterocycle together with the nitrogen to which $R^{55}$ and $R^{56}$ are attached), a cycloalkyl, or form a nitrogen-containing heterocycle together with the nitrogen to which $R^{53}$ and $R^{54}$ are attached), or —$OCOR^{58}$ (wherein $R^{58}$ is an optionally substituted lower alkyl, an aryl which is optionally substituted with $R^{57}$ ($R^{57}$ is the same as the above), a heteroaryl which is optionally substituted with $R^{57}$ ($R^{57}$ is the same as the above), —$NR^{59}R^{60}$ (wherein $R^{59}$ and $R^{60}$ are independently a hydrogen atom, an optionally substituted lower alkyl, an aryl which is optionally substituted with $R^{57}$ ($R^{57}$ is the same as the above), a heteroaryl which is optionally substituted with $R^{57}$ ($R^{57}$ is the same as the above) or form a nitrogen-containing heterocycle together with the nitrogen to which $R^{59}$ and $R^{60}$ and attached)), and the like. At least one substituent of these substituents may be attached to any of the substitutable position(s).

"A lower alkoxycarbonyl" refers to an alkoxycarbonyl whose alkyl moiety is the same as defined in the above lower alkyl. For example, there include straight or branched $C_1$ to $C_6$ alkoxycarbonyl groups such as methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbony, tert-amyloxycarbonyl, 3-methylbutoxycarbonyl, neopentyloxycarbonyl, n-hexyloxycarbonyl.

As the specific examples of "a lower alkylthio", there include straight or branched $C_1$ to $C_6$ alkylthio groups such as methylthio, ethylthio, n-propylthio, isopropylthio, n-butylthio, sec-butylthio and tert-butylthio.

As a substituent in "an optionally substituted cycloalkyl", "an optionally substituted cycloalkylalkyl", "an optionally substituted heterocycloalkyl", "an optionally substituted heterocycloalkylalkyl", "an optionally substituted heterocycloalkenyl" or "an optionally substituted heterocycloalkenylalkyl", there include hydroxyl, a halogen atom, cyano, nitro, trifluoromethyl, an optionally substituted lower alkyl, an optionally substituted lower alkoxy, mercapto, an optionally substituted lower alkylthio, an optionally substituted lower alkylsulfonyl, a cycloalkyl, carboxyl, a lower alkoxycarbonyl, —NR$^{53}$R$^{54}$ (where R$^{53}$ and R$^{54}$ are the same as the above), —OCOR$^{58}$ (where R$^{58}$ is the same as the above) and the like. At least one substituent of these substitutents may be attached to any of the substitutable position(s).

As a substituent on the aromatic rings in "an optionally substituted arylsulfonyl" or "an optionally substituted heteroarylsulfonyl", there include a halogen atom, cyano, nitro, trifluoromethyl, a lower alkyl, an optionally substituted lower alkoxy and the like. At least one substituent of these substitutents may be attached to any of the substitutable position(s).

As a substituent in "an optionally substituted lower alky" or "an optionally substituted lower alkenyl", there include hydroxyl, a halogen atom, cyano, nitro, trifluoromethyl, an optionally substituted lower alkoxy, mercapto, an optionally substituted lower alkylthio, an optionally substituted lower alkylsulfonyl, a cycloalkyl, carboxyl, a lower alkoxycarbonyl, —NR$^{61}$R$^{62}$ (wherein R$^{61}$ and R$^{62}$ are independently a hydrogen atom, a lower alkyl, formyl, an optionally substituted acyl, an optionally substituted alkylsulfonyl, an optionally substituted arylsulfonyl, an optionally substituted heteroarylsulfonyl, —CONR$^{63}$R$^{64}$ (wherein R$^{63}$ and R$^{64}$ are independently a hydrogen atom, a lower alkyl, aryl which is optionally substituted with R$^{57}$ (where R$^{57}$ is the same as the above), a heteroaryl which is optionally substituted with R$^{57}$ (where R$^{57}$ is the same as the above), or form a nitrogen-containing heterocycle together with the nitrogen to which R$^{63}$ and R$^{64}$ are attached), a cycloalkyl, or form a nitrogen-containing heterocycle together with the nitrogen to which R$^{61}$ and R$^{62}$ are attached), or —OCOR$^{65}$ (wherein R$^{65}$ represents a lower alkyl, an aryl which is optionally substituted with R$^{57}$ (where R$^{57}$ is the same as the above), a heteroaryl which is optionally substituted with R$^{57}$ (R$^{57}$ is the same as the above) or —NR$^{66}$R$^{67}$ (wherein R$^{66}$ and R$^{67}$ are independently a hydrogen atom, a lower alkyl, an aryl which is optionally substituted with R$^{57}$ (where R$^{57}$ is the same as the above), a heteroaryl which is optionally substituted with R$^{57}$ (where R$^{57}$ is the same as the above), or form a nitrogen-containing heterocycle together with the nitrogen R$^{66}$ and R$^{67}$ are attached)) and the like. At least one substituent of these substitutents may be attached to any of the substitutable position(s).

As a substituent in "an optionally substituted lower alkoxy", "an optionally substituted acyl", "an optionally substituted lower alkylthio", "an optionally substituted lower alkylsulfonyl" or "an optionally substituted lower alkoxycarbonyl", there include hydroxyl, a halogen atom, cyano, nitro, a lower alkoxy groups and the like. At least one substituent of these substitutents may be attached to any of the substitutable position(s).

When there is an asymmetric carbon in the compound represented by the general formula (I) of the present invention or the compound represented by the general formula (Ia) of the present invention, the racemic forms, diastereoisomers and individual optically active forms are all included in the present invention, and when there is a geometric isomer, all of the (E) form, (Z) form and their mixture are included in the present invention.

Salts of the compounds of the present invention represented by the general formula (I) or (Ia) are not specifically limited as long as they are pharmaceutically acceptable. Such salts include salts with an inorganic base, an organic base, an organic acid, an inorganic acid and an amino acid. Examples of the salt with an inorganic base include alkali metal salts and alkaline-earth metal salts, such as lithium salt, sodium salt, potassium salt, calcium salt, magnesium salt. Examples of the salt with an organic base include triethylamine salt, pyridine salt, ethanolamine salt, cyclohexylamine salt, dicyclohexylamine salt, dibenzylethanolamine salt and the like. Examples of the salt with an organic acid include salts with formic acid, acetic acid, tartaric acid, maleic acid, succinic acid, lactic acid, malic acid, ascorbic acid, oxalic acid, glycolic acid, phenylacetic acid, methanesulfonic acid and the like. Examples of the salt with an inorganic acid include salts with hydrochloric acid, hydrobromic acid, phosphoric acid, sulfamic acid, nitric acid and the like. Further, examples of the salt with an amino acid include salts with glycine, alanine, arginine, glutamic acid, aspartic acid and the like.

The compounds of the present invention represented by the general formula (I) or (Ia) may be in a prodrug form. The prodrugs of the present invention include compounds in which the carboxyl, amino or hydroxyl group of the compounds of general formula (I) or (Ia) is modified so as to generate free carboxyl, amino or hydroxyl group by degradation in vivo when administered. Examples of the prodrug include methyl ester, ethyl ester and aminoalkyl ester derivatives of the carboxyl group in the compounds of the general formula (I) or (Ia), acetate, formate and benzoate derivatives of the hydroxyl and amine functional groups in the lo compounds of the general formula (I) or (Ia) and the like, but are not limited thereto.

Specific examples of the reverse hydroxamic acid derivatives represented by the general formula (I) of the present invention may include the compounds shown in Tables 1 to 28, but are not limited thereto as a matter of course.

TABLE 1

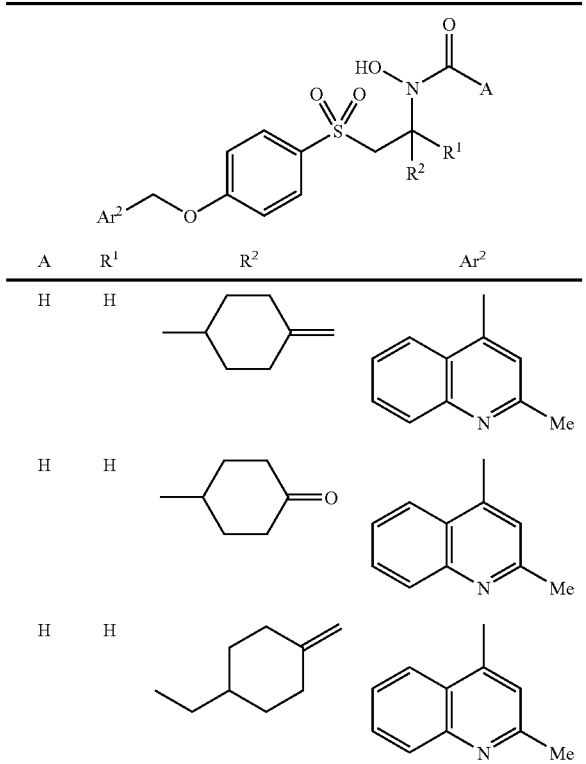

TABLE 1-continued
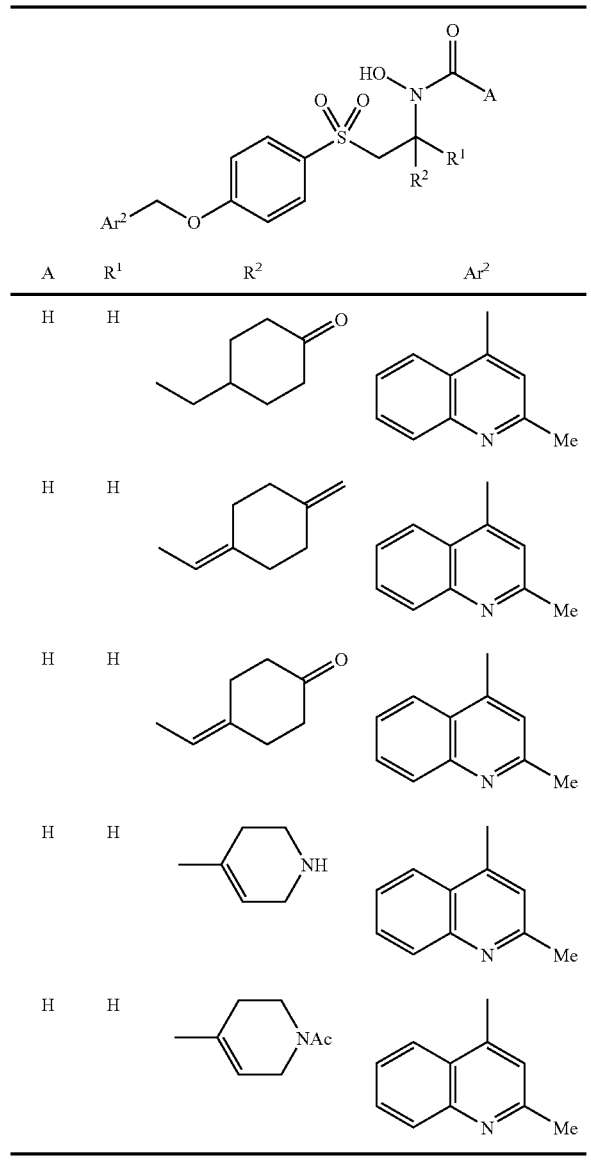
TABLE 2
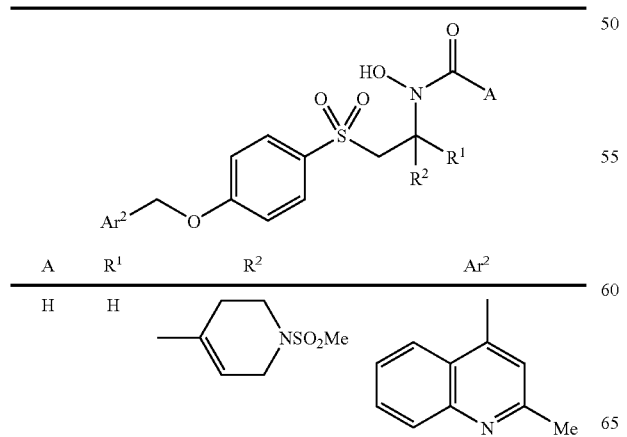
TABLE 2-continued
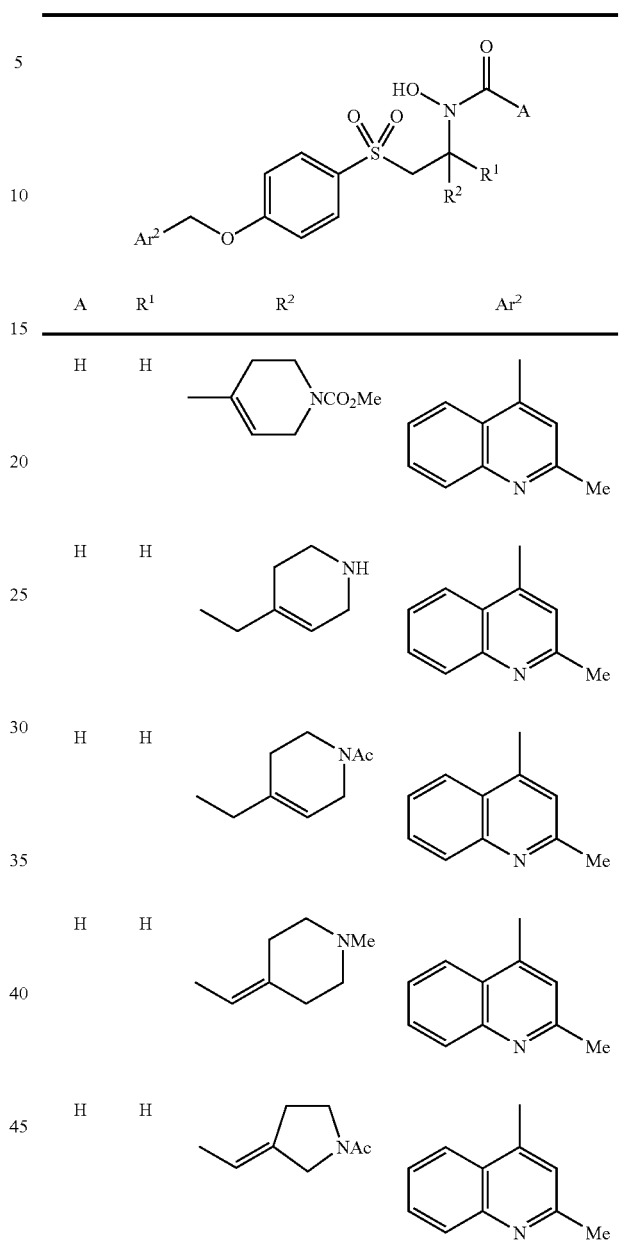
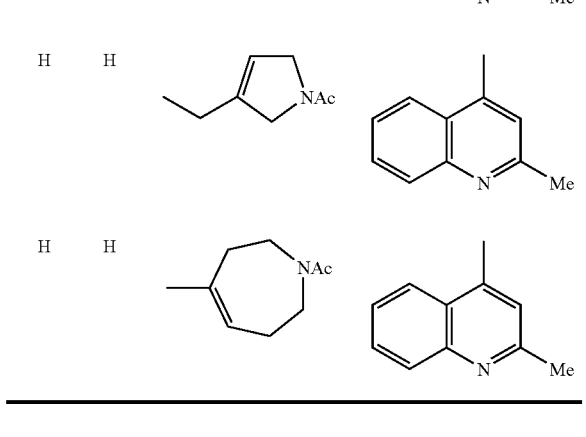

TABLE 3

Structure: Ar²-CH₂-O-C₆H₄-SO₂-CH₂-C(R¹)(R²)-N(OH)-C(=O)-A

| A | R¹ | R² | Ar² |
|---|---|---|---|
| H | H | 4-methyl-3,6-dihydro-2H-pyran-4-yl | 4-methyl-2-methylquinolin-? |
| H | H | 4-methyl-3,6-dihydro-2H-thiopyran-4-yl | 4-methyl-2-methylquinolin-? |
| H | H | 4-ethyl-3,6-dihydro-2H-pyran-4-yl | 4-methyl-2-methylquinolin-? |
| H | H | 4-methyl-thiazolidin-2-one-4-yl (NH) | 4-methyl-2-methylquinolin-? |
| H | H | 3-methyl-4-methyl-thiazolidin-2-one-4-yl (MeN) | 4-methyl-2-methylquinolin-? |
| H | H | 4-ethyl-thiazolidin-2-one-4-yl (NH) | 4-methyl-2-methylquinolin-? |
| H | H | 3-methyl-4-ethyl-thiazolidin-2-one-4-yl (MeN) | 4-methyl-2-methylquinolin-? |
| H | H | 4-(but-1-enyl)tetrahydro-2H-pyran-4-yl | 4-methyl-2-methylquinolin-? |

TABLE 4

Structure: Ar²-CH₂-O-C₆H₄-SO₂-CH₂-C(R¹)(R²)-N(OH)-C(=O)-A

| A | R¹ | R² | Ar² |
|---|---|---|---|
| H | H | 4-methylphenyl | 4-methyl-2-methylquinolin-? |
| H | H | 4-(hydroxymethyl)phenyl | 4-methyl-2-methylquinolin-? |
| H | H | 3-methylphenyl | 4-methyl-2-methylquinolin-? |
| H | H | 2,4-dimethylpyridin-? | 4-methyl-2-methylquinolin-? |
| H | H | 4-ethyl-2-methylpyridin-? | 4-methyl-2-methylquinolin-? |
| H | H | 4-ethyl-2-(hydroxymethyl)pyridin-? | 4-methyl-2-methylquinolin-? |
| H | H | 4-ethyl-2-(methoxymethyl)pyridin-? | 4-methyl-2-methylquinolin-? |
| H | H | 4-ethyl-1-methyl-1H-imidazol-?-yl | 4-methyl-2-methylquinolin-? |

TABLE 5
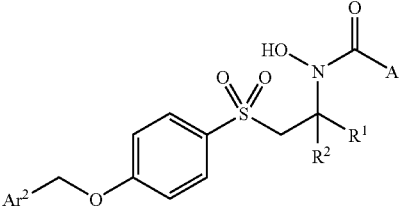
| A | R¹ | R² | Ar² |
|---|----|----|-----|
| H | H |  | 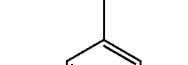 |
| H | H | 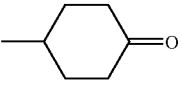 | 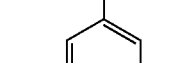 |
| H | H | 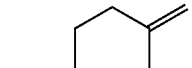 | 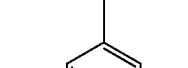 |
| H | H | 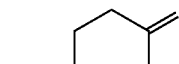 | 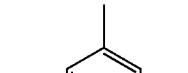 |
| H | H | 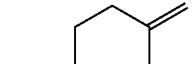 | 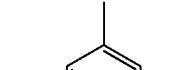 |
| H | H | 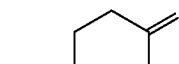 | 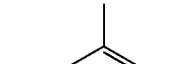 |
| H | H | 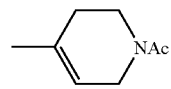 | 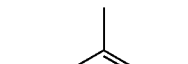 |
| H | H | 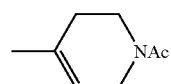 | 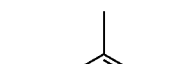 |
TABLE 6
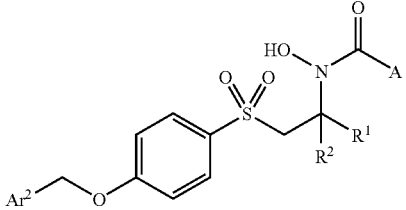
| A | R¹ | R² | Ar² |
|---|----|----|-----|
| H | H | 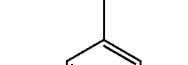 | 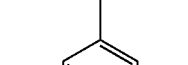 |
| H | H | 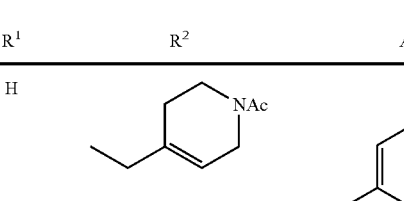 | 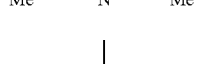 |
| H | H | 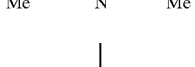 |  |
| H | H | 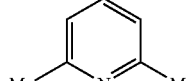 | 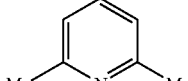 |

TABLE 7

Structure: Ar²-CH₂-O-C₆H₄-SO₂-CH₂-C(R¹)(R²)-N(OH)-C(=O)-A

| A | R¹ | R² | Ar² |
|---|----|----|-----|
| H | H | 4-methylenecyclohexyl | 3,5-dimethylphenyl |
| H | H | 4-oxocyclohexyl | 3,5-dimethylphenyl |
| H | H | 4-ethyl-methylenecyclohexyl | 3,5-dimethylphenyl |
| H | H | 4-ethyl-4-oxocyclohexyl | 3,5-dimethylphenyl |
| H | H | 4-ethylidenecyclohexyl-methylene | 3,5-dimethylphenyl |
| H | H | 4-ethylidene-4-oxocyclohexyl | 3,5-dimethylphenyl |
| H | H | 1-acetyl-1,2,3,6-tetrahydropyridin-4-yl | 3,5-dimethylphenyl |
| H | H | 1-(methoxycarbonyl)-1,2,3,6-tetrahydropyridin-4-yl | 3,5-dimethylphenyl |

TABLE 8

Structure: Ar²-CH₂-O-C₆H₄-SO₂-CH₂-C(R¹)(R²)-N(OH)-C(=O)-A

| A | R¹ | R² | Ar² |
|---|----|----|-----|
| H | H | 1-acetyl-4-ethyl-1,2,3,6-tetrahydropyridin-4-yl | 3,5-dimethylphenyl |
| H | H | 1-(methanesulfonyl)-4-ethylidenepiperidin-4-yl | 3,5-dimethylphenyl |
| H | H | 1-acetyl-3-ethyl-2,5-dihydro-1H-pyrrol-3-yl | 3,5-dimethylphenyl |
| H | H | 3-methyl-4-methylthiazolidin-2-one-4-yl | 3,5-dimethylphenyl |
| H | H | 4-ethylthiazolidin-2-one-4-yl | 3,5-dimethylphenyl |
| H | H | 4-ethyl-2-methylpyridin-?-yl | 3,5-dimethylphenyl |
| H | H | 4-ethyl-2-(hydroxymethyl)pyridin-?-yl | 3,5-dimethylphenyl |
| H | H | 4-ethyl-2-(methoxymethyl)pyridin-?-yl | 3,5-dimethylphenyl |

TABLE 9

Structure: Ar²-CH₂-O-C₆H₄-SO₂-CH₂-C(R¹)(R²)-N(OH)-C(=O)-A

| A | R¹ | R² | Ar² |
|---|----|----|-----|
| H | H | 4-methylenecyclohexyl-methyl | 3-Me-5-Cl-phenyl |
| H | H | 4-oxocyclohexyl-methyl | 3-Me-5-Cl-phenyl |
| H | H | (4-methylcyclohexyl)ethyl | 3-Me-5-Cl-phenyl |
| H | H | (4-oxocyclohexyl)ethyl | 3-Me-5-Cl-phenyl |
| H | H | 4-ethylidene-cyclohexyl-CH₂OH | 3-Me-5-Cl-phenyl |
| H | H | 4-ethylidene-cyclohexanone | 3-Me-5-Cl-phenyl |
| H | H | 1-Ac-4-methyl-tetrahydropyridinyl | 3-Me-5-Cl-phenyl |
| H | H | 1-CO₂Me-4-methyl-tetrahydropyridinyl | 3-Me-5-Cl-phenyl |

TABLE 10

Structure: Ar²-CH₂-O-C₆H₄-SO₂-CH₂-C(R¹)(R²)-N(OH)-C(=O)-A

| A | R¹ | R² | Ar² |
|---|----|----|-----|
| H | H | 4-ethyl-1-Ac-tetrahydropyridinyl | 3-Me-5-Cl-phenyl |
| H | H | 4-ethylidene-1-SO₂Me-piperidinyl | 3-Me-5-Cl-phenyl |
| H | H | 3-ethyl-1-Ac-dihydropyrrolyl | 3-Me-5-Cl-phenyl |
| H | H | N-Me-4-methyl-thiazolidin-2-one | 3-Me-5-Cl-phenyl |
| H | H | 4-ethyl-thiazolidin-2-one | 3-Me-5-Cl-phenyl |
| H | H | 4-ethyl-2-methylpyridinyl | 3-Me-5-Cl-phenyl |
| H | H | 4-ethyl-2-(hydroxymethyl)pyridinyl | 3-Me-5-Cl-phenyl |
| H | H | 4-ethyl-2-(methoxymethyl)pyridinyl | 3-Me-5-Cl-phenyl |

TABLE 11

| A | R¹ | R² | Ar² |
|---|----|----|-----|
| H | H | 4-methylenecyclohexyl | 3-Me-5-OMe-phenyl |
| H | H | 4-oxocyclohexylmethyl | 3-Me-5-OMe-phenyl |
| H | H | 4-methylcyclohexylmethyl | 3-Me-5-OMe-phenyl |
| H | H | 4-oxocyclohexylmethyl | 3-Me-5-OMe-phenyl |
| H | H | 4-(hydroxymethyl)cyclohexylidenemethyl | 3-Me-5-OMe-phenyl |
| H | H | 4-oxocyclohexylidenemethyl | 3-Me-5-OMe-phenyl |
| H | H | 1-Ac-1,2,3,6-tetrahydropyridin-4-ylmethyl | 3-Me-5-OMe-phenyl |
| H | H | 1-CO₂Me-1,2,3,6-tetrahydropyridin-4-ylmethyl | 3-Me-5-OMe-phenyl |

TABLE 12

| A | R¹ | R² | Ar² |
|---|----|----|-----|
| H | H | 1-Ac-1,2,3,6-tetrahydropyridin-4-ylethyl | 3-Me-5-OMe-phenyl |
| H | H | 1-SO₂Me-tetrahydropyridin-4-ylidenemethyl | 3-Me-5-OMe-phenyl |
| H | H | 1-Ac-2,5-dihydro-1H-pyrrol-3-ylethyl | 3-Me-5-OMe-phenyl |
| H | H | 3-Me-2-oxothiazolidin-4-ylmethyl | 3-Me-5-OMe-phenyl |
| H | H | 2-oxothiazolidin-4-ylethyl | 3-Me-5-OMe-phenyl |
| H | H | 2-methylpyridin-4-ylethyl | 3-Me-5-OMe-phenyl |
| H | H | 4-(hydroxymethyl)phenylethyl | 3-Me-5-OMe-phenyl |
| H | H | 2-(methoxymethyl)pyridin-4-ylethyl | 3-Me-5-OMe-phenyl |

TABLE 13
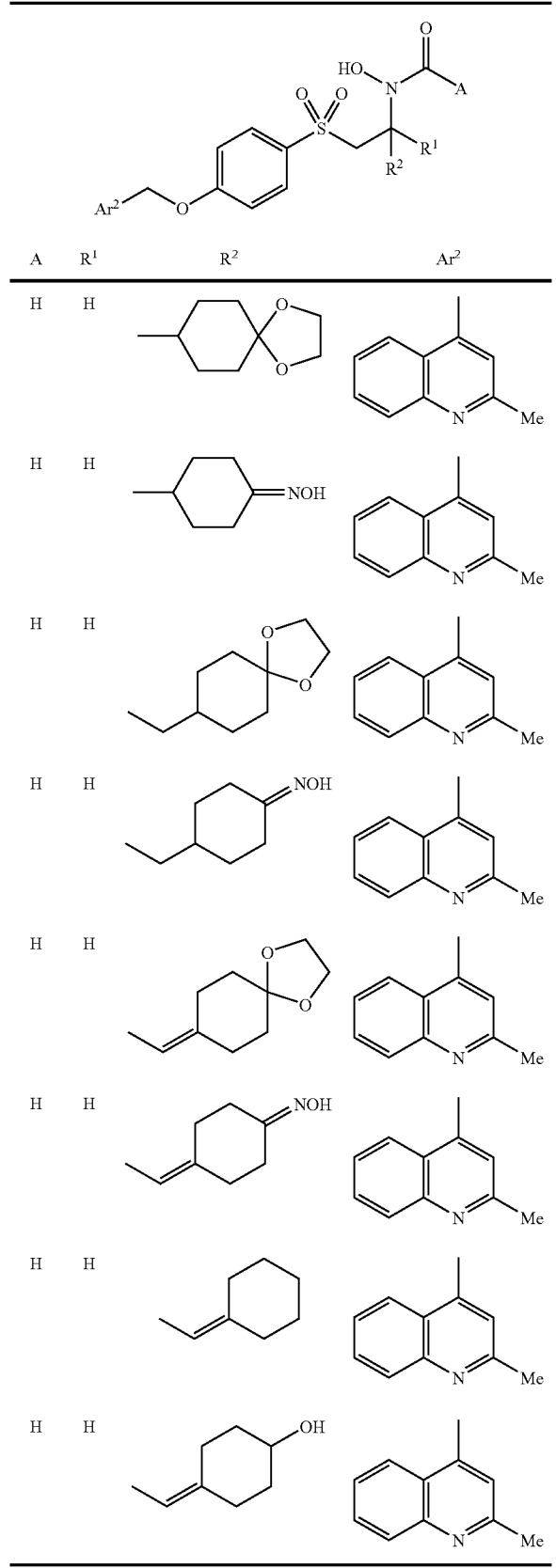
TABLE 14
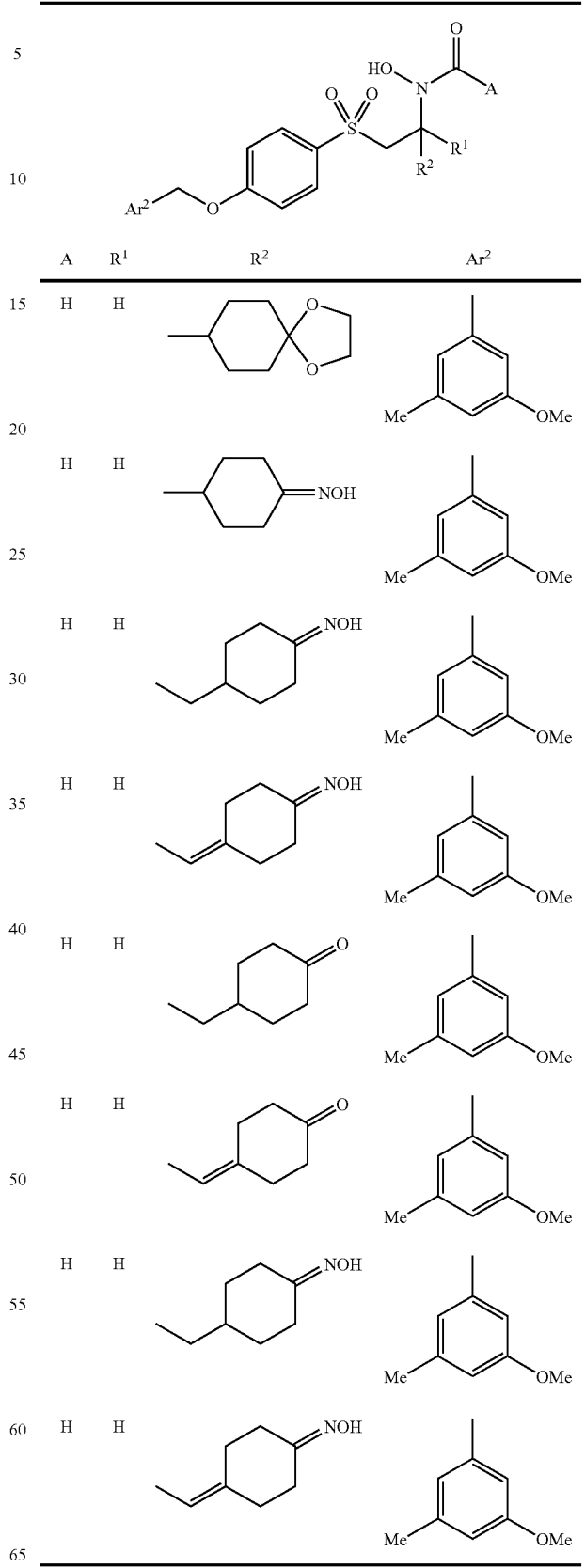

TABLE 15
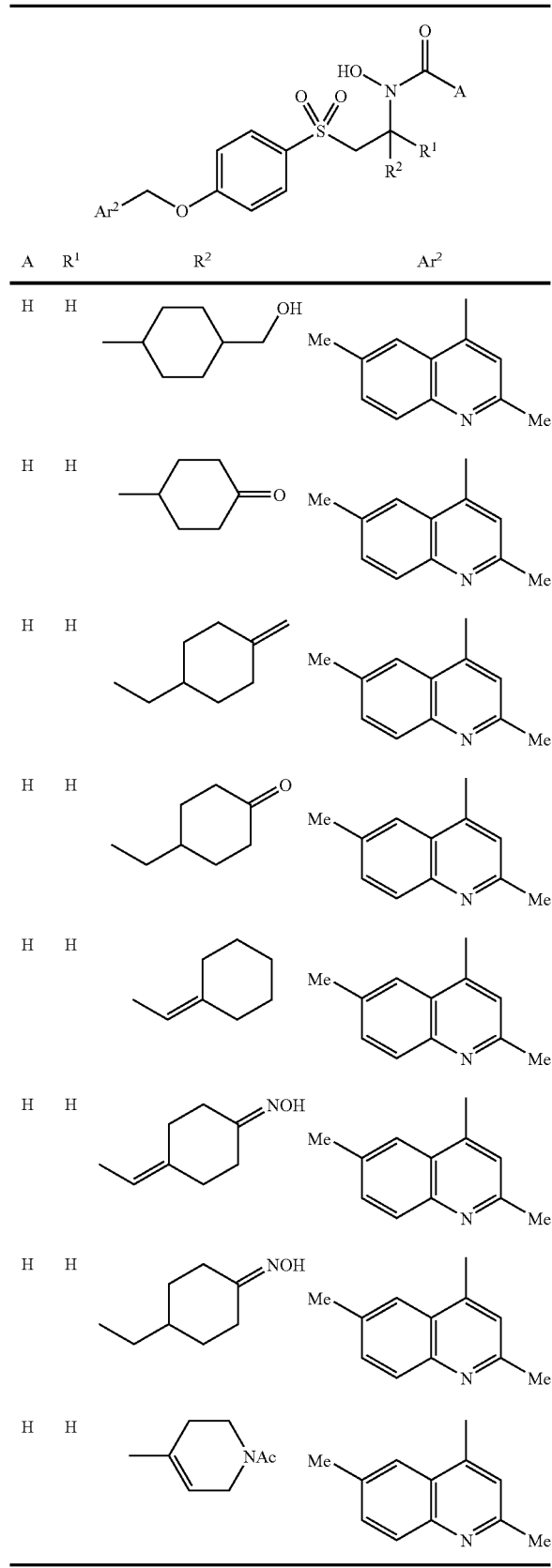
TABLE 16
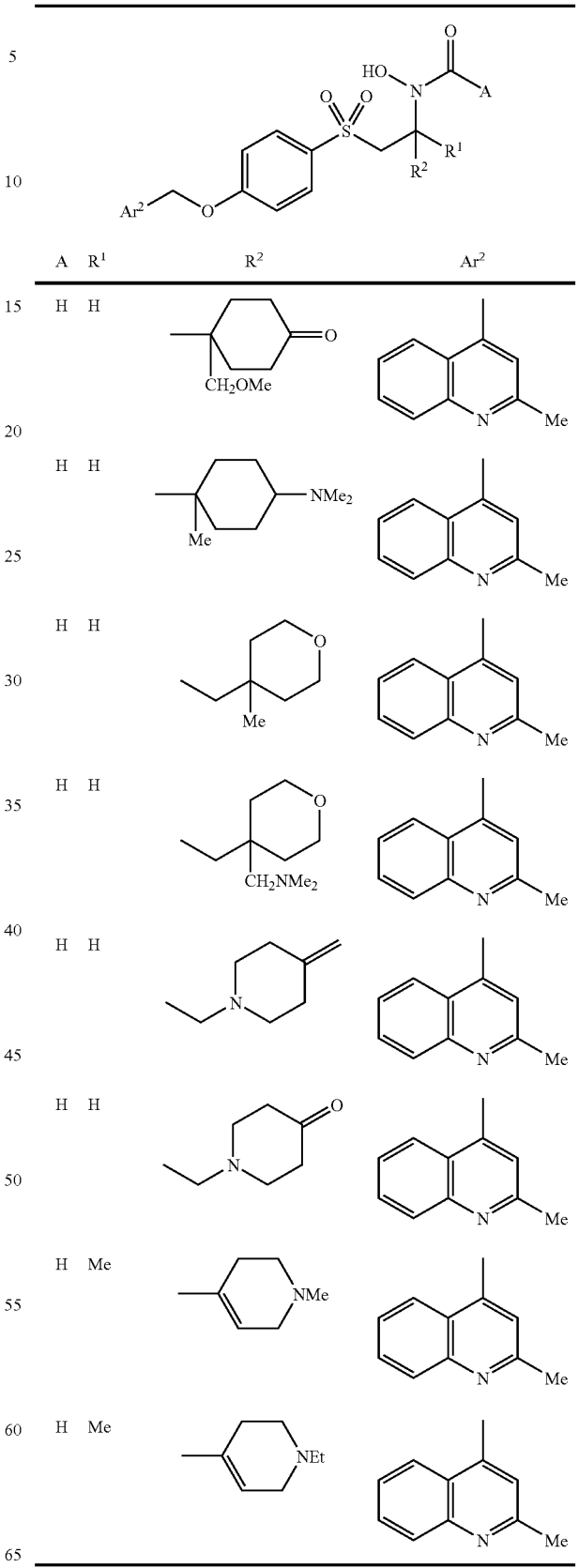

TABLE 17

| A | R¹ | R² | Ar² |
|---|----|----|-----|
| H | H | 5-methyl-5-(methoxymethyl)-1,3-dioxane | 2-methyl-4-quinolinyl |
| H | H | 5,5-dimethyl-1,3-dioxane | 2-methyl-4-quinolinyl |
| H | H | 5-ethyl-5-methyl-1,3-dioxane | 2-methyl-4-quinolinyl |
| H | H | 4-methyl-4-(dimethylaminomethyl)tetrahydropyran | 2-methyl-4-quinolinyl |
| H | H | 4-ethyl-4-methylcyclohexanone | 2-methyl-4-quinolinyl |
| H | H | 4-ethyl-4-(methoxymethyl)cyclohexanone | 2-methyl-4-quinolinyl |
| H | Me | 4-ethylcyclohexanone | 2-methyl-4-quinolinyl |
| H | Me | 4-ethyl-4-methylcyclohexanone | 2-methyl-4-quinolinyl |

TABLE 18

| A | R¹ | R² | Ar² |
|---|----|----|-----|
| H | Me | 4-methylcyclohexanone | 2-methyl-4-quinolinyl |
| H | Me | 4-methyl-4-(dimethylamino)cyclohexane | 2-methyl-4-quinolinyl |
| H | Me | 4-ethyl-4-methyltetrahydropyran | 2-methyl-4-quinolinyl |
| H | Me | 1-ethyl-4-methylpiperidine | 2-methyl-4-quinolinyl |
| H | Me | 1-ethyl-4-methylenepiperidine | 2-methyl-4-quinolinyl |
| H | Me | 1-ethylpiperidin-4-one | 2-methyl-4-quinolinyl |
| H | Me | 1-methyl-4-ethylidene-1,2,3,6-tetrahydropyridine | 2-methyl-4-quinolinyl |
| H | Me | 4-ethylidenecyclohexanol | 2-methyl-4-quinolinyl |

TABLE 19

TABLE 20

TABLE 21
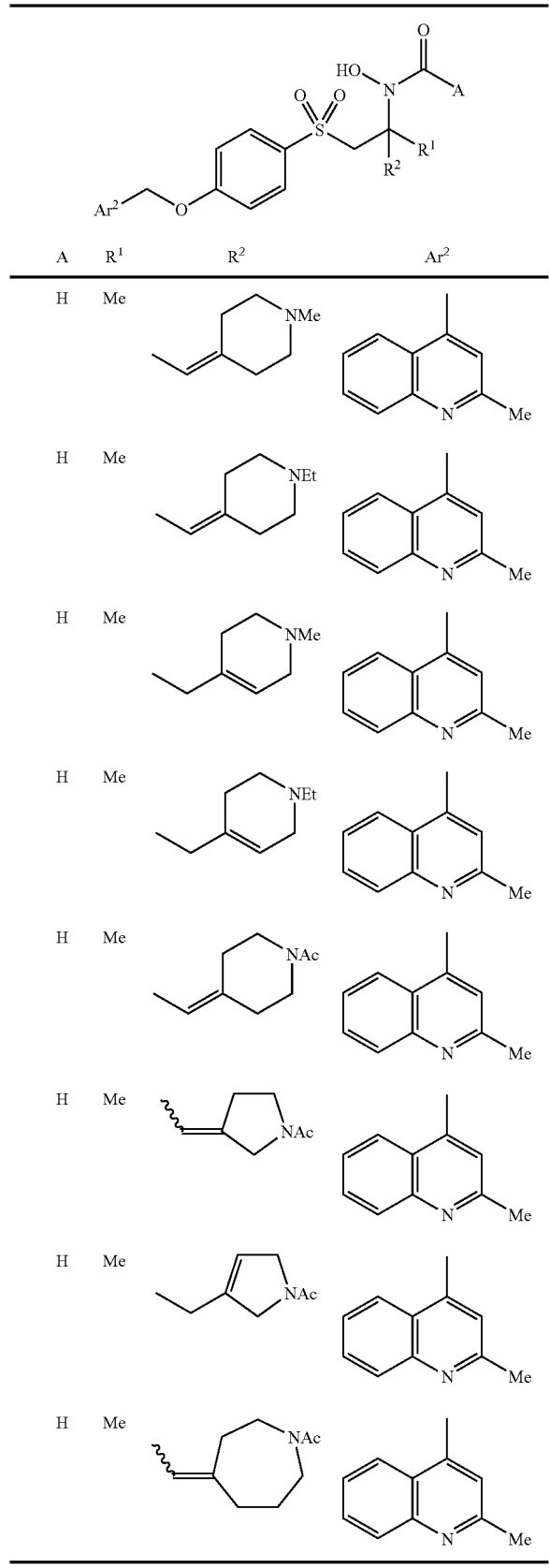
TABLE 22
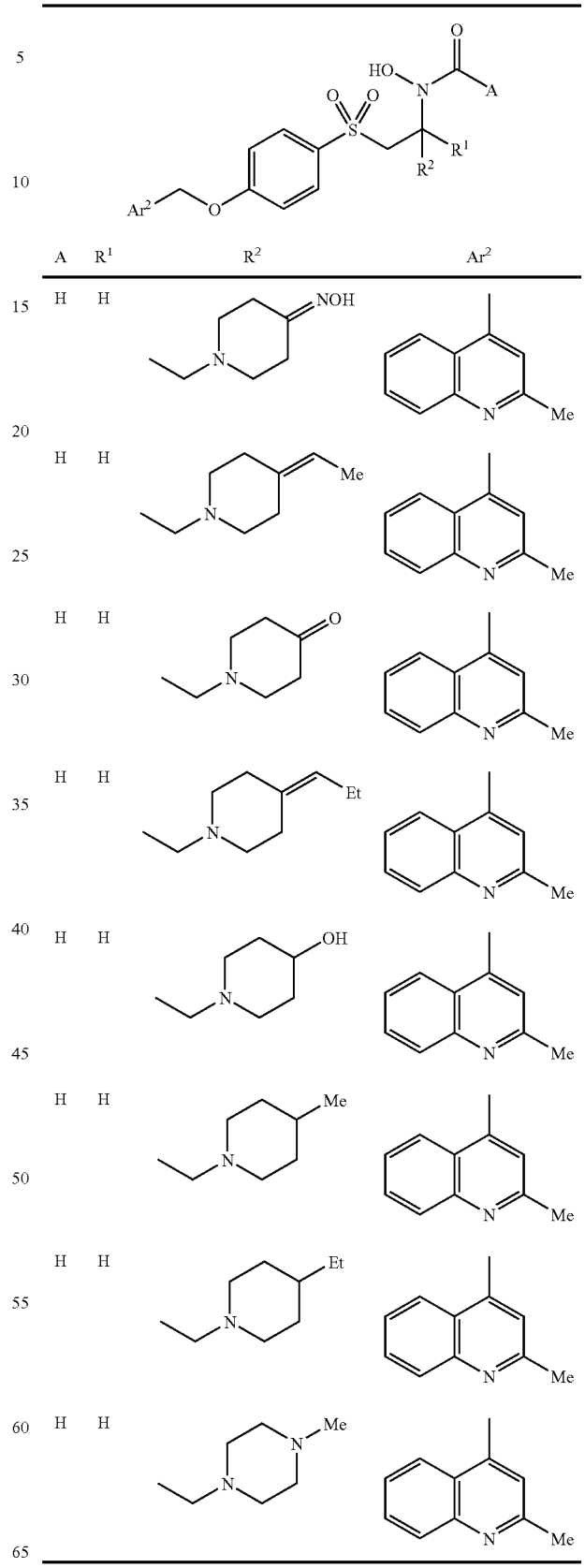

TABLE 23
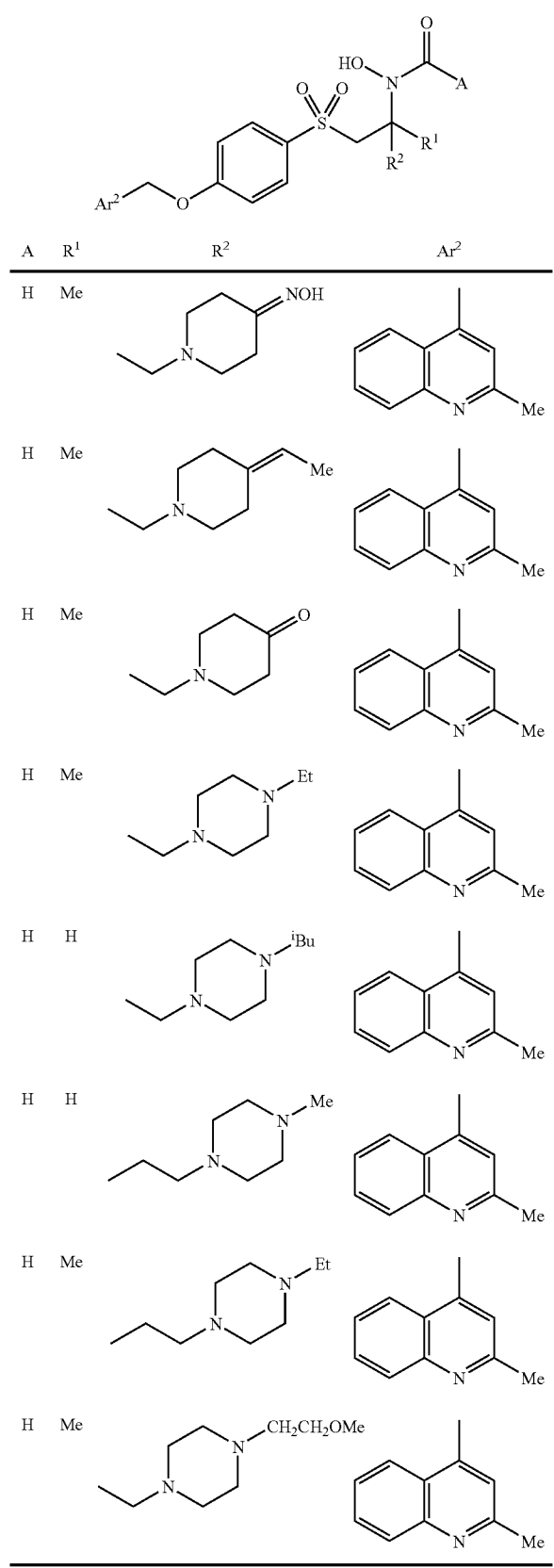
TABLE 24
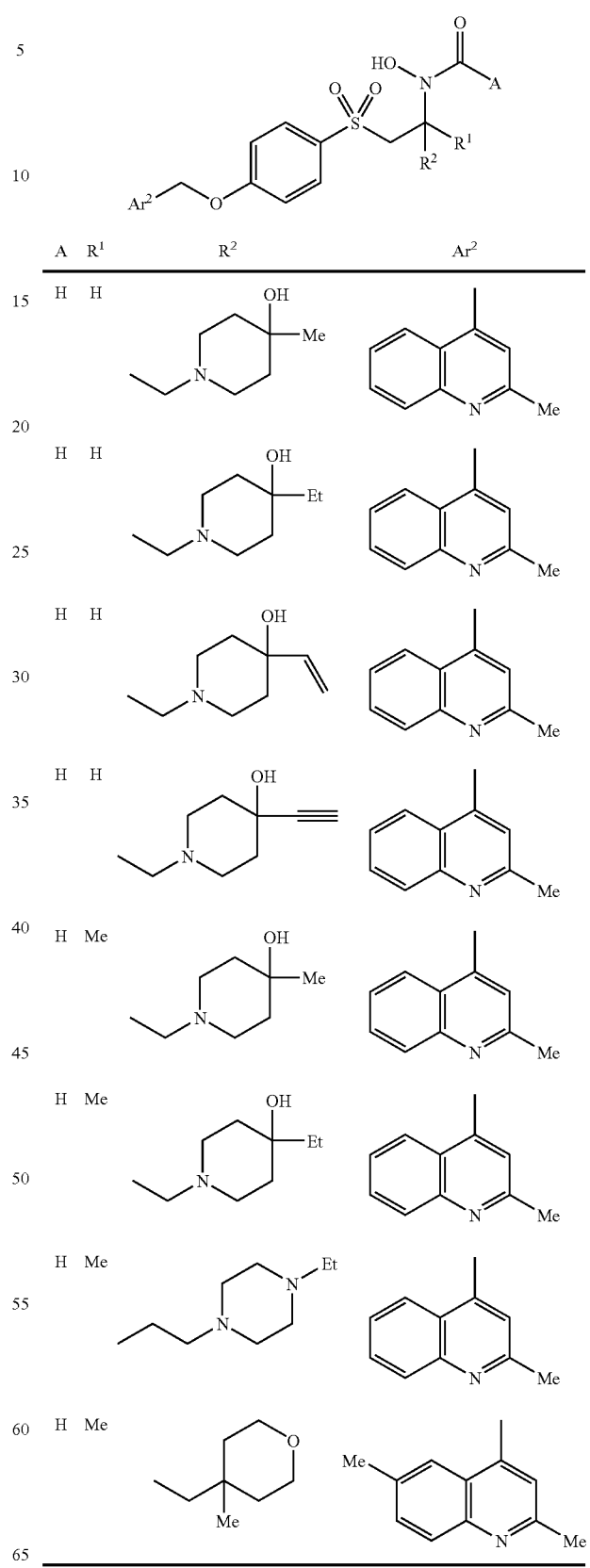

TABLE 25
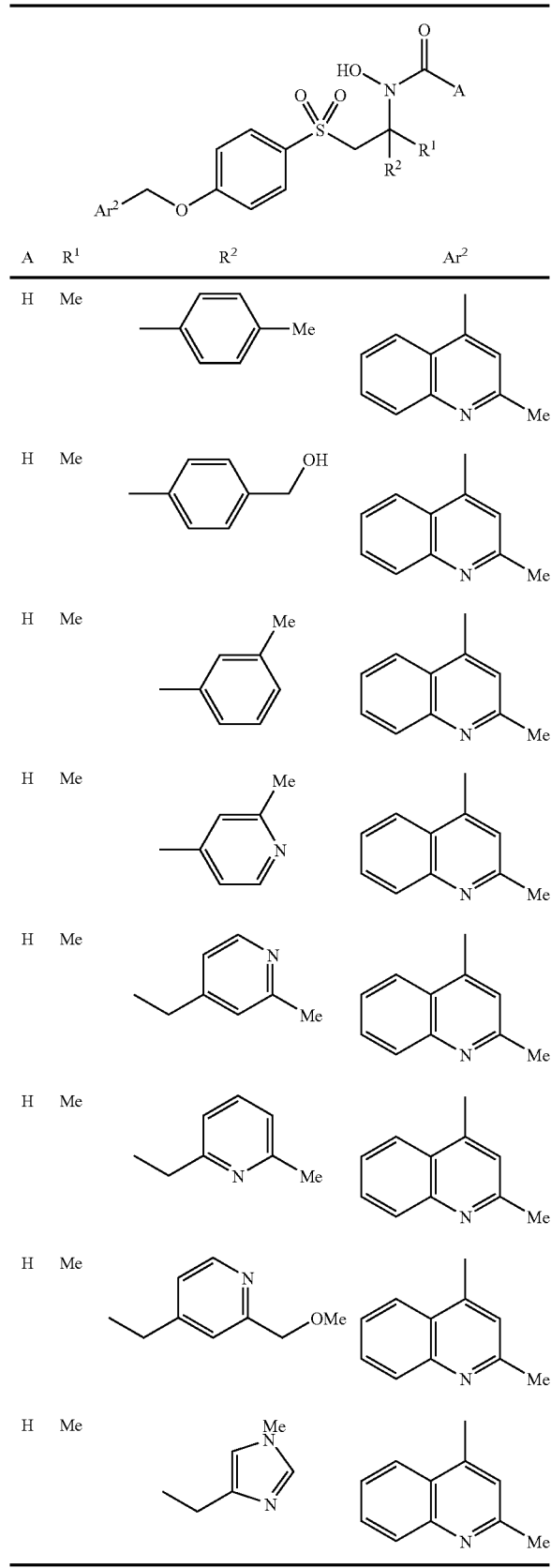
TABLE 26
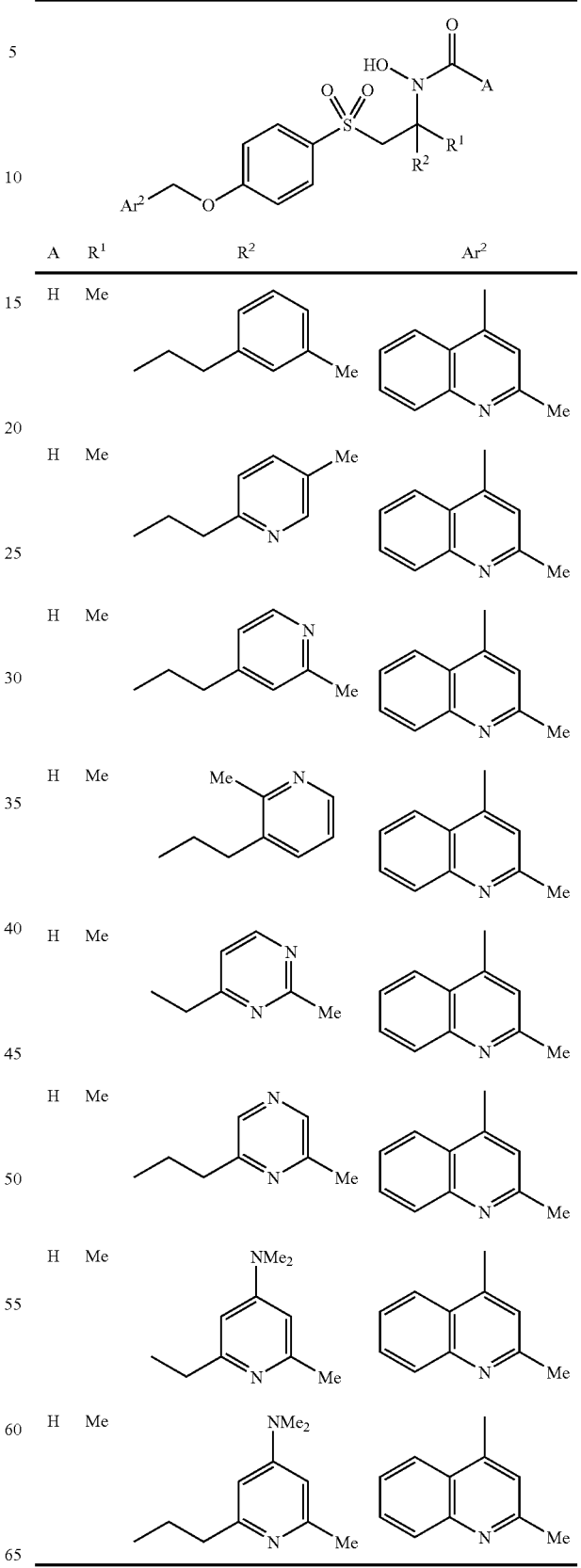

TABLE 27
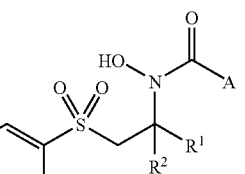
| A | R¹ | R² | | Ar² |
|---|----|----|----|-----|
| H | H | 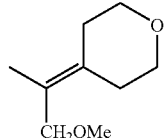 | | 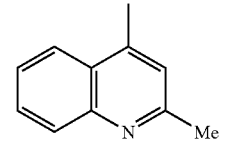 |
| H | H | 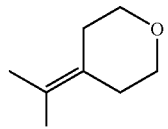 | | 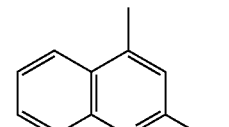 |
| H | H | 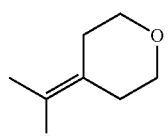 | | 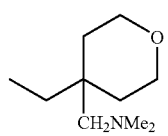 |
| H | Me | 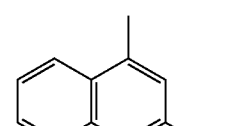 | | 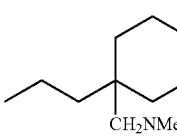 |
| H | Me | 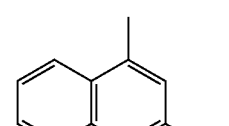 | | 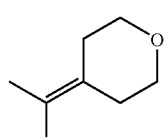 |
| H | Me | 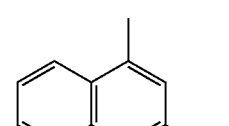 | | 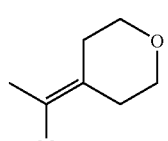 |
| H | Me | 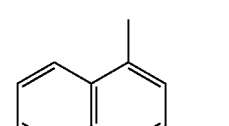 | | 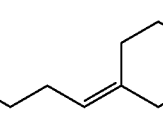 |
| H | Me | 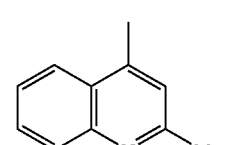 | | 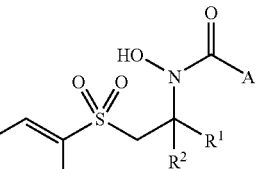 |
TABLE 28
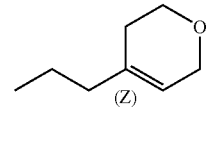
| A | R¹ | R² | Ar² |
|---|----|----|-----|
| H | Me | 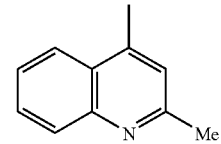 | 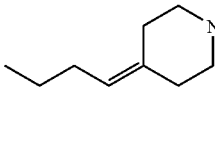 |
| H | Me | 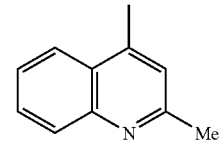 | 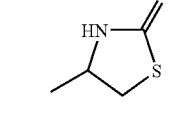 |
| H | Me | 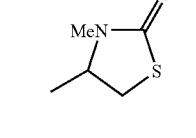 | 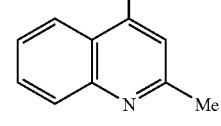 |
| H | Me | 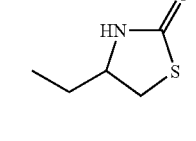 | 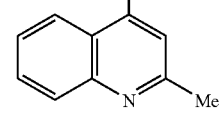 |
| H | Me | 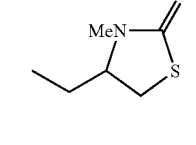 | 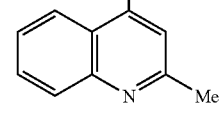 |
| H | Me | 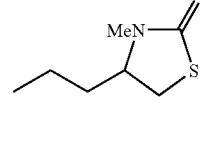 | 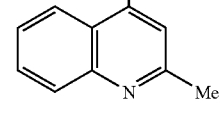 |
| H | Me | 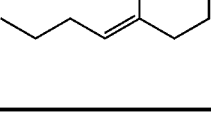 | 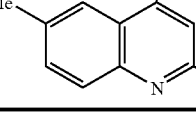 |
The reverse hydroxamic acid derivatives represented by the general formula (I) or (Ia) of the present invention may be prepared by a variety of methods, but their preparation is carried out effectively by the following method. Hereinafter, the preparation method is explained as that for the compounds of the general formula (I), while the same preparation method may also be applied to prepare the compounds of the general formula (Ia), because the compounds of the general formula (Ia) is encompassed in the compounds of the general formula (I).

Specific examples of "protective group" used in the following preparation method include tert-butyl, benzyl, o-methylbenzyl, p-nitrobenzyl, p-methoxybenzyl, o-chlorobenzyl, 2,4-dichlorobenzyl, p-bromobenzyl, allyl, tert-butoxycarbonyl, benzyloxycarbonyl, o-methylbenzyloxycarbonyl, p-nitrobenzyloxycarbonyl, p-methoxybenzyloxycarbonyl, o-chlorobenzyloxycarbonyl, 2,4-dichlorobenzyloxycarbonyl, p-bromobenzyloxycarbonyl, allyloxycarbonyl, tert-butyldimethylsilyl, tert-butyldiphenylsilyl, triethylsilyl, trimethylsilyl, triisopropylsilyl, methoxymethyl, tetrahydropyranyl, protective groups for carbonyl (e.g. ethanediol, propanediol, mercaptoethanol, mercaptopropanol, ethanedithiol, propanedithiol) and the like.

The compounds represented by the general formula (I) may be prepared by the reactions in the following steps 1 to 5.

chloride, acetatic acid salt or the like), this addition reaction is carried out in the presence of an inorganic base such as potassium carbonate, sodium carbonate, sodium bicarbonate, sodium hydroxide, potassium hydroxide and lithium hydroxide. The reaction solvent is not particularly limited so far as it does not significantly inhibit the reaction. A preferred solvent is water, tetrahydrofuran, 1,4-dioxane, diethyl ether or a mixture thereof.

The reaction temperature is not particularly limited and usually between 0 to 100° C., and a preferred reaction time is from 2 hours to 1 week.

<Step 2>

In Step 2, the compound (IIIa) obtained in Step 1 is condensed with an intermediate represented by the general formula (IV) to prepare a compound represented by the general formula (I). When A is hydrogen in the intermediate (IV), the intermediate (IV) is an active intermediate obtained from a mixed anhydride of formic acid (a mixed anhydride of formic acid and acetic acid, and the like), from pentafluorophenyl formate, or from formic acid and carbodiimide (dicyclohexylcarbodiimide, diisopropylcarbodiimide or water-soluble carbodiimide). When A is a lower alkyl group or a cycloalkyl

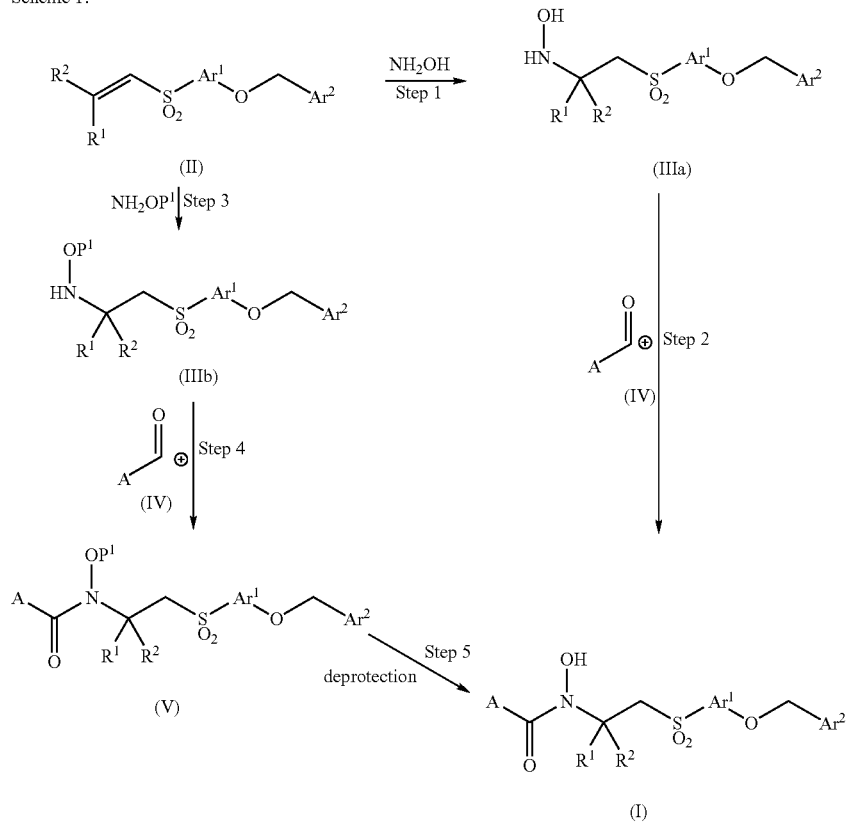

(wherein A, $Ar^1$, $Ar^2$, $R^1$ and $R^2$ are the same as defined above, and $P^1$ is a protective group for the hydroxyl group in hydroxylamine).

<Step 1>

In Step 1, hydroxylamine or its salt is added to a compound (II) to prepare a compound represented by the general formula (IIIa). When hydroxylamine is in a salt form (hydrogroup, it is an active intermediate obtained from the corresponding acid anhydride or the corresponding carboxylic acid and carbodiimide (dicyclohexylcarbodiimide, diisopropylcarbodiimide or water-soluble carbodiimide). When A is —$NR^3R^4$ ($R^3$ and $R^4$ are the same as defined above) and both $R^3$ and $R^4$ are hydrogen atoms, the intermediate (IV) is trimethylsilyl isocyanate; when either $R^3$ or $R^4$ is hydrogen atom, it is the corresponding isocyanate or the corresponding amine and carbonylation agent (carbonyldiimidazole, triphosgene and the like); and when neither $R^3$ nor $R^4$ is hydrogen atom, it is the corresponding carbamyl chloride or the corresponding amine and carbonylation agent (carbonyldiimidazole, triphosgene and the like). The reaction may be facilitated by the coexistence of an organic base such as triethylamine, diisopropylethylamine, pyridine, lutidine, collidine, dimethylaminopyridine. In some of these cases, (particularly when the active intermediate is obtained from carbodiimide), the reaction is accelerated by the addition of 1-hydroxybenzotriazole and/or 4-dimethylaminopyridine. The reaction solvent is not particularly limited so far as it does not significantly inhibit the reaction. A preferred solvent is chloroform, methylene chloride, tetrahydrofuran, 1,4-dioxane, dimethylformamide, dimethyl sulfoxide, pyridine and the like. The reaction temperature is not particularly limited and usually between 0 and 100° C., and a preferred reaction time is from 1 to 24 hours. It should be noted that in certain cases in the present step the ACO group may be added to the hydroxyl group in hydroxylamino group depending on chemical properties of the raw material, but this can be converted to the objective compound (I) by treating with a lower alcohol under acidic, basic or neutral condition. A preferred lower alcohol is methanol, ethanol, propanol or the like. An auxiliary solvent may be used, and in this case, the auxiliary solvent to be used is not particularly limited.

<Step 3>

In Step 3, hydroxylamine in which the hydroxyl group is protected by an appropriate protective group $P^1$ or its salt is added to a compound (II) to prepare a compound represented by the general formula (IIIb). The protective group includes benzyl, 4-methoxybenzyl, tert-butyl, tetrahydropyranyl, 2-propene-1-yl or the like. In this addition reaction, when the protected hydroxylamine is in a salt form (hydrochloride, acetic acid salt or the like), the reaction is carried out in the presence of an inorganic base such as potassium carbonate, sodium carbonate, sodium bicarbonate, sodium hydroxide, potassium hydroxide or lithium hydroxide. The reaction solvent is not particularly limited so far as it does not significantly inhibit the reaction. A preferred solvent is water, tetrahydrofuran, 1,4-dioxane, diethyl ether, toluene, dimethoxyethane, a mixed solvent thereof, or the like.

The reaction temperature is not particularly limited and usually between 0 and 100° C., and a preferred reaction time is from 2 hours to 1 week.

<Step 4>

In Step 4, the compound (IIIb) obtained in Step 3 is condensed with an intermediate represented by the general formula (IV) to prepare a compound represented by the general formula (V), in the same manner as in Step 2.

<Step 5>

In Step 5, the deprotection is carried out by a known method in accordance with the kind of the protective group $P^1$ used for the compound (V) obtained in Step 4 to give the compound represented by the general formula (I). As to the deprotection condition, refer to "Protective Group in Organic Synthesis", 2nd edition, Greene, T. W. et al., John Wiley & Sons, Inc., New York (1991)".

It goes without saying that, depending on the properties of $Ar^1$, $Ar^2$, $R^1$ and $R^2$, the protective groups are used in advance for the reactions in Steps 1 to 5 and that the removal of the protective groups is required after the reaction. If unprotected, the product yield may become lower in the next step or the step after the next, or a difficulty in handling each intermediate may be encountered.

The above compound (II) may be prepared by Steps a to d as described below.

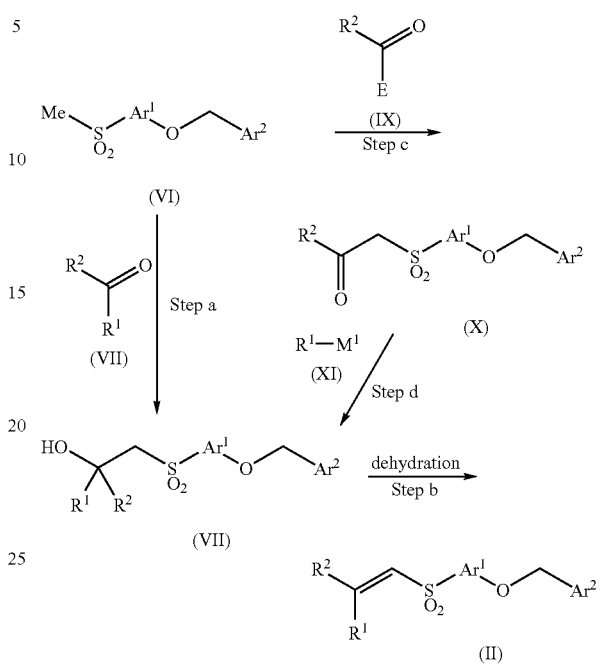

(wherein, $Ar^1$, $Ar^2$, $R^1$ and $R^2$ are the same as defined above; E is a leaving functional group such as a lower alkoxy group, a halogen atom or a N,O-dimethylhydroxyamino group; $M^1$ is Li, $CeCl_2$, ZnBr, ZnCl, $ZnR^1$, $NaBH_3$, $LiBH_3$, $LiBEt_3$, $KBEt_3$, $LiB[CH(CH_3)C_2H_5]_3$, $KB[CH(CH_3)C_2H_5]_3$, $Al[CH(CH_3)C_2H_5]_2$ or the like).

<Step a>

In Step a, a compound represented by a general formula (VI) is converted to the corresponding anion by a base, followed by reacting it with a compound represented by a general formula (VII) to give a compound (VIII). The base to be used includes lithium diisopropylamide, lithium(bistrimethylsilyl)amide, lithium tetramethylpiperazide, sodium(bistrimethylsilyl)amide, potassium (bistrimethylsilyl)amide, n-butyllithium, sec-butyllithium, tert-butyllithium and the like. These bases are used alone or in combination of two or more in some cases. The reaction solvent is not particularly limited so far as it does not significantly inhibit the reaction. A preferred solvent is tetrahydrofuran, tetrahydropyran, diethyl ether, tert-butyl methyl ether, a mixed solvent thereof, or the like.

The reaction temperature is usually between −100 and 40° C., and a preferred reaction time is from 1 to 12 hours. It should be noted that the compound (II) may occasionally be obtained depending on the chemical properties of the compound (VI), but it does not become an issue in light of the purpose of the present production.

<Step b>

In Step b, the compound (II) is prepared by a dehydration reaction of the compound (VIII) obtained in Step a. The dehydration reaction is performed by a combination of a reagent to activate the hydroxyl group and an organic base. The reagent to activate the hydroxyl group includes methanesulfonyl chloride, p-toluenesulfonyl chloride, benzenesulfonyl chloride, chloromethanesulfonyl chloride, thionyl chloride, sulfuryl chloride, phosphorus pentachloride or the like. The organic base includes triethylamine, diisopropylethylamine, diazabicycloundecene, diazabicyclononene, pyridine, dimethylaminopyridine, lutidine, collidine or the like. A preferred combination is a combination of methanesulfonyl chloride and triethylamine. Further, as other dehydration reagents, there include triphenylphosphine-diethylazodicarboxylate, triphenylphosphine-diisopropylazodicarboxylate, tri-n-butylphosphine-diethylazodicarboxylate, tri-n-butylphosphine-diisopropylazodicarboxylate and the like. The reaction solvent is not particularly limited so far as it does not significantly inhibit the reaction. A preferred solvent is chloroform, methylene chloride, tetrahydrofuran, 1,4-dioxane, dimethylformamide or the like. The reaction temperature is not particularly limited and usually between 0 and 100° C., and a preferred reaction time is from 1 to 24 hours.

It should be noted that, during or after the reaction in Step a or d, the hydroxyl group in the generated compound (VIII) leaves spontaneously in certain cases owing to the chemical property of $R^1$ or $R^2$ to give the compound (II) partially or wholly. When it occurs partially, Step b can be carried out without purification, and when it occurs wholly, Step b can be omitted.

<Step c>

In Step c, a compound represented by the general formula (VI) is converted to its anion by a base in the same manner as in Step a, followed by reacting it with a compound (IX) to give a compound (X).

<Step d>

In Step d, the compound (X) obtained in Step c is reacted with a compound represented by the general formula (XI) to prepare a compound represented by the general formula (VIII). When the compound (XI) is sodium borohydride or lithium borohydride, a preferred solvent is methanol, ethanol, isopropanol, tetrahydrofuran, dichloromethane, chloroform, a mixed solvent thereof or the like. When the compound (XI) is neither of the above two compounds, a preferred solvent is tetrahydrofuran, tetrahydropyran, diethyl ether, tert-butyl methyl ether, a mixed solvent thereof or the like. The reaction temperature is usually between −100 and 30° C., and a preferred reaction time is from 1 to 12 hours.

It goes without saying that, depending on the properties of $Ar^1$, $Ar^2$, $R^1$ and $R^2$, protective groups and the like are used in advance for the reactions in Steps a to d and that removal of the protective groups and the like are required after the reactions.

The above compound (VI) may be prepared by Steps e to i as described below.

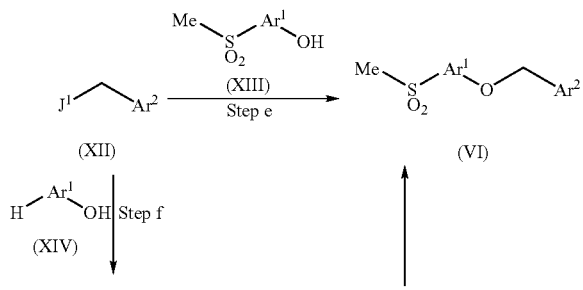

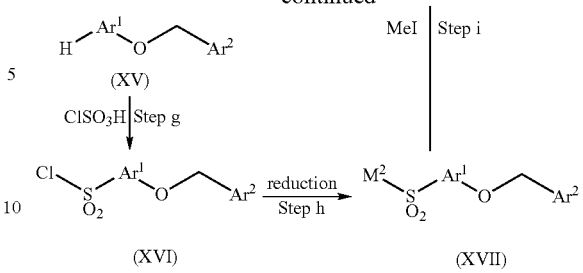

(wherein, $Ar^1$ and $Ar^2$ are the same as defined above; $J^1$ is a halogen atom, a methanesulfonyloxy group, a p-toluenesulfonyloxy group, a benzenesulfonyloxy group or a trifluoromethanesulfonyloxy group; $M^2$ is hydrogen, lithium, sodium or potassium).

<Step e>

In Step e, a compound represented by the general formula (XII) or its salt and a compound represented by the general formula (XIII) are condensed in the presence of an inorganic base to prepare a compound (VI). A preferred inorganic base is sodium hydroxide, potassium hydroxide, lithium hydroxide, sodium carbonate, potassium carbonate, cesium carbonate, calcium hydroxide or the like. The reaction solvent is not particularly limited so far as it does not significantly inhibit the reaction. A preferred solvent is water, ethanol, ethanol, tert-butanol, tetrahydrofuran, 1,4-dioxane, 2-methoxyethanol, a mixed solvent thereof or the like. The reaction temperature is not particularly limited and usually set at a boiling temperature of the reaction solution. A preferred reaction time is from 1 to 24 hours.

<Step f>

In Step f, a compound represented by the general formula is (XII) or its salt and a compound represented by the general formula (XIV) are condensed in the presence of an inorganic base to prepare a compound (XV). A preferred inorganic base is sodium hydroxide, potassium hydroxide, lithium hydroxide, sodium carbonate, potassium carbonate, cesium carbonate, calcium hydroxide or the like. The reaction solvent is not particularly limited so far as it does not significantly inhibit the reaction. A preferred solvent is water, methanol, ethanol, tert-butanol, tetrahydrofuran, 1,4-dioxane, 2-methoxyethanol, a mixed solvent thereof or the like. The reaction temperature is not particularly limited and usually set at a boiling temperature of the reaction solution. A preferred reaction time is from 1 to 24 hours.

<Step g>

In Step g, the compound (XV) obtained in Step f is reacted with chlorosulfonic acid to prepare a compound represented by the general formula (XVI). The reaction solvent is not particularly limited so far as it does not significantly inhibit the reaction. No solvent, or chloroform, methylene chloride, carbon tetrachloride or the like is preferred. The reaction temperature is not particularly limited and usually between 0 and 70° C. A preferred reaction time is from 1 to 72 hours.

<Step h>

In Step h, the chlorosulfonyl group in the compound (XVI) obtained in Step g is reduced with a reducing agent to prepare a compound represented by the general formula (XVII). The reducing agent includes zinc, sodium sulfite, sodium bisulfite, lithium aluminum hydride, magnesium, iron, tin chloride, sodium sulfide, sodium iodide, potassium iodide and the like. The reaction solvent is not particularly limited so far as it does not significantly inhibit the reaction. The solvent includes water, ethanol, methanol, ether and the like. The reaction temperature is not particularly limited and usually between 20 and 100° C. A preferred reaction time is from 1 to 12 hours.

<Step i>

In Step i, the compound (XVII) obtained in Step h is reacted with methyl iodide to produce the compound represented by the general formula (VI). In case where $M^2$ in the compound (XVII) is hydrogen, a base is used. The base includes sodium hydroxide, potassium hydroxide, lithium hydroxide, tetra-n-butylammonium hydroxide and the like. In the reaction of the present step, the reaction is accelerated by the addition of a phase-transfer catalyst such as tetra-n-butylammonium chloride, tetra-n-butylammonium bromide or the like. The reaction solvent is not particularly limited so far as it does not significantly inhibit the reaction, and a preferred solvent is tetrahydrofuran, dimethoxyethane, ethanol, methanol, dimethylformamide, dioxane, water, dimethylsulfoxide or the like. The reaction temperature is not particularly limited and usually between 0 and 100° C. A preferred reaction time is from 1 to 24 hours.

It goes without saying that, depending on the properties of $Ar^1$ and $Ar^2$, protective groups and the like are used in advance for the reactions in Steps e to i and that removal of the protective groups and the like is required after the reaction.

The above compound (X) may be prepared by Step j as described below.

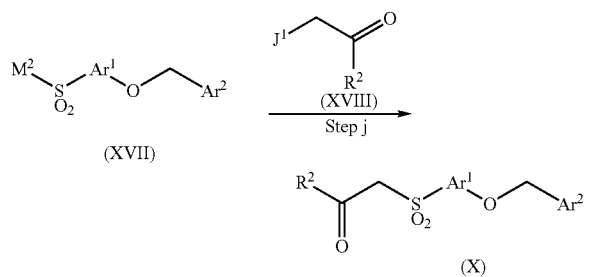

(wherein, $Ar^1$, $Ar^2$, $R^2$, $J^1$ and $M^2$ are the same as defined above).

<Step j>

In Step j, a compound represented by the general formula (XVII) and a compound represented by the general formula (XVIII) are condensed to prepare the compound represented by the general formula (X). When $M^2$ in the compound (XVII) is hydrogen, the condensation is carried out in the presence of a base. The base includes sodium hydroxide, potassium hydroxide, lithium hydroxide, tetra-n-butylammonium hydroxide and the like. When a phase-transfer catalyst such as tetra-n-butylammonium chloride or tetra-n-butylammonium bromide is added in the present reaction step, the reaction is accelerated. The reaction solvent is not particularly limited so far as it does not significantly inhibit the reaction. A preferred solvent is tetrahydrofuran, dimethoxyethane, ethanol, methanol, dimethylformamide, dioxane, water, dimethylsulfoxide or the like. The reaction temperature is not particularly limited and usually between 0 and 100° C., and a preferred reaction time is from 1 to 24 hours.

It goes without saying that, depending on the properties of $Ar^1$, $Ar^2$ and $R^2$, protective groups and the like are used in advance for the reaction in Step j and that removal of the protective groups and the like is required after the reaction.

It should be noted that the above compound (XVI) may be prepared by Steps k to l as described below.

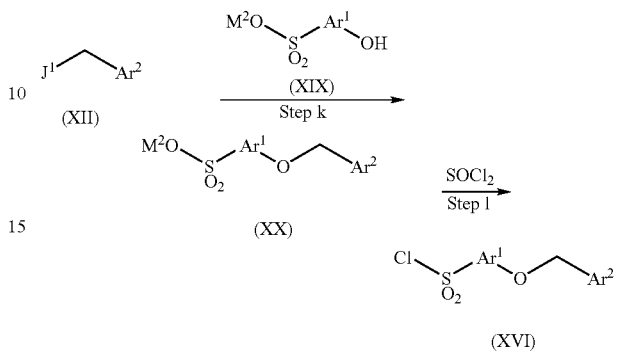

(wherein $Ar^1$, $Ar^2$, $J^1$ and $M^2$ are the same as defined above).

<Step k>

In Step k, a compound represented by the general formula (XII) or its salt and a compound represented by the general formula (XIX) are condensed in the presence of an inorganic base to prepare a compound (XX). A preferred inorganic base is sodium hydroxide, potassium hydroxide, lithium hydroxide, sodium carbonate, potassium carbonate, cesium carbonate or the like. The reaction solvent is not particularly limited so far as it does not significantly inhibit the reaction. A preferred solvent is water, methanol, ethanol, tetrahydrofuran, 1,4-dioxane, 2-methoxyethanol, a mixed solvent thereof or the like. The reaction temperature is not particularly limited and usually set at a boiling temperature of the reaction solution. A preferred reaction time is from 1 to 24 hours.

<Step l>

In Step l, the compound (XX) obtained in Step k is reacted with thionyl chloride or phosgene to prepare the compound represented by the general formula (XVI). A catalytic amount of dimethylformamide may be added as a reaction accelerator. The reaction solvent is not particularly limited so far as it does not significantly inhibit the reaction. No solvent, or chloroform, methylene chloride, carbon tetrachloride or the like is preferred. The reaction temperature is not particularly limited and usually between 0 and 100° C. A preferred reaction time is from 1 to 72 hours.

It goes without saying that, depending on the properties of $Ar^1$ and $Ar^2$, protective groups are used in advance for the reaction in Steps k and l and that removal of the protective groups and the like is required after the reaction.

It should be noted that the above compound (XVII) may be prepared by Steps m and n as described below.

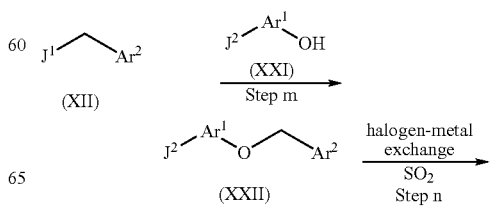

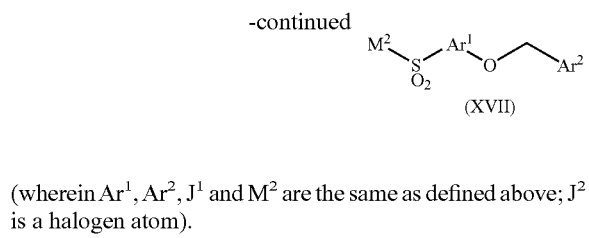

(wherein $Ar^1$, $Ar^2$, $J^1$ and $M^2$ are the same as defined above; $J^2$ is a halogen atom).

<Step m>

In Step m, a compound represented by the general formula (XII) or its salt and a compound represented by the general formula (XXI) are condensed in the presence of an inorganic base to prepare a compound (XXII). A preferred inorganic base is sodium hydroxide, potassium hydroxide, lithium hydroxide, sodium carbonate, potassium carbonate, cesium carbonate, calcium hydroxide or the like. The reaction solvent is not particularly limited so far as it does not significantly inhibit the reaction. A preferred solvent is water, methanol, ethanol, tetrahydrofuran, 1,4-dioxane, 2-methoxyethanol, a mixed solvent thereof, or the like. The reaction temperature is not particularly limited and usually set at a boiling temperature of the reaction solution. A preferred reaction time is from 1 to 24 hours.

<Step n>

In Step n, the halogen atom ($j^2$) in the compound (XXII) obtained in Step m is converted to lithium by a halogen-metal exchange reaction, followed by a reaction with sulfur dioxide to prepare the compound represented by the general formula (XVII). The reaction solvent is not particularly limited so far as it does not significantly inhibit the reaction. A preferred solvent is tetrahydrofuran, tetrahydropyran, diethyl ether, a mixed solvent thereof or the like. The reaction temperature is not particularly limited and usually between –100 and 30° C., and a preferred reaction time is from 1 to 6 hours.

It goes without saying that, depending on the properties of $Ar^1$ and $Ar^2$, protective groups are used in advance for the reactions in Steps m and n and that removal of the protective groups and the like is required after reaction.

The compound represented by the general formula (IIIa) in the Scheme 1 may also be prepared by the reactions in Steps o to s as described below.

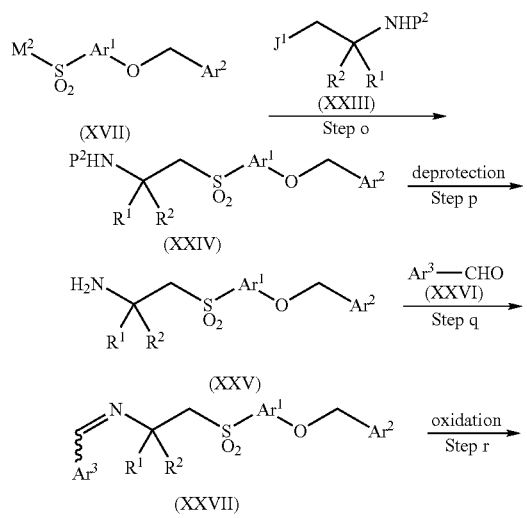

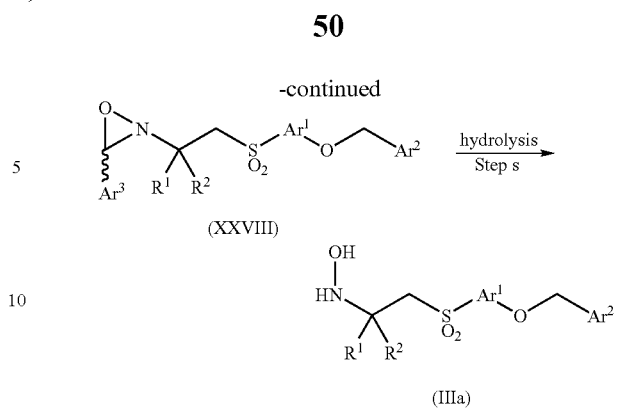

(wherein $Ar^1$, $Ar^2$, $R^1$, $R^2$, $J^1$ and $M^2$ are the same as defined above; $P^2$ is a protective group for an amino group; $Ar^3$ is an aromatic hydrocarbon group such as a phenyl grorp, a 4-methoxyphenyl group, a 4-tolyl group or a 4-chlorophenyl group).

<Step o>

In Step o, a compound represented by the general formula (XVII) and a compound represented by the general formula (XXIII) are condensed to prepare a compound represented by the general formula (XXIV). When $M^2$ in the compound (XVII) is hydrogen, the condensation is carried out in the presence of a base. The base includes sodium hydroxide, potassium hydroxide, lithium hydroxide, tetra-n-butylammonium hydroxide and the like. When a phase-transfer catalyst such as tetra-n-butylammonium chloride or tetra-n-butylammonium bromide is added in the present reaction step, the reaction is accelerated. The reaction solvent is not particularly limited so far as it does not significantly inhibit the reaction, and a preferred solvent is tetrahydrofuran, dimethoxyethane, ethanol, methanol, dimethylformamide, dioxane, water, dimethylsulfoxide or the like. The reaction temperature is not particularly limited and usually between 0 and 100° C., and a preferred reaction time is from 1 to 24 hours.

<Step p>

In Step p, the deprotection of the protective group is carried out by a well-known method according to the kinds of the protective group $P^2$ which has been used for the compound (XXIV) obtained in Step o to prepare a compound represented by the general formula (XXV). For example, when $P^2$ is a tert-butoxycarbonyl group, the deprotection of the amino group is carried out under an acidic condition to generate the compound (XXV). The deprotection under an acidic condition may be carried out by the well-known method. As the acid, there include trifluoroacetic acid, hydrogen chloride, hydrogen bromide, trimethylsilyl iodide and the like. The reaction solvent is not particularly limited so far as it does not significantly inhibit the reaction, and a preferred solvent is chloroform, methylene chloride, tetrahydrofuran, 1,4-dioxane, ethyl acetate, acetic acid, a mixed solvent thereof or the like. The reaction temperature is not particularly limited and usually between 0 and 100° C., and a preferred reaction time is from 1 to 24 hours.

<Step q>

In Step q, the dehydration condensation between the compound (XXV) obtained in Step p or its salt and a compound represented by the general formula (XXVI) is carried out to generate a compound represented by the general formula (XXVII). For acceleration of the reaction, sodium carbonate, magnesium sulfate, molecular sieve and the like may be added, or azeotropic removal of water formed as the by-product may be performed. The reaction solvent is not particularly limited so far as it does not significantly inhibit the reaction, a preferred solvent is ethanol, methanol, chloroform, methylene chloride, tetrahydrofuran, 1,4-dioxane, ethyl acetate, benzene, toluene, a mixture thereof or the like. The reaction temperature is not particularly limited and usually between 0 to 120° C., and the reaction time is from 1 to 48 hours.

<Step r>

In Step r, the imine moiety in the compound (XXVII) obtained in Step q is oxidized with an oxidizing reagent to prepare a compound represented by the general formula (XXVIII). The oxidizing reagent includes m-chloroperbenzoic acid, perbenzoic acid, peracetic acid, peroxycamphoric acid, p-nitroperbenzoic acid, monoperoxyphthalic acid, performic acid, trifluoroperacetic acid, p-toluenepersulfonic acid, oxone and the like. In order to prevent a side reaction, sodium bicarbonate, sodium carbonate, potassium carbonate, disodium hydrogenphosphate, magnesium sulfate, sodium sulfate or the like may coexist therein. The reaction solvent is not particularly limited so far as it does not significantly inhibit the reaction, and a preferred solvent is chloroform, methylene chloride, benzene, toluene, a mixed solvent thereof or the like. The reaction temperature is not particularly limited and usually between −40 and 50° C. A preferred reaction time is from 1 to 48 hours.

<Step s>

In Step s, the compound (XXVIII) obtained in Step r is subjected to solvolysis to generate the compound represented by the general formula (IIIa). As an accelerating agent for the reaction, there includes an inorganic acid such as hydrochloric acid or sulfuric acid, an organic acid such as oxalic acid, citric acid, tartaric acid, acetic acid, trifluoroacetic acid, methanesulfonic acid or p-toluenesulfonic acid, an amine salt such as ammonium chloride, ammonium sulfate or hydroxylamine hydrochloride, and the like. Methanol, ethanol, water and the like are included for the solvent, and tetrahydrofuran, dimethoxyethane, dimethyl sulfoxide, dioxane, ether and the like are included as the auxiliary solvent. The reaction temperature is not particularly limited and usually between 0 and 100° C. The preferred reaction time is from 1 to 24 hours.

It goes without saying that, depending on the properties of $Ar^1$, $Ar^2$ and $R^2$, protective groups and the like are used in advance for the reactions in steps o to s and that removal of the protective groups and the like is required after reaction.

The compound represented by the general formula (IIIb) in Scheme 1 may be prepared by the reactions in Steps t to u as described below.

<Step t>

A compound represented by the general formula (VII) and hydroxylamine protected by the protective group $p^1$ or its salt are condensed to generate a compound represented by the general formula (XXIX). When the protected hydroxylamine is in a salt form (hydrochloride, acetic acid salt or the like), this reaction is carried out in the presence of a weak base such as sodium bicarbonate, sodium acetate or pyridine. The reaction solvent is not particularly limited so far as it does not significantly inhibit the reaction, and a preferred solvent is tetrahydrofuran, 1,4-dioxane, benzene, toluene, xylene, ethanol, methanol, dimethoxyethane, a mixed solvent thereof or the like. The reaction temperature is not particularly limited and usually between 20 and 150° C. A preferred reaction time is from 2 to 72 hours.

<Step u>

In Step u, a compound represented by the general formula (VI) is converted to its anion by a base, followed by reaction with the compound (XXIX) obtained in Step t to give the compound (IIIb). The base to be used includes lithium diisopropylamide, lithium(bistrimethylsilyl)amide, lithium tetramethylpiperazide, sodium(bistrimethylsilyl)amide, potassium(bistrimethylsilyl)amide, n-butyl lithium, sec-butyl lithium, tert-butyl lithium and the like. Lewis acid such as trifluoroboron-ether complex may be present as an accelerating agent. The reaction solvent is not particularly limited so far as it does not significantly inhibit the reaction, and a preferred solvent is tetrahydrofuran, tetrahydropyran, diethyl ether, tert-butyl methyl ether, hexane, a mixed solvent thereof or the like.

The reaction temperature is usually between −100 and 30° C. A preferred reaction time is from 1 to 24 hours.

It goes without saying that, depending on the properties of $Ar^1$, $Ar^2$, $R^1$ and $R^3$, protective groups and the like are used in advance for the reactions in Steps t and u and that removal of the protective groups and the like is required after reaction.

The above compound (VIII) may be prepared by Steps v to z as described below.

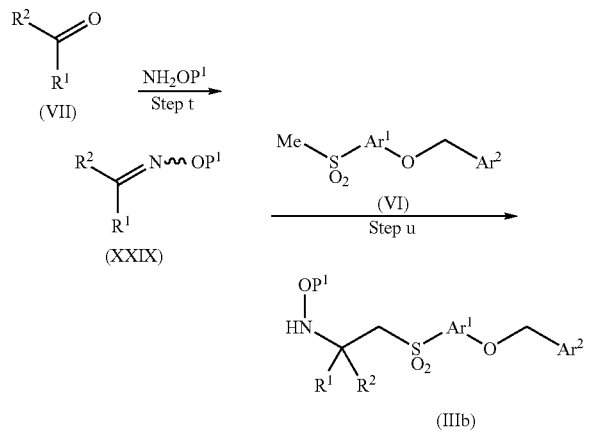

(wherein $Ar^1$, $Ar^2$, $R^1$, $R^2$ and $p^1$ are the same as defined above).

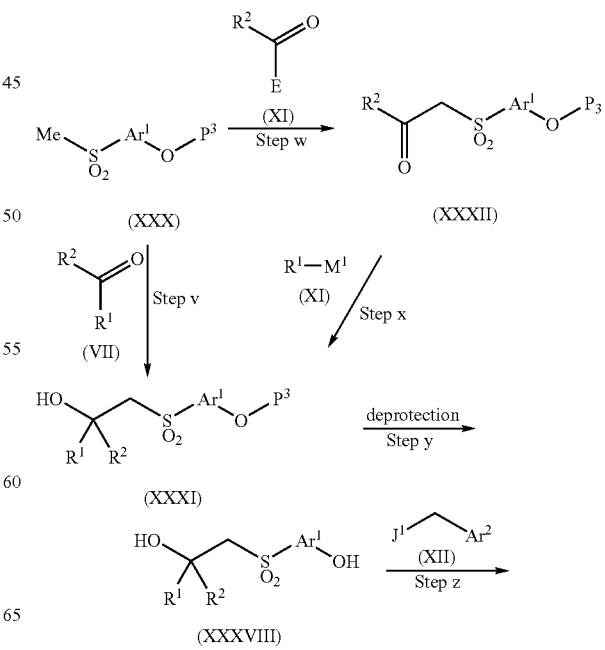

-continued

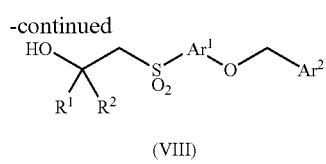

(VIII)

(wherein $Ar^1$, $Ar^2$, $R^2$, $R^2$, E, $M^1$ and $J^1$ are the same as defined above, and $P^3$ is a protective group for the hydroxyl group).

<Step v>

In Step v, a compound represented by the general formula (XXX) is converted to its anion by a base, followed by reacting with a compound (VII) to give a compound (XXXI) in the same manner as in Step a.

<Step w>

In Step w, a compound represented by the general formula (XXX) is converted to its anion by a base, followed by reacting it with a compound (IX) to give a compound (XXXII) in the same manner as in Step c.

<Step x>

In Step x, the compound represented by the general formula (XXXII) is reacted with a compound represented by the general formula (XI) to give a compound (XXXI) in the same manner as in Step d.

<Step y>

In Step y, the deprotection is carried out for the compound represented by the general formula (XXXI) by a well-known method according to the kind of its protective group $P^3$ to prepare a compound represented by the general formula (XXXIII).

It should be noted that, during or after the reaction in Step v or x, the protective group $P^3$ in the generated compound (XXXI) leaves spontaneously in certain cases owing to the chemical property of $R^1$, $R^2$ and $P^3$ to give the compound (XXXIII) partially or wholly. When it occurs partially, Step y can be carried out without purification, and when it occurs wholly, Step y can be omitted.

<Step z>

In Step z, the compound (XXXIII) obtained in Step y and a compound represented by the general formula (XII) or its salt are condensed in the presence of an inorganic base to give the compound (VIII). A preferred inorganic base is sodium hydroxide, potassium hydroxide, lithium hydroxide, sodium carbonate, potassium carbonate, cesium carbonate, sodium bicarbonate, calcium hydroxide, sodium hydride, potassium hydride, potassium-tert-butoxide or the like. The reaction solvent is not particularly limited so far as it does not significantly inhibit the reaction, and a preferred solvent is water, methanol, ethanol, tert-butanol, tetrahydrofuran, 1,4-dioxane, 2-methoxyethanol, dimethylformamide, dimethylacetamide, dimethyl sulfoxide, a mixed solvent thereof or the like. The reaction temperature is not particularly limited, and usually between 0 and 100° C. A preferred reaction time is from 1 to 24 hours.

It goes without saying that, depending on the properties of $Ar^1$, $Ar^2$, $R^1$ and $R^2$, protective groups and the like are used in advance for the reactions in Steps v to z and that removal of the protective groups and the like is required after the reaction.

The compounds of the present invention prepared by the methods described above are isolated and purified as free compounds, salts thereof, various solvated forms such as hydrate or ethanol solvate, or polymorphic crystalline products. Pharmaceutically acceptable salts of the compounds of the present invention may be prepared by conventional salt formation reactions. Isolation and purification may be carried out by application of chemical operations such as fractional extraction, crystallization and chromatography for fractionation. Further, an optical isomer may be obtained as a stereochemically pure isomer either by selecting an appropriate starting compound or by the optical resolution of a racemic compound.

The reverse hydroxamic acid derivatives I or the reverse hydroxamic acid derivatives Ia of the present invention show an excellent TACE-selective inhibitory action, suppress the production of active TNF-α in a soluble form, and are useful as a therapeutic agent for various disease conditions caused by TNF-α which have been described above. These include, for example, autoimmune diseases such as rheumatoid arthritis, systemic lupus erythematosus, multiple sclerosis, Behchet's disease and Sjoegren's syndrome, and their associated organ inflammations of various kinds, allergic diseases such as asthma, atopic dermatitis, rhinostenosis and rhinitis, inflammatory bowel disease including Crohn's disease and the like, nephritis, hepatitis, inflammatory diseases of central nervous system, cardiovascular diseases, arteriosclerosis, diabetes mellitus, myasthenia gravis, acute infectious disease, fever, anemia, sepsis, various malignant tumors, prevention of damage to transplanted organ, inhibition of tumor growth or metastasis, and the like.

The medicine containing the reverse hydroxamic acid derivatives Ia or the TACE inhibitor containing the reverse hydroxamic acid derivatives I of the present invention may be administered systematically or locally by oral, transnasal, airway route, transpulmonary route, instillation of drop, intravenous injection, subcutaneous injection, intrarectal route and the like. The dosage form may be appropriately selected depending on its administration route, including, for example, tablet, troche, sublingual tablet, sugar coated tablet, capsules, pill, powder, granule, liquid, emulsion, syrup, eye-drops, collunarium, inhalant, injection and the like. These products may be prepared by combining with excipient, preservative, wetting agent, emulsifier, stabilizer, solubilizing agent and the like.

The dosage of the drug containing the reverse hydroxamic acid derivatives Ia or the TACE inhibitor containing the reverse hydroxamic acid derivatives I of the present invention may be appropriately determined depending on the conditions, for example, administration subject, administration route, symptoms and the like. For example, the oral dose of the present compound as an effective ingredient for an adult patient may be generally in the range of about 0.1 to 100 mg/kg, preferably in the range of 1 to 40 mg/kg, in one dose, and is preferably administered once to three times a day.

The effect of TACE inhibition by the reverse hydroxamic acid derivatives I or Ia of the present invention which is indicated by the concentration required for 50% inhibition ($IC_{50}$) should be preferably attained at 0.01 to 1000 nM.

Hereinafter, the present invention is more specifically explained by means of the following examples, but is not limited only to these examples.

$^1$H-NMR spectra were measured with a Model JNM-EX270 spectrometer (270 MHz, manufactured by JEOL) using tetramethylsilane (TMS) as an internal standard and δ value was shown in ppm. The measurement of low resolution mass spectra (FABMS) was conducted with a Model JMS-HX-110A, JEOL.

EXAMPLE 1

Preparation of N-hydroxy-N-[1-(4-methylenecyclohexyl)-2-{4-(2-methylquinolin-4-ylmethoxy)benzenesulfonyl}ethyl]formamide (I-1)

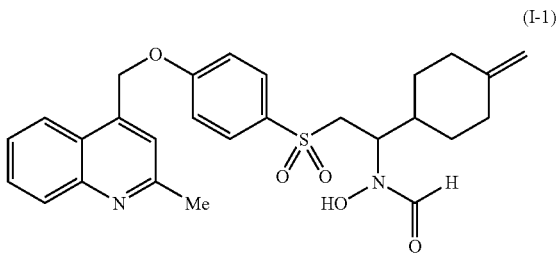

(1-1): 4-(4-Methanesulfonylphenoxymethyl)-2-methylquinoline (VI-1)

To a solution of 7.23 g (29.6 mmol) of 4-chloromethyl-2-methylquinoline hydrochloride and 5.61 g (32.6 mmol) of 4-methylsulfonylphenol in ethanol (26 mL) was added 17.1 mL (68.1 mmol) of 4 N aqueous sodium hydroxide, followed by heating under reflux for 5 hours. After standing to cool, water (150 mL) and 4 N aqueous sodium hydroxide (2.5 mL) were added and stirred for 20 minutes at room temperature. The precipitates were collected by filtration, washed thoroughly with water and hexane, and then dried at 40° C. in vacuo in the presence of phosphorus pentoxide to give 9.06 g (yield 93.5%) of 4-(4-methanesulfonylphenoxymethyl)-2-methylquinoline (VI-1). Its physical properties are shown below.

$^1$H-NMR(CDCl$_3$) δ value: 2.76(3H, s), 3.06(3H, s), 5.59 (2H, s), 7.17(2H, dt, J=8.9, 3.0), 7.43(1H, s), 7.56(1H, t, J=7.3), 7.74(1H, td, J=8.6, 1.3), 7.92(3H, m), 8.10(1H, d, J=8.3).

FAB-MS: Calculated (M$^+$+1): 328; Found: 328.

(1-2): 1-(4-Methylenecyclohexyl)-2-[4-(2-methylquinolin-4-ylmethoxy)benzenesulfonyl]ethanone (X-1)

Into a solution of 1.95 g (5.94 mmol) of 4-(4-methanesulfonylphenoxymethyl)-2-methylquinoline (VI-1) obtained in the above (1-1) in tetrahydrofuran (150 mL) was dropped 3.7 mL (7.43 mmol) of 2 mol/L lithium diisopropylamide solution in hexane-heptane-ethylbenzene (available from Aldrich) at −78° C. under an atmosphere of argon, followed by stirring for 1 hour. Into this solution, a solution of 1.1 g (6.54 mmol) of methyl 4-methylenecyclohexane carboxylate in tetrahydrofuran (5 mL) was dropped at −78° C., and then stirred for 4 hours. After 1 N sulfuric acid (4 mL) was added to the reaction mixture and stirred for 10 minutes, the solution was neutralized with saturated aqueous sodium bicarbonate. The reaction mixture was concentrated under a reduced pressure, and the residue was extracted with ethyl acetate. The organic layer was washed with saturated brine, dried over anhydrous magnesium sulfate, and followed by evaporation of the solvent. The obtained residue was purified by column chromatography (silica gel 50 g, developing solvent: hexane:ethyl acetate=1:3) to give 1.67 g (yield 60.0%) of 1-(4-methylenecyclohexyl)-2-[4-(2-methylquinolin-4-ylmethoxy)benzenesulfonyl]ethanone (X-1) as a colorless crystal. Its physical properties are shown below.

$^1$H-NMR(CDCl$_3$) δ value: 1.40(2H, m), 2.05(4H, m), 2.36 (2H, m), 2.76(3H, s), 2.85(1H, tt, J=11.2, 3.6), 4.22(2H, s), 4.66(2H, s), 5.58(2H, s), 7.16(2H, dt, J=8.9, 3.0), 7.42(1H, s), 7.56(1H, td, J=7.6, 1.0), 7.74(1H, m), 7.85(2H, dt, J=8.9, 3.0), 7.90(1H, d, J=8.3), 8.10(1H, d, J=8.6).

FAB-MS: Calculated (M$^+$+1): 450; Found: 450.

(1-3): 1-(4-Methylenecyclohexyl)-2-[4-(2-methylquinolin-4-ylmethoxy)benzenesulfonyl]ethanol (VIII-1)

To a solution of 400 mg (0.89 mmol) of 1-(4-methylenecyclohexyl)-2-[4-(2-methylquinolin-4-ylmethoxy)benzenesulfonyl]ethanone (X-1) obtained in the above (1-2) in mixed methanol and tetrahydrofuran (6.5 mL+2.5 mL) was added 33.6 mg (0.89 mmol) of sodium borohydride at 0° C., and stirred for 30 minutes at room temperature. After water was added to the reaction mixture, the reaction mixture was concentrated under a reduced pressure and the residue was extracted with ethyl acetate. The organic layer was washed with water and saturated brine successively and dried over anhydrous magnesium sulfate. Upon removal of the solvent by evaporation, 410 mg (yield 100%) of 1-(4-methylenecyclohexyl)-2-[4-(2-methylquinolin-4-ylmethoxy) benzenesulfonyl]ethanol (VIII-1) was obtained as white solid. Its physical properties are shown below.

$^1$H-NMR(CDCl$_3$) δ value: 1.11(2H, m), 1.50-1.83(3H, m), 1.98(2H, m), 2.29(2H, m), 2.77(3H, s), 3.21(2H, d, J=5.9), 3.33(1H, d, J=2.3), 3.99(1H, m), 4.60(2H, s), 5.60(2H, s), 7.19(2H, d, J=8.9), 7.43(1H, s), 7.57(1H, t, J=8.3), 7.75(1H, t, J=8.3), 7.90(3H, m), 8.12(1H, d, J=8.6).

FAB-MS: Calculated (M$^+$+1): 452; Found: 452.

(1-4): 2-Methyl-4-[4-{2-(4-methylenecyclohexyl) ethenesulfonyl}phenoxymethyl]quinoline (II-1).

Methanesulfonyl chloride, 183 mg (1.60 mmol) was added, at 0° C., to a solution of 410 mg (0.89 mmol) of 1-(4-methylenecyclohexyl)-2-[4-(2-methylquinolin-4-ylmethoxy)benzenesulfonyl]ethanol (VIII-1) obtained in the above (1-3) and 360 mg (3.60 mmol) of triethylamine in methylene chloride (6.0 mL), and stirred for 6 hours at room temperature. The reaction mixture was treated with saturated aqueous sodium bicarbonate and then extracted with ethyl acetate. The organic layer was washed with water and saturated brine successively, and dried over anhydrous magnesium sulfate. Upon removal of the solvent by evaporation, 415 mg (yield 100%) of 2-methyl-4-[4-{2-(4-methylenecyclohexyl)ethenesulfonyl}phenoxymethyl]quinoline (II-1) was obtained as white solid. Its physical properties are shown below.

$^1$H-NMR(CDCl$_3$) δ value: 1.25(2H, m), 1.87(2H, m), 2.05 (2H, m), 2.33(3H, m), 2.76(3H, s), 4.64(2H, t, J=1.3), 5.57 (2H, s), 6.26(1H, dd, J=15.2, 1.3), 6.92(1H, dd, J=15.2, 6.3), 7.14(2H, dt, J=8.9, 3.0), 7.42(1H, s), 7.55(1H, m), 7.73(1H, m), 7.83(2H, dt, J=8.9, 3.0), 7.89(1H, dd, J=8.2, 1.0), 8.10 (1H, d, J=7.9).

FAB-MS: Calculated (M$^+$+1): 434; Found: 434.

(1-5): N-[1-(4-Methylenecyclohexyl)-2-{4-(2-methylquinolin-4-ylmethoxy)benzenesulfonyl}ethyl]hydroxylamine (III-1)

A 50% aqueous solution of hydroxylamine (1.1 mL) was added to a solution of 415 mg (0.89 mmol) of 2-methyl-4-[4-{2-(4-methylenecyclohexyl)ethenesulfonyl}phenoxymethyl]quinoline (II-1) obtained in the above (1-4) in tetrahydrofuran (9.3 mL) at 0° C., and stirred for 2 hours at room temperature. The reaction mixture was concentrated under a reduced pressure. The obtained residue was diluted with ethyl acetate, then washed with water and saturated brine successively, and dried over anhydrous magnesium sulfate. Upon removal of the solvent by evaporation, 443 mg (yield 100%) of N-[1-(4-methylenecyclohexyl)-2-{4-(2-methylquinolin-4-ylmethoxy)benzenesulfonyl}ethyl]hydroxylamine (III-1) was obtained as white solid. Its physical properties are shown below.

$^1$H-NMR(CDCl$_3$) δ value: 1.01(2H, m), 1.50-2.04(5H, m), 2.28(2H, m), 2.76(3H, s), 3.12(2H, m), 3.44(1H, dd, J=15.2, 9.9), 4.60(2H, s), 4.71(1H, bs), 5.59(2H, s), 7.17(2H, d, J=8.9), 7.43(1H, s), 7.56(1H, t, J=7.3), 7.74(1H, m), 7.91(3H, m), 8.10(1H, d, J=8.6).

FAB-MS: Calculated (M$^+$+1): 467; Found: 467.

(1-6): N-Hydroxy-N-[1-(4-methylenecyclohexyl)-2-{4-(2-methylquinolin-4-ylmethoxy)benzenesulfonyl}ethyl]formamide (I-1)

A solution of formic acid (2.2 mL) and acetic anhydride (0.54 mL) premixed for 30 minutes at 0° C. was dropped into a solution of 443 mg (0.89 mmol) of N-[1-(4-methylenecyclohexyl)-2-{4-(2-methylquinolin-4-ylmethoxy)benzenesulfonyl}ethyl]hydroxylamine (III-1) obtained in the above (1-5) in mixed tetrahydrofuran and formic acid (5.4 mL+2.2 mL) at 0° C. and then stirred for 1 hour at room temperature. The reaction mixture was concentrated under a reduced pressure, the obtained residue was subjected to azeotropic distillation with xylene, diluted with chloroform (5.8 mL) and methanol (1.5 mL), and stirred for 40 hours at room temperature. The reaction mixture was concentrated under a reduced pressure, followed by purification by medium pressure column chromatography on silica gel (developing solvent for silica gel: ethyl acetate) to give 326 mg (yield 74.1%) of the title compound. Its physical properties are shown below.

$^1$H-NMR(CDCl$_3$) δ value: 1.06(2H, m), 1.65-2.07(5H, m), 2.32(2H, m), 2.76(3H, s), 3.27(1H, m), 3.57-3.93(1.7H, m), 4.39(0.3H, m), 4.61(2H, m), 5.58(2H, m), 7.17(2H, m), 7.42(1H, s), 7.55(1H, t, J=7.3), 7.65-7.92(4.7H, m), 8.10(1H, d, J=8.6), 8.47(0.3H, s).

FAB-MS: Calculated (M$^+$+1): 495; Found: 495.

EXAMPLE 2

Preparation of N-hydroxy-N-[2-{4-(2-methylquinolin-4-ylmethoxy)benzenesulfonyl}-1-(4-oxocyclohexylmethyl)ethyl]formamide (I-2)

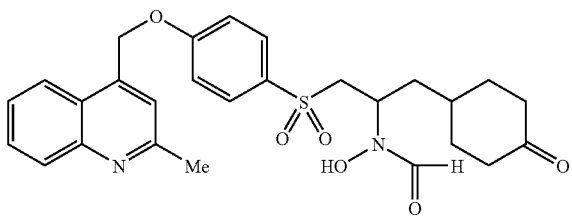

(2-1): 1-(1,4-Dioxaspiro[4.5]dec-8-yl)-3-[4-(2-methylquinolin-4-ylmethoxy) benzenesulfonyl]propan-2-ol (VIII-2)

To a solution of 5.0 g (15.3 mmol) of 4-(4-methanesulfonylphenoxymethyl)-2-methylquinoline (VI-1) obtained in the above (1-1) in tetrahydrofuran (250 mL) was dropped 8.4 mL (16.8 mmol) of 2 mol/L lithium diisopropylamide solution in hexane-heptane-ethylbenzene (available from Aldrich) at −78° C. under an atmosphere of argon and stirred for 50 minutes.

To this solution, a solution of 3.1 g (16.8 mmol) of (1,4-dioxaspiro[4.5]dec-8-yl)acetaldehyde in tetrahydrofuran (5mL) was added and stirred for 20 minutes. To the resulting reaction mixture, acetic acid (1.3 mL) was added and stirred for 10 minutes, and then saturated aqueous sodium bicarbonate (40 mL) was added and stirred for 15 minutes at room temperature. The organic solvent was evaporated under a reduced pressure, and the residue was extracted with ethyl acetate. The extract was washed with saturated aqueous sodium bicarbonate and saturated brine successively, dried over anhydrous magnesium sulfate. The extract was concentrated and the obtained residue was purified by medium pressure column chromatography on silica gel (developing solvent: hexane-ethyl acetate=25:75 to 0:100) to give 6.24 g (yield 79.7%) of 1-(1,4-dioxaspiro[4.5]dec-8-yl)-3-[4-(2-methylquinolin-4-ylmethoxy)benzenesulfonyl]propan-2-ol (VIII-2) as colorless oil. Its physical properties are shown below.

$^1$H-NMR(CDCl$_3$) δ value: 1.22(2H, m), 1.40-1.83(9H, m), 2.77(3H, s), 3.13(1H, dd, J=14.2, 2.3), 3.21(1H, dd, J=14.2, 8.6), 3.39(1H, bs), 3.92(4H, s), 4.29(1H, m), 5.59(2H, s), 7.19(2H, dt, J=8.9, 3.0), 7.43(1H, s), 7.56(1H, m), 7.74(1H, m), 7.90(3H, m), 8.12(1H, d, J=8.3).

FAB-MS: Calculated (M$^+$+1): 512; Found: 512.

(2-2): 4-[4-{3-(1,4-Dioxaspiro[4.5]dec-8-yl)-prop-1-ene-1-sulfonyl}phenoxymethyl]-2-methylquinoline (II-2)

Into a solution of 6.20 g (12.12 mol) of 1-(1,4-dioxaspiro[4.5]dec-8-yl)-3-[4-(2-methylquinolin-4-ylmethoxy)benzenesulfonyl]propan-2-ol (VIII-2) obtained in the above (2-1) and 4.42 g (43.64 mol) of triethylamine in methylene chloride (60 mL) was dropped 1.94 g (16.97 mmol) of methanesulfonyl chloride over 15 minutes at −10° C. The reaction mixture was stirred for 3 hours at 0° C., and then allowed to warm to room temperature gradually. The reaction mixture was treated with saturated aqueous sodium bicarbonate and then extracted with ethyl acetate. The extract was washed with saturated aqueous sodium bicarbonate and saturated brine successively, and dried over anhydrous magnesium sulfate. Upon removal of the solvent by evaporation, 6.0 g (yield 100%) of 4-[4-{3-(1,4-dioxaspiro[4.5]dec-8-yl)-prop-1-ene-1-sulfonyl}phenoxymethyl]-2-methylquinoline (II-2) was obtained as white solid. Its physical properties are shown below.

$^1$H-NMR(CDCl$_3$) δ value: 1.26(2H, m), 1.52(2H, m), 1.70 (4H, m), 2.16(2H, t, J=7.3), 2.77(3H, s), 3.92(4H, s), 5.57(2H, s), 6.30(1H, d, J=14.8), 6.93(1H, dt, J=14.9, 7.3), 7.14(2H, d, J=8.6), 7.43(1H, s), 7.56(1H, t, J=7.9), 7.74(1H, t, J=7.9), 7.84(2H, d, J=8.9), 7.90(1H, d, J=7.9), 8.11(1H, d, J=8.3).

FAB-MS: Calculated (M$^+$+1): 494; Found: 494.

(2-3): N-[1-(1,4-Dioxaspiro[4.5]dec-8-ylmethyl)-2-{4-(2-methylquinolin-4-ylmethoxy)benzenesulfonyl}ethyl]hydroxylamine (III-2a)

According to the same manner as in Example 1 (1-5), 6.4 g (yield 100%) of N-[1-(1,4-dioxaspiro[4.5]dec-8-ylmethyl)-2-{4-(2-methylquinolin-4-ylmethoxy)benzenesulfonyl}ethyl]hydroxylamine (III-2a) was obtained from 6.0 g (12.12 mmol) of 4-[4-{3-(1,4-dioxaspiro[4.5]dec- 8-yl)prop-1-ene-1-sulfonyl}phenoxymethyl]-2-methylquinoline (II-2) obtained in the above (2-2) and a 50% aqueous solution of hydroxylamine (17 mL). Its physical properties are shown below.

$^1$H-NMR(CDCl$_3$) δ value: 1.05-1.78(11H, m), 2.76(3H, s), 2.99(1H, dd, J=14.2, 3.0), 3.45(1H, m), 3.61(1H, dd, J=14.2, 8.3), 3.91(4H, s), 5.06(1H, bs), 5.58(2H, s), 7.17(2H, d, J=8.8), 7.43(1H, s), 7.56(1H, t, J=7.9), 7.74(1H, t, J=8.3), 7.91(3H, m), 8.10(1H, d, J=8.6).

FAB-MS: Calculated (M$^+$+1): 527; Found: 527.

(2-4): 4-[2-Hydroxyamino-3-{4-(2-methylquinolin-4-ylmethoxy)benzenesulfonyl}propyl]cyclohexanone (III-2b)

To a solution of 6.40 g (12.12 mmol) of N-[1-(1,4-dioxaspiro[4.5]dec-8-ylmethyl)-2-{4-(2-methylquinolin-4-ylmethoxy)benzenesulfonyl}ethyl]hydroxylamine (III-2a) obtained in the above (2-3) in tetrahydrofuran (70 mL) was added 2 N hydrochloric acid (17 mL) at 0° C., and stirred for 14 hours at room temperature. The resulting reaction mixture was treated with saturated aqueous sodium bicarbonate and then extracted with ethyl acetate. The organic layer was washed with saturated aqueous sodium bicarbonate and saturated brine successively, and dried over anhydrous magnesium sulfate. Upon removal of the solvent by evaporation, 6.25 g (yield 100%) of 4-[2-hydroxyamino-3-{4(2-methylquinolin-4-ylmethoxy)benzenesulfonyl}propyl]cyclohexanone (III-2b) was obtained as oil. Its physical property is shown below.

FAB-MS: Calculated (M$^+$+1): 483; Found: 483.

(2-5): N-Hydroxy-N-[2-{4-(2-methylquinolin-4-ylmethoxy)benzenesulfonyl}-1-(4-oxocyclohexylmethyl)ethyl]formamide (I-2)

According to the same manner as in Example 1 (1-6), 3.6 g (yield 58.2%) of the title compound was obtained from 6.25 g (12.12 mmol) of 4-[2-hydroxyamino-3-{4-(2-methylquinolin-4-ylmethoxy)benzenesulfonyl}propyl]cyclohexanone (III-2b) obtained in the above (2-4), formic acid (60 mL) and acetic anhydride (7.2 mL). Its physical properties are shown below.

$^1$H-NMR(CDCl$_3$) δ value: 1.15-2.50(11H, m), 2.76(3H, s), 3.07(0.6H, dd, J=14.5, 3.0), 3.22(0.4H, dd, J=14.5, 4.0), 3.59 (0.4H, dd, J=14.5, 9.9), 3.75(0.6H, dd, J=14.5, 8.6), 4.41 (0.6H, m), 4.78(0.4H, m), 5.59(2H, s), 7.18(2H, m), 7.43(1H, s), 7.57(1H, t, J=7.9), 7.75(1H, t, J=8.3), 7.82(3H, m), 7.98 (0.6H, s), 8.10(1H, d, J=8.6), 8.51(0.4H, s).

FAB-MS: Calculated (M$^+$+1): 511; Found: 511.

EXAMPLE 3

Preparation of N-Hydroxy-N-[2-{4-(2-methylquinolin-4-ylmethoxy)benzenesulfonyl}-1-(4-oxocyclohexylidenemethyl)ethyl]formamide (I-3)

(I-3)

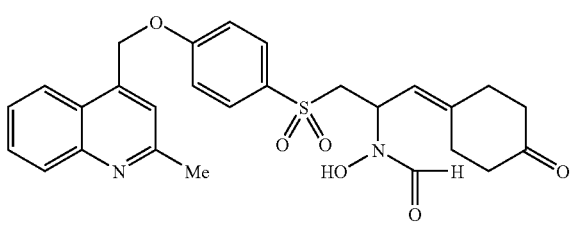

(3-1): 1-(1,4-Dioxaspiro[4.5]dec-8-ylidene)-3-[4-(2-methylquinolin-4-ylmethoxy)benzenesulfonyl]propan-2-ol (VIII-3)

According to the same manner as in Example 2 (2-1), 2.50 g (yield 88.3%) of 1-(1,4-dioxaspiro[4.5]dec-8-ylidene)-3-[4-(2-methylquinolin-4-ylmethoxy)benzenesulfonyl]propan-2-ol (VIII-3) was obtained from 1.8 g (5.50 mmol) of 4-(4-methanesulfonylphenoxymethyl)-2-methylquinoline (VI-1) obtained in the above (1-1) and 1.11 g (6.09 mmol) of (1,4-dioxaspiro[4.5]dec-8-ylidene)acetaldehyde. Its physical properties are shown below.

$^1$H-NMR(CDCl$_3$) δ value: 1.65(4H, m), 2.21(4H, m), 2.77 (3H, s), 3.12(1H, dd, J=14.2, 2.4), 3.20(1H, d, J=1.7), 3.35 (1H, dd, J=14.2, 9.2), 3.95(4H, s), 4.99(1H, bt, J=8.6), 5.17 (1H, bt, J=8.3), 5.60(2H, s), 7.19 (2H, t, J=8.9), 7.43(1H, s), 7.57(1H, t, J=7.3), 7.75(1H, m), 7.91(3H, m), 8.10(1H, d, J=8.6).

FAB-MS: Calculated (M$^+$+1): 510; Found: 510.

(3-2): 4-[4-{3-(1,4-Dioxaspiro[4.5]dec-8-ylidene)-prop-1-ene-1-sulfonyl}phenoxymethyl]-2-methylquinoline (II-3)

According to the same manner as in Example 2 (2-2), 2.05 g (yield 85.2%) of 4-[4-{3-(1,4-dioxaspiro[4.5]dec-8-ylidene)-prop-1-ene-1-sulfonyl}phenoxymethyl]-2-methylquinoline (II-3) was obtained from 2.50 g (4.91 mmol) of 1-(1,4-dioxaspiro[4.5]dec-8-ylidene)-3-[4-(2-methylquinolin-4-ylmethoxy)benzenesulfonyl]propan-2-ol (VIII-3) obtained in the above (3-1). Its physical properties are shown below.

$^1$H-NMR(CDCl$_3$) δ value: 1.75(4H, t, J=6.6), 2.39(2H, t, J=6.6), 2.57(2H, d, J=6.6), 2.76(3H, s), 3.98(4H, s), 5.57(2H, s), 5.92(1H, d, J=11.5), 6.26(1H, d, J=14.5), 7.13(2H, d, J=8.9), 7.42(1H, s), 7.54(2H, m), 7.74(1H, t, J=7.6), 7.88(3H, m), 8.11(1H, d, J=8.6).

FAB-MS: Calculated (M$^+$+1): 492; Found: 492.

(3-3): N-[1-(1,4-Dioxaspiro[4.5]dec-8-ylidenemethyl)-2-{4-(2-methylquinolin-4-ylmethoxy)benzenesulfonyl}ethyl]hydroxylamine (III-3a)

According to the same manner as in Example 1 (1-5), 2.20 g (yield 100%) of N-[1-(1,4-dioxaspiro[4.5]dec-8-ylidenemethyl)-2-{4-(2-methylquinolin-4-ylmethoxy) benzenesulfonyl}ethyl]hydroxylamine (III-3a) was obtained from 2.05 g (4.17 mmol) of 4-[4-{3-(1,4-dioxaspiro[4.5]dec-8-ylidene)-prop-1-ene-1-sulfonyl}phenoxymethyl]-2-methylquinoline (II-3) obtained in the above (3-2) and a 50% aqueous solution of hydroxylamine (10 mL). Its physical property is shown below.

FAB-MS: Calculated (M$^+$+1): 525; Found: 525.

(3-4): 4-[2-Hydroxyamino-3-{4-(2-methylquinolin-4-ylmethoxy)benzenesulfonyl}propyliden]cyclohexanone (III-3b)

According to the same manner as in Example 2 (2-4), 2.10 g (yield 100%) of 4-[2-Hydroxyamino-3-{4-(2-methylquinolin-4-ylmethoxy)benzenesulfonyl}propyliden]cyclohexanone (III-3b) was obtained from 2.20 g (4.17 mmol) of N-[1-(1,4-dioxaspiro[4.5]dec-8-ylidenemethyl)-2-{4-(2-methylquinolin-4-ylmethoxy)benzenesulfonyl}ethyl]hydroxylamine (III-3a) obtained in the above (3-3). Its physical property is shown below.

FAB-MS: Calculated (M$^+$+1): 481; Found: 481.

(3-5): N-Hydroxy-N-[2-{4-(2-methylquinolin-4-ylmethoxy)benzenesulfonyl}-1-(4-oxocyclohexylidenmethyl)ethyl]formamide (I-3)

According to the same manner as in Example 1 (1-6), 1.12 g (yield 52.8%) of the title compound was obtained from 2.10 g (4.17 mmol) of 4-[2-hydroxyamino-3-{4-(2-methylquinolin-4-ylmethoxy)benzenesulfonyl}propyliden]cyclohexanone (III-3b) obtained in the above (3-4), formic acid (20 mL) and acetic anhydride (2.4 mL). Its physical properties are shown below.

$^1$H-NMR(CDCl$_3$) δ value: 1.56-2.65(8H, m), 2.76(3H, s), 3.20(1H, m), 3.60-3.97(2H, m), 5.00-5.50(2H, m), 5.60(2H, s), 7.18(2H, m), 7.43(1H, s), 7.57(1H, t, J=7.6), 7.74(1H, t, J=7.9), 7.87(3H, m), 8.00(0.4H, S), 8.09(1H, d, J=8.3), 8.39 (0.6H, s).

FAB-MS: Calculated (M$^+$+1) 509; Found: 509.

EXAMPLE 4

Preparation of N-[2-{4-(2,6-dimethylpyridin-4-ylmethoxy)benzenesulfonyl}-1-(4-methylenecyclohexyl)ethyl]-N-hydroxyformamide (I-4)

(I-4)

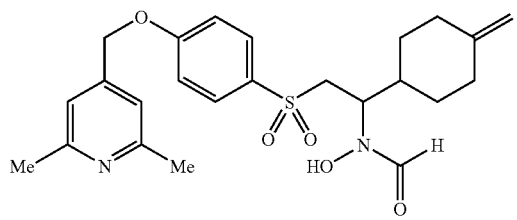

(4-1): 4-(4-Methanesulfonylphenoxymethyl)-2,6-dimethylpyridine (VI-4)

To a solution of 1.0 g (5.21 mmol) of 4-chloromethyl-2,6-dimethylpyridine hydrochloride and 1.1 g (6.25 mmol) of 4-methylsulfonylphenol in ethanol (3.5 mL) was added 3.5 mL (14.0 mmol) of 4 N aqueous sodium hydroxide solution, followed by heating under reflux for 90 minutes. After standing to cool, ethanol was evaporated under a reduced pressure. To the obtained residue, water was added and the precipitates were collected by filtration and then dried under a reduced pressure to obtain 707 mg (yield 46.6%) of 4-(4-methanesulfonylphenoxymethyl)-2,6-dimethylpyridine (VI-4) as a colorless crystal. Its physical property is shown below.

$^1$H-NMR(CDCl$_3$) δ value: 2.55(6H, s), 3.04(3H, s), 5.09 (2H, s), 7.01(2H, s), 7.08(2H, d, J=8.9), 7.89(2H, d, J=8.9).

(4-2): 2-[4-(2,6-Dimethylpyridin-4-ylmethoxy)benzenesulfonyl]-1-(4-methylenecyclohexyl)ethanone (X-4)

According to the same manner as in Example 1 (1-2), 377 mg (yield 53.2%) of 2-[4-(2,6-dimethylpyridin-4-ylmethoxy)benzenesulfonyl]-1-(4-methylenecyclohexyl)ethanone (X-4) was obtained from 500 mg (1.72 mmol) of 4-(4-methanesulfonylphenoxymethyl)-2,6-dimethylpyridine (VI-4) obtained in the above (4-1) and 290 mg (1.72 mmol) of methyl 4-methylenecyclohexane carboxylate, as a colorless crystal. Its physical properties are shown below.

$^1$H-NMR(CDCl$_3$) δ value: 1.33-1.48(2H, m), 1.94-2.12 (4H, m), 2.34-2.39(2H, m), 2.55(6H, s), 2.84(1H, tt, J=3.3, 11.2), 4.21(2H, s), 4.66(2H, s), 5.08(2H, s), 7.00(1H, s), 7.07(2H, d, J=8.9), 7.82(2H, d, J=8.9).

FAB-MS: Calculated (M$^+$+1): 414; Found: 414.

(4-3): 2-[4-(2,6-Dimethylpyridin-4-ylmethoxy)benzenesulfonyl]-1-(4-methylenecyclohexyl)ethanol (VIII-4)

According to the same manner as in Example 1 (1-3), 329 mg(yield 91.6%) of 2-[4-(2,6-dimethylpyridin-4-ylmethoxy)benzenesulfonyl]-1-(4-methylenecyclohexyl)ethanol (VIII-4) was obtained from 357 mg (0.86 mmol) of 2-[4-(2,6-dimethylpyridin-4-ylmethoxy)benzenesulfonyl]-1-(4-methylenecyclohexyl)ethanone (X-4) obtained in the above (4-2), as colorless amorphous. Its physical properties are shown below.

$^1$H-NMR(CDCl$_3$) δ value: 1.02-1.18(2H, m), 1.52-1.65 (1H, m), 1.73-1.84(2H, m), 1.92-2.10(2H, m), 2.27-2.34(2H, m), 2.55(6H, s), 3.19-3.21(2H, m), 3.42(1H, s), 3.98(1H, q, J=5.3), 4.59(2H, s), 5.09(2H, s), 7.01(2H, s), 7.09(2H, d, J=9.2), 7.86(2H, d, J=8.9).

FAB-MS: Calculated (M$^+$+1): 416; Found: 416.

(4-4): 2,6-Dimethyl-4-[4-{2-(4-methylenecyclohexyl)ethenesulfonyl}phenoxymethyl]pyridine (II-4)

According to the same manner as in Example 1 (1-4), 293 mg (yield 100%) of 2,6-dimethyl-4-[4-{2-(4-methylenecyclohexyl)ethenesulfonyl}phenoxymethyl]pyridine (II-4) was obtained from 306 mg (0.74 mmol) of 2-[4-(2,6-dimethylpyridin-4-ylmethoxy)benzenesulfonyl]-1-(4-methylenecyclohexyl)ethanol (VIII-4) obtained in the above (4-3), as a colorless crystal. Its physical properties are shown below.

$^1$H-NMR(CDCl$_3$) δ value: 1.17-1.32(2H, m), 1.79-1.90 (2H, m), 2.00-2.11(2H, m), 2.30-2.36(3H, m), 2.54(6H, s), 4.64(2H, s), 5.07(2H, s), 6.25(1H, dd, J=1.3, 15.2), 6.91(1H, dd, J=6.6, 15.2), 7.00(2H, s), 7.04(2H, d, J=8.9), 7.80(2H, d, J=8.9).

FAB-MS: Calculated (M$^+$+1): 398; Found: 398.

(4-5): N-[2-{4-(2,6-Dimethylpyridin-4-ylmethoxy)benzenesulfonyl}-1-(4-methyleneccylohexyl)ethyl]hydroxylamine (III-4)

According to the same manner as in Example 1 (1-5), 306 mg (yield 96.4%) of N-[2-{4-(2,6-dimethylpyridin-4-ylmethoxy)benzenesulfonyl}-1-(4-methylenecyclohexyl)ethyl]hydroxylamine (III-4) was obtained from 293 mg (0.74 mmol) of 2,6-dimethyl-4-[4-{2-(4-methylenecyclohexyl)ethenesulfonyl}phenoxymethyl]pyridine (II-4) obtained in the above (4-4) and a 50% aqueous solution of hydroxylamine (1.2 mL), as a colorless crystal. Its physical properties are shown below.

$^1$H-NMR(CDCl$_3$) δ value: 0.89-1.10(2H, m), 1.75-2.04 (4H, m), 2.28-2.32(2H, m), 2.55(6H, s), 3.08-3.17(2H, m), 3.37-3.46(1H, m), 4.60(2H, s), 4.78(1H, s), 5.09(2H, s), 7.01 (2H, s), 7.08(2H, d, J=8.9), 7.88(2H, d, J=8.9).

FAB-MS: Calculated (M$^+$+1): 431; Found: 431.

(4-6): N-[2-{4-(2,6-Dimethylpyridin-4-ylmethoxy)benzenesulfonyl}-1-(4-methylenecyclohexyl)ethyl]-N-hydroxyformamide (I-4)

According to the same manner as in Example 1 (1-6), 68.3 mg (yield 32.1%) of the title compound was obtained from 200 mg (0.46 mmol) of N-[2-{4-(2,6-dimethylpyridin-4-yl-methoxy)benzenesulfonyl}-1-(4-methylenecyclohexyl)ethyl]hydroxylamine (III-4) obtained in the above (4-5), formic acid (2.4 mL) and acetic anhydride (0.3 mL), as brown amorphous. Its physical properties are shown below.

$^1$H-NMR(CDCl$_3$) δ value: 1.01-1.15(2H, m), 1.77-2.05 (5H, m), 2.28-2.40(2H, m), 2.55(6H, s), 3.23-3.89(3H, m), 4.60-4.64(2H, m), 5.09(2H, s), 7.01(2H, s), 7.06-7.12(2H, m), 7.78-7.83(2H, m), 8.47(1H, s).

FAB-MS: Calculated (M$^+$+1): 459; Found: 459.

EXAMPLE 5

Preparation of N-[2-{4-(3,5-Dimethylbenzyloxy)benzenesulfonyl}-1-(4-methylenecyclohexyl)ethyl]-N-hydroxyformamide (I-5)

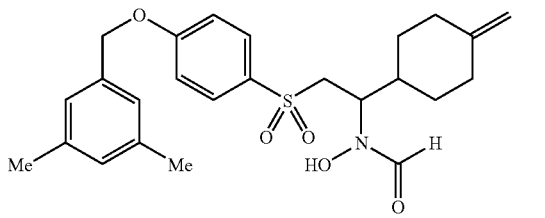

(I-5)

(5-1): 1-(4-methanesulfonylphenoxymethyl)-3,5-dimethylbenzene (VI-5)

To a solution of 2.9 g (18.9 mmol) of 1-chloromethyl-3,5-dimethylbenzene and 3.9 g (22.7 mmol) of 4-methylsulfonylphenol in ethanol (10 mL) was added 10 mL (20.0 mmol) of 2 N aqueous sodium hydroxide solution, followed by heating under reflux for 2 hours. After standing to cool, water was added and the precipitates were collected by filtration and dried under a reduced pressure to obtain 4.1 g (yield 75.3%) of 1-(4-methanesulfonylphenoxymethyl)-3,5-dimethylbenzene (VI-5). Its physical properties are shown below.

$^1$H-NMR(CDCl$_3$) δ value: 2.34(6H, s), 3.03(3H, s), 5.06 (2H, s), 7.00(1H, s), 7.03(2H, s), 7.09(2H, d, J=9.2), 7.87(2H, d, J=8.9).

FAB-MS: Calculated (M$^+$+1): 291; Found: 291.

(5-2): 2-[4-(3,5-Dimethylbenzyloxy)benzenesulfonyl]-1-(4-methylenecyclohexyl)ethanone (X-5)

According to the same manner as in Example 1 (1-2), 288 mg (yield 40.5%) of 2-[4-(3,5-dimethylbenzyloxy)benzenesulfonyl]-1-(4-methylenecyclohexyl)ethanone (X-5) was obtained from 500 mg (1.72 mmol) of 1-(4-methanesulfonylphenoxymethyl)-3,5-dimethylbenzene (VI-5) obtained in the above (5-1) and 290 mg (1.72 mmol) of methyl 4-methylenecyclohexane carboxylate, as a colorless crystal. Its physical properties are shown below.

$^1$H-NMR(CDCl$_3$) δ value: 1.33-1.48(2H, m), 1.94-2.13 (4H, m), 2.25-2.40(2H, m), 2.34(6H, s), 2.84(1H, tt, J=3.3, 11.2), 4.20(2H, s), 4.65(2H, d, J=1.3), 5.06(2H, s), 7.00(1H, s), 7.03(2H, s), 7.08(2H, d, J=8.9), 7.80(2H, d, J=8.9).

FAB-MS: Calculated (M$^+$+1): 413; Found: 413.

(5-3): 2-[4-(3,5-Dimethylbenzyloxy)benzenesulfonyl]-1-(4-methylenecyclohexyl)ethanol (VIII-5)

According to the same manner as in Example 1 (1-3), 270 mg (yield 93.1%) of 2-[4-(3,5-dimethylbenzyloxy)benzenesulfonyl]-1-(4-methylenecyclohexyl)ethanol (VIII-5) was obtained from 288 mg (0.70 mmol) of 2-[4-(3,5-dimethylbenzyloxy)benzenesulfonyl]-1-(4-methylenecyclohexyl)ethanone (X-5) obtained in the above (5-2), as pale yellow oil. Its physical properties are shown below.

$^1$H-NMR(CDCl$_3$) δ value: 1.02-1.22(2H, m), 1.53-1.65 (1H, m), 1.73-1.84(2H, m), 1.92-2.02(2H, m), 2.28-2.34(2H, m), 2.34(6H, s), 3.17-3.19(2H, m), 3.36(1H, d, J=2.3), 3.96 (1H, m), 4.60(2H, s), 5.06(2H, s), 7.00(1H, s), 7.03(2H, s), 7.10(2H, d, J=8.9), 7.84(2H, d, J=8.9).

FAB-MS: Calculated (M$^+$+1): 415; Found: 415.

(5-4): 1,3-Dimethyl-5-[4-{2-(4-methylenecyclohexyl)ethenesulfonyl}phenoxymethyl]benzene (II-5)

According to the same manner as in Example 1 (1-4), 224 mg (yield 96.4%) of 1,3-dimethyl-5-[4-{2-(4-methylenecyclohexyl)ethenesulfonyl}phenoxymethyl]benzene (II-5) was obtained from 243 mg (0.59 mmol) of 2-[4-(3,5-dimethylbenzyloxy)benzenesulfonyl]-1-(4-methylenecyclohexyl)ethanol (VIII-5) obtained in the above (5-3), as yellow oil. Its physical properties are shown below.

$^1$H-NMR(CDCl$_3$) δ value: 1.17-1.32(2H, m), 1.83-1.89 (2H, m), 2.00-2.11(2H, m), 2.26-2.39(3H, m), 2.33(6H, s), 4.64(2H, s), 5.04(2H, s), 6.25(1H, dd, J=1.3, 15.2), 6.89(1H, dd, J=6.3, 15.2), 6.99(1H, s), 7.03(2H, s), 7.05(2H, d, J=8.9), 7.78(2H, d, J=8.9).

FAB-MS: Calculated (M$^+$+1): 397; Found: 397.

(5-5): N-[2-{4-(3,5-Dimethylbenzyloxy)benzenesulfonyl}-1-(4-methylenecyclohexyl)ethyl]hydroxylamine (III-5)

According to the same manner as in Example 1 (1-5), 223 mg (yield 91.7%) of N-[2-{4-(3,5-dimethylbenzyloxy)benzenesulfonyl}-1-(4-methylenecyclohexyl)ethyl]hydroxylamine (III-5) was obtained from 243 mg (0.59 mmol) of 1,3-dimethyl-5-[4-{2-(4-methylenecyclohexyl)ethenesulfonyl}phenoxymethyl]benzene (II-5) obtained in the above (5-4) and a 50% aqueous solution of hydroxylamine (1.0 mL), as a colorless crystal. Its physical properties are shown below.

$^1$H-NMR(CDCl$_3$) δ value: 1.02-1.22(2H, m), 1.53-1.65 (1H, m), 1.73-1.84(2H, m), 1.92-2.02(2H, m), 2.28-2.34(2H, m), 2.34(6H, s), 3.17-3.19(2H, m), 3.36(1H, d, J=2.3), 3.96 (1H, m), 4.60(2H, s), 5.06(2H, s), 7.00(1H, s), 7.03(2H, s), 7.10(2H, d, J=8.9), 7.84(2H, d, J=8.9).

FAB-MS: Calculated (M$^+$+1): 430; Found: 430.

(5-6): N-[2-{4-(3,5-Dimethylbenzyloxy)benzenesulfonyl}-1-(4-methylenecyclohexyl)ethyl]-N-hydroxyformamide (I-5)

According to the same manner as in Example 1 (1-6), 223 mg (yield 91.7%) of the title compound was obtained from 223 mg (0.52 mmol) of N-[2-{4-(3,5-dimethylbenzyloxy)

benzenesulfonyl}-1-(4-methylenecyclohexyl)ethyl]hydroxylamine (III-5) obtained in the above (5-5), formic acid (2.4 mL) and acetic anhydride (0.3 mL), as a colorless crystal. Its physical properties are shown below.

$^1$H-NMR(CDCl$_3$) δ value: 1.10(2H, m), 1.48-2.32(7H, m), 2.34(6H, s), 3.05-3.42(1H, m), 3.52-3.96(1.6H, m), 4.39(0.4H, m), 4.62(2H, m), 5.06(2H, m), 6.95-7.16(5H, m), 7.70-7.92(2.6H, m), 8.48(0.4H, s).

FAB-MS: Calculated (M$^+$+1): 458; Found: 458.

EXAMPLE 6

Preparation of N-Hydroxy-N-[1-(4-hydroxyiminocyclohexylidenemethyl)-2-{4-(2-methylquinolin-4-ylmethoxy)benzenesulfonyl}ethyl]formamide (I-6)

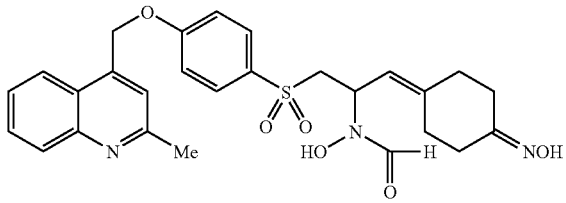

(I-6)

(6-1): 4-[2-Hydroxyamino-3-{4-(2-methylquinolin-4-ylmethoxy)benzenesulfonyl}propylidene]cyclohexanonoxime (III-6)

A 50% aqueous solution of hydroxylamine (0.8 mL) and 2N hydrochloric acid (11 mL) was added to a solution of 1.60 g (3.05 mmol) of N-[1-(1,4-dioxaspiro[4.5]dec-8-ylidenemethyl)-2-{4-(2-methylquinolin-4-ylmethoxy)benzenesulfonyl}ethyl]hydroxylamine (III-3a) in tetrahydrofuran (20 mL) at 0° C., and stirred for 14 hours at room temperature. The resulting mixture was treated with saturated aqueous sodium bicarbonate and then extracted with ethyl acetate. The organic layer was washed with saturated aqueous sodium bicarbonate and saturated brine successively, and dried over anhydrous magnesium sulfate. Upon removal of the solvent by evaporation, 1.68 g (yield 100%) of 4-[2-hydroxyamino-3-{4-(2-methylquinolin-4-ylmethoxy) benzenesulfonyl}propylidene]cyclohexanoneoxime (III6) was obtained as a solid. Its physical property is shown below.

FAB-MS: Calculated (M$^+$+1): 496; Found: 496.

(6-2): N-Hydroxy-N-[1-(4-hydroxyiminocyclohexylidenemethyl)-2-{4-(2-methylquinolin-4-ylmethoxy) benzenesulfonyl}ethyl]formamide (I-6)

According to the same manner as in Example 1 (1-6), 0.92 g (yield 57.6%) of the title compound was obtained from 1.68 g (3.05 mmol) of 4-[2-hydroxyamino-3-{4-(2-methylquinolin-4-ylmethoxy)benzenesulfonyl}propylidene]cyclohexanoneoxime (III6) obtained in the above (6-1). Its physical properties are shown below.

$^1$H-NMR(CDCl$_3$) δ value: 1.95-2.40(8H, m), 2.67(3H, s), 3.49(1H, dd, J=14.5, 5.0), 3.68(1H, m), 4.71-5.42(2H, m), 5.74(2H, s), 7.39(2H, d, J=8.6), 7.56(1H, s), 7.60(1H, t, J=7.6), 7.76(1H, t, J=7.9), 7.88(2H, d, J=8.6), 7.98(1H, d, J=8.6), 8.07(2H, m), 9.65(0.5H, bs), 10.03(0.5H, bs), 10.31 (1H, m).

FAB-MS: Calculated (M$^+$+1): 524; Found: 524.

EXAMPLE 7

Preparation of N-Hydroxy-N-[2-{4-(3-methoxy-5-methylbenzyloxy)benzenesulfonyl)-1-(4-methylenecyclohexyl)ethyl]formamide (I-7)

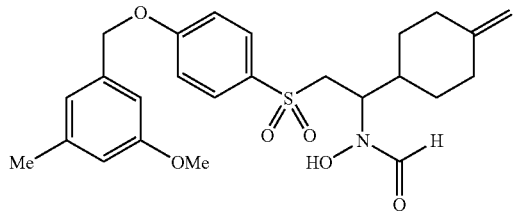

(I-7)

(7-1): 1-(4-Methanesulfonylphenoxymethyl)-3-methoxy-5-methylbenzene (VI-7)

To a solution of 5.0 g (36.7 mmol) of 3,5-dimethylanisole in carbon tetrachloride (35 mL) was added 5.2 g (29.4 mmol) of N-bromosuccinimide and 0.2 g (0.74 mmol) of benzoyl peroxide at room temperature, followed by heating under reflux for 2 hours. The reaction mixture was left standing to cool and then filtered. The filtrate was concentrated under a reduced pressure. The obtained residue was dissolved in ethanol (7.5 mL), and treated with 4.5 g (26.1 mmol) of 4-methylsulfonylphenol and 7.5 mL (30.0 mmol) of a 4 N aqueous sodium hydride, and heated under reflux for 1 hour. After standing to cool, water and hexane was added to the reaction mixture, and the precipitates were collected by filtration and washed with ether. The residue was purified by column chromatography (silica gel 80 g, developing solvent: chloroform-ethyl acetate=4: 1) to obtain 4.5 g (yield 40.4%) of 1-(4-methanesulfonylphenoxymethy)-3-methoxy-5-methylbenzene (VI-7) as a colorless crystal. Its physical properties are shown below.

$^1$H-NMR(CDCl$_3$) δ value: 2.35(3H, s), 3.03(3H, s), 3.80 (3H, s), 5.08(2H, s), 6.71(1H, s), 6.77(1H, s), 6.82(1H, s), 7.09 (2H, d, J=8.6), 7.86(2H, d, J=8.6).

FAB-MS: Calculated (M$^+$+1): 307; Found: 307.

(7-2): 2-[4-(3-Methoxy-5-methylbenzyloxy)benzenesulfonyl]-1-(4-methylenecyclohexyl) ethanone (X-7)

According to the same manner as in Example 1 (1-2), 485 mg (yield 49.5%) of 2-[4-(3-methoxy-5-methylbenzyloxy) benzenesulfonyl]-1-(4-methylenecyclohexyl)ethanone (X-7) was obtained from 700 mg (2.29 mmol) of 1-(4-methanesulfonylphenoxymethy)-3-methoxy-5-methylbenzene (VI-7) obtained in the above (7-1) and 385 mg (2.29 mmol) of methyl 4-methylenecyclohexane carboxylate, as colorless oil. Its physical properties are shown below.

$^1$H-NMR(CDCl$_3$) δ value: 1.33-1.48(2H, m), 1.93-2.12 (4H, m), 2.31-2.39(2H, m), 2.35(3H, s), 2.77-2.88(1H, m), 3.80(3H, s), 4.20(2H, s), 4.65(2H, s), 5.07(2H, s), 6.71(1H, s), 6.76(1H, s), 6.81(1H, s), 7.08(2H, d, J=8.9), 7.80(2H, d, J=8.9).

FAB-MS: Calculated (M$^+$+1): 429; Found: 429.

(7-3): 2-[4-(3-Methoxy-5-methylbenzyloxy)benzenesulfonyl]-1-(4-methylenecyclohexyl)ethanol (VIII-7)

According to the same manner as in Example 1 (1-3), 482 mg (yield 100%) of 2-[4-(3-methoxy-5-methylbenzyloxy)benzenesulfonyl]-1-(4-methylenecyclohexyl)ethanol (VIII-7) was obtained from 480 mg (1.12 mmol) of 2-[4-(3-methoxy-5-methylbenzyloxy)benzenesulfonyl]-1-(4-methylenecyclohexyl)ethanone (X-7) obtained in the above (7-2), as colorless oil. Its physical properties are shown below.

$^1$H-NMR(CDCl$_3$) δ value: 1.02-1.18(2H, m), 1.51-1.62 (2H, m), 1.73-1.83(2H, m), 1.93-2.05(2H, m), 2.28(1H, m), 2.35(3H, s), 3.18(2H, d, J=5.3), 3.35(1H, d, J=2.3), 3.80(3H, s), 3.93-4.00(1H, m), 4.60(2H, s), 5.08(2H, s), 6.71(1H, s), 6.76(1H, s), 6.81(1H, s), 7.10(2H, d, J=8.9), 7.84(2H, d, J=8.9).

FAB-MS: Calculated (M$^+$+1): 431; Found: 431.

(7-4): 1-Methoxy-3-methyl-5-[4-{2-(4-methylenecyclohexyl)ethenesulfonyl}phenoxymethyl]benzene (II-7)

According to the same manner as in Example 1 (1-4), 462 mg (yield 100%) of 1-methoxy-3-methyl-5-[4-{2-(4-methylenecyclohexyl)ethenesulfonyl}phenoxymethyl]benzene (II-7) was obtained from 482 mg (1.12 mmol) of 2-[4-(3-methoxy-5-methylbenzyloxy)benzene sulfonyl]-1-(4-methylenecyclohexyl) ethanol (VIII-7) obtained in the above (7-3), as brown oil. Its physical properties are shown below.

$^1$H-NMR(CDCl$_3$) δ value: 1.22-1.36(2H, m), 1.38-1.50 (2H, m), 1.84-1.89(2H, m), 2.00-2.11(2H, m), 2.31(1H, m), 2.35(3H, s), 3.80(3H, s), 4.64 (2H, s), 5.06(2H, s), 6.25(1H, dd, J=1.3, 15.2), 6.70(1H, s), 6.76(1H s), 6.81(1H, s), 6.89 (1H, dd, J=6.6, 15.2), 7.05(2H, d, J=8.9), 7.78(2H, d, J=8.9).

FAB-MS: Calculated (M$^+$+1): 413; Found: 413.

(7-5): N-[2-{4-(3-Methoxy-5-methylbenzyloxy)benzenesulfonyl}-1-(4-methylenecyclohexyl)ethyl]hydroxylamine (III-7)

According to the same manner as in Example 1 (1-5), 359 mg (yield 71.9%) of N-[2-{4-(3-methoxy-5-methylbenzyloxy)benzenesulfonyl}-1-(4-methylenecyclohexyl)ethyl]hydroxylamine (III-7) was obtained from 462 mg (1.12 mmol) of 1-methoxy-3-methyl-5-[4-{2-(4-methylenecyclohexyl)ethenesulfonyl}phenoxymethyl]benzene (II-7) obtained in the above (7-4) and a 50% aqueous solution of hydroxylamine (3.0 mL), as a colorless crystal. Its physical properties are shown below.

$^1$H-NMR(CDCl$_3$) δ value: 0.99-1.09(2H, m), 1.77-1.85 (3H, m), 1.90-2.03(2H, m), 2.27-2.28(1H, m), 2.35(3H, s), 3.07-3.17(2H, m), 3.36-3.45(1H, m), 3.80(3H, s), 4.50(1H, s), 4.60(2H, s), 5.08(2H, s), 6.71(1s), 6.76(1H, s), 6.82(1H, s), 7.09(2H, d, J=8.9), 7.85(2H, d, J=8.9).

FAB-MS: Calculated (M$^+$+1): 446; Found: 446.

(7-6): N-Hydroxy-N-[2-14-(3-methoxy-5-methylbenzyloxy)benzenesulfonyl)-1-(4-methylenecyclohexyl)ethyl]formamide (I-7)

According to the same manner as in Example 1 (1-6), 121 mg (yield 32.6%) of the title compound was obtained from 350 mg (0.79 mmol) of N-[2-{4-(3-methoxy-5-methylbenzyloxy)benzenesulfonyl}-1-(4-methylenecyclohexyl)ethyl] hydroxylamine (III-7) obtained in the above (7-5), formic acid (4.0 mL) and acetic anhydride (0.5 mL), as brown amorphous. Its physical properties are shown below.

$^1$H-NMR(CDCl$_3$) δ value: 1.04-1.20(2H, m), 1.75-2.10 (5H, m), 2.25-2.40(2H, m), 2.35(3H, s), 3.21-3.31(1H, m), 3.71-3.91(1H, m), 3.80(3H, s), 4.06-4.20(0.6H, m), 4.35-4.45(0.4H, m), 4.59-4.63(2H, m), 5.07(2H, s), 6.71(1H, s), 6.76(1H, s), 6.81(1H, s), 7.06-7.12(2H, m), 7.76-7.81(2.6H, m), 8.47(0.4H, s).

FAB-MS: Calculated (M$^+$+1): 474; Found: 474.

EXAMPLE 8

Preparation of N-[1-(1,4-Dioxaspiro[4.5]dec-8-yl)-2-{4-(3-methoxy-5-methylbenzyloxy)benzenesulfonyl}ethyl]-N-hydroxyformamide (I-8)

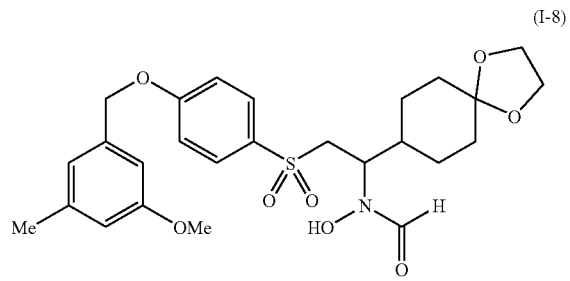

(I-8)

(8-1): 1-(1,4-Dioxaspiro[4.5]dec-8-yl)-2-[4-(3-methoxy-5-methylbenzyloxy)benzenesulfonyl]ethanone (X-8)

According to the same manner as in Example 1 (1-2), 838 mg (yield 54.1%) of 1-(1,4-Dioxaspiro[4.5]dec-8-yl)-2-[4-(3-methoxy-5-methylbenzyloxy)benzenesulfonyl]ethanone (X-8) was obtained from 1 g (3.26 mmol) of 1-(4-methanesulfonylphenoxymethy)-3-methoxy-5-methylbenzene (VI-7) obtained in the above (7-1) and 700 mg (3.27 mmol) of ethyl 1,4-dioxaspiro[4.5]decane-8-carboxylate, as colorless oil. Its physical properties are shown below.

$^1$H-NMR(CDCl$_3$) δ value: 1.52-1.93(8H, m), 2.35(3H, s), 2.66-2.75(1H, m), 3.80(3H, s), 3.90-3.96(4H, m), 4.19(2H, s), 5.07(2H, s), 6.71(1H, s), 6.76(1H, s), 6.82(1H, s), 7.08(2H, d, J=8.9), 7.79(2H, d, J=8.9).

FAB-MS: Calculated (M$^+$+1): 475; Found: 475.

(8-2): 1-(1,4-dioxaspiro[4.5]dec-8-yl)-2-[4-(3-methoxy-5-methylbenzyloxy)benzenesulfonyl]ethanol (VIII-8)

According to the same manner as in Example 1 (1-3), 834 mg (yield 100%) of 1-(1,4-dioxaspiro[4.5]dec-8-yl)-2-[4-(3-methoxy-5-methylbenzyloxy)benzenesulfonyl]ethanol (VIII-8) was obtained from 830 mg (1.73 mmol) of 1-(1,4-dioxaspiro[4.5]dec-8-yl)-2-[4-(3-methoxy-5-methylbenzyloxy)benzenesulfonyl]ethanone (X-8) was obtained in the above (8-1), as colorless oil. Its physical properties are shown below.

$^1$H-NMR(CDCl$_3$) δ value: 1.21-1.37(2H, m), 1.43-1.54 (2H, m), 1.66-1.77(5H, m), 2.36(3H, s), 3.17-3.19(2H, m), 3.41(1H, d, J=2.0), 3.81(3H, s), 3.86-3.96(5H, m), 5.08(2H, s), 6.71(1H, s), 6.76(1H, s), 6.83(1H, s), 7.09(2H, d, J=8.9), 7.83(2H, d, J=8.9).

FAB-MS: Calculated (M$^+$+1): 477; Found: 477

(8-3): 8-[2-{4-(3-Methoxy-5-methylbenzyloxy)benzenesulfonyl}vinyl]-1,4-dioxaspiro[4.5]decane (II-8)

According to the same manner as in Example 1 (1-4), 794 mg (yield 100%) of 8-[2-{4-(3-methoxy-5-methylbenzyloxy)benzenesulfonyl}vinyl]-1,4-dioxaspiro[4.5]decane (II-8) was obtained from 834 mg (1.73 mmol) of 1-(1,4-dioxaspiro[4.5]dec-8-yl)-2-[4-(3-methoxy-5-methylbenzyloxy)benzenesulfonyl]ethanol (VIII-8) obtained in the above (8-2), as brown oil. Its physical properties are shown below.

$^1$H-NMR(CDCl$_3$) δ value: 1.36-1.66(4H, m), 1.76-1.79 (4H, m), 2.21-2.31(1H, m), 2.35(3H, s), 3.80(3H, s), 3.90-3.94(4H, m), 5.06(2H, s), 6.26(1H, dd, J=1.3, 15.2), 6.71(1H, s), 6.76(1H, s), 6.82(1H, s), 6.90(1H, dd, J=6.6, 15.2), 7.05 (2H, d, J=8.9), 7.78(2H, d, J=8.9).

FAB-MS: Calculated (M$^+$+1): 459; Found: 459.

(8-4): N-[1-(1,4-Dioxaspiro[4.5]dec-8-yl)-2-{4-(3-methoxy-5-methylbenzyloxy)benzenesulfonyl}ethyl]hydroxylamine (III-8)

According to the same manner as in Example 1 (1-5), 699 mg (yield 71.9%) of N-[1-(1,4-dioxaspiro[4.5]dec-8-yl)-2-{4-(3-methoxy-5-methylbenzyloxy)benzenesulfonyl}ethyl]hydroxylamine (III-8) was obtained from 462 mg (1.12 mmol) of 8-[2-{4-(3-methoxy-5-methylbenzyloxy)benzenesulfonyl}vinyl]-1,4-dioxaspiro[4.5]decane (II-8) obtained in the above (8-3) and a 50% aqueous solution of hydroxylamine (5.0 mL), as a colorless crystal. Its physical properties are shown below.

$^1$H-NMR(CDCl$_3$) δ value: 1.11-1.31(2H, m), 1.44-1.56 (2H, m), 1.67-1.77(5H, m), 2.35(3H, s), 3.08-3.19(2H, m), 3.34-3.44(1H, m), 3.80(3H, s), 3.85-3.96(4H, m), 4.86(1H, s), 5.08(2H, s), 6.71(1H, s), 6.77(1H, s), 6.82(1H, s), 7.08(2H, d, J=8.9), 7.85(2H, d, J=8.9).

FAB-MS: Calculated (M$^+$+1): 492; Found: 492.

(8-5): N-[1-(1,4-Dioxaspiro[4.5]dec-8-yl)-2-{4-(3-methoxy-5-methylbenzyloxy)benzenesulfonyl}ethyl]-N-hydroxyformamide (I-8)

According to the same manner as in Example 1 (1-6), 30.0 mg (yield 11.4%) of the title compound was obtained from 250 mg (0.51 mmol) of N-[1-(1,4-dioxaspiro[4.5]dec-8-yl)-2-{4-(3-methoxy-5-methylbenzyloxy)benzenesulfonyl}ethyl]hydroxylamine (III-8) obtained in the above (8-4), formic acid (2.4 mL) and acetic anhydride (0.3 mL), as brown amorphous. Its physical properties are shown below.

$^1$H-NMR(CDCl$_3$) δ value: 1.23-1.34(2H, m), 1.44-1.81 (7H, m), 2.35(3H, s), 3.22-3.32(2H, m), 3.80(3H, s), 3.83-3.93(4H, m), 4.40(1H, m), 5.07(2H, s), 6.71(1H, s), 6.76(1H, s), 6.82(1H, s), 7.06-7.12(2H, m), 7.75-7.83(2.6H, m), 8.46 (0.4H, s).

FAB-MS: Calculated: M$^+$+1 520; Found: 520.

EXAMPLE 9

Preparation of N-Hydroxy-N-{2-[4-(2-methylquinolin-4-ylmethoxy)benzenesulfonyl]-1-(tetrahydropyran-4-ylidenemethyl)ethyl}formamide (I-9)

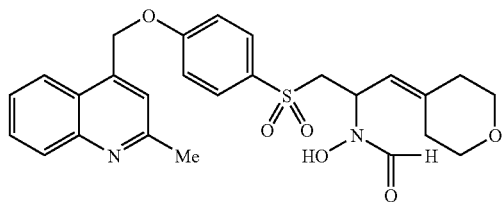

(I-9)

(9-1): 1-[4-(2-Methylquinolin-4-ylmethoxy)benzenesulfonyl]-3-(tetrahydropyran-4-ylidene)propan-2-ol (VIII-9)

Into a solution of 12.0 g (36.7 mmol) of 4-(4-methanesulfonylphenoxymethyl)-2-methylquinoline (VI-1) obtained in the above (1-1) in tetrahydrofuran (450 mL) was dropped 22.0 mL (44.0 mmol) of 2 mol/L lithium diisopropylamide in hexane-heptane-ethylbenzene (available from Aldrich) at −78° C. under an atmosphere of argon, followed by stirring for 30 minutes. Into this solution, a solution of 5.55 g (44.0 mmol) of (tetrahydropyran-4-ylidene)acetaldehyde in tetrahydrofuran (10 mL) was dropped at −78° C. and stirred for 30 minutes. To the resulting reaction mixture was added ethanol (100 mL), and the reaction mixture was concentrated under a reduced pressure, followed by an addition of water to the residue and an extraction with ethyl acetate. The organic layer was washed with saturated brine, dried over anhydrous magnesium sulfate, and concentrated. Then, ethanol was added to the obtained residue and heated. The insoluble material was collected by filtration, followed by drying at 50° C. under a reduced pressure to obtain 12.9 g (yield 77%) of 1-[4-(2-methylquinolin-4-ylmethoxy)benzenesulfonyl]-3-(tetrahydropyran-4-ylidene)propan-2-ol (VIII-9). Its physical property is shown below.

$^1$H-NMR(CDCl$_3$) δ value: 2.15-2.35(4H, m), 2.76(3H, s), 3.13(1H, dd, J=14.2, 1.7), 3.36(1H, dd, J=14.2, 8.9), 3.64(4H, m), 5.02(1H, m), 5.22(1H, d, J=8.3), 5.30(2H, s), 7.19(2H, d, J=8.6), 7.42(1H, s), 7.56(1H, m), 7.74(1H, m), 7.90(3H, m), 8.10(1H, d, J=8.3).

(9-2): 2-Methyl-4-{4-[3-(tetrahydropyran-4-ylidene)prop-1-ene-1-sulfonyl]phenoxymethyl}quinoline (II-9).

To a solution of 12.9 g (28.4 mmol) of 1-[4-(2-methylquinolin-4-ylmenthoxy)benzenesulfonyl]-3-(tetrahydropyran-4-ylidene)propan-2-ol (VIII-9) obtained in the above (9-1) and 14.3 g (141.3 mmol) of triethylamine in methylene chloride (240 mL) was added 6.66 g (58.1 mmol) of methanesulfonyl chloride at -10° C. and stirred for 12 hours at room temperature. The resulting reaction mixture was treated with saturated aqueous sodium bicarbonate and then extracted with ethyl acetate. The organic layer was washed with water and saturated brine successively and dried over anhydrous magnesium sulfate, followed by evaporation of the solvent to obtain 2.4 g (yield 100%) of crude 2-methyl-4-{4-[3-(tetrahydropyran-4-ylidene)prop-1-ene-1-sulfonyl]phenoxymethyl}quinoline (II-9). Its physical property is shown below.

$^1$H-NMR(CDCl$_3$) δ value: 2.35(2H, t, J=5.3), 2.56(2H, t, J=5.3), 2.76(3H, s), 3.73(4H, t, J=5.3), 5.57(2H, s), 5.95(1H, d, J=11.6), 6.29(1H, d, J=14.5), 7.13(2H, d, J=8.6), 7.42(1H, s), 7.48-7.58(2H, m), 7.74(1H, m) 7.84-7.72(3H, m), 8.10 (1H, d, J=8.3).

(9-3): N-Hydroxy-N-{2-[4-(2-methylquinolin-4-ylmethoxy)benzenesulfonyl]-1-(tetrahydropyran-4-ylidenemethyl)ethyl}formamide (I-9)

To a solution of 12.4 g (28.4 mmol) of crude 2-methyl-4-{4-[3-(tetrahydropyran-4-ylidene)prop-1-ene-1-sulfonyl]phenoxymethyl}quinoline (II-9) obtained in the above (9-2) in tetrahydrofuran (150 mL) was added a 50% aqueous solution of hydroxylamine (70 mL) at room temperature and stirred for 64 hours. The reaction mixture was evaporated under a reduced pressure, and the obtained residue was diluted with ethyl acetate, washed with water and saturated brine successively, dried over anhydrous magnesium sulfate, and the solvent was evaporated. To the obtained residue, tetrahydrofuran (60 mL) was added, and a mixture of formic acid (20 mL) and acetic anhydride (5.0 mL) premixed for 30 minutes at 0° C. was added thereto at 0° C., followed by stirring for 1 hour at room temperature. The reaction mixture was concentrated under a reduced pressure, subjected to azeotropic distillation with toluene, diluted with chloroform (25 mL), and then treated with methanol (100 mL), followed by stirring for 16 hours at room temperature. The reaction mixture was concentrated under a reduced pressure and then purified by medium pressure column chromatography on silica gel (developing solvent: ethyl acetate-ethanol=96:4) to give 3.80 g (yield 27.0%) of the title compound (I-9). Its physical properties are shown below.

$^1$H-NMR(CDCl$_3$) δ value: 1.82-2.15(4H, m), 2.67(3H, s), 3.25-3.78(6H, m), 4.90(0.4H, m), 5.10-5.40(1.6H, m), 5.76 (2H, s), 7.39(2H, d, J=8.9), 7.57(1H, s), 7.60(1H, t, J=8.3), 7.76(1H, t, J=7.3), 7.87(2H, d, J=8.9), 7.98(1H, d, J=8.6), 8.05(1H, s), 8.12(1H, d, J=7.9), 9.65(0.4H, bs), 10.04(0.6H, bs).

FAB-MS: Calculated (M$^+$+1): 497; Found: 497.

EXAMPLE 10

Preparation of N-Hydroxy-N-{2-[4-(2-methylquinolin-4-ylmethoxy)benzenesulfonyl]-1-(4-oxocyclohexyl)ethyl}formamide (I-11)

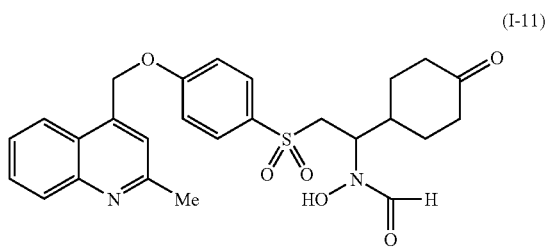

(I-11)

(10-1): N-Hydroxy-N-{2-[4-(2-methylquinolin-4-ylmethoxy)benzenesulfonyl]-1-(4-oxocyclohexyl)ethyl}formamide (I-11)

To a solution of 7.6 g (14.06 mmol) of N-{1-(1,4-dioxaspiro[4.5]dec-8-yl)-2-[4-(2-methylquinolin-4-ylmethoxy)benzenesulfonyl]ethyl}-N-hydroxyformamide (I-28) obtained by the same manner as in Example 1 in tetrahydrofuran (220 mL) was added, at 0° C., 160 mL (80 mmol) of 0.5 N hydrochloric acid precooled to 0° C., and stirred for 24 hours at room temperature. To the reaction mixture, sodium bicarbonate was added to neutralize, and then tetrahydrofuran was removed under a reduced pressure. The residue was extracted with ethyl acetate, and the organic layer was washed with saturated aqueous sodium bicarbonate (twice) and saturated brine successively, dried over anhydrous magnesium sulfate, and the solvent was evaporated. Upon recrystallization from ethyl acetate, 5.9 g (yield 84.5%) of the title compound was obtained. Its physical properties are shown below.

$^1$H-NMR(CDCl$_3$) δ value: 1.10-2.40(9H, m), 2.67(3H, s), 3.50-4.05(2.64H, m), 4.40(0.36H, bt, J=7.6), 5.76(2H, s), 7.39(2H, m), 7.57(1H, s), 7.60(1H, t, J=7.3), 7.76(1H, t, J=7.6), 7.80-8.18(5H, m), 9.66(0.64H, s), 9.99(0.36H, s).

FAB-MS: Calculated (M$^+$+1): 497; Found: 497.

EXAMPLE 11

Preparation of N-Hydroxy-N-{2-[4-(2-methylquinolin-4-ylmethoxy)benzenesulfonyl]-1-(tetrahydrothiopyran-4-ylidenemethyl)ethyl}formamide (I-17)

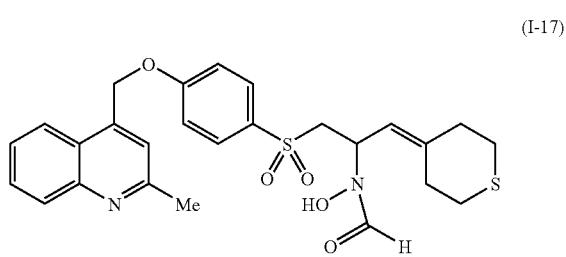

(I-17)

(11-1): N-{2-[4-(2-Methylquinolin-4-ylmethoxy)benzenesulfonyl]-1-(tetrahydrothiopyran-4-ylidenemethyl)ethyl}hydroxylamine (III-17)

A 50% aqueous solution of hydroxylamine (2 mL) was added to a solution of 0.18 g (0.40 mmol) of 2-methyl-4-{4-[3-(tetrahydrothiopyran-4-ylidene)-1-propene-1-sulfonyl]phenoxymethyl}quinoline obtained in the same manner as Example 9 (9-1) and (9-2) in tetrahydrofuran (5 mL) at room temperature and stirred for 54 hours. After the reaction was completed, the solvent was removed under a reduced pressure, the residue was extracted with chloroform, and the organic layer was dried over magnesium sulfate. After drying, the solution was filtered and the filtrate was concentrated under a reduced pressure, and the obtained residue was subjected to column chromatography on silica gel (silica gel 4 g, developing solvent; chloroform:methanol=20:1) to obtain 0.12 g (yield 63%) of N-{2-[4-(2-methylquinolin-4-ylmethoxy)benzenesulfonyl]-1-(tetrahydrothiopyran-4-ylidenemethyl)ethyl}hydroxylamine (III-17) as a white crystal. Its physical properties are shown below.

$^1$H-NMR(CDCl$_3$) δ value: 2.35-2.65(8H, m), 2.77(3H, s), 3.08(1H, dd, J=14.5, 5.0), 3.59(1H, dd, J=14.2, 7.3), 4.30(1H, m), 5.17(1H, d, J=8.6), 5.59(2H, s), 7.17(2H, d, J=6.9), 7.43 (1H, s), 7.57(1H, t, J=7.3), 7.75(1H, t, J=7.3), 7.84-7.92(3H, m), 8.11(1H, d, J=8.3).

FAB-MS: Calculated (M$^+$+1): 484; Found: 484.

(11-2): N-hydroxy-N-{2-[4-(2-methylquinolin-4-ylmethoxy)benzenesulfonyl]-1-(tetrahydrothiopyran-4-ylidenemethyl)ethyl}formamide (I-17)

A mixture of formic acid (3.0 mL) and acetic anhydride (0.4 mL) premixed for 30 minutes at 0° C. was added to a solution of 0.28 g (0.58 mmol) of N-{2-[4-(2-methylquinolin-4-ylmethoxy)benzenesulfonyl]-1-(tetrahydrothiopyran-4-ylidenemethyl)ethyl}hydroxylamine (III-17) in tetrahydrofuran (4 mL) at 0° C., and stirred for another 2 hours at room temperature. After the reaction was completed, the solvent was removed under a reduced pressure, and then subjected to azeotropic distillation with toluene. The resulting residue was dissolved in a mixed solution of methanol (1 mL) and chloroform (3 mL) and stirred for 1 hour at room temperature. Then, the solvent was removed under a reduced pressure, and the obtained residue was subjected to medium pressure column chromatography on silica gel (developing solvent; chloroform:methanol=30: 1) to obtain 0.1 g (yield 34%) of the title compound as a white crystal. Its physical properties are shown below.

$^1$H-NMR(CDCl$_3$) δ value: 2.21-2.28(4H, m), 2.50-2.61 (4H, m), 2.67(3H, s), 3.37-3.70(2H, m), 4.92-5.35(2H, m), 5.76(2H, s), 7.40(2H, d, J=8.6), 7.58(1H, s), 7.61(1H, d, J=7.9), 7.76(1H, m), 7.88(2H, d, J=8.3), 7.98(1H, d, J=8.3), 8.06(1H, s), 8.12(1H, d, J=8.3), 9.65(0.4H, s), 10.04(0.6H, s).

FAB-MS: Calculated (M$^+$+1): 513; Found: 513.

EXAMPLE 12

Preparation of N-hydroxy-N-{1-(1-isobutylpiperidin-4-ylidenemethyl-2-[4-(2-methylquinolin-4-ylmethoxy)benzenesulfonyl]ethyl}formamide (I-24)

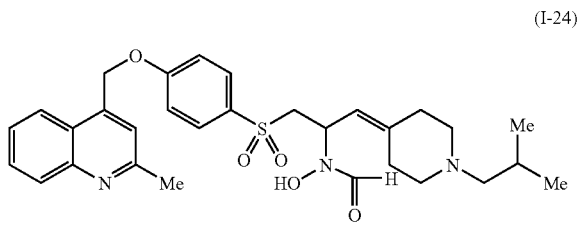

(I-24)

(12-1): tert-Butyl ester of 4-{2-hydroxy-3-[4-(2-methylquinolin-4-ylmethoxy)benzenesulfonyl] propylidene}piperidine-1-carboxylic acid (VIII-24)

Into a solution of 11.0 g (33.6 mmol) of 4-(4-methanesulfonylphenoxymethyl)-2-methylquinoline in tetrahydrofuran (400 mL) was dropped 19.3 mL (38.6 mmol) of 2 mol/L lithium diisopropylamide solution in hexane-heptane-ethylbenzene at −78° C. under an atmosphere of argon, and then, stirred for 40 minutes at the same temperature. To this solution, a solution of 8.0 g (35.6 mmol) of tert-butyl ester of 4-(2-oxoethylidene)piperidine-1-carboxylic acid in tetrahydrofuran (50 mL) was added and stirred for 1 hour. Then a saturated aqueous ammonium chloride solution was added thereto, which was extracted with ethyl acetate. The organic layer was washed with saturated brine, dried over anhydrous magnesium sulfate and concentrated under a reduced pressure. The obtained residue was subjected to column chromatography on silica gel (silica gel 400 g, developing solvent; hexane:ethyl acetate=1:3) to obtain 15.7 g (yield 84%) of tert-butyl ester of 4-{2-hydroxy-3-[4-(2-methylquinolin-4-ylmethoxy)benzenesulfonyl]propylidene}piperidine-1-carboxylic acid (VIII-24) as a pale yellow crystal. Its physical properties are shown below.

$^1$H-NMR(CDCl$_3$) δ value: 1.45(9H, s), 2.12(4H, t, J=5.6), 2.77(3H, s), 3.31-3.48(4H, m), 5.02(1H, m), 5.25(1H, d, J=8.2), 5.60(2H, s), 7.19(2H, d, J=8.6), 7.43(1H,s), 7.57(1H, m), 7.74(1H, m), 7.91(3H, d, J=8.6), 8.10(1H, d, J=8.6).

FAB-MS: Calculated (M$^+$+1): 553; Found: 553.

(12-2): tert-Butyl ester of 4-{3-[4-(2-methylquinolin-4-ylmethoxy)benzenesulfonyl]allylidene]piperidine-1-carboxylic acid (II-24)

A solution of 4.0 mL (51.1 mmol) of methanesulfonyl chloride in methylene chloride (50 mL) was slowly dropped, over 30 minutes at −10° C., into a solution of 15.7 g (28.4 mmol) of tert-butyl ester of 4-{2-hydroxy-3-[4-(2-methylquinolin-4-ylmethoxy)benzenesulfonyl] propylidene}piperidine-1-carboxylic acid (VIII-24) obtained in the above (12-1) and 16.6 mL (120 mmol) of triethylamine in methylene chloride (320 mL), and stirred for 2 hours. Saturated aqueous sodium bicarbonate was then added thereto, followed by extraction with chloroform. The organic layer was washed with saturated brine, then dried over anhydrous magnesium sulfate, and concentrated under a reduced pressure. The obtained residue was subjected to column chromatography on silica gel (silica gel 300 g, developing solvent; hexane:ethyl acetate=1:2) to obtain 11.5 g (yield 76%) of tert-butyl ester of 4-{3-[4-(2-methylquinolin-4-ylmethoxy) benzenesulfonyl]allylidene}piperidine-1-carboxylic acid (II-24a) as a pale yellow crystal. Its physical properties are shown below.

$^1$H-NMR(CDCl$_3$) δ value: 1.48(9H, s), 2.26-2.30(2H, m), 2.47-2.51(2H, m), 2.76(3H, s), 3.47(4H, m), 5.57(2H, s), 5.97(1H, d, J=11.6), 6.29(1H, d, J=14.5), 7.13(2H, d, J=8.9), 7.42(1H, s), 7.48-7.58(2H, m), 7.73(1H, m) 7.86(2H, d, J=8.9), 7.90(1H, d, J=8.6), 8.09 (1H, d, J=8.3).

FAB-MS: Calculated (M$^+$+1): 535; Found: 535.

(12-3): 4-{4-[3-(1-Isobutylpiperidin-4-ylidene)-1-propene-1-sulfonyl]phenoxymethyl}-2-methylquinoline (II-24b)

To a solution of 9.0 g (16.9 mmol) of tert-butyl ester of 4-{3-[4-(2-methylquinolin-4-ylmethoxy)benzenesulfonyl] allylidene}piperidine-1-carboxylic acid (II-24a) obtained in the above (12-2) was added 4N hydrochloric acid-dioxane solution (60 mL) at 0° C., and stirred for 4 hours at room temperature. After the reaction was completed, the solvent was removed under a reduced pressure. Saturated sodium bicarbonate was added to the residue, followed by extraction with chloroform. The organic layer was dried over anhydrous magnesium sulfate and filtered. The filtrate was concentrated under a reduced pressure to obtain crude 2-methyl-4-[4-(3-piperidin-4-ylidene-1-propene-1-sulfonyl)phenoxymethyl] quinoline. This compound was dissolved in methanol (300 mL), treated with 2.4 mL (26.5 mmol) of isobutylaldehyde, 8.1 g (38.2 mmol) of sodium triacetoxyborohydride and 25 mL of acetic acid at 0° C. and stirred for 15 hours. After the reaction was completed, the solvent was removed under a reduced pressure, and then saturated aqueous sodium bicarbonate was added to the residue, followed by extraction with chloroform. The organic layer was dried over anhydrous magnesium sulfate, and then filtered. The filtrate was concentrated under a reduced pressure. The resulting residue was subjected to column chromatography on silica gel (silica gel 200 g, developing solvent; ethyl acetate) to obtain 6.1 g (yield 73%) of 4-{4-[3-(1-isobutylpiperidin-4-ylidene)-1-propene-1-sulfonyl]phenoxymethyl}-2-methylquinoline (II-24b) as a pale yellow crystal. Its physical properties are shown below.

$^1$H-NMR(CDCl$_3$) δ value: 0.90(6H, d, J=6.6), 1.77(1H, m), 2.08(2H, d, J=7.3), 2.43(2H, d, J=5.0), 2.44(4H, t, J=5.6), 2.52(2H, d, J=5.6), 2.76(3H, s), 5.57(2H, s), 5.88(1H, d, J=11.5), 6.25(1H, d, J=14.5), 7.13(2H, d, J=8.9), 7.42(1H, s), 7.49-7.59(2H, m), 7.70-7.77(1H, m), 7.85(2H, d, J=8.9), 7.90 (1H, d, J=7.8), 8.09(1H, d, J=7.9).

FAB-MS: Calculated (M$^+$+1): 491; Found: 491.

(12-4): N-{1-(1-Isobutylpiperidin-4-ylidenemethyl)-2-[4-(2-methylquinolin-4-ylmethoxy)benzenesulfonyl]ethyl}hydroxylamine (III-24)

A 50% aqueous solution of hydroxylamine (60 mL) was added to a solution of 6.1 g (12.4 mmol) of 4-{4-[3-(1-isobutylpiperidin-4-ylidene)-1-propene-1-sulfonyl]phenoxymethyl}-2-methylquinoline (II-24b) obtained in the above (12-3) in tetrahydrofuran (200 mL) at room temperature and stirred for 72 hours. After the reaction was completed, the solvent was removed under a reduced pressure, the residue was extracted with chloroform, and the organic layer was dried over magnesium sulfate and concentrated under a reduced pressure. The obtained residue was subjected to column chromatography on silica gel (silica gel 150 g, developing solvent; chloroform:methanol=10:1) to obtain 6.2 g (yield 95%) of N-{1-(1-isobutylpiperidin-4-ylidenemethyl)-2-[4-(2-methylquinolin-4-ylmethoxy)benzenesulfonyl]ethyl}hydroxylamine (III-24) as a white crystal. Its physical properties are shown below.

$^1$H-NMR(CDCl$_3$) δ value: 0.88(6H, d, J=6.6), 1.74(1H, m), 2.03-2.52(8H, m), 2.76(3H, s), 3.10(1H, dd, J=14.2, 5.3), 3.62(1H, dd, J=14.2, 6.9), 4.22(1H, dd, J=14.2, 6.9), 5.05(1H, d, J=8.6), 5.58(2H, s), 7.16(2H, d, J=8.9), 7.43(1H, s), 7.56(1H, m), 7.73(1H, m), 7.88(2H, d, J=8.9), 7.90(1H, d, J=7.9), 8.10(1H, d, J=8.3).

FAB-MS: Calculated (M$^+$+1) 524; Found: 524.

(12-5): N-Hydroxy-N-{1-(1-isobutylpiperidin-4-ylidenemethyl)-2-[4-(2-methylquinolin-4-ylmethoxy)benzenesulfonyl]ethyl}formamide (I-24)

Formic acid (55 mL) and acetic anhydride (7.1 mL) were mixed at 0° C. and stirred for 30 minutes. This mixture was added to a solution of N-{1-(1-isobutylpiperidin-4-ylidenemethyl)-2-[4-(2-methylquinolin-4-ylmethoxy)benzenesulfonyl]ethyl}hydroxylamine (III-20 24) obtained in the above (12-4) in tetrahydrofuran (65 mL) at 0° C., and stirred for another 2 hours at room temperature. The solvent was then removed under a reduced pressure, subjected to azeotropic distillation with toluene, and then the obtained residue was dissolved in a mixed solvent of methanol (60 mL) and chloroform (90 mL), and stirred for 12 hours at room temperature. The reaction mixture was concentrated under a reduced pressure, and the residue was subjected to medium pressure column chromatography on silica gel (developing solvent; chloroform:methanol=87: 13) to give 5.3 g (yield 90%) of the title compound as a white crystal. Its physical properties are shown below.

$^1$H-NMR(CDCl$_3$) δ value: 0.80(6H, d, J=6.6), 1.70(1H, m), 1.99-2.11(6H, m), 2.27-2.37(4H, m), 2.67(3H, s), 3.43-3.78(2H, m), 4.80-5.35(2H, m), 5.76(2H, m), 7.39(2H, d, J=8.6), 7.56(1H, s), 7.60(1H, d, J=7.3), 7.76(1H, m), 7.87(2H, d, J=8.6), 7.98(1H, d, J=8.6), 8.05(0.5H, s), 8.11(1H, d, J=8.3), 8.16(0.5H, s).

FAB-MS: Calculated (M$^+$+1): 552; Found: 552.

EXAMPLE 13

Preparation of N-{1-[1-(2,2-Dimethylpropionyl)piperidin-4-ylidenemethyl]-2-[4-(2-methylquinolin-4-ylmethoxy)benzenesulfonyl]ethyl}-N-hyroxyformamide (I-25)

(I-25)

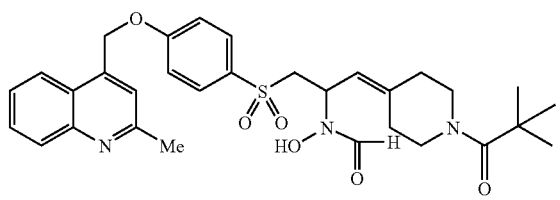

(13-1): 2,2-Dimethyl-1-(4-{3-[4-(2-methylquinolin-4-ylmethoxy)benzenesulfonyl]allylidene}piperidin-1-yl)propan-1-one (X-25)

To a solution of 0.2 g (0.37 mmol) of tert-butyl ester of 4-{3-[4-(2-methylquinolin-4-ylmethoxy)benzenesulfonyl]allylidene}piperidine-1-carboxylic acid (II-24a) obtained in Example 12 (12-2) in methanol (2.0 mL) was added 4N hydrochloric acid-dioxane solution (2.0 mL) at 0° C. and stirred for 2 hours at room temperature. The reaction mixture was then concentrated under a reduced pressure, treated with saturated aqueous sodium bicarbonate, extracted with chloroform, and dried over anhydrous magnesium sulfate. After drying, the solution was filtered, and the filtrate was concentrated under a reduced pressure to give crude 2-methyl-4-[4-(3-piperidin-4-ylidene-1-propene-1-sulfonyl)phenoxymethyl]quinoline. This was dissolved in dichloromethane (10 mL), treated with triethylamine (0.077 mL, 0.56 mmol) and pivaloyl chloride (0.058 g, 0.48 mmol) at 0° C., and stirred for 2 hours. The reaction mixture was then concentrated under a reduced pressure, diluted with ethyl acetate, washed with saturated aqueous sodium bicarbonate and saturated brine, and dried over magnesium sulfate. The filtrate was concentrated under a reduced pressure to obtain 0.18 g (yield 94.7%) of 2,2-dimethyl-1-(4-{3-[4-(2-methylquinolin-4-ylmethoxy)benzenesulfonyl]allylidene}piperidin-1-yl)propan-1-one (X-25). Its physical property is shown below.

$^1$H-NMR(CDCl$_3$) δ value: 1.21(9H, s), 2.28(2H, brs), 2.49(2H, brs), 2.68(3H, s), 3.52-3.61(4H, m), 5.73(2H, s), 6.10(1H, d, J=11.6), 6.77(1H, d, J=14.5), 7.35-7.49(3H, m), 7.57-7.62(2H, m), 7.73-7.86(3H, m), 7.99(1H, d, J=7.6), 8.10(1H, d, J=8.3).

(13-2): 1-(4-{2-Hydroxyamino-3-[4-(2-methylquinolin-4-ylmethoxy)benzenesulfonyl]propylidene}piperidin-1-yl)-2,2-dimethylpropan-1-one (III-25)

According to the same manner as in Example 1 (1-5), 70 mg (yield 38.9%) of 1-(4-{2-hydroxyamino-3-[4-(2-methylquinolin-4-ylmethoxy)benzenesulfonyl]propylidene}piperidin-1-yl)-2,2-dimethylpropan-1-one (III-25) was obtained from 0.17 g (0.33 mmol) of 2,2-dimethyl-1-(4-{3-[4-(2-methylquinolin-4-ylmethoxy)benzenesulfonyl]allylidene}piperidin-1-yl)propan-1-one (X-25) obtained in the above (13-1) and a 50% aqueous solution of hydroxylamine (1.5 mL). Its physical property is shown below.

$^1$H-NMR(CDCl$_3$) δ value: 1.28(9H, s), 2.08-2.34(3H, m), 2.77(3H, s), 3.10(1H, dd, J=14.2, 5.3), 3.55-3.85(6H, m), 4.31(1H, m), 5.24(1H, d, J=9.2), 5.59(2H, s), 7.18(2H, d, J=8.9), 7.44(1H, s), 7.57(1H, t, J=8.3), 7.75(1H, m), 7.88-7.92(3H, m), 8.10(1H, d, J=7.9).

(13-3): N-{ 1-[1-(2,2-Dimethylpropionyl)piperidin-4-ylidenemethyl]-2-[4-(2-methylquinolin-4-ylmethoxy)benzenesulfonyl]ethyl}-N-hyroxyformamide (I-25)

According to the same manner as in Example 1 (1-6), 40 mg (yield 63.6%) of the title compound was obtained from 60 mg (0.011 mmol) of 1-(4-{2-hydroxyamino-3-[4-(2-methylquinolin-4-ylmethoxy)benzenesulfonyl]propylidene}piperidin-1-yl)-2,2-dimethylpropan-1-one (III-25) obtained in the above (13-2), formic acid (1.0 mL) and acetic anhydride (0.15 mL). Its physical properties are shown below.

¹H-NMR(CDCl₃) δ value: 0.77-1.01(2H, m), 1.25-1.73 (5H, m), 1.36(9H, s), 2.51-2.60(2H, m), 2.67(3H, s), 3.39-3.67(2H, m), 3.81-3.90(2H, m), 4.12(0.5H, m), 4.65(0.5H, m), 5.75(2H, s), 7.40(2H, d, J=7.3), 7.57(1H, s), 7.61(1H, d, J=7.6), 7.76(1H, m), 7.86-8.00(3H, m), 8.12(1H, m), 9.53 (0.4H, s), 9.86(0.6H, s).

FAB-MS: Calculated (M⁺+1): 598; Found: 598.

EXAMPLE 14

Preparation of optically active N-hydroxy-N-{2-[4-(2-methylquinolin-4-ylmethoxy)benzenesulfonyl]-1-(tetrahydropyran-4-ylidenemethyl)ethyl}formamide (I-33)

(I-33)

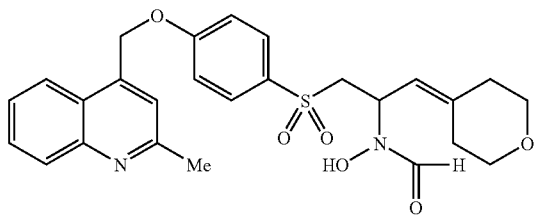

(14-1): N-((R)-4-Benzyl-2-oxooxazolidine-3-carbonyloxy)-N-{2-[4-(2-methylquinolin-4-ylmethoxy)benzenesulfonyl]-1-(tetrahydropyran-4-ylidenemethyl)ethyl}formamide Into a solution of 241 mg (1.36 mmol) of (R)-4-benzyl-2-oxazolidinone in tetrahydrofuran (4.5 mL) was dropped 0.9 mL (1.42 mmol) of 1.58 mol/L butyllithium in hexane at −78° C. and then stirred for 30 minutes. To this solution, a solution of 400 mg (1.35 mmol) of bistrichloromethylcarbonate in tetrahydrofuran (4.5 mL) was added at −78° C., stirred for 1 hour, and then concentrated under a reduced pressure. To the obtained colorless solid, 300 mg (0.60 mmol) of N-hydroxy-N-{2-[4-(2-methylquinolin-4-ylmethoxy)benzenesulfonyl]-1-(tetrahydropyran-4-ylidenemethyl)ethyl}formamide (I-9), 12 mL of methylene chloride and 0.5 mL (3.59 mmol) of triethylamine were added successively, and stirred for 2 hours at room temperature. Then, water was added to the reaction mixture, followed by an extraction with ethyl acetate. The organic layer was washed with saturated brine, dried, and then concentrated under a reduced pressure. The obtained oil was purified by column chromatography (silica gel 20 g, developing solvent; ethyl acetate) and high pressure liquid chromatography [5SL-II Waters (inner diameter 20 mm, length 250 mm), hexane-ethyl acetate-ethanol (14:14:1), flow rate 7.0 mL/minute, UV 254 nm], which yielded 92 mg (yield 21.8%, retention time 23 minutes) of N-((R)-4-benzyl-2-oxooxazolidine-3-carbonyloxy)-N-{2-[4-(2-methylquinolin-4-ylmethoxy)benzenesulfonyl]-1-(tetrahydropyran-4-ylidenemethyl)ethyl}formamide and 52 mg (yield 12.3%, retention time 24.5 minutes) of its diastereomer, N-((R)-4-benzyl-2-oxooxazolidine-3-carbonyloxy)-N-{2-[4-(2-methylquinolin-4-ylmethoxy)benzenesulfonyl]-1-(tetrahydropyran-4-ylidenemethyl)ethyl}formamide. Their physical properties are shown below.

N-((R)-4-Benzyl-2-oxooxazolidine-3-carbonyloxy)-N-{2-[4-(2-methylquinolin-4-ylmethoxy)benzenesulfonyl]-1-(tetrahydropyran-4-ylidenemethyl)ethyl}formamide (retention time 23 minutes)

¹H-NMR(CDCl₃) δ value: 2.07-2.27(2H, m), 2.27-2.49 (2H, m), 2.76(3H, s), 2.90(1H, dd, J=13.2, 9.2), 3.28(1H, dd, J=13.2, 3.3), 3.37(1H, m), 3.55-3.80(4H, m), 3.88(1H, dd, J=14.2, 6.3), 4.21(1H, m), 4.31(1H, m), 4.57(1H, m), 5.24 (1H, bd, J=8.6), 5.57(2H, s), 7.13-7.23(1H, m), 7.17(1H, d, J=8.6), 7.25-7.40(3H, m), 7.42(1H, s), 7.55(1H, t, J=7.3), 7.73(1H, J=7.3), 7.84-7.94(1H, m), 7.87(2H, d, J=8.9), 8.09 (1H, d, J=7.9), 8.20(¹H, bs).

FAB-MS: Calculated (M⁺+1): 700; Found: 700.

N-((R)-4-Benzyl-2-oxooxazolidine-3-carbonyloxy)-N-{2-[4-(2-methylquinolin-4-ylmethoxy)benzenesulfonyl]-1-(tetrahydropyran-4-ylidenemethyl)ethyl}formamide (retention time 24.5 minutes)

¹H-NMR(CDCl₃) δ value: 2.10-2.26(2H, m), 2.26-2.48 (2H, m), 2.76(3H, s), 2.93(1H, dd, J=13.5, 9.2), 3.27-3.43 (2H, m), 3.56-3.79(4H, m), 3.85(1H, dd, J=14.5, 6.3), 4.22 (1H, dd, J=9.2, 3.6), 4.32(1H, m), 4.60(1H, m), 5.25(1H, bd, J=8.6), 5.58(2H, s), 7.11-7.24(2H, m), 7.18(1H, d, J=8.6), 7.24-7.38(3H, m), 7.43(1H, s), 7.56(1H, t, J=7.3), 7.74(1H, t, J=7.3), 7.89(2H, d, J=8.6), 7.90(1H, d, J=8.6), 8.10(1H, d, J=8.6), 8.21(1H, bs).

FAB-MS: Calculated (M⁺+1): 700; Found: 700.

(14-2): Optically active N-hydroxy-N-{2-[4-(2-methylquinolin-4-ylmethoxy)benzenesulfonyl]-1-(tetrahydropyran-4-ylidenemethyl)ethyl}formamide (I-33)

To a solution of 92 mg (0.13 mmol) of N-((R)-4-benzyl-2-oxooxazolidine-3-carbonyloxy)-N-[2-[4-(2-methylquinolin-4-ylmethoxy)benzenesulfonyl]-1-(tetrahydropyran-4-ylidenemethyl)ethyl]formamide (retention time 23 minutes) obtained in the above (14-1) were added 3 mL of methanol, 3 mL of tetrahydrofuran and 1 mL (2.0 mmol) of aqueous 2.0 mol/L lithium hydroxide solution successively and stirred for 3 hours at room temperature. The reaction mixture was concentrated under a reduced pressure and then diluted with water, followed by an adjustment of pH to 8 with a saturated aqueous ammonium chloride solution. After this solution was extracted with ethyl acetate, the organic layer was washed with saturated brine, dried, and then concentrated under a reduced pressure. The obtained oil was purified by preparative thin layer chromatography [silica gel, 200 mm×200 mm×0.5 mm, 3 sheets, ethyl acetate-ethanol (10:1)] to yield 40 mg (62%) of the title compound. Its physical properties are shown below.

¹H-NMR(CDCl₃) δ value: 2.03-2.22(2H, m), 2.26-2.39 (2H, m), 2.76(3H, s), 3.18(1H, m), 3.45-3.92(5H, m), 5.04-5.48(1H, m), 5.30(1H, bs), 5.60(2H, bs), 7.10-7.24(2H, m), 7.43(1H, s), 7.57(1H, t, J=7.6), 7.75(1H, t, J=7.6), 7.80-7.94 (3H, m), 7.96(0.45H, bs), 8.10(1H, d, J=8.3), 8.38(0.55H, bs).

FAB-MS: Calculated (M⁺+1): 497; Found: 497.

EXAMPLE 15

Preparation of Optically Active N-hydroxy-N-{2-[4-(2-methylquinolin-4-ylmethoxy)benzenesulfonyl]-1-(tetrahydropyran-4-ylidenemethyl)ethyl}formamide (I-34)

(I-34)

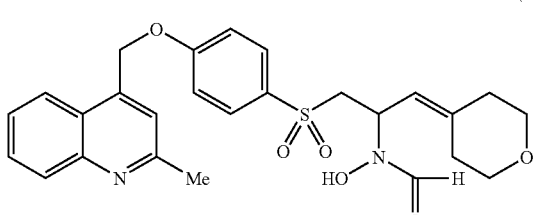

According to the same manner as in Example 14 (14-2), 27 mg (yield 73%) of the title compound was obtained from 52 mg (0.074 mmol) of N-((R)-4-benzyl-2-oxooxazolidine-3-carbonyloxy)-N-{2-[4-(2-methylquinolin-4-ylmethoxy)benzenesulfonyl]-1-(tetrahydropyran-4-ylidenemethyl)ethyl}formamide (retention time 24.5 minutes) obtained in the above (14-1), 3 mL of methanol, 3 mL of tetrahydrofuran and 1 mL (2.0 mmol) of aqueous 2.0 M lithium hydroxide solution. Its physical properties are shown below.

$^1$H-NMR(CDCl$_3$) δ value: 2.03-2.22(2H, m), 2.26-2.40 (2H, m), 2.77(3H, s), 3.18(1H, m), 3.45-3.92(5H, m), 5.04-5.48(1H, m), 5.30(1H, bs), 5.60(2H, bs), 7.10-7.24(2H, m), 7.43(1H, s), 7.57(1H, m), 7.75(1H, t, J=7.3), 7.80-7.94(3H, m), 7.97(0.4H, br s), 8.10(1H, d, J=8.6), 8.38(0.6H, bs).

FAB-MS: Calculated (M$^+$+1): 497; Found: 497.

EXAMPLE 16

Preparation of N-hydroxy-N-{2-[4-(2-methylquinolin-4-ylmethoxy)benzenesulfonyl]-1-p-tolylethyl}formamide (I-57)

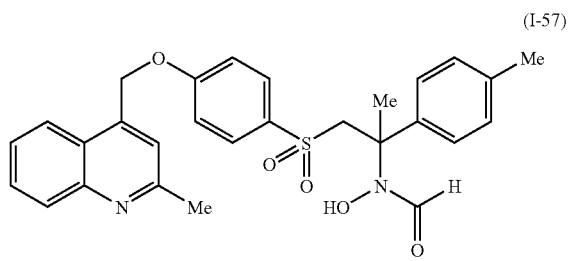

(16-1): 1-[4-(2-Methylquinolin4-ylmethoxy)benzenesulfonyl]-2-p-tolylpropan-2-ol (VIII-57)

Under an atmosphere of argon, a solution of 473 mg (1.44 mmol) of 4-(4-methanesulfonylphenoxymethyl)-2-methylquinoline in tetrahydrofuran was cooled to −78° C. and then, 1.44 mL (1.44 mmol) of 2 M lithium diisopropylamide was added thereto and stirred for 40 minutes. Into this solution was dropped a solution of 194 mg (1.59 mmol) of p-methylacetophenone in tetrahydrofuran, followed by stirring for 2.5 hours. The reaction was stopped by the addition of saturated brine, extracted with ethyl acetate, dried over anhydrous magnesium sulfate, and filtered, and the filtrate was concentrated under a reduced pressure. The obtained residue was purified by column chromatography on silica gel (developing solvent; hexane:ethyl acetate=1:1 to 1:2) to obtain 440 mg (0.95 mmol) of 1-[4-(2-methylquinolin-4-ylmethoxy)benzenesulfonyl]-2-p-tolylpropan-2-ol (VIII-57). Its physical property is shown below.

$^1$H-NMR(CDCl$_3$) δ value: 1.69(3H, s), 2.27(3H, s), 2.77 (3H, s), 3.58(1H, d, J=14.5), 3.70(1H, d, J=14.5), 4.59(1H, s), 5.53(2H, s), 6.95-7.01(4H, m 7.17(2H, d, J=8.3), 7.41(1H, s), 7.53-7.59(3H, m), 7.75(1H, t, J=7.5), 7.88(1H, d, J=7.9), 8.10(1H, d, J=8.6).

(16-2): 2-Methyl-4-[4-(2-p-tolylprop-1-ene-1-sulfonyl)phenoxymethyl]quinoline (II-57)

To stirred, cooled (0° C.) a solution of 434 mg (0.94 mmol) of 1-[4-(2-methylquinolin-4-ylmethoxy)-benzenesulfonyl]-2-p-tolylpropan-2-ol (VIII-57) obtained in the above (16-1) in methylene chloride was added 0.66 mL (4.70 mmol) of triethylamine and then 0.15 mL (1.88 mmol) of methanesulfonyl chloride. Thereafter, another 0.66 mL of triethylamine and 0.15 mL of methanesulfonyl chloride were added to the reaction mixture at room temperature. After the reaction was completed, water was added to the reaction mixture, and the mixture was extracted with chloroform. The extract was dried over anhydrous magnesium sulfate and filtered, and then filtrate was concentrated under a reduced pressure. The residue was purified by column chromatography on silica gel (developing solvent; hexane:ethyl acetate=6:4 to 1:1) to give 393 mg (0.89 mmol) of 2-methyl-4-[4-(2-p-tolylprop-1-ene-1-sulfonyl)phenoxymethyl]quinoline (II-57) as colorless oil. Its physical property is shown below.

FAB-MS: Calculated (M$^+$+1): 444; Found: 444.

(16-3): N-{2-[4-(2-Methylquinolin-4-ylmethoxy)benzenesulfonyl]-1-p-tolylethyl}hydroxylamine (III-57)

A 50% aqueous solution of hydroxylamine (3 mL) was added to a solution of 2-methyl-4-[4-(2-p-tolylprop-1-ene-1-sulfonyl)phenoxymethyl]quinoline (II-57) obtained in the above (16-2) in tetrahydrofuran and stirred for 6 days at room temperature. After the reaction mixture was concentrated under a reduced pressure, saturated brine was added thereto, followed by extraction with ethyl acetate. The extract was dried over anhydrous magnesium sulfate, filtered, and then purified by column chromatography on silica gel (developing solvent; hexane:ethyl acetate=1:1 to 1:2) to give 202 mg (0.42 mmol) of N-{2-[4-(2-methylquinolin-4-ylmethoxy)benzenesulfonyl]-1-p-tolylethyl}hydroxylamine (III-57) as colorless powder. Its physical property is shown below.

FAB-MS: Calculated (M$^+$+1): 477; Found: 477.

(16-4): Synthesis of N-hydroxy-N-{2-[4-(2-methylquinolin-4-ylmethoxy)benzenesulfonyl]-1-p-tolylethyl}formamide (I-57)

A solution of formic acid (12 mL) and acetic anhydride (3 mL) premixed for 30 minutes at 0° C. was dropped into a solution of 187 mg (0.39 mmol) of N-{2-[4-(2-methylquinolin-4-ylmethoxy)benzenesulfonyl]-1-p-tolylethyl}hydroxylamine (III-57) obtained in the above (16-3) in tetrahydrofuran at 0° C., and then stirred for 4 hours at room temperature. The reaction mixture was concentrated under a reduced pressure, the obtained residue was subjected to azeotropic distillation with toluene, then diluted with chloroform (2 mL), and methanol (8 mL) was added thereto, followed by stirring for 12 hours at room temperature. The reaction mixture was concentrated under a reduced pressure, and then purified by medium pressure column chromatography on silica gel (developing solvent; ethyl acetate:hexane=2:1 to ethyl acetate) to give 139 mg (0.28 mmol) of the title compound as colorless powder. Its physical properties are shown below.

$^1$H-NMR(CDCl$_3$) δ value: 2.10(3H, s), 2.30(3H, s), 2.76 (3H, s), 3.76(1H, d, J=14.5), 4.17(1H, d, J=14.5), 5.56(2H, s), 7.12(6H, s), 7.41(1H, s), 7.55(1H, t, J=7.4), 7.73(1H, t, J=7.4), 7.80-7.90(3H, m), 8.09(1H, d, J=8.3), 8.29(1H, s).

FAB-MS: Calculated (M$^+$+1): 505; Found: 505.

EXAMPLE 17

Preparation of N-hydroxy-N-{2-[4-(2-methylquinolin-4-ylmethoxy)benzenesulfonyl]-1-(4-methyltetrahydropyran-4-yl)ethyl}formamide (1-60)

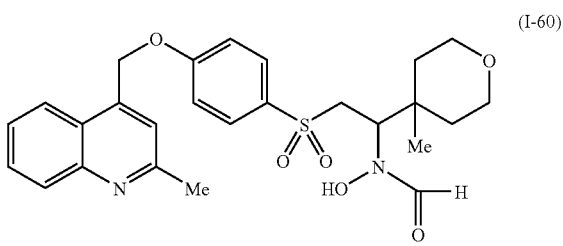

(I-60)

(17-1): 2-[4-(2-Methylquinolin-4-ylmethoxy)benzenesulfonyl]-1-(4-methyltetrahydropyran-4-yl)ethanol (VIII-60)

Under an atmosphere of argon, 1.7 mL (3.45 mmol) of 2 mol/L lithium diisopropylamide in hexane-heptane-ethylbenzene was dropped, at −78° C., into a solution of 1.03 g (3.14 mmol) of 4-(4-methanesulfonylphenoxymethyl)-2-methylquinoline (VI-1) in tetrahydrofuran (40 mL), and then stirred for 50 minutes. Into this solution, 3.1 mL (3.10 mmol) of 1 mol/L lithium(bistrimethylsilyl)amide in tetrahydrofuran was dropped at −78° C., and then 745 mg (4.71 mmol) of methyl 4-methyltetrahydropyran-4-carboxylate was dropped and stirred for 6 hours. To the reaction mixture, 471 mg (7.85 mmol) of acetic acid was added, and after stirring for 5 minutes, the reaction mixture was concentrated under a reduced pressure. After the residue was dissolved in ethanol (5 mL), 415 mg (11.0 mmol) of sodium borohydride was added thereto at 0° C. and stirred for 1 hour. Water (15 mL) was added to the reaction mixture, and after stirring for 5 minutes, the reaction mixture was concentrated under a reduced pressure. The residue was extracted by partition between ethyl acetate and water, the organic layer was washed with saturated brine and dried over anhydrous magnesium sulfate, and the solvent was removed. The obtained residue was purified by medium pressure column chromatography (developing solvent; hexane-ethyl acetate) to give 1.06 g (yield 74.2%) of 2-[4-(2-methylquinolin-4-ylmethoxy)benzenesulfonyl]-1-(4-methyltetrahydropyran-4-yl)ethanol (VIII-60). Its physical properties are shown below.

$^1$H-NMR(CDCl$_3$) δ value: 0.97(3H, s), 1.06(1H, m), 1.42 (2H, m), 1.64(1H, m), 2.77(3H, s), 3.00-3.29(2H, m), 3.37 (1H, d, J=2.3), 3.51(2H, m), 3.65-3.88(3H, m), 5.59(2H, s), 7.20(2H, d, J=8.9), 7.43(1H, s), 7.57(1H, m), 7.74(1H, m), 7.90(3H, m), 8.10(1H, d, J=7.9).

FAB-MS: Calculated (M$^+$+1): 456; Found: 456.

(17-2): 2-Methyl-4-{4-[2-(4-methyltetrahydropyran-4-yl)ethenesulfonyl]phenoxymethyl}quinoline (II-60)

At 0° C., 1.03 g (9.04 mmol) of methanesulfonyl chloride was added to a solution of 1.03 g (2.26 mmol) of 2-[4-(2-methylquinolin-4-ylmethoxy)benzenesulfonyl]-1-(4-methyltetrahydropyran-4-yl)ethanol (VIII-60) obtained in the above (17-1) and 3.56 g (29.15 mmol) of dimethylaminopyridine in methylene chloride (30 mL), and stirred for 10 minutes at 0° C. and then for 1 hour at room temperature. After the reaction mixture was diluted with ethyl acetate, it was passed through a silica gel column. The filtrate was concentrated and the obtained residue was purified by medium pressure column chromatography (developing solvent; hexane-ethyl acetate) to give 850 mg (yield 86.0%) of 2-methyl-4-{4-[2-(4-methyltetrahydropyran-4-yl)ethenesulfonyl]phenoxymethyl}quinoline (II-60). Its physical properties are shown below.

$^1$H-NMR(CDCl$_3$) δ value: 1.15(3H, s), 1.50(2H, m), 1.68 (2H, m), 2.76(3H, s), 3.64(4H, m), 5.58(2H, s), 6.25(1H, d, J=15.5), 6.94(1H, d, J=15.5), 7.15(2H, d, J=8.9), 7.43(1H, s), 7.56(1H, t, J=7.6), 7.74(1H, t, J=7.5), 7.88(3H, m), 8.10(1H, d, J=8.6).

FAB-MS: Calculated (M$^+$+1): 438; Found: 438.

(17-3): N-{2-[4-(2-Methylquinolin-4-ylmethoxy)benzenesulfonyl]-1-(4-methyltetrahydropyran-4-yl)ethyl}hydroxyamine (III-60)

To a solution of 514 mg (1.17 mmol) of 2-methy-4-{4-[2-(4-methyltetrahydropyran-4-yl)ethenesulfonyl]phenoxymethyl}quinoline (II-60) obtained in the above (17-2) in tetrahydrofuran (8.0 mL) was added a 50% aqueous solution of hydroxylamine (1.5 mL) at room temperature, and stirred for 24 hours. The reaction mixture was concentrated under vacuum to obtain 570 mg (yield 100%) of crude N-[2-[4-(2-methylquinolin-4-ylmethoxy)benzenesulfonyl]-1-(4-methyltetrahydropyran-4-yl)ethyl}hydroxyamine (III-60).

(17-4): N-Hydroxy-N-{2-[4-(2-methylquinolin-4-ylmethoxy)benzenesulfonyl]-1-(4-methyltetrahydropyran-4-yl)ethyl}formamide (1-60)

Into a solution of 570 mg (1.17 mmol) of crude N-{2-[4-(2-methylquinolin-4-ylmethoxy)benzenesulfonyl]-1-(4-methyltetrahydropyran-4-yl)ethyl}hydroxyamine (III-60) obtained in the above (17-3) and 700 mg (15.21 mmol) of formic acid in pyridine (3.5 mL) was dropped 478 mg (4.68 mmol) of acetic anhydride over 15 minutes at 0° C., and stirred for 10 minutes at 0° C. and then for 1 hour at room temperature. The reaction mixture was concentrated under vacuum. The residue was dissolved in chloroform (8.0 mL) and methanol (4.0 mL) was added, followed by stirring for 4 hours at room temperature. The reaction mixture was concentrated under a reduced pressure. The residue was extracted by partition between ethyl acetate-saturated aqueous sodium bicarbonate. The organic layer was washed with saturated aqueous sodium bicarbonate and saturated brine successively, and dried over anhydrous magnesium sulfate, followed by an evaporation of the solvent. The obtained residue was purified by medium pressure column chromatography (developing solvent: ethyl acetate-ethanol) to obtain 238 mg (yield 40.8%) of the title compound as white powder. Its physical properties are shown below.

$^1$H-NMR(CDCl$_3$) δ value: 1.08(0.9H, s), 1.13(2.1H, s), 1.14-1.80(4H, m), 2.77(3H, s), 3.12-3.95(6.7H, m), 4.39(1H, m), 5.60(2H, m), 7.09-7.25(2H, m), 7.43(1H, s), 7.56(1H, m), 7.65-7.92(4.7H, m), 8.10(1H, d, J=8.3), 8.52(0.3H, m).

FAB-MS: Calculated (M$^+$+1): 499; Found: 499.

EXAMPLE 18

Preparation of N-{2-[4-(2,6-dimethylquinolin-4-ylmethoxy)benzenesulfonyl]-1-(tetrahydropyran-4-ylidenemethyl)ethyl}-N-hydroxyformamide (I-74)

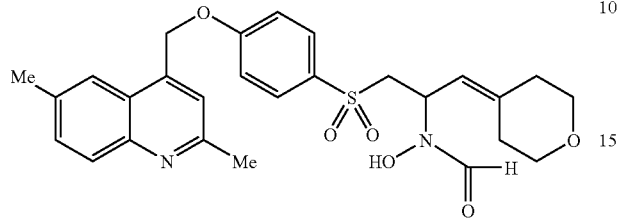

(I-74)

(18-1): (2,6-Dimethylquinolin-4-yl)methanol

To a solution of 10.0 g (63.6 mmol) of 2,6-dimethylquinoline and 29.1 g (127.5 mmol) of ammonium peroxodisulfate in a mixed solvent of methanol (140 mL)-water (110 mL) was added 4.0 mL of concentrated sulfuric acid and heated under reflux for 24 hours. After the reaction mixture was left to cool, methanol was evaporated under a reduced pressure. The remaining solution was adjusted to pH 10 by adding sodium carbonate, and then extracted with chloroform. The organic layer was washed with saturated brine and dried over anhydrous magnesium sulfate, and the solvent was removed. The obtained residue was purified by column chromatography (silica gel 200 g, developing solvent: chloroform:ethyl acetate:triethyamine=1:1:0.01) to obtain 5.50 g (yield 46%) of (2,6-dimethylquinolin-4-yl)methanol. Its physical properties are shown below.

$^1$H-NMR(CDCl$_3$) δ value: 2.52(3H, s), 2.67(3H, s), 5.15 (2H, s), 7.36(1H, s), 7.49(1H, dd, J=8.6, 2.0), 7.69(1H, s), 7.92(1H, d, J=8.6).

FAB-MS: Calculated (M$^+$+1): 188; Found: 188.

(18-2): 4-Chloromethyl-2,6-dimethylquinoline hydrochloride (XII-74)

Into a solution of 5.50 g (29.4 mmol) of (2,6-dimethylquinolin-4-yl)methanol obtained in the above (18-1) in chloroform (35 mL) was dropped 4.2 mL (58.4 mmol) of thionyl chloride at 0° C. and stirred for 18 hours at room temperature. After the reaction mixture was concentrated under a reduced pressure, the residue was washed with ethyl acetate to obtain 6.96 g (yield 98%) of 4-chloromethyl-2,6-dimethylquinoline hydrochloride (XII-74). Its physical propertied are shown below.

$^1$H-NMR(CDCl$_3$) δ value: 2.66(3H, s), 3.19(3H, s), 5.12 (2H, s), 7.76(1H, s), 7.84(1H, dd, J=8.7, 1.8), 7.93(1H, s), 8.92(1H, d, J=8.7).

FAB-MS: Calculated (M$^+$+1): 206; Found: 206.

(18-3): 4-(4-Methanesulfonylphenoxymethyl)-2,6-dimethylquinoline (VI-74)

To a suspension of 6.96 g (28.7 mmol) of 4-chloromethyl-2,6-dimethylquinoline hydrochloride (XII-74) obtained in the above (18-2) and 5.20 g (30.2 mmol) of 4-methanesulfonylphenol in ethanol (25 mL) was added 25 mL (100.0 mL) of 4 mol/L aqueous sodium hydroxide solution, followed by heating under reflux for 3 hours. After standing to cool, water and 4 mol/L aqueous sodium hydroxide solution were added thereto. The precipitates were collected by filtration and dried at 50° C. under a reduced pressure to obtain 3.70 g (yield 38%) of 4-(4-methanesulfonylphenoxymethyl)-2,6-dimethylquinoline (VI-74). Its physical propertied are shown below.

$^1$H-NMR(CDCl$_3$) δ value: 2.56(3H, s), 2.74(3H, s), 3.06 (3H, s), 5.57(2H, s), 7.18(2H, d, J=8.9), 7.39(1H, s), 7.55-7.70(2H, m), 7.90-8.00(3H, m).

FAB-MS: Calculated (M$^+$+1): 342; Found: 342.

(18-4): 1-[4-(2,6-Dimethylquinolin-4-ylmethoxy)benzenesulfonyl]-3-(tetrahydropyran-4-ylidene)propan-2-ol (VIII-74)

Into a solution of 500 mg (1.46 mmol) of 4-(4-methanesulfonylphenoxymethyl)-2,6-dimethylquinoline (VI-74) obtained in the above (18-3) in tetrahydrofuran (25 mL) was dropped, at −78° C. under an atmosphere of argon, a solution of 0.8 mL (1.60 mmol) of 2 mol/L lithium diisopropylamide in hexane-heptane-ethylbenzene (available from Aldrich), and stirred for 30 minutes. Into this solution, a solution of 200 mg (1.59 mmol) of (tetrahydopyran-4-ylidene)acetaldehyde in tetrahydrofuran (5.0 mL) was dropped at −78° C. and stirred for 1 hour. To the reaction mixture, ethanol (20 mL) was added, and the reaction mixture was concentrated under a reduced pressure. Water was added to the residue, followed by extraction with ethyl acetate. The organic layer was washed with saturated brine and dried over anhydrous magnesium sulfate, and the solvent was removed. The obtained residue was purified by column chromatography (silica gel 40 g, developing solvent: ethyl acetate:hexane:triethylamine=10:1:0.1) to obtain 334 mg (yield 49%) of 1-[4-(2,6-dimethylquinolin-4-ylmethoxy)benzenesulfonyl]-3-(tetrahydropyran-4-ylidene)propan-2-ol (VIII-74). Its physical properties are shown below.

$^1$H-NMR(CDCl$_3$) δ value: 2.15-2.30(4H, m), 2.56(3H, s), 2.74(3H, s), 3.13(1H, dd, J=14.2, 2.3), 3.36(1H, dd, J=14.2, 9.2), 3.65(4H, m), 5.03(1H, m), 5.22(1H, d, J=8.6), 5.57(2H, s), 7.20(2H, d, J=9.2), 7.39(1H, s), 7.57(1H, dd, J=8.6, 2.0), 7.64(1H, s), 7.91(2H, d, J=8.9), 7.99(1H, d, J=8.6).

FAB-MS: Calculated (M$^+$+1): 468; Found: 468.

(18-5) N-{2-[4-(2,6-Dimethylquinolin-4-ylmethoxy)benzenesulfonyl]-1-(tetrahydropyran-4-ylmethyl)ethyl}hydroxylamine (III-74)

To a solution of 330 mg (0.71 mmol) of 1-[4-(2,6-dimethylquinolin-4-ylmethoxy)benzenesulfonyl]-3-(tetrahydropyran-4-ylidene)propan-2-ol (VIII-74) and 363 mg (3.59 mmol) of triethylamine in methylene chloride (3.0 mL) was added 148 mg (1.29 mmol) of methanesulfonyl chloride at −10° C. and stirred for 4 hours at room temperature. To the reaction mixture, saturated aqueous sodium bicarbonate was added and extracted with ethyl acetate. The organic layer was washed with water and saturated brine successively, dried over anhydrous magnesium sulfate, and the solvent was removed. The obtained residue was dissolved in tetrahydrofuran (6.0 mL), and then a 50% aqueous solution of hydroxylamine (2.5 mL) was added thereto at room temperature, followed by stirring for 65 hours. The reaction mixture was concentrated under a reduced pressure, and the obtained residue was diluted with ethyl acetate, washed with water and saturated brine successively, and dried over anhydrous magnesium sulfate. Upon removal of the solvent by evaporation, 341 mg (yield 100%) of crude N-{2-[4-(2,6-dimethylquinolin-4-ylmethoxy)benzenesulfonyl]-1-(tetrahydropyran-4-ylmethyl)ethyl}hydroxylamine (III-74) was obtained. Its physical properties are shown below.

$^1$H-NMR(CDCl$_3$) δ value: 2.15-2.30(4H, m), 2.56(3H, s), 2.74(3H, s), 3.11(1H, dd, J=14.2, 5.0), 3.60-3.70(4H, m), 4.28(1H, m), 5.18(1H, d, J=8.9), 5.57(2H, s), 7.18(2H, d, J=8.9), 7.39(1H, s), 7.57(1H, m), 7.64(1H, s), 7.70-7.85(1H, m), 7.90(2H, d, J=8.9), 7.99(1H, d, J=8.2).

FAB-MS: Calculated (M$^+$+1): 483; Found: 483.

(18-6): N-{2-[4-(2,6-Dimethylquinolin-4-ylmethoxy)benezenesulfonyl]-1-(tetrahydropyran-4-ylidenemethyl)ethyl}-N-hydroxyformamide (I-74)

Into a solution of 341 mg (0.71 mmol) of crude N-{2-[4-(2,6-dimethylquinolin-4-ylmethoxy)benzenesulfonyl]-1-(tetrahydropyran-4-ylmethyl)ethyl}hydroxylamine (III-74) obtained in the above (18-5) in tetrahydrofuran (4.0 mL) was dropped, at 0° C., a mixture of formic acid (4.0 mL) and acetic anhydride (1.0 mL) premixed for 30 minutes at 0° C., and then stirred for 2 hours at room temperature. The reaction mixture was concentrated under a reduced pressure. After the residue was subjected to azeotropic distillation with toluene, it was diluted with chloroform (1.5 mL), and methanol (6.0 mL) was added thereto, followed by stirring for 12 hours at room temperature. The reaction mixture was concentrated under a reduced pressure and then purified by medium pressure column chromatography on silica gel to obtain 53.7 mg (yield 15%) of the title compound (I-74). Its physical propertied are shown below.

$^1$H-NMR(CDCl$_3$) δ value: 1.90-2.20(4H, m), 2.50(6H, s), 2.60-2.80(1H, m), 3.40-3.55(4H, m), 3.60-3.80(1H, m), 4.90 (0.4H, m), 5.19(1H, m), 5.31(0.6H, m), 5.72(2H, s), 7.39(2H, d, J=8.9), 7.51(3H, s), 7.59(1H, d, J=10.2), 7.85-7.95(3.6H, m), 8.05(1H, s), 8.32(0.4H, s), 9.65(0.4H, s), 10.05(0.6H, s).

FAB-MS: Calculated (M$^+$+1): 511; Found: 511.

EXAMPLE 19

Preparation of N-{2-[4-(6-fluoro-2-methylquinolin-4-ylmethoxy)benzenesulfonyl]-1-o-tolylethyl}-N-hydroxyformamide (I-79)

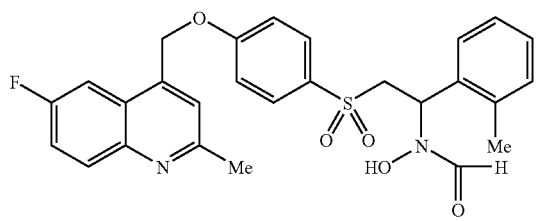

(I-79)

(19-1): (6-Fluoro-2-methylquinolin-4-yl)methanol

To a solution of 10.0 g (62.0 mmol) of 6-fluoro-2-methylquinoline and 28.3 g (124.0 mmol) of ammonium peroxodisulfate in a mixture of methanol (140 mL)-water (110 mL) was added 4.0 mL of concentrated sulfuric acid, and heated under reflux for 18 hours. The reaction mixture was left to cool, and methanol was removed under a reduced pressure. The residue was adjusted to pH 10 by adding sodium carbonate, and then extracted with chloroform. The organic layer was washed with saturated brine and dried over anhydrous magnesium sulfate, and the solvent was removed to obtain 9.61 g (yield 81%) of (6-fluoro-2-methylquinolin-4-yl)methanol. Its physical properties are shown below.

$^1$H-NMR(CDCl$_3$) a value: 2.73(3H, s), 5.12(2H, s), 7.40-7.55(3H, m), 8.04(1H, dd, J=8.6, 5.6).

FAB-MS: Calculated (M$^+$+1): 192; Found: 192.

(19-2): 4-Chloromethyl-6-fluoro-2-methylquinoline hydrochloride (XII-79)

Into a solution of 9.60 g (50.2 mmol) of (6-fluoro-2-methylquinolin-4-yl)methanol obtained in the above (19-1) in chloroform (120 mL) was dropped 7.2 mL (100.1 mmol) of thionyl chloride at 0° C. and stirred for 15 hours at room temperature. After the reaction mixture was concentrated under a reduced pressure, the residue was washed with ethyl acetate to obtain 11.99g (yield 97%) of 4-chloromethyl-6-fluoro-2-methylquinoline hydrochloride (XII-79). Its physical properties are shown below.

$^1$H-NMR(CDCl$_3$) a value: 2.86(3H, s), 5.37(2H, s), 7.85-8.00(2H, m), 8.12-8.17(1H, m), 8.35-8.38(1H, m).

FAB-MS: Calculated (M$^+$+1): 210; Found: 210.

(19-3): 6-Fluoro-4-(4-methanesulfonylphenoxymethyl)-2-methylquinoline (VI-79)

To a suspension of 7.99 g (32.5 mmol) of 4-chloromethyl-6-fluoro-2-methylquinoline hydrochloride (XII-79) obtained in the above (19-2) and 6.71 g (39.0 mmol) of methanesulfonylphenol in ethanol (30 mL) was added 18 mL (72.0 mmol) of 4 mol/L aqueous sodium hydroxide solution and heated under reflux for 1 hour. After standing to cool, water and 4 mol/L aqueous sodium hydroxide solution were added, and the precipitates were collected by filtration, followed by drying at 50° C. under a reduced pressure to obtain 9.22 g (yield 82%) of 6-fluoro-4-(4-methanesulfonylphenoxymethyl)-2-methylquinoline (VI-79). Its physical property is shown below.

$^1$H-NMR(CDCl$_3$) δ value: 2.76(3H, s), 3.06(3H, s), 5.51 (2H, s), 7.17(2 H, d, J=9.2), 7.45-7.55(3H, m), 7.93(2H, d, J=8.9), 8.06-8.12(1H, m).

(19-4): 2-[4-ylmethoxy)benzenesulfonyl]-1-o-tolylethanol (VIII-79)

Into a solution of 650 mg (1.88 mmol) of 6-fluoro-4-(4-methanesulfonylphenoxymethyl)-2-methylquinoline (VI-79) obtained in the above (19-3) in tetrahydrofuran (35 mL) was dropped, at −78° C. under an atmosphere of argon, 1.0 mL (2.00 mmol) of 2 mol/L lithium diisopropylamide in hexane-heptane-ethylbenzene (available from Aldrich), and stirred for 40 minutes. Into the solution, 0.26 mL (2.25 mmol) of 2-methylbenzaldehyde was dropped at −78° C. and stirred for 30 minutes. Ethanol (20 mL) was added to the reaction mixture, followed by concentrating under a reduced pressure. The residue was extracted with ethyl acetate after addition of water. The organic layer was washed with saturated brine and dried over anhydrous magnesium sulfate, and the solvent was removed. The obtained residue was washed with ether to obtain 620 mg (yield 71%) of 2-[4-(6-fluoro-2-methylquinolin-4-ylmethoxy)benzenesulfonyl]-1-o-tolylethanol (VIII-79). Its physical properties are shown below.

$^1$H-NMR(CDCl$_3$) δ value: 2.12(3H, s), 2.75(3H, s), 3.25 (1H, m), 3.43(1H, dd, J=14.2, 9.9), 5.52(2H, s), 7.05-7.30 (5H, m), 7.40-7.60(4H, m), 7.96(2H, d, J=8.9), 8.09(1H, m).

FAB-MS: Calculated (M$^+$+1): 466; Found: 466.

(19-5): 6-Fluoro-2-methyl-4-[4-(2-o-tolylethene-sulfonyl)phenoxymethyl]quinoline (II-79)

To a solution of 610 mg (1.31 mmol) of 2-[4-(6-fluoro-2-methylquinolin-4-ylmethoxy)benzenesulfonyl]-1-o-tolyle-thanol (VIII-79) obtained in the above (19-4) and 653 mg (6.46 mmol) of triethylamine in methylene chloride (10 mL) was added 296 mg (2.58 mmol) of methanesulfonyl chloride at −10° C., and stirred for 3 hours at room temperature. Saturated aqueous sodium bicarbonate was added to the reaction mixture, followed by extraction with ethyl acetate. The organic layer was washed with water and saturated brine successively, and dried over anhydrous magnesium sulfate. The solvent was removed and the obtained residue was purified by column chromatography (silica gel 70 g, developing solvent: ethyl acetate:hexane:triethylamine=2:1:0.02) to obtain 437 mg (yield 74%) of 6-fluoro-2-methyl-4-[4-(2-o-tolylethenesulfonyl)phenoxymethyl]quinoline (II-79). Its physical properties are shown below. $^1$H-NMR(CDCl$_3$) δ value: 2.46(3H, s), 2.75(3H, s), 5.49(2H, s), 6.78(1H, d, J=15.2), 7.10-7.35(5H, m), 7.40-7.55(4H, m), 7.90-8.00(3H, m), 8.08(1m).

FAB-MS: Calculated (M$^+$+1): 448; Found: 448.

(19-6): N-{2-[4-(6-Fluoro-2-methylquinolin-4-yl-methoxy)benzenesulfonyl]-1-o-tolylethyl}hydroxylamine (III-79)

To a solution of 420 mg (0.94 mmol) of 6-fluoro-2-methyl-4-[4-(2-o-tolylethenesulfonyl)phenoxymethyl]quinoline (II-79) obtained in the above (19-5) in tetrahydrofuran (7.0 mL) was added a 50% aqueous solution of hydroxylamine (3.0 mL) at room temperature, and stirred for 65 hours. The reaction mixture was concentrated under a reduced pressure, and then the obtained residue was diluted with ethyl acetate, washed with water and saturated brine successively, and dried over anhydrous magnesium sulfate. Upon removal of the solvent by evaporation, 451 mg (yield 100%) of crude N-{2-[4-(6-fluoro-2-methylquinolin-4-ylmethoxy)benzenesulfo-nyl]-1-o-tolylethyl}hydroxylamine (III-79) was obtained. Its physical properties are shown below.
$^1$H-NMR(CDCl$_3$) δ value: 2.21(3H, s), 2.75(3H, s), 3.25 (1H, dd, J=14.5, 3.0), 3.65(1H, dd, J=14.9, 9.9), 4.70(1H, bs), 4.83(1H, dd, J=9.2, 3.3), 5.50(2H, s), 7.10-7.20(5H, m), 7.32 (1H, m), 7.44(1H, s), 7.50(2H, m), 7.88(2H, d, J=8.9), 8.09 (1H, m).

FAB-MS: Calculated (M$^+$+1): 481; Found: 481.

(19-7): N-{2-[4-(6-Fluoro-2-methylquinolin-4-yl-methoxy)benzenesulfonyl]-1-o-tolylethyl}-N-hy-droxyforamide (I-79).

Into a solution of 451 mg (0.94 mmol) of crude N-{2-[4-(6-fluoro-2-methylquinolin-4-ylmethoxy)benzenesulfonyl]-1-o-tolylethyl}hydroxylamine (III-79) obtained in the above (19-6) in tetrahydrofuran (4.0 mL) was dropped, at 0° C., a mixture of formic acid (8.0 mL) and acetic anhydride (2.0 mL) premixed for 30 minutes at 0° C., and stirred for 3 hours at room temperature. The reaction mixture was concentrated under a reduced pressure. After azeotropic distillation with toluene, the obtained residue was diluted with chloroform (2.0 mL), and methanol (8.0 mL) was added thereto, followed by stirring for 18 hours at room temperature. After concentration of the reaction mixture under a reduced pressure, the residue was purified by medium pressure column chromatography on silica gel (developing solvent: ethyl acetate-hex-ane=80:20 to 93:7) to obtain 396 mg (yield 83%) of the title compound (1-79). Its physical properties are shown below.
$^1$H-NMR(CDCl$_3$) δ value: 2.15(3H, s), 2.67(3H, s), 3.80-3.95(1H, m), 4.05-4.20(1H, m), 5.36(0.4H, m), 5.70(2H, s), 5.92(0.6H, m), 7.05-7.20(2.5H, m), 7.30-7.40(3H, m), 7.60-7.75(2H, m), 7.80-7.95(3H, m), 8.00-8.15(1.54H, m), 8.65-10.10(total 1H, s×2).

FAB-MS: Calculated (M$^+$+1): 509; Found: 509.

EXAMPLE 20

Preparation of N-{2-[4-(8-fluoro-2-methylquinolin-4-ylmethoxy)benzenesulfonyl]-1-o-tolylethyl}-N-hydroxyformamide (I-124)

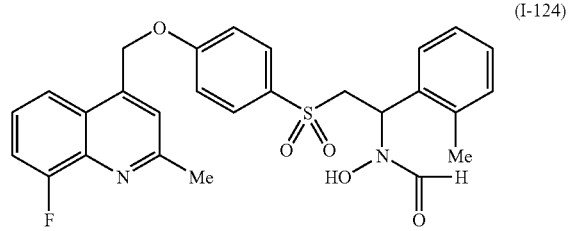

(20-1): 4-(2-Hydroxy-2-o-tolylethanesulfonyl)phe-nol (VI-124)

Into a solution of 1.50 g (5.24 mmol) of tert-butyl-(4-methanesulfonylphenoxy)dimethylsilane in tetrahydrofuran (30 mL) was dropped, at −78° C. under an atmosphere of argon, 3.1 mL (6.20 mmol) of 2 mol/L lithium diisopropylamide in hexane-heptane-ethylbenzene (available from Aldrich), and stirred for 1 hour. Into this solution, 0.72 mL (6.23 mmol) of 2-methylbenzaldehyde was dropped at −78° C., and stirred for 30 minutes. Ethanol (30 mL) was added to the reaction mixture and stirred for 18 hours. The reaction mixture was concentrated under a reduced pressure. After addition of 1 N hydrochloric acid to the residue, it was extracted with ethyl acetate. The organic layer was washed with saturated brine and dried over anhydrous magnesium sulfate, and the solvent was removed. The obtained residue was purified by medium pressure column chromatography on silica gel (developing solvent: hexane:ethyl acetate=2:1 to 1:1) to obtain 930 mg (yield 60.8%) of 4-(2-hydroxy-2-o-tolyle-thanesulfonyl)phenol (XXXI-124) as a colorless crystal. Its physical property is shown below.
$^1$H-NMR(CDCl$_3$) δ value: 2.10(3H, s), 3.23(1H, dd, J=14.5, 1.3), 3.41(1H, dd, J=14.5, 9.6), 5.43(1H, dd, J=9.6, 1.3), 6.42(1H, brs), 6.99(2H, d, J=8.6), 7.10(1H, m), 7.15-7.25(2H, m), 7.50(1H, m), 7.85(2H, d, J=8.6).

(20-2): 2-[4-(8-Fluoro-2-methylquinolin-4-yl-methoxy)benzenesulfonyl]-1-o-tolylethanol (VIII-124)

To a solution of 360 mg (1.23 mmol) of 4-(2-hydroxy-2-o-tolylethanesulfonyl)phenol (XXXI-124) obtained in the above (20-1) and 400 mg (1.23 mmol) of cesium carbonate in dimethylsulfoxide (3 mL) was added 300 mg (1.22 mmol) of 4-chloromethyl-8-fluoro-2-methylquinoline hydrochloride at room temperature, and stirred for 3 days. After dilution of the reaction mixture with ethyl acetate, it was washed with water and saturated brine successively and dried over anhydrous magnesium sulfate. Upon removal of the solvent by evaporation, 567 mg (yield 100%) of crude 2-[4-(8-fluoro-2-methylquinolin-4-ylmethoxy)benzenesulfonyl]-1-o-tolylethanol (VIII-124) was obtained. Its physical properties are shown below.

$^1$H-NMR(CDCl$_3$) δ value: 2.23(3H, s), 3.25(1H, dd, J=14.5, 3.3), 3.66(1H, dd, J=14.5, 9.2), 3.90(3H, s), 4.85(1H, dd, J=9.2, 3.3), 5.28(2H, s), 6.45(1H, s), 6.85-6.95(2H, m), 7.05-7.15(5H, m), 7.30(1H, m), 7.40-7.50(1H, m), 7.85-7.90 (2H, m).

FAB-MS: Calculated (M$^+$+1): 466; Found: 466.

(20-3): 8-Fluoro-2-methyl-4-[4-(2-o-tolylethenesulfonyl)phenoxymethyl]quinoline (II-124)

To a solution of 567 mg (1.22 mmol) of 2-[4-(8-fluoro-2-methylquinolin-4-ylmethoxy)benzenesulfonyl]-1-o-tolylethanol (VIII-124) obtained in the above (20-2) and 617 mg (6.10 mmol) of triethylamine in methylene chloride(10 mL) was added 281 mg (2.45 mmol) of methanesulfonyl chloride at −10° C., and stirred for 15 hours at room temperature. To the reaction mixture, saturated aqueous sodium bicarbonate was added, followed by extraction with ethyl acetate. The organic layer was washed with water and saturated brine successively, and dried over anhydrous magnesium sulfate. The solvent was removed and the obtained residue was purified by column chromatography (silica gel 70 g, developing solvent: hexane:ethyl acetate=3:2) to obtain 440 mg (yield 80.7%) of 8-fluoro-2-methyl-4-[4-(2-o-tolylethenesulfonyl)phenoxymethyl]quinoline (II-124) as brown amorphous. Its physical property is shown below.

FAB-MS: Calculated (M$^+$+1): 448; Found: 448.

(20-4): N-{2-[4-(8-Fluoro-2-methylquinolin-4-ylmethoxy)benzenesulfonyl-1-o-tolylethyl}hydroxylamine (III-124)

To a solution of 546 mg (0.98 mmol) of 8-fluoro-2-methyl-4-[4-(2-o-tolylethenesulfonyl)phenoxymethyl]quinoline (II-124) obtained in the above (20-3) in tetrahydrofuran (9.0 mL) was added a 50% aqueous solution of hydroxylamine (4.0 mL) at room temperature, and stirred for 30 hours. After evaporation of the reaction mixture under a reduced pressure, the obtained residue was diluted with ethyl acetate, washed with water and saturated brine successively, and dried over anhydrous magnesium sulfate. Upon removal of the solvent by evaporation, 472 mg (yield 100%) of crude N-{2-[4-(8-fluoro-2-methylquinolin-4-ylmethoxy)benzenesulfonyl]-1-o-tolylethyl}hydroxylamine (III-124) was obtained. Its physical properties are shown below.

$^1$H-NMR(CDCl$_3$) δ value: 2.21(3H, s), 2.81(3H, s), 3.24 (1H, dd, J=14.5, 3.3), 3.64(1H, dd, J=14.5, 9.6), 4.55(1H, m), 4.83(1H, dd, J=9.2, 3.0), 5.57(2H, s), 7.10-7.20(5H, m), 7.30-7.40(1H, m), 7.40-7.55(3H, m), 7.65-7.75(1H, m), 7.85-7.95 (2H, m).

FAB-MS: Calculated (M$^+$+1): 481; Found: 481.

(20-5): N-{2-[4-(8-Fluoro-2-methylquinolin-4-ylmethoxy)benzenesulfonyl]-1-o-tolylethyl}-N-hydroxyformamide (I-124)

Into a solution of 472 mg (0.98 mmol) of N-{2-[4-(8-fluoro-2-methylquinolin-4-ylmethoxy)benzenesulfonyl]-1-o-tolylethyl}hydroxylamine (III-124) obtained in the above (20-4) in tetrahydrofuran (4.0 mL) was dropped, at 0° C., a mixture of formic acid (8.0 mL) and acetic anhydride (2.0 mL) premixed for 30 minutes at 0° C., and stirred for 1 hour at room temperature. The reaction mixture was concentrated under a reduced pressure. After azeotropic distillation of the obtained residue with toluene, it was diluted with chloroform (2.0 mL), and then methanol (8.0 mL) was added thereto, followed by stirring for 40 hours at room temperature. After concentration of the reaction mixture under a reduced pressure, the residue was purified by medium pressure column chromatography on silica gel (developing solvent: ethyl acetate-hexane=2:1 to 4:1) to obtain 392 mg (yield 78.4%) of the title compound. Its physical properties are shown below.

$^1$H-NMR(CDCl$_3$) δ value: 2.18(1.8H, s), 2.39(1.2H, s), 2.81(3H, s), 3.20-3.45(1H, m), 3.95-4.35(1H, m), 5.55-5.80 (1H, m), 5.60(2H, s), 7.05-7.25(6H, m), 7.35-7.65(3H, m), 7.68(1H, d, J=7.9), 7.84(0.6H, d, J=7.9) 7.92(1H, d, J=8.9), 8.02(0.4H, d, J=8.9), 8.07(0.4H, s), 8.46(0.6H, s).

FAB-MS: Calculated (M$^+$+1): 509; Found: 509.

EXAMPLE 21

Preparation of 1-hydroxy-1-{2-[4-(2-methylquinolin-4-ylmethoxy)benzenesulfonyl]-1-(tetrahydrothiopyran-4-ylidenemethyl)ethyl}urea (I-125)

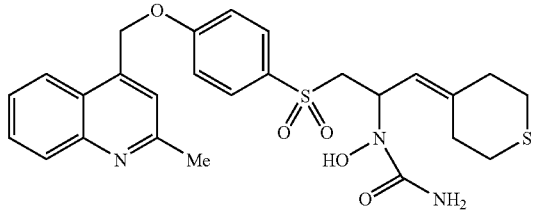

(I-125)

To a solution of 0.2 g (0.41 mmol) of N-{2-[4-(2-methylquinolin-4-ylmethoxy)benzenesulfonyl]-1-(teterhydrothiopyran-4-ylidenemethyl)ethyl}hydroxylamine (III-17) obtained in Example 11 (11-1) in tetrahydrofuran (5 mL) was added 0.073 mL (0.53 mmol) of trimethylsilylisocyanate at 0° C., and stirred for 1 hour at room temperature. After the reaction was completed, the solvent was removed under a reduced pressure, ether was added thereto, and the precipitates were collected by filtration to obtain 35 mg (yield 16.7%) of the title compound as white solid. Its physical properties are shown below.

$^1$H-NMR(CDCl$_3$) δ value: 2.34-2.61(6H, m), 2.76(3H, m), 3.08(1H, dd, J=14.2, 5.0), 3.60(1H, m), 4.48-5.51(2H, m), 5.58(2H, s), 7.17(2H, d, J=8.9), 7.43(1H, s), 7.56(1H, m), 7.74(1H, m), 7.85-7.92(3H, m), 8.09(1H, d, J=8.6).

FAB-MS: Calculated (M$^+$+1): 528; Found: 528.

EXAMPLE 22

Preparation of N-hydroxy-N-{2-[4-(2-methylquinolin-4-ylmethoxy)benzenesulfonyl]-1-(tetrahydrothipyran-4-ylidenemethyl)ethyl}acetamide (I-126)

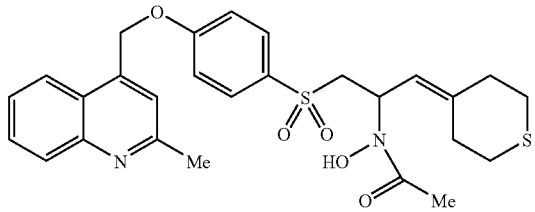

(I-126)

A mixture of acetic acid (2 mL) and acetic anhydride (0.3 mL) premixed for 30 minutes at 0° C. was added to a solution of 0.15 g (0.31 mmol) of N-{2-[4-(2-methylquinolin-4-ylmethoxy)benzenesulfonyl]-1-(tetrahydrothiopyran-4- ylidenemethyl)ethyl}hydroxylamine (III-17) obtained in Example 11 (11-1) in tetrahydrofuran (3 mL) at 0° C., and stirred for 1 hour. After the reaction was completed, the solvent was removed under a reduced pressure. Ethyl acetate was added to the residue and washed with saturated aqueous sodium bicarbonate and saturated brine, and the organic layer was dried over anhydrous magnesium sulfate. The filtrate was concentrated under a reduced pressure, the obtained residue was dissolved in methanol (3 mL), and then aqueous 2 N sodium hydroxide solution (1 mL) was added thereto and stirred for 1 hour at room temperature. After the reaction was completed, the solvent was removed under a reduced pressure, followed by extraction with chloroform and drying with magnesium sulfate. The filtrate was concentrated under a reduced pressure and subjected to column chromatography on silica gel (developing solvent, ethyl acetate: ethanol=50:1) to obtain 50 mg (yield 31.3%) of the title compound. Its physical properties are shown below.

$^1$H-NMR(CDCl$_3$) δ value: 2.14(3H, s), 2.31-2.60(8H, m), 2.75(3H, m), 3.15(1H, m), 3.72(1H, m), 5.21-5.42(2H, m), 5.59(2H, s), 7.18(2H, d, J=8.6), 7.44(1H, s), 7.57(1H, m), 7.74(1H, m), 7.85-7.92(3H, m), 8.07(1H, d, J=8.3).

FAB-MS: Calculated (M$^+$+1): 527; Found: 527.

According to the same manner as in Example 1, the compounds I-10, I-16, I-19, I-22, I-23, I-28, I-29, I-31, I-32, I-35, I-36, I-37, I-38, I-39, I-40, I-49, I-56, I-58, I-59, I-67, I-68, I-72, I-72, I-80, I-81, I-87, I-90, I-93, I-98, I-105, I-121, I-127, I-129, I-135, I-136, I-144, I-145, I-146, I-147, I-148, I-149, I-150, I-165, I-166, I-169 and I-170 were synthesized. The structure and physical properties of each compound are shown in Tables 29 to 36, 38 and 39.

According to the same manner as in Example 6, the compounds I-12, I-13, I-14, I-27, I-75, I-76, I-85, I-86, I-88, I-100, I-102, I-107, I-109, I-111, I-112, I-120 and I-122 were synthesized. The structure and physical properties of each compound are shown in Tables 29, 30, 32 and 35 to 38.

According to the same manner as in Example 9, the compounds I-15, I-18, I-20, I-61, I-77, I-82, I-83, I-91, I-95, I-99, I-103, I-104, I-106, I-110, I-115, I-116, I-117, I-118, I-143, I-152 and I-163 were synthesized. The structure and physical properties of each compound are shown in Tables 29, 30 and 32 to 38.

According to the same manner as in Example 10, the compounds I-48, I-84, I-89, I-92, I-94, I-101, I-108, I-113, I-114, I-119, I-123 and I-137 were synthesized. The structure and physical properties of each compound are shown in Tables 29 and 32 to 38.

According to the same manner as in Example 12, the compounds I-26, 1-30, I-44, I-45, I-46, I-65, I-66, I-71, I-140, I-142, I-153, I-154, I-155, I-156, I-158, I-159, I-160, I-164, I-167 and I-174 were synthesized. The structure and physical properties of each compound are shown in Tables 29 and 30.

According to the same manner as in Example 13, the compounds I-21, I-41, I-43, I-50, I-51, I-52, I-53, I-54, I-55, I-62, I-63, I-64, I-69, I-70, I-73, 1-130, I-131, I-132, I-133, I-138, I-139, I-141, I-157, I-171, I-172, I-173 and I-175 were synthesized. The structure and physical properties of each compound are shown in Tables 29 and 30.

According to the same manner as in Example 16, the compounds I-134 and I-162 were synthesized. The structure and physical properties of each compound are shown in Table 29.

According to the same manner as in Example 17, the compounds I-47, I-128, I-161 and I-168 were synthesized. The structure and physical properties of each compound are shown in Table 29.

According to the same manner as in Example 22, the compound I-151 was synthesized. Its structure and physical properties are shown in Table 40.

TABLE 29

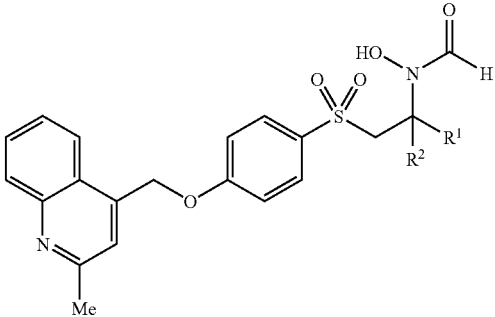

| Compound | R$^1$ | R$^2$ | $^1$H—NMR | FABMS (M + 1) |
|---|---|---|---|---|
| I-10 | H | 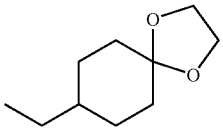 | 1.05-2.00(11H, m), 2.76(3H, s), 2.94-3.23(1H, m), 3.45-3.82(1H, m), 3.91(4H, m), 4.33(0.6H, m), 4.72(0.4H, m), 5.57(2H, m), 7.17(2H, d, J=8.9), 7.43(1H, s), 7.56(1H, t, J=7.5), 7.74(1H, m), 7.80-7.96(3.6H, m), 8.10(1H, d, J=8.6), 8.44(0.4H, s). (solvent: CDCl3) | 555 |
| I-12 | H | NOMe | 1.20(2H, m), 1.62-2.55(7H, m), 2.76(3H, s), 3.25(2H, m), 3.55-4.00(4.6H, m), 4.42(0.4H, m), 5.59(2H, m), 7.08-7.23(2H, m), 7.43(1H, s), 7.56(1H, m), 7.68-8.50(6H, m). (solvent: CDCl3) | 526 |

TABLE 29-continued

| Compound | R¹ | R² | ¹H—NMR | FABMS (M + 1) |
|---|---|---|---|---|
| I-13 | H | 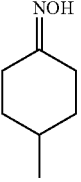 | 1.05-52.67(9H, m), 2.76(3H, s), 3.20(2H, m), 3.50-4.20(2.65H, m), 4.47(0.35H, m), 5.59(2H, s), 7.18(2H, m), 7.42(1H, s), 7.56(1H, m), 7.62-7.92(4H, m), 8.10(1H, d, J=8.3), 8.35-8.65(1H, m). (solvent: CDCl3) | 540 |
| I-14 | H | 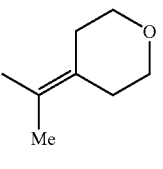 | 1.05-2.47(9H, m), 2.75(3H, s), 3.24(2H, m), 3.55-4.10(2.65H, m), 4.46(0.35H, m), 5.57(2H, s), 7.16(2H, m), 7.42(1H, m), 7.55(1H, m), 7.65-7.95(4.65H, m), 8.10(1H, d, J=8.3), 8.43(0.35H, s). (solvent: CDCl3) | 512 |
| I-15 | H | 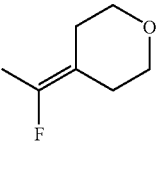 | 1.46(3H, s), 1.80-2.32(4H, m), 2.67(3H, s), 3.30-3.88(6H, m), 5.05(0.4H, m), 5.55(0.6H, m), 5.77(2H, s), 7.38(2H, d, J=8.9), 7.56(1H, s), 7.60(1H, t, J=8.3), 7.76(1H, t, J=7.3), 7.77-8.20(5H, m), 8.92(1H, s), 10.03(0.4H, bs), 10.45(0.6H, bs). (solvent: DMSO-d6) | 511 |
| I-16 | H | 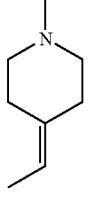 | 2.00-2.45(4H, m), 2.75(3H, s), 3.25-4.15(6H, m), 5.26(0.23H, m), 5.50-5.73(2.77H, m), 7.20(2H, d, J=8.9), 7.43(1H, s), 7.57(1H, t, J=7.3), 7.75(1H, m), 7.89(3H, m), 8.00-8.11(1.23H, m), 8.39(0.77H, s). (solvent: CDCl3) | 515 |
| I-18 | H | 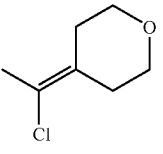 | 1.44(9H, d, J=4.6), 2.03-2.25(4H, m), 2.75(3H, s), 3.13-3.28(2H, m), 3.37-3.92(4H, m), 5.12-5.49(2H, m), 5.58(2H, s), 7.17(2H, s), 7.44(1H, s), 7.57(1H, s), 7.74(1H, s), 7.85-7.92(3H, m), 7.97(0.4H, s), 8.08(1H, d, J=8.6), 8.33(0.6H, s). (solvent: CDCl3) | 596 |
| I-19 | H | 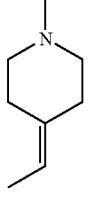 (Cl) | 2.20-2.70(4H, m), 2.76(3H, s), 3.12-4.30(6H, m), 5.61(2.35H, m), 5.86(0.65H, m), 7.20(2H, d, J=8.9), 7.42(1H, s), 7.57(1H, t, J=8.3), 7.74(1H, m), 7.89(3.35H, m), 8.09(1H, d, J=8.3), 8.39(0.65H, s). (solvent: CDCl3) | 533 |

TABLE 29-continued
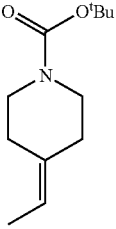
| Compound | R¹ | R² | ¹H—NMR | FABMS (M + 1) |
|---|---|---|---|---|
| I-20 | H | 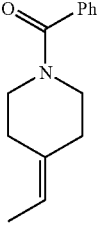 | 1.25(9H, s), 2.08-2.37(4H, m), 2.76(3H, s), 3.17-3.42(2H, m), 3.59-3.91(4H, m), 512-5.48(2H, m), 5.59(2H, s), 7.18(2H, s), 7.44(1H, s), 7.56(1H, m), 7.74(1H, m), 7.85-7.92(3H, m), 7.98(0.3H, s), 8.09(1H, d, J=8.3), 8.34(0.7H, s). (solvent: CDCl3) | 580 |
| I-21 | H | 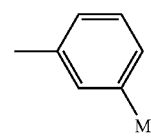 | 2.08-2.39(4H, m), 2.75(3H, s), 3.19-3.50(4H, m), 3.65-3.91(2H, m), 5.15-5.51(2H, m), 5.58(2H, m), 7.16(2H, d, J=7.9), 7.32-7.45(6H, m), 7.56(1H, m), 7.74(1H, m), 7.84-7.91(3H, m), 7.94(0.4H, s), 8.08(1H, d, J=8.6), 8.22(0.6H, s). (solvent: CDCl3) | 600 |
| I-22 | H | 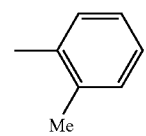 | 2.22(3H, s), 2.68(3H, s), 3.80-4.20(2H, m), 5.33(0.45H, m), 5.68(0.55H, m), 5.73(2H, s), 6.90-7.20(4H, m), 7.33(2H, d, J=8.9), 7.58(1H, s), 7.61(1H, m), 7.70-7.88(3H, m), 7.99(1H, d, J=7.9), 8.05-8.25(2H, m), 9.59(0.45H, bs), 10.01(0.55H, bs). (solvent: DMSO-d6) | 491 |
| I-23 | H | 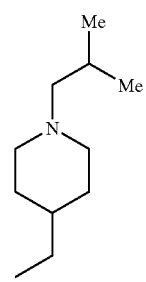 | 2.16(3H, s), 2.68(3H, s), 3.85(1H, dd, J=14.8, 4.3), 4.07(1 H, m), 5.36(0.35H, m), 5.74(2H, 5), 5.91(0.65H, m), 6.90-7.40(6H, m), 7.57(1H, s), 7.61(1H, t, J=7.9), 7.70-7.90(3H, m), 7.99(1H, d, J=8.6), 8.05-8.25(2H, m), 9.69(0.35H, bs), 10.03(0.65H, bs). (solvent: DMSO-d6) | 491 |
| I-26 | H |  | 0.94-1.35(5H, m), 1.59-1.67(2H, m), 2.68(3H, m), 3.09-3.22(2H, m), 3.35-3.44(2H, m), 3.74-3.78(2H, m), 4.12(0.5H, m), 4.67(0.5H, m), 5.75(2H, s), 7.39(2H, d, J=8.9), 7.57(1H, s), 7.61(1H, d, J=7.9), 7.76(1H, m), 7.86-8.00(3H, m), 8.10(0.7H, s), 8.12(1H, s), 8.31 (0.3H, d, J=2.0), 9.54(0.5H, s), 9.86(0.5H, s). (solvent: DMSO-d6) | 499 |

TABLE 29-continued

| Compound | R¹ | R² | ¹H—NMR | FABMS (M + 1) |
|---|---|---|---|---|
| I-27 | H | 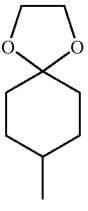 | 0.85-2.42(11H, m), 2.76(3H, s), 3.00-3.32(2H, m), 3.46-3.80(1H, m), 4.34(0.65H, m), 4.74(0.35H, m), 5.59(2H, s), 7.06-7.25(2H, m), 7.42(1H, s), 7.56(1H, 7.9), 7.65-7.92(4.65H, m), 8.10(1H, d, J=8.6), 8.47(0.35H, s). (solvent: CDCl3) | 526 |
| I-28 | H | 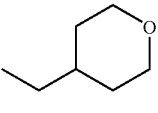 | 1.15-1.88(9H, m), 2.77(3H, m), 3.26(1H, m), 3.55-4.00(5.7H, m), 4.40(0.3H, m), 5.58(2H, m), 7.17(2H, m), 7.43(1H, s), 7.50-7.93(5.7H, m), 8.10(1H, d, J=8.6), 8.47(0.3H, s). (solvent: CDCl3) | 541 |
| I-29 | H | 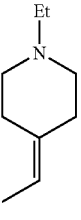 | 0.95-1.35(5H, m), 1.59-1.66(2H, m), 2.67(3H, m), 3.09-3.22(2H, m), 3.39(1H, m), 3.62(1H, m), 3.74-3.78(2H, m), 4.12(0.5H, m), 4.68(0.5H, s), 5.75(3H, s), 7.40(2H, d, J=8.6), 7.56(1H, s), 7.61(1H, d, J=7.9), 7.76(1H, m), 7.87-7.97(3H, m), 8.05(1H, d, J=5.7), 8.13(1H, s), 9.54(0.5H, s), 9.86(0.5H, s). (solvent: DMSO-d6) | 499 |
| I-30 | H | 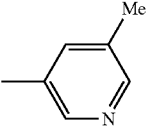 | 0.97-1.02(3H, m), 2.04-2.20(4H, m), 2.36-2.2.51(6H, m), 2.67(3H, s), 3.45-3.75(2H, m), 4.83-5.32(2H, m), 5.76(2H, s), 7.39(2H, d, J=8.9), 7.57(1H, s), 7.62 (1H, d, J=7.6), 7.76(1H, m), 7.87(1H, d, J=8.3), 7.97-8.13(3H, m). (solvent: DMSO-d6) | 524 |
| I-31 | H | 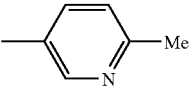 | 2.20(3H, s), 2.68(3H, s), 4.10(2H, m), 5.47(0.5H, m), 5.72(2.5H, m), 7.31(2H, d, J=8.9), 7.40-7.84(6H, m), 7.99(1H, d, J=7.9), 8.03-8.42(2H, m), 9.68(0.5H, bs), 10.03(0.5H, bs). (solvent: DMSO-d6) | 492 |
| I-32 | H | 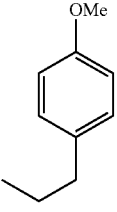 | 2.41 (3H, s), 2.68(3H, s), 4.05(2H, m), 5.46(0.5H, m), 5.72(2.5H, m), 7.1 5(1H, d, J=7.9), 7.32(1H, d, J=8.9), 7.57(1H, s), 7.60(1H, m), 8.45(3H, m), 9.63(0.5H, bs), 10.06(0.5H, bs). (solvent: DMSO-d6) | 492 |
| I-35 | H | OMe | 1.82(1H, m), 2.18(1H, m), 2.47(1H, m), 2.68(1H, m), 2.76(0.9H, s), 277(2.1H, s), 3.09(0.7H, dd, J=14.5, 3.3), 3.21(0.3H, dd, J=14.5, 3.3), 3.68(0.3H, m), 3.71(0.7H, m), 3.75(0.9H, s), 3.77(2.1H, s), 4.13(0.7H, s), 4.60(0.3H, m), 5.57(1.4H, s), 5.59(0.6H, s), 6.80(2H, m), 7.03(2H, m), 7.15(2H, m), 7.42(1H, s), 7.56(1H, bt, J=7.1), 7.71-7.90(4.7H, m), 8.10(1H, d, J=8.6), 8.48(0.3H, s). (solvent: CDCl3) | 535 |

TABLE 29-continued

| Compound | R¹ | R² | ¹H—NMR | FABMS (M + 1) |
|---|---|---|---|---|
| I-36 | H | 4-propyl-2-methylphenyl (Me on ring, propyl para) | 1.88(1H, m), 2.18(1H, m), 2.29(0.75H, s), 2.31(2.25H, s), 2.49(1H, m), 2.71(1H, m), 2.76(3H, s), 3.09(0.75H, dd, J=14.5, 3.0), 3.24(0.25H, dd, J=14.5, 3.0), 3.56(0.25H, dd, J=14.5, 9.0), 3.73(0.75H, dd, J14.5, 9.0), 4.15(0.75H, m), 4.62(0.25H, m), 5.59(0.5H, s), 7.00-7.20(6H, m), 7.41(1H, s), 7.56(1H, bt, J=6.9), 7.71-7.90(4.75H, m), 8.09(1H, d, J=8.6), 8.48(0.25H, s). (solvent: CDCl3) | 519 |
| I-37 | H | 4-butyl-methylphenyl | 1.43-1.68(3H, m), 1.88(1H, m), 2.28(0.9H, s), 2.30(2.1H, s), 2.54(2H, m), 2.76(3H, s), 3.05(0.7H, dd, J=3.0, 14.8), 3.18(0.3H, dd, J=3.6, 14.8), 3.56(0.3H, dd, J=10.4, 14.8), 3.71(0.7H, dd, J=8.9, 14.8), 4.18(0.7H, m), 4.59(0.3H, m), 5.56(1.4H, s), 5.57(0.6H, s), 6.94-7.19(6H, m), 7.42(1H, s), 7.55(1H, t, J=6.9), 7.70-7.90(4.7H, m), 8.10(1H, d, J=8.3), 8.45(0.3H, s). (solvent: CDCl3) | 533 |
| I-38 | H | OHCO-cyclohexenyl-propyl | 1.66-2.27(9H, m), 2.76(3H, s), 3.10(0.7H, m), 3.24(0.3H, m), 3.58 (0.3H, dd, J=14.5, 10.2), 3.72(0.7H, dd, J=8.3, 14.5), 4.20(0.7H, m), 4.55(0.3H, m), 5.15(1H, m), 5.35(0.3H, m), 5.44(0.7H, m), 5.58(2H, s), 7.18(2H, m), 7.43(1 H, s), 7.56(1H, t, J=7.0), 7.74(1H, t, J=7.0), 7.82-7.91(3.7H, m), 8.02-8.11(2H, m), 8.45(0.3H, s). (solvent: CDCl3) | 553 |
| I-39 | H | 3-methyl-propylphenyl | 1.85(1H, m), 2.22(1H, m), 2.26(0.9H, s), 2.29(2.1H, s), 2.49(1H, m), 2.68(1H, m), 2.75(2.1H, s), 2.76(0.9H, s), 3.07(0.7H, dd, J=14.5, 3.2), 3.20(0.3H, dd, J=14.5, 3.6), 3.62(0.3H, dd, J=14.5, 9.7), 3.74(0.7H, dd, J=14.5, 8.6), 4.15(0.7H, m), 4.67(0.3H, s), 5.54(1.4H, s), 5.56(0.6H, s), 6.83-7.02(3H, m), 7.10-7.18(3H, m), 7.41(1H, s), 7.55(1H, m), 7.70-7.91(4.7H, m), 8.09(1H, d, J=8.2), 8.47(0.3H, s). (solvent: CDCl3) | 519 |
| I-40 | H | 2-methyl-propylphenyl | 1.82(1H, m), 2.17(1H, m), 2.23(0.9H, s), 2.26(2.1H, s), 2.52(1H, m), 2.67(1H, m), 2.75(2.1H, s), 2.76(0.9H, s), 3.09(0.7H, dd, J=14.5, 3.3), 3.23(0,3H, dd, J=14.5, 4.0), 3.61(0.3H, dd, J=14.5, 9.9), 3.74(0.7H, dd, J=14.5, 8.2), 4.25(0.7H, m), 4.70(0.3H, m), 5.5(1.4H, s), 5.57(0.6H, s), 7.04-7.19(6H, m), 7.41(1H, s), 7.55(1H, m), 7.70-7.91(4.7H, m), 8.09(1H, d, J=8.6), 8.52(0.3H, s). (solvent: CDCl3) | 519 |
| I-41 | H | 1-acetyl-4-ethylidenepiperidinyl | 2.00-2.14(4H, m), 2.67(3H, s), 3.19(3H, s), 3.38-3.53(4H, m), 3.68 (1H, m), 4.11(1H, m), 4.95-5.26(2H, m), 5.74(2H, s), 7.40(2H, d, J=7.9), 7.57-7.60(2H, m), 7.76(1H, m), 7.87-8.12(5H, m), 9.65(0.3H, s), 10.06(0.7H, m). (solvent DMSO-d6) | 538 |

TABLE 29-continued
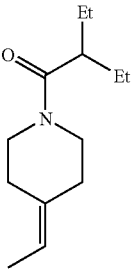
| Compound | R¹ | R² | ¹H—NMR | FABMS (M + 1) |
|---|---|---|---|---|
| I-42 | H | 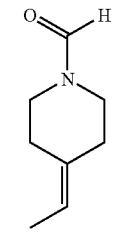 | 0.74(6H, s), 1.33-1.56(4H, m), 1.95-2.12(3H, m), 2.51-2.65(2H, m) 2.68(3H, s), 3.30-3.77(6H, m), 4.92-5.39(2H, m), 5.75(2H, s), 7.40(2H, d, J=8.6), 7.57(1H, s), 7.61(1H, d, J=6.3), 7.76(1H, m), 7.89(2H d, J=8.6), 7.99(1H, d, J=8.2), 8.08(1H, s), 8.12(1H, d, J=8.2), 9.66(0.3H, s), 10.04(0.7H, s). (solvent: DMSO-d6) | 594 |
| I-43 | H | 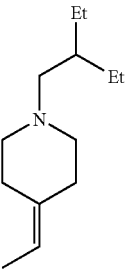 | 1.95-2.11(4H, m), 2.67(3H, s), 3.18-3.72(6H, m), 4.95-5.33(2H, m), 5.75(2H, s), 7.40(2H, d, J=8.2), 7.57(1H, s), 7.62(1H, d, J=6.6), 7.76(1H, m), 7.88(2H, d, J=8.2), 7.97-8.07(3H, m), 8.12(1H, d, J=8.2), 9.71(0.4H, s), 10.04(0.6H, s). (solvent: DMSO-d6) | 524 |
| I-44 | H | 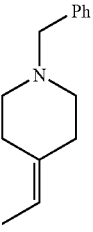 | 0.80-0.95(10H, m), 1.35-1.78(5H, m), 2.30-2.59(4H, m), 2.75(3H, s), 2.76-2.91(2H, m), 3.34(1H, m), 3.70(1H, m), 5.02-5.52(2H, m), 5.61(2H, s), 7.21(2H, d, J=6.6), 7.46(1H, d, J=4.0), 7.56(1H, s), 7.73(1H, m), 7.86-8.14(4H, m), 8.37(1H, s). (solvent: CDCl3) | 580 |
| I-45 | H |  | 212-2.55(6H, m), 2.75(3H, m), 3.19(1H, m), 3.51-3.60(2H, m), 3.85(1H, m), 5.20-5.41(2H, m), 5.57(2H, m), 7.16(2H, d, J=6.3), 7.42(1H, s), 7.55(1H, m), 7.73(1H, m), 7.76-7.90(2H, m), 7.95(0.5H, s), 8.09(1H, d, J=8.3), 8.24(0.5H. s). (solvent: CDCl3) | 586 |

TABLE 29-continued

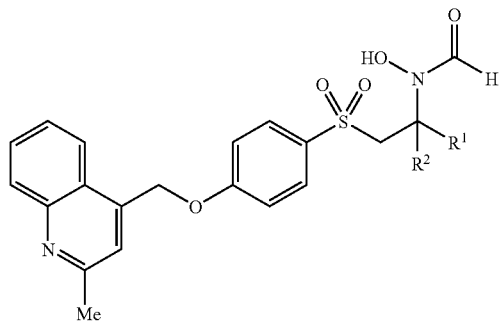

| Compound | R¹ | R² | ¹H—NMR | FABMS (M + 1) |
|---|---|---|---|---|
| I-46 | H | (1-ethylpiperazin-4-yl)methyl with isopropyl | 0.83-0.98(6H, m), 1.81(1H, m), 2.29(1.4H, d, J=6.9), 2.37(0.6H, d, J=6.9), 2.48-3.19(10H, m), 2.76(3H, s), 3.24-3.42(1H, m), 3.60(0.7H, dd, J=14.6, 6.9), 3.69(0.3H, m), 4.24(0.3H, m), 5.10(0.7H, m), 5.58(2H, s), 7.17(2H, d, J=8.9), 7.42(1H, s), 7.56(1H, t, J=7.6), 7.74(1H, m), 7.80-7.95(1.3H, m), 7.88(2H, d, J=8.9), 8.09(1H, d, J=8.3), 8.39(0.7H, bs). (solvent: CDCl3) | 555 |
| I-47 | H | 8-methyl-1,4-dioxaspiro[4.5]decyl | 0.99(0.84H, s), 1.04(2.16H, s), 1.28-1.80(8H, m), 2.76(2.16H, s), 2.77(0.84H, s), 3.13-3.35(0.84H, m), 3.65-4.00(5.8H, m), 4.41(0.36H, bd, J=9.6), 5.58(1.44H, s), 5.60(0.56H, s), 7.18(2H, m), 7.38-7.97(6.76H, m), 8.10(1H, d, J=8.6), 8.46(0.24H, m). (solvent: CDCl3) | 555 |
| I-48 | H | 4-methyl-4-(oxocyclohexyl) | 0.99(1.3H, s), 1.05(1.7H, s), 1.33-2.40(8H, m), 3.34(3H, s), 3.25-3.78(2H, m), 3.90(0.57H, d, J=6.6), 4.46(0.43H, d, J=7.9), 5.76(2H, s), 7.40(2H, m), 7.57(1H, s), 7.61(1H, t, J=6.9), 7.76(1H, t, J=6.9), 7.80-8.05(3.57H, m), 8.11(1H, d, J=8.3), 8.18(0.43H, s), 9.69(0.57H, s), 10.10(0.43H, s). (solvent: CDCl3) | 511 |
| I-49 | H | tetrahydropyran-4-yl | 0.75-1.82(5H, m), 2.67(3H, s), 3.16(2H, m), 3.42-3.88(6.6H, m), 4.23(0.4H, t, J=8.6), 5.76(2H, s), 7.39(2H, m), 7.57(1H, s), 9.92(0.4H, s). (solvent: DMSO-d6) | 485 |
| I-50 | H | 1-benzoyl-4-piperidyl | 1.05-2.02(4H, m), 2.76(3H, s), 2.82-3.29(4H, m), 3.42-3.84(2H, m), 4.21-4.81(1H, m), 5.59(2H, s), 7.18(2H, m), 7.38(5H, m), 7.42(1H, s), 7.56(1H, m), 7.74(1H, dd, J=7.9, 7.3), 7.86(3H, m), 7.91(0.7H, s), 8.10(1H, d, J=8.3), 8.39(0.3H, s). (solvent: CDCl3) | 602 |
| I-51 | H | 1-(2-ethylbutanoyl)-4-piperidyl | 0.82(6H, m), 0.98-2.13(11H, m), 2.36-2.58(2H, m), 2.49(1H, m), 2.76(3H, s), 2.86-3.25(2H, m), 3.50-4.09(2H, m), 4.29-4.89(1H, m), 5.59(2H, s), 7.19(2H, m), 7.43(1H, s), 7.56(1H, dd, J=7.9, 6.9), 7.74(1H, dd, J=7.9, 7.3), 7.87(3H, m), 8.08(0.6H, s), 8.09(1H, d, J=8.6), 8.43(0.4H, s). (solvent: CDCl3) | 596 |

TABLE 29-continued

| Compound | R¹ | R² | ¹H—NMR | FABMS (M + 1) |
|---|---|---|---|---|
| I-52 | H | (1-(4-ethylpiperazinyl)-SO₂Me) | 2.37-2.83(6H, m), 2.60(3H, bs), 2.75(3H, s), 3.06-3.42(5H, m), 3.57(0.3H, dd, J=9.6, 14,5), 3.66(0.7H, dd, J=14.5, 8.6), 4.30(0.7H, m), 4.81(0.3H, m), 5.57(1.4H, s), 5.58(0.6H, s), 7.16(1.4H, d, J=8.9), 7.18(0.6H, d, J=8.9), 7.42(1H, s), 7.56(1H, m), 7.74(1H, m), 7.80-7.95(3.7H, m), 8.09(1H, d, J=8.6), 8.38(0.3H, bs). (solvent: CDCl3) | 577 |
| I-53 | H | (1-(4-ethylpiperazinyl)-C(O)CH₂OMe) | 2.29-2.80(6H, m), 2.76(3H, s), 3.06-3.74(6H, m), 3.39(1.2H, s), 3.40(1.8H, s), 4.06(0.8H, s), 4.08(1.2H, s), 4.29(0.6H, m), 4.80(0.4H, m), 5.59(2H, bs), 7.18(2H, m), 7.43(1H, s), 7.57(1H, t, J=7.6), 7.74(1H, t, J=7.6), 7.80-7.96(3.6H, m), 8.10(1H, d, J=8.6), 8.37(0.4H, bs). (solvent: CDCl3) | 571 |
| I-54 | H | (1-(4-ethylpiperazinyl)-C(O)-PhOMe-p) | 2.24-2.80(6H, m), 2.76(3H, s), 3.22-3.86(6H, m), 3.81(1.2H, s), 3.82(1.8H, s), 4.29(0.6H, m), 4.81(0.4H, m), 5.58(2H, bs), 6.90(2H, m), 7.17(2H, m), 7.35(2H, m), 7.43(1H, s), 7.56(1H, m), 7.74(1 H, t, J=7.6), 7.79-7.96(3.6H, m), 8.10(1H, d, J=8.6), 8.32(0.4H, bs). (solvent: CDCl3) | 633 |
| I-55 | H | (1-(4-ethylpiperazinyl)-C(O)tBu) | 1.44(9H, s), 2.26-2.92(6H, m), 2.76(3H, s), 3.22-3.75(6H, m), 4.27(0.7H, m), 4.94(0.3H, m), 5.57(2H, s), 7.17(2H, m), 7.42(1H, s), 7.43(1H, s), 7.56(1H, m), 7.74(1H, m), 7.80-7.97(3.7H, m), 8.10(1H, d, J=8.3), 8.28(0.3H, bs). (solvent: CDCl3) | 599 |
| I-56 | H | (3-pyridyl-propyl) | 1.91(1H, m), 2.25(1H, m), 2.60(2H, m), 2.76(3H, s), 3.14(0.6H, dd, m), 4.24(0.6H, m), 4.75(0.4H, m), 5.58(0.8H, s), 5.59(1.2H, s), 7.14-7.25(3H, m), 7.42(1H, s), 7.50-7.58(2H, m), 7.71-7.92(4.6H, m), 8.09(1H, d, J=12.9), 8.29-8.45(2.4H, m). (solvent: CDCl3) | 506 |

TABLE 29-continued

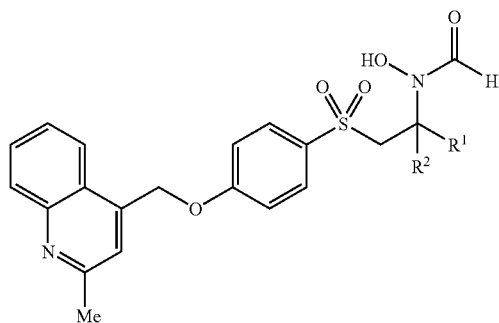

| Compound | R¹ | R² | ¹H—NMR | FABMS (M + 1) |
|---|---|---|---|---|
| I-58 | H | MeN-thiazolidinone-Me | 2.77(3H, s), 2.80(1H, s), 2.96(2H, s), 3.15-4.10(4.6H, m), 4.50-4.65(0.4H, m), 4.95-5.10(0.6H, m), 5.55-5.65(0.4H, m), 5.61(2H, s), 7.15-7.25(2H, m), 7.43(1H, s), 7.57(1H, d, J=7.3), 7.75(1H, d, J=6.9), 7.80-7.95(3.6H, m), 8.10(1H, d, J=8.3), 8.48(0.4H, s). (solvent: CDCl3) | 516 |
| I-59 | H | PhOMe-p, thiazolidinone-Me | 2.70-2.80(3H, m), 3.05-3.40(3H, m), 3.65-4.25(6H, m), 4.45-4.60(0.6H, m), 5.00-5.15(1.4H, m), 5.60(2H, s), 6.70-6.90(2H, m), 7.04(1H, d, J=6.8), 7.10-7.30(4H, m), 7.40-7.50(1H, m), 7.50-7.60(1H, m), 7.70-7.95(3H, m), 8.07(1.4H, d, J=8.3), 8.35-8.45(0.6H, m). (solvent: CDCl3) | 622 |
| I-61 | H | O=C(OᵗBu)-piperidine-Me (ethylidene) | 0.76-0.82(3H, m), 1.37(9H, s), 1.76-2.30(5H, m), 2.68(3H, s), 3.13(1H, m), 3.40-3.72(3H, m), 4.97-5.35(2H, m), 5,74(2H, s), 7.34-7.7.41(2H, m), 7.57(1H, s), 7.76(1H, m), 7.84-8.12(5H, m), 9.55(1H, s). (solvent: DMSO-d6) | 610 |
| I-62 | H | O₂S-Pr piperidine (ethylidene) | 1.02-1.10(6H, m), 1.70-1.91(2H, m), 2.22-2.65(4H, m), 2.76(3H, s), 2.79-2.91(3H, m), 3.21(1H, m), 3.62-3.91(3H, m), 5.13-15.53(2H, m), 5.60(2H, s), 7.19(2H, s), 7.43(1H, s), 7.57(1H, m), 7.75(1H, m), 7.85-7.92(2H, m), 7.95(0.4H, s), 8.09(1H, d, 8.6), 8.38(0.6H, s). (solvent: CDCl3) | 616 |
| I-63 | H | O=C(CHEt₂)-piperidine-Me (ethylidene) | 0.72-0.84(9H, m), 1.23-1.52(4H, m), 1.73-2.35(3H, m), 2.53-2.92(2H, m), 2.67(3H, s), 3.27-3.82(5H, m), 4.93-5.34(2H, m), 5.74(2H, s), 7.37-7.42(2H, m), 7.56(1H, s), 7.62(1H, d, J=8.2), 7.76(1H, m), 7.85-7.91 (2H, m), 7.99(1H, d, J=8.6), 8.06-8.13(2H, m), 9.66(0.4H, s), 10.04(0.6H, s). (solvent: DMSO-d6) | 608 |

TABLE 29-continued
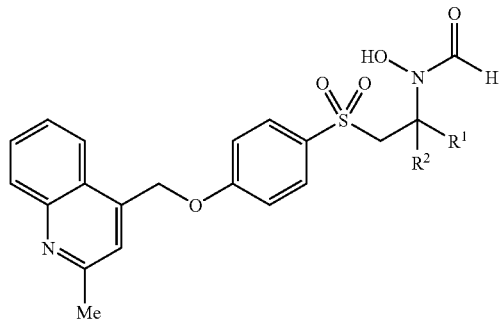
| Compound | R¹ | R² | ¹H—NMR | FABMS (M + 1) |
|---|---|---|---|---|
| I-64 | H | 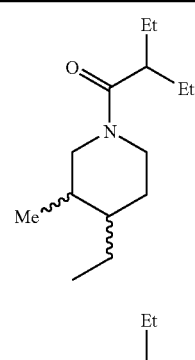 | 0.53-0.92(9H, m), 1.17-1.80(10H, m), 2.58-2.91(2H, m), 2.68(3H, m), 3.39-3.63(3H, m), 3.88-4.61(3H, m), 5.75(2H, s), 7.40(2H, d, J=8.2), 7.58(1H, s), 7.62(1H, d, J=7.9), 7.76(1H, m), 7.87-8.21(5H, m), 9.53-9.58(0.5H, m), 9.88(0.5H, d, J=6.6). (solvent: DMSO-d6) | 610 |
| I-65 | H | 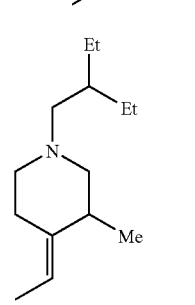 | 0.94-1.13(9H, m), 1.90-2.61(8H, m), 2.76(3H, s), 2.96-3.70(4H, m), 5.15-5.42(2H, m), 5.59(2H, s), 7.18(2H, d, J=6.6), 7.44(1H, s), 7.56(1H, m), 7.73(1H, m), 7.83-7.89(3H, m), 8.09(1H, d, J=8.2), 8.23(0.3H, s), 8.44(0.7H, s). (solvent: CDCl3) | 566 |
| I-66 | H | 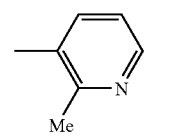 | 0.97-1.03(9H, m), 1.97-2.71(8H, m), 2.76(3H, s), 2.81-3.58(4H, m), 5.11-5.80(2H, m), 5.59(2H, s), 7.18(2H, d, J=8.9), 7.43(1H, s), 7.56(1H, m), 7.74(1H, m), 7.84-7.92(3H, m), 8.09(1H, d, J=8.6), 8.19(0.3H, s), 8.52(0.7H, s). (solvent: CDCl3) | 566 |
| I-67 | H | 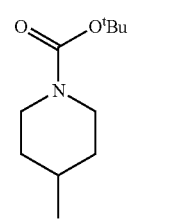 | | 492 |
| I-68 | H |  | 1.13(2H, m), 1.44(9H, s), 1.54-1.98(3H, m), 2.60(1H, m), 2.76(3H, s), 3.11-3.35(4H, m), 3.55-3.94(2H, m), 4.13(1H, m), 5.57(2H, s) 7.17(2H, m), 7.43(1H, s), 7.56(1H, m), 7.74(1H, m), 7.83(1H, m), 7.90(0.7H, s), 8.10(1H, d, J=8.3), 8.48(0.3H, s). (solvent: CDCl3) | 585 |

TABLE 29-continued

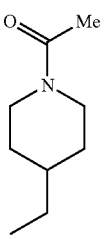

| Compound | R¹ | R² | ¹H—NMR | FABMS (M + 1) |
|---|---|---|---|---|
| I-69 | H | 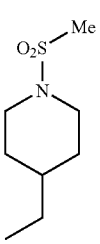 | 0.83-1.97(6H, m), 2.04(1.5H, s), 2.06(1.5H, s), 2.47(1H, m), 2.76(3H, s), 2.80-3.28(4H, m), 3.50-3.88(2H, m), 4.30-4.65(1H, m), 5.59(2H, s) 7.18(2H, m), 7.43(1H, s), 7.56(1H, dd, J=7.3, 6.8), 7.74(1H, dd, J=7.6, 7.3), 7.87(1H, d, J=8.4), 7.92(0.6H, s), 8.09(1 H, d, J=8.6), 8.41(0.4H, s). (solvent: CDCl3) | 540 |
| I-70 | H | 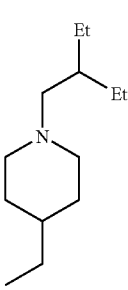 | 1.38(4H, m), 1.69(2H, m), 1.96(1H, m), 2.05(3H, s), 2.60(2H, m), 2.77(3H, s), 2.94-3.29(2H, m), 3.45-3.88(2H, m), 4.31-4.87(1H, m), 5.60(2H, s), 7.19(2H, m), 7.43(1H, s), 7.57(1H, dd, J=7.3, 7.3), 8.48(0.5H, s). (solvent: CDCl3) | 576 |
| I-71 | H | 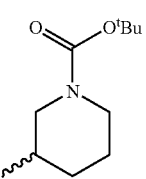 | 0.87(6H, t, J=7.3), 1.31-1.53(4H, m), 1.54-2.11(8H, m), 2.46-2.70(6H, m), 2.76(3H, s), 3.00-3.29(1H, m), 3.68(1H, m), 4.24-4.89(1H, m), 5.58(2H, s), 7.18(2H, d, J=7.9), 7.43(1H, s), 7.55(1H, m), 7.73(1H, dd, J=7.6, 7.3), 7.86(1H, m), 7.91(1H, m), 8.08(1H, d, J=8.6), 8.28(0.5H, s). (solvent: CDCl3) | 582 |
| I-72 | H | 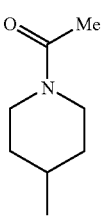 | 1.01-1.29(2H, m), 1.44(9H, s), 1.54-2.04(3H, m), 2.60(3H, m), 2.77(3H, s), 3.10-3.42(4H, m), 3.53-3.95(2H, m), 4.01-4.47(1H, m), 5.59(2H, s), 7.18(2H, m), 7.43(1H, s), 7.56(1H, m), 7.74(1H, m), 7.79-7.93(1.7H, m), 8.10(1H, d, J=8.3), 8.49(0.3H, s). (solvent: CDCl3) | 584 |
| I-73 | H | (see structure) | 1.16(1H, m), 1.71(2H, m), 1.92(1H, m), 2.03(1.5H, s), 2.06(1.5H, s), 2.42(1H, m), 2.76(3H, s), 2.96(2H, m), 3.22(2H, m), 3.63-3.99(2H, m), 4.31-4.74(1H, m), 5.57(2H, s), 7.17(2H, m), 7.43(1H, s), 7.55(1H, m), 7.73(1H, dd, J=7.6, 7.3), 7.78-7.94(1.6H, m), 8.09(1H, d, J=8.6), 8.43(0.4H, s). (solvent: CDCl3) | 526 |

TABLE 29-continued

| Compound | R¹ | R² | ¹H—NMR | FABMS (M + 1) |
|---|---|---|---|---|
| I-127 | H | (propylidene-tetrahydropyran) | 1.43(1H, m), 1.66(1H, m), 1.87(2H, m), 2.10(4H, m), 3.33(3H, m), 3.27-3.68(6H, m), 4.02(0.6H, m), 4.52(0.4H, m), 5.04(1H, m), 5.75(2H, s), 7.39(2H, d, J=8.9), 7.57(1H, s), 7.60(1H, t, J=7.6), 7.71-7.89(3.6H, m), 7.99(1H, d, J=8.6), 8.12(1.4H, m), 9.54(0.6H, s), 9.85(0.4H, s). (solvent: DMSO-d6) | 525 |
| I-128 | H | (4-methyl-4-(methoxymethoxy)cyclohexyl) OCH₂OMe / Me | 0.84(1.5H, s), 0.86(1.5H, s), 0.90-1.60(8H, m), 2.68(3H, s), 3.13(1.5H, s), 3.18(1.5H, s), 3.30-3.78(3.5H, m), 4.40-4.60(2.5H, m), 5.73(2H, s), 7.40(2H, m), 7.60(2H, m), 7.76(1H, t, J=6.9), 7.80-8.20(5H, m), 9.62(0.5H, s), 9.95(0.5H, s). (solvent: DMSO-d6) | 557 |
| I-129 | H | (6-methylpyridin-2-yl)ethyl | 2.11-2.29(2H, m), 2.50(2.4H, s), 2.54(0.6H, s), 2.61-2.77(1H, m), 2.77(3H, s), 2.93(2H, m), 3.20-3.27(1H, m), 3.75(0.8H, m), J=14.5, 7.3), 3.80(0.2H, dd, J=14.5, 7.3), 4.28(0.2H, m), 4.92(0.8H, m), 5.60(2H, s), 6.97(1H, d, J=7.6), 7.05(1H, d, J=7.6), 7.18(2H, d, J=8.9), 7.44(1H, s), 7.56(2H, t, J=7.7), 7.74(1H, t, J=6.9), 7.85-7.96(3H, m), 8.10-8.12(1.8H, m), 8.18(0.2H, s). (solvent: CDCl3) | 520 |
| I-130 | H | (3-methylpiperidin-1-yl)(2-ethylbutanoyl) | 0.83(6H, t, J=7.3), 0.96-2.11(8H, m), 2.47(1H, m), 2.76(3H, s), 2.84-3.39(1H, m), 3.51-4.17(1H, m), 4.32-4.87(1H, m), 5.59(2H, s), 7.18(2H, m), 7.43(1H, s), 7.56(1H, dd, J=8.3, 6.9), 7.74(1H, dd, J=8.6, 6.9), 7.79-7.95(2.7H, m), 8.10(1H, d, J=8.6), 8.48(0.3H, s). (solvent: CDCl3) | 582 |
| I-131 | H | (3-methylpiperidin-1-yl)(phenyl)methanone | 0.96-1.41(2H, m), 1.52-1.89(4H, m), 1.90-2.12(1H, m), 2.76(3H, s), 2.88(2H, m), 3.10-3.38(1H, m), 3.49-4.03(1H, m), 4.32-4.90(1H, m), 5.58(2H, s), 7.18(2H, m), 7.38(5H, s), 7.42(1H, s), 7.56(1H, m), 7.74(1H, dd, J=7.9, 6.9), 7.78-7.96(2.6H, m), 8.10(1H, d, J=8.6), 8.38(0.4H, s). (solvent: CDCl3) | 588 |
| I-132 | H | (4-methylpiperidin-1-yl)(2-ethylbutanoyl) | 0.81(6H, m), 0.95-1.20(2H, m), 1.32-2.10(8H, m), 2.31-2.58(2H, m), 2.76(3H, s), 2.81-3.36(2H, m), 3.55-4.18(2H,m), 4.33-4.88(1H, m), 5.57(2H, s), 7.17(2H, m), 7.43(1H, s), 7.55(1H, m), 7.73(1H, m), 7.75-7.99(2.8H, m), 8.10(1H, d, J=7.9), 8.42(0.2H, s). (solvent: CDCl3) | 582 |

TABLE 29-continued

[Structure: quinoline-2-methyl with CH2-O linked to phenyl-SO2-CH2-C(R1)(R2)-N(OH)-CHO]

| Compound | R¹ | R² | ¹H—NMR | FABMS (M + 1) |
|---|---|---|---|---|
| I-133 | H | 1-acetyl-3-methylpiperidin-yl | 0.99-1.41(2H, m), 1.49-2.21(4H, m), 2.07(3H, s), 2.44(1H, m), 2.76(3H, s), 2.88-3.38(2H, m), 3.51-4.00(2H,m), 4.26-4.79(1H, m), 5.59(2H, s), 7.18(2H, m), 7.43(1H, s), 7.56(1H, m), 7.74(1H, m), 7.77-8.01(2.5H, m), 8.09(1H, d, J=7.3), 8.46(0.5H, s). (solvent: CDCl3) | 526 |
| I-134 | H | 2,4-dimethylpyridin-yl | 0.84(0.9H, s), 2.10(2.1H, s), 2.32(0.9H, s), 2.35(2.1H, s), 2.77(3H, s), 3.85(0.3H, d, J=14), 4.00(0.3H, d, J=14), 4.09(0.7H, d, J=14), 4.22(0.7H, d, J=14), 5.56(0.6H, s), 5.58(1.4H, s), 7.01-7.20(3H, m), 7.41(1H, s), 7.56(1H, m), 7.63-7.80(2H, m), 7.81-8.00(3H, m), 8.08-8.11(1.3H, m), 8.13-8.31(1H, m), 8.48(0.7H, s). (solvent: CDCl3) | 506 |
| I-135 | H | 2,6-dimethylpyridin-yl | 2.46(3H, s), 2.75(3H, s), 3.58(0.7H, dd, J=14.8, 3.3), 3.90(0.3H, dd, J=14.8, 3.0), 4.10-4.25(1H, m), 5.46(0.3H, m), 5.59(2H, s), 5.97(0.7H, dd, J=9.9, 3.3), 7.05-7.20(4H, m), 7.43(1H, s), 7.50-7.65(2H, m), 7.70-7.80(1H, m), 7.85-7.95(3H, m), 8.05-8.15(1.3H, m), 8.27(0.7H, s). (solvent: CDCl3) | 492 |
| I-136 | H | (4S)-3-methyl-4-methyl-thiazolidin-2-one | 2.76(4H, s), 2.95(2H, s), 3.10-3.65(2.4H, m), 3.70-4.10(1.6H, m), 4.50-4.65(0.6H, m), 4.95-5.15(0.4H, m), 5.61(2H, s), 7.15-7.25(2H, m), 7.43(1H, s), 7.57(1H, m), 7.74(1H, m), 7.80-7.95(3.4H, m), 8.10(1H, d, J=8.6), 8.34(0.4H, s), 8.47(0.2H, s). (solvent: CDCl3) | 516 |
| I-137 | H | 4-hydroxy-4-methylcyclohexyl | 0.82(1.5H, s), 0.85(1.5H, s), 0.85-1.62(8H, m), 2.68(3H, s), 3.28-3.82(3.5H, m), 4.28(1H, bs), 4.47(0.5H, t, J=9.6), 5.75(2H, s), 7.39(2H, m), 7.60(2H, m), 7.76(1H, t, J=7.6), 7.83-8.35(5H, m), 9.62(0.5H, s), 9.92(0.5H, s). (solvent: DMSO-d6) | 513 |
| I-138 | H | 1-(methylsulfonyl)azepan-4-ylidene | 1.74-1.78(2H, m), 2.13-2.21(3H, m), 2.67(3H, s), 2.83(3H, s), 3.20-3.27(4H, m), 3.57-3.62(3H, m), 4.80-5.25(2H, m), 5.25(2H, s), 7.39(2H, d, J=8.9), 7.61(1H, d, J=7.6), 7.76(1H, m), 7.87(2H, d, J=8.9), 7.98(1H, d, J=8.6), 8.06(1H, s), 8.08(1H, d, J=8.6), 9.67(0.4H, s), 10.0(0.6H, s). (solvent: DMSO-d6) | 588 |

TABLE 29-continued

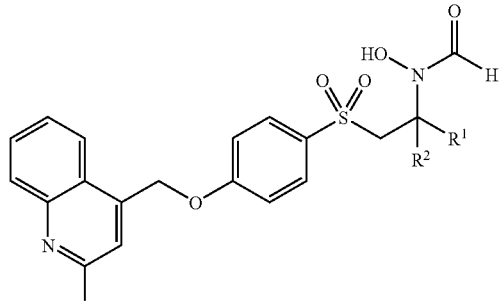

| Compound | R¹ | R² | ¹H—NMR | FABMS (M + 1) |
|---|---|---|---|---|
| I-139 | H | 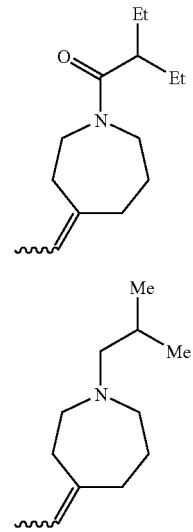 | 0.67-0.77(6H, m), 1.31-1.41(5H, m), 2.14-2.51(8H, m), 2.67(3H, s), 3.20-3.81(4H, m), 4.75-5.40(2H, m), 5.76(2H, s), 7.38-7.41(2H, m), 7.58(1H, s), 7.73-8.14(6H, m), 9.62(0.4H, s), 10.0(0.6H, s). (solvent: DMSO-d6) | 608 |
| I-140 | H | 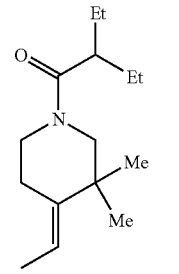 | 0.76-0.81(6H, m), 1.47-1.65(3H, m), 2.07-2.22(4H, m), 2.68(3H, s), 3.35-4.10(8H, m), 4.79-5.23(2H, m), 5.75(2H, 5), 7.39-7.42(2H, m), 7.58(1H, s), 7.62(1H, d, J=7.9), 7.76(1H, m), 7.89(1H, d, J=8.6), 7.99(1H, d, J=8.2), 8.12(1H, d, J=8.2), 8.24(1H, m). (solvent: DMSO-d6) | 566 |
| I-141 | H | 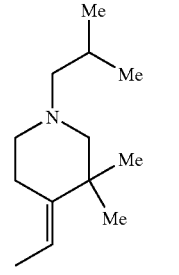 | 0.76-0.94(12H, m), 1.23-1.52(4H, m), 2.03-2.20(2H, m), 2.68(3H, s), 3.17-3.18(2H, m), 3.41-3.78(3H, m), 4.91-5.38(2H, m), 5.74(2H, s), 7.41 (2H, d, J=8.6), 7.58(2H, s), 7.77(1H, m), 7.89(2H, d, J=8.3), 7.94(1H, d, J=8.3), 8.06-8.16(2H, m), 9.67(1H, brs). (solvent: DMSO-d6) | 622 |
| I-142 | H | 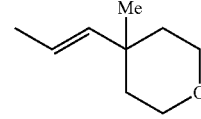 | 0.80-0.94(12H, m), 1.68(1H, m), 2.01-2.19(6H, m), 2.68(3H, s), 3.32-3.43(2H, m), 3.62-3.71(2H, m), 4.81-5.33(2H, m), 5.75(2H, s), 7.40(2H, d, J=8.3), 7.57(1H, m), 7.76(1H, m), 7.88(2H, d, J=8.6), 7.98-8.13(3H, m), 8.19(1 H, s). (solvent: DMSO-d6) | 580 |
| I-143 | H | Me (with propenyl-tetrahydropyran group) | 1.03(3H, d, J=9.6), 1.35-1.65(4H, m), 2.77(3H, s), 3.27(1H, m), 3.50-3.65(4H, m), 3.81(1H, m), 4.80-5.10(1H, m), 5.32-5.54(1H, m), 5.59(2H, s), 5.64-5.78(1H, m), 7.19(2H, m), 7.43(1H, s) 7.57(1H, m), 7.74(1H, m), 7.80-7.92(3H, m), 7.99(0.4H, s), 8.10(1H, d, J=7.9), 8.45(0.6H, s). (solvent: CDCl3) | 525 |

TABLE 29-continued

| Compound | R¹ | R² | ¹H—NMR | FABMS (M + 1) |
|---|---|---|---|---|
| I-144 | H | 4-methyl-4-propyl-tetrahydropyran | 0.93(1H, s), 0.95(2H, s), 1.10-1.90(8H, m), 2.77(3H, s), 3.10-3.35(1H, m), 3.50-3.80(5H, m), 4.10-4.60(1H, m), 5.59(2H, s), 7.19(2H, m), 7.43(1H, s), 7.57(1H, m), 7.74(1H, m), 7.80-7.95(3.6H, m), 8.10(1H, d, J=8.3), 8.49(0.4H, s). (solvent: CDCl3) | 527 |
| I-145 | H | 2,3-dimethyl-4-methoxy-propylbenzene | 1.76(1H, m), 2.14(7H, m), 2.47(1H, m), 2.64(1H, m), 2.76(3H, s), 3.10(0.7H, m), 3.21(0.3H, m), 3.70(1H, m), 3.76(0.9H, s), 3.77(2.1H, s), 4.21(0.7H, m), 4.67(0.3H, s), 5.55(1.4H, s), 5.56(0.6H, s), 6.63(1H, m), 6.86(1H, m), 7.12-7.20(2H, m), 7.41(1H, s), 7.55(1H, m), 7.69-7.95(4.7H, m), 8.08-8.11(1H, m), 8.52(0.3H, s). (solvent: CDCl3) | 563 |
| I-146 | H | 3-propyl-cyclohexenol | 1.50-1.83(3H, m), 1.83-2.25(7H, m), 2.76(3H, s), 3.04-3.29(1H, m), 3.48-3.74(1H, m), 3.94-4.12(1H, m), 4.20(0.7H, m), 4.52(0.3H, m), 5.31(0.3H, m), 5.38(0.7H, m), 5.58(2H, s), 7.14-7.18(2H, m), 7.42(1H, s), 7.56(1H, t, J=7.6), 7.70-7.92(5H, m), 8.10(1H, m). (solvent: CDCl3) | 525 |
| I-152 | H | N-Boc-3,3-dimethyl-4-ethyl-tetrahydropyridine | 0.77(3H, s), 0.81(3H, s), 1.38(9H, s), 2.17-2.31(2H, m), 2.68(3H, s), 2.90(1H, m), 3.17(2H, d, J=5.0), 3.46-3.85(3H, m), 4.01(0.5H, brs), 4.65(0.5H, brs), 5.17(1H, brs), 5.75(2H, s), 7.40(2H, d, J=6.6), 7.57(1H, m), 7.76(1H, m), 7.84-7.88(2H, m), 8.00(1H, d, J=8.2), 8.12(1H, d, J=7.9), 8.15(1H, s), 9.61(0.5H, s), 9.92(0.5H, s). (solvent: DMSO-d6) | 624 |
| I-153 | H | (3-methylpiperidin-1-yl)ethyl | 0.92-1.20(5H, m), 1.40-1.90(3H, m), 1.91-2.28(2H, m), 2.30-2.63(2H, m), 2.72(3H, s), 2.76-3.06(2H, m), 3.21(1H, m), 3.77(1H, m), 4.31-5.14(1H, m), 5.56(2H, s), 7.16(2H, m), 7.42(1H, s), 7.54(1H, dd, J=8.3, 6.9), 7.69(1H, dd, J=6.9, 6.6), 7.88(2H, m), 7.99(0.6H, s), 8.08(1H, d, J=8.6), 8.27(0.4H, s). (solvent: CDCl3) | 512 |
| I-154 | H | (3-methylpiperidin-1-yl)-2-methylpropyl | 0.74-0.99(8H, m), 1.31-1.77(2H, m), 1.78-2.24(4H, m), 2.27-2.61(2H, m), 2.75(3H, s), 2.78-3.00(2H, m), 3.12-3.43(1H, m), 3.61-3.90(1H, m), 4.13-5.16(1H, m), 5.57(2H, s), 7.16(2H, m), 7.42(1H, s), 7.54(1H, dd, J=7.7, 7.3), 7.75(1H, dd, J=8.6, 7.6), 7.88(2H, m), 8.02(0.5H, s), 8.09(1H, d, J=8.3), 8.33(0.5H, s). (solvent: CDCl3) | 540 |

TABLE 29-continued

| Compound | R¹ | R² | ¹H—NMR | FABMS (M + 1) |
|---|---|---|---|---|
| I-155 | H | 1-(4-methylpiperidin-1-yl)-2-methylpropyl group (N-CH2-CH(Me)-... piperidine with 4-Me) | 1.18-1.32(8H, m), 1.33-1.55(2H, m), 1.56-1.84(2H, m), 1.85-2.21(2H, m), 2.27-2.60(2H, m), 2.76(3H, s), 3.09(2H, m), 3.18-3.41(1H, m), 3.58-4.86(1H, m), 5.58(2H, s), 7.17(2H, m), 7.42(1H, s), 7.56(1H, dd, J=8.2, 6.9), 7.73(1H, dd, J=8.3, 7.3), 7.86(2H, m), 8.10(1H, d, J=8.3), 8.24(0.5H, s), 8.47(0.5H, s). (solvent: CDCl3) | 512 |
| I-156 | H | 1-(4-methylpiperidin-1-yl)propan-2-yl | 0.78-0.95(6H, m), 1.13-1.38(2H, m), 1.39-2.18(4H, m), 2.76(3H, s), 2.90(2H, m), 3.18-3.38(1H, m), 3.53-3.91(1.7H, m), 4.47(0.3H, m), 5.59(2H, s), 7.17(2H, m), 7.43(1H, s), 7.56(1H, dd, J=8.3, 6.9), 7.73(1H, m) 7.79-7.94(2.6H, m), 8.10(1H, d, J=8.6), 8.40(0.4H, s). (solvent: CDCl3) | 512 |
| I-157 | H | N-Boc-3-ethylpiperidin-1-yl | 1.08-1.33(3H, m), 1.45(9H, s), 1.53-2.12(8H, m), 2.76(3H, s), 2.82-3.28(1H, m), 3.36-3.86(2.8H, m), 4.23-4.98(0.2H, m), 5.58(2H, s), 7.17(2H, m), 7.43(1H, s), 7.56(1H, m), 7.74(1H, m), 7.79-7.98(2.8H, m), 8.10(1H, d, J=8.3), 8.21(0.2H, s). (solvent: CDCl3) | 598 |
| I-158 | H | 1-(3-ethylpiperidin-1-yl)propan-2-yl | 0.83-1.42(8H, m), 1.43-2.18(4H, m), 2.36-2.65(3H, m), 2.74(3H, s), 2.90-3.28(2H, m), 3.40-3.81(1.5H, m), 4.20(0.5H, m), 5.53(2H, s), 7.04-7.25(2H, m), 7.41(1H, s), 7.53(1H, m), 7.71(1H, m), 7.77-7.95(2H, m), 8.07(1H, d, J=8.6), 8.15(0.3H, s), 8.49(0.7H, s). (solvent: CDCl3) | 526 |
| I-159 | H | 2-ethyl-1-(4-methylpiperidin-1-yl)butyl | 1.02(6H, d, J=6.6), 1.07(3H, s), 1.14-1.61(2H, m), 1.86-2.17(2H, m), 5.58(2H, s), 7.17(2H, m), 7.43(1H, s), 7.56(1H, d, J=8.3, 6.9), 7.73(1H, dd, J=7.9, 7.3), 7.79-8.00(2H, m), 8.09(1H, d, J=8.3), 8.45(1H, s). (solvent: CDCl3) | 554 |

TABLE 29-continued

[Structure: quinoline-CH2-O-phenyl-SO2-CH2-C(R1)(R2)-N(OH)-CHO, with 2-methyl on quinoline]

| Compound | R¹ | R² | ¹H—NMR | FABMS (M + 1) |
|---|---|---|---|---|
| I-160 | H | [3-methylpiperidin-1-yl-CH2-CH(Et)(Et)] | 0.85(6H, t, J=7.3), 1.04-1.56(6H, m), 1.57-1.89(2H, m), 2.07-2.67(5H, m), 2.76(3H, s), 3.31(JH, m), 3.73-3.94(1H, m), 4.09-4.29(1H, m), 5.57(2H, s), 7.15(2H, d, J=8.6), 7.42(1H, s), 7.55(1H, m), 7.73(1H, m), 7.79-7.97(2H, m), 8.09(1H, d, J=8.3), 8.22(0.4H, s), 8.40(0.6H, s). (solvent: CDCl3) | 568 |
| I-161 | H | [4-methyl-4-(N-Boc-piperidinyl)] (N-CO-OtBu, 4-Me piperidine) | 1.07(3H, s), 1.44(9H, s), 1.32-1.57(4H, m), 2.76(3H, s), 2.82-3.03(2H, m), 3.08-3.30(1H, m), 3.60-3.78(1H, m), 3.79-3.96(1.7H, m), 4.38(0.3H, m), 5.60(2H, s), 7.10-7.25(2H, m), 7.43(1H, s), 7.56(1H, d, J=8.3, 7.3), 7.74(1H, dd, J=8.6, 6.9), 7.79-7.97(2.6H, m), 8.10(1H, d, J=8.3), 8.48(0.4H, s). (solvent: CDCl3) | 598 |
| I-162 | Me | [p-tolyl-CH(nBu)] | 0.90(3H, t, J=7.3), 1.26-1.39(2H, m), 1.53-1.60(2H, m), 2.10(3H, s), 2.56(2H, t, J=7.6), 2.75(3H, s), 3.76(1H, d, J=15), 4.18(1H, d, J=15), 5.56(2H, s), 7.09-7.19(6H, m), 7.41(1H, s), 7.55(1H, t, J=7.0), 7.73(1H, t, J=7.0), 7.80-7.90(3H, m), 8.10(1H, d, J=8.3), 8.29(1H, s). (solvent: CDCl3) | 547 |
| I-163 | Me | [4-ethylidene-N-Boc-piperidinyl] (OC-OtBu) | 1.45(9H, s), 1.84(3H, s), 2.18(2H, m), 2.28(2H, m), 2.77(3H, s), 3.34-3.51(4H, s), 5.59(2H, s), 5.68(1H, m), 7.16(2H, m), 7.42(1H, s), 7.56(1H, t, J=7.5), 7.74(1H, t, J=7.6), 7.82-7.92(3H, m), 8.10(1H, d, J=8.3), 8.37(1H, s). (solvent: CDCl3) | 610 |
| I-164 | H | [4-ethylidenepiperidin-1-yl-CH2-CH(Me)(Me)] | 0.95-1.10(7H, m), 1.83-2.04(5H, m), 2.26(1H, m), 2.32-2.61(3H, m), 2.70-2.81(3H, m), 2.76(3H, s), 2.90(1H, m), 3.30(2H, m), 3.75(1H, bs), 5.44-5.49(1H, m), 5.59(2H, s), 7.14-7.18(2H, m), 7.43(1H, s), 7.56(1H, t, J=7.6), 7.74(1H, t, J=7.8), 7.80-7.94(3H, m), 8.10(1H, d, J=8.3), 8.43(1H, s). (solvent: CDCl3) | 566 |

TABLE 29-continued

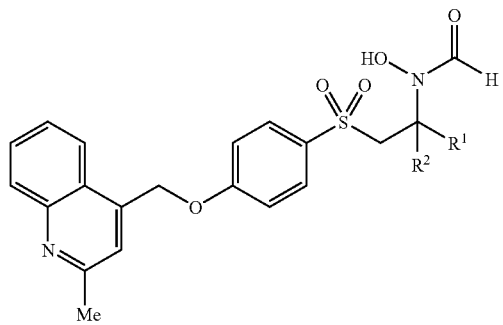

| Compound | R¹ | R² | ¹H—NMR | FABMS (M + 1) |
|---|---|---|---|---|
| I-165 | H | (1,4-dioxa-8-azaspiro[4.5]dec-8-yl)ethyl | 1.60-2.03(4H, m), 2.47-4.15(6H, m), 2.77(3H, s), 3.36(1H, dd, J=14.4, 6.9), 3.55(1H, dd, J=14.4, 5.6), 3.86-4.03(4H, m), 4.25, 5.16(1H, m), 5.59(2H, s), 7.12-7.22(2H, m), 7.42(1H, s), 7.56(1H, t, J=7.3), 7.74(1H, t, J=7.3), 7.82-7.95(3H, m), 8.11(1H, d, J=8.3), 8.19(0.45H, s), 8.37(0.55H, bs). (solvent: CDCl3) | 556 |
| I-166 | H | 1-(tetrahydropyran-4-yl)ethyl | 0.85(1.5H, d, J=6.9), 0.91(1.5H, d, J=7.3), 1.25-1.95(6H, m), 2.77(3H, s), 3.15-4.65(7H, m), 5.60(2H, d, J=3.0), 7.19(2H, m), 7.43(1H, s), 7.56(1H, m), 7.74(1H, m), 7.87(3.5H, m), 8.10(1H, d, J=8.6), 8.48(0.5H, s). (solvent: CDCl3) | 513 |
| I-167 | H | (4-methylpiperidin-1-yl)-CH₂-CH(Et)-Et | 0.82(6H, t, J=7.3), 1.30(4H, m), 1.59(2H, m), 1.80(2H, m), 2.09(2H, m), 2.76(3H, s), 2.85(2H, m), 3.06-3.38(1H, m), 3.40-3.90(6H, m), 5.57(2H, s), 7.16(2H, m), 7.43(1H, s), 7.55(1H, m), 7.73(1H, d, J=8.9, 6.6), 7.78-7.95(2.6H, m), 8.09(1H, d, J=8.6), 8.43(0.4H, s). (solvent: CDCl3) | 568 |
| I-168 | H | 4-(methoxymethyl)-4-methyltetrahydropyran | 1.04-1.58(4H, m), 2.67(3H, s), 3.03(1.5H, s), 3.08(1.5H, s), 3.14-3.88(8.5H, m), 4.56(0.5H, d, J=9.6), 5.77(2H, s), 7.39(2H, m), (2H, m), 7.64-8.02(4.5H, m), 8.12(1H, d, J=7.9), 8.19(0.5H, s), 9.74(0.5H, s), 10.00(0.5H, s). (solvent: DMSO-d6) | 529 |
| I-169 | H | 4-methyl-4-(2-methylprop-1-enyl)tetrahydropyran | | 539 |
| I-170 | H | 4-methyl-4-isobutyltetrahydropyran | | 541 |
| I-171 | H | 4-methyl-1-(methylsulfonyl)piperidine | 1.29-1.47(2H, m), 1.30-1.70(3H, m), 1.71-1.90(2H, m), 2.61(1H, m), 2.76(3H, s), 2.76(3H, s), 3.11-3.36(1H, m), 3.51-4.00(2.5H, m), 4.47(0.5H, m), 5.59(2H, s), 7.19(2H, m), 7.42(1H, s), 7.56(1H, dd, J=7.6, 6.9), 7.74(1H, dd, J=7.9, 7.3), 7.77-7.95(2.5H, m), 8.10(1H, d, J=8.3), 8.48(0.5H, s). (solvent: CDCl3) | 562 |

TABLE 29-continued

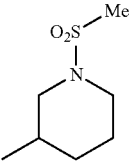

| Compound | R¹ | R² | ¹H—NMR | FABMS (M + 1) |
|---|---|---|---|---|
| I-172 | H | (3-methylpiperidinyl with N-SO₂Me) | 1.29-1.47(2H, m), 1.30-1.70(3H, m), 1.71-1.90(2H, m), 2.61(1H, m), 2.76(3H, s), 2.76(3H, s), 3.11-3.36(1H, m), 3.51-4.00(2.5H, m), 4.47(0.5H, m), 5.59(2H, s), 7.19(2H, m), 7.42(1H, s), 7.56(1H, dd, J=7.6, 6.9), 7.74(1H, dd, J=7.9, 7.3), 7.77-7.95(2.5H, m), 8.10(1H, d, J=8.3), 8.48(0.5H, s). (solvent: CDCl3) | 562 |

TABLE 30

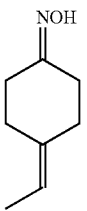

| Compound | R¹ | R² | ¹H—NMR | FABMS (M + 1) |
|---|---|---|---|---|
| I-75 | H | =cyclohexyl=NOH | 2.10-2.80(8H, m), 2.56(3H, s), 2.73(3H, s), 3.20(1H, m), 3.60-4.00(1H, m). 5.10(0.4H, m), 5.33(1H, m), 5.45(0.6H, m), 5.57(2H, s), 7.00-7.25(2H, m), 7.39(1H, s), 7.57(1H, d, J=8.6), 7.63(1 H, m), 7.80-7.90(2H, m), 7.98(1.6H, d, J=8.2), 8.38(0.4H, s). (solvent: CDCl3) | 538 |
| I-76 | H | =4-ethylcyclohexyl=NOH | 0.95-2.10(9H, m), 2.25-2.45(2H, m), 2.56(3H, s), 2.73(3H, s), 3.00-3.15(1H, m), 3.45-3.80(1H, m), 4.36(0.6H, m), 4.70-4.80(0.4H, m), 5.56(2H, s), 7.15-7.25(2H, m), 7.38(1H, s), 7.57(1H, d, J=8.9), 7.63(1H, s), 7.80-8.05(3.6H, m), 8.48(0.4H, s). (solvent: CDCl3) | 540 |
| I-77 | H | 2,3-dimethylphenyl | 2.18(1.8H, s), 2.39(1.2H, s), 2.57(3H, s), 2.73(3H, s), 3.15-3.40(1H, m), 3.95-4.10(1H, m), 5.55-5.80(3H, m), 7.05-7.25(5H, m), 7.39(1H, s), 7.45-7.65(3H, m), 7.80-8.05(3H, m), 8.09(0.4H, s), 8.48(0.6H, s). (solvent: CDCl3) | 505 |

TABLE 30-continued
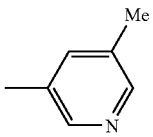
| Compound | R¹ | R² | ¹H—NMR | FABMS (M + 1) |
|---|---|---|---|---|
| I-78 | H | 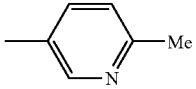 | 2.20(3H, s), 2.53(3H, s), 2.65(3H, s), 4.00-4.15(2H, m), 5.45-5.55(1H, m), 5.69(2H, s), 7.32(2H, d, J=8.9), 7.45-7.65(3H, m), 7.75-7.85(2H, m), 7.85-7.95(2H, m), 8.10-8.40(2H, m), 9.65-10.15(total 1H, sX2). (solvent: DMSO-d6) | 506 |
| I-147 | H | 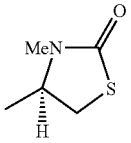 | 2.41(3H, s), 2.52(3H, s), 2.65(3H, s), 4.00-4.15(2H, m), 5.45(1H, m), 5.69(2H, s), 7.15(1H, d, J=7.9), 7.33(2H, d, J=8.9), 7.53(1H, s), 10.07(0.6H, s). (solvent: DMSO-d6) | 506 |
| I-148 | H | 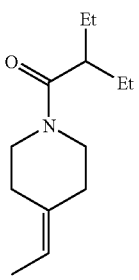 | 2.56(3H, s), 2.74(3H, s), 2.81(0.4H, s), 2.91(0.6H, s), 2.97(2H, s), 3.10-3.65(2.7H, m), 3.70-4.15(1.3H, m), 4.55-4.70(0.7H, m), 4.95-5.15(1.3H, m), 5.59(2H, s), 7.15-7.25(2H, m), 7.39(1H, s), 7.57(1H, m), 7.64(1H, s), 7.85-7.90(2H, m), 7.95-8.00(1.3H, m), 8.36(0.5H, s), 8.49(0.2H, s). (solvent: CDCl3) | 530 |
| I-173 | H | 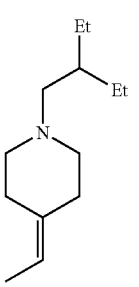 | 0.74(3H, s), 0.76(3H, s), 1.23-1.51(4H, m), 1.92-2.14(2H, m), 2.52(3H, s), 2.64(3H, s), 3.36-3.71(9H, m), 4.91-5.33(2H, m), 5.72(2H, s), 7.42-7.61(4H, m), 7.90-7.98(3H, m), 8.07(1H, s), 9.65(0.4H, s), 10.05(0.6H, s). (solvent: DMSO-d6) | 608 |
| I-174 | H |  | 0.47-0.79(6H, m), 1.19-1.24(5H, m), 1.91-2.04(6H, m), 2.10-2.28(3H, m), 2.52(3H, s), 2.54(3H, s), 3.46(1H, m), 3.66(1H, m), 4.80-5.32(2H, m), 5.72(2H, s), 7.40(2H, d, J=8.6), 7.51(1H, s), 7.59(1H, d, J= 8.6), 7.86(1H, s), 7.89(3H, s), 8.05(0.7H, s), 8.20(0.3H, s). (solvent: DMSO-d6) | 594 |

TABLE 30-continued

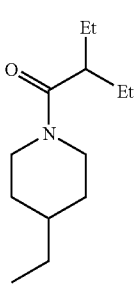

| Compound | R¹ | R² | ¹H—NMR | FABMS (M + 1) |
|---|---|---|---|---|
| I-175 | H | (4-ethylpiperidin-1-yl)-C(O)-CH(Et)- | 0.74-0.90(6H, m), 1.24-1.73(11H, m), 2.43-2.60(2H, m), 2.52(3H, s), 2.64(3H, s), 2.89(1H, m), 3.41(1H, brs), 3.56(1H, m), 3.96(1H, m), 4.12(1H, m), 4.41(0.5H, m), 4.68(0.5H, m), 5.71(1H, s), 7.40-7.43(2H, m), 7.52(1H, s), 7.59(1H, m), 7.86-7.89(4H, m), 7.90(0.5H, s), 8.13(0.5H, s), 9.54(0.5H, s), 9.87(0.5H, s). (solvent: DMSO-d6) | 610 |

TABLE 31

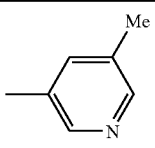

| Compound | R¹ | R² | ¹H-NMR | FABMS (M + 1) |
|---|---|---|---|---|
| I-80 | H | 5-methylpyridin-3-yl | 2.20(3H, s), 2.68(3H, s), 4.09(2H, m), 5.47(0.4H, m), 5.65-5.80(0.6H, m), 5.68(2H, s), 7.33(2H, d, J=8.6), 7.45-7.75(2H, m), 7.80(2H, d, J=8.3), 7.92(1H, m), 8.05(1H, dd, J=9.1, 5.6), 8.13(0.4H, s), 8.20-8.35(3H, m), 8.38(0.6H, m), 9.68(0.4H, s), 10.11(0.6H, s). (solvent: DMSO-d6) | 510 |
| I-81 | H | 6-methylpyridin-3-yl | 2.41(3H, s), 2.67(3H, s), 4.00-4.15(2H, m), 5.46(0.4H, m), 5.65-5.75(0.6H, m), 5.68(2H, s), 7.15(1H, d, J=7.9), 7.35(2H, d, J=8.9), 7.55-7.75(3H, m), 7.81(2H, d, J=8.6), 7.92(1H, m), 8.05(1H, dd, J=9.2, 5.6), 8.10-8.45(2H, m), 9.68(0.4H, s), 10.77(0.6H, s). (solvent: DMSO-d6) | 510 |
| I-149 | H | 6-methylpyridin-2-yl | 2.49(3H, s), 2.76(3H, s), 3.45-3.85(1H, m), 4.16(1H, m), 5.40-5.50(0.4H, m), 5.52(2H, s), 5.97(0.6H, dd, J=9.9, 3.0), 7.10-7.20(4H, m), 7.45-7.55(3H, m), 7.55-7.70(1H, m), 7.85-8.00(2H, m), 8.05-8.15(1.4H, m), 8.25(0.6H, s). (solvent: CDCl3) | 510 |

TABLE 32

[Structure: quinoline-CH2-O-phenyl-SO2-CH2-C(R1)(R2)-N(OH)-CHO]

| Compound | R¹ | R² | ¹H-NMR | FABMS (M + 1) |
|---|---|---|---|---|
| I-82 | H | 2-methylphenyl | 2.17, 2.35(total 3H, each s), 3.25-3.45(1H, m), 3.90-4.30(1H, m), 5.43-5.46(2H, m), 5.60-5.85(1H, m), 7.05-7.25(5H, m), 7.35-7.50(1H, m), 7.55-7.65(2H, m), 7.70-7.80(2H, m), 7.80-7.90(2H, m), 8.00-8.10(1H, m), 8.09(0.4H, s), 8.22(1H, d, J=8.3), 8.44(0.6H, s). (solvent: CDCl3) | 477 |
| I-83 | H | 8-ethylidene-1,4-dioxaspiro[4.5]decane | 1.65-1.75(4H, m), 2.15-2.35(4H, m), 3.10-3.20(1H, m), 3.55-3.70(1H, m), 3.75-3.90(1H, m), 3.94(4H, s), 5.20-5.40(1H, m), 5.46(2H, s), 7.10-7.25(2H, m), 7.55-7.65(2H, m), 7.70-7.90(4H, m), 7.96(0.4H, s), 8.09(1H, d, J=8.3), 8.22(1H, d, J=8.6), 8.37(0.6H, s). (solvent: CDCl3) | 539 |
| I-84 | H | 4-ethylidenecyclohexanone | 2.01-2.70(8H, m), 3.10-3.25(1H, m), 3.60-3.90(2H, m), 4.95-5.55(3H, m), 7.10-7.25(2H, m), 7.55-7.70(2H, m), 7.70-7.90(4H, m), 7.97(0.4H, s), 8.09(1H, d, J=8.9), 8.24(1H, d, J=8.3), 8.37(0.6H, s). (solvent: CDCl3) | 495 |
| I-85 | H | 4-ethylidenecyclohexanone O-formyl oxime | 2.10-2.80(8H, m), 3.10-3.20(1H, m), 3.60-3.90(1H, m), 5.00-5.60(4H, m), 7.10-7.25(2H, m), 7.55-7.70(2H, m), 7.70-7.90(4H, m), 7.96(0.4H, s), 8.09(1H, d, J=8.6), 8.23(1H, d, J=8.6), 8.37(0.6H, s), 8.61(1H, s). (solvent: CDCl3) | 538 |
| I-86 | H | 4-ethylidenecyclohexanone oxime | 2.30-2.70(8H, m), 3.15-3.25(1H, m), 3.60-3.90(1H, m), 3.90-4.00(1H, m), 5.00-5.60(2H, m), 5.46(2H, s), 7.15-7.25(2H, m), 7.50-7.65(2H, m), 7.70-7.90(4H, m), 7.98(0.4H, s), 8.09(1H, d, J=8.3), 8.23(1H, d, J=8.6), 8.39(0.6H, s). (solvent: CDCl3) | 510 |
| I-87 | H | 8-ethyl-1,4-dioxaspiro[4.5]decane | 1.20-1.40(4H, m), 1.40-1.75(6H, m), 1.75-1.95(1H, m), 3.00-3.25(1H, m), 3.40-3.75(1H, m), 3.85-3.95(4H, m), 4.25-4.40(1H, m), 4.65-4.80(1H, m), 7.15-7.25(2H, m), 7.55-7.65(2H, m), 7.75-7.90(4H, m), 7.91(0.6H, s), 8.09(1H, d, J=8.3), 8.22(1H, d, J=8.6), 8.46(0.4H, s). (solvent: CDCl3) | 541 |
| I-88 | H | 4-ethylcyclohexanone oxime | 1.05-1.30(2H, m), 1.30-2.10(9H, m), 3.00-3.30(1H, m), 3.45-3.75(1H, m), 4.35(1H, m), 4.75(1H, m), 5.46(2H, d, J=4.3), 7.15-7.25(2H, m), 7.55-7.65(2H, m), 7.70-7.90(4H, m), 7.92(0.6H, s), 8.09(1H, d, J=8.3), 8.23(1H, d, J=8.6), 8.47(0.4H, s). (solvent: CDCl3) | 512 |
| I-89 | H | 4-ethylcyclohexanone | 1.20-1.35(2H, m), 1.35-1.50(1H, m), 1.55-1.80(2H, m), 1.90-2.10(2H, m), 2.10-2.40(4H, m), 3.07(0.6H, dd, J=3.3, 14.5), 3.21(0.4H, dd, J=3.6, 14.5), 3.45-3.80(1H, m), 4.38(1H, m), 4.76(1H, m), 5.47(2H, d, J=2.3), 7.15-7.25(2H, m), 7.55-7.65(2H, m), 7.75-7.90(4H, m), 7.97(0.6H, s), 8.09(1H, d, J=8.6), 8.23(1H, d, J=8.6), 8.50(0.4H, s). (solvent: CDCl3) | 497 |

TABLE 33
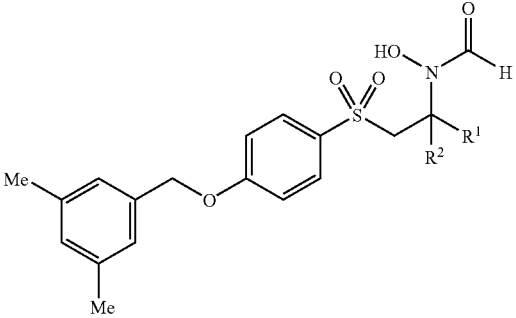
| Compound | R¹ | R² | ¹H-NMR | FABMS (M + 1) |
|---|---|---|---|---|
| I-90 | H | 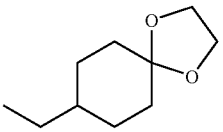 | 1.20-2.00(11H, m), 2.33(6H, s), 2.95-3.20(1H, m), 3.50-3.75(1H, m), 3.85-4.00(4H, m), 4.30(1H, m), 4.65-4.75(1H, m), 5.05(2H, s), 6.99(1H, s), 7.03(2H, s), 7.05-7.15(2H, m), 7.75-7.85(2H, m), 7.89(0.7H, s), 8.43(0.3H, s). (solvent: CDCl3) | 518 |
| I-91 | H | 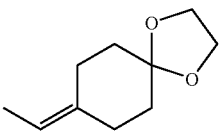 | 1.55-1.75(4H, m), 2.15-2.40(4H, m), 2.34(6H, s), 3.10-3.20(1H, m), 3.60-3.90(1H, m), 3.94-3.96(4H, m), 5.00-5.10(0.5H, m), 5.06(2H, s), 5.25-5.40(1.5H, m), 7.00(1H, s), 7.03(2H, s), 7.05-7.15(2H, m), 7.75-7.85(2H, m), 7.97(0.5H, s), 8.37(0.5H, s). (solvent: CDCl3) | 516 |
| I-92 | H | 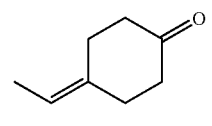 | 2.15-2.70(8H, m), 2.33(6H, s), 3.17(1H, m), 3.65-4.00(1H, m), 4.95-5.15(0.6H, m), 5.06(2H, s), 5.30-5.65(1.4H, m), 6.99(1H, s), 7.03(2H, s), 7.05-7.15(2H, m), 7.75-7.85(2H, m), 7.90-7.80(0.4H, m), 8.35-8.45(0.6H, s). (solvent: CDCl3) | 472 |
TABLE 34
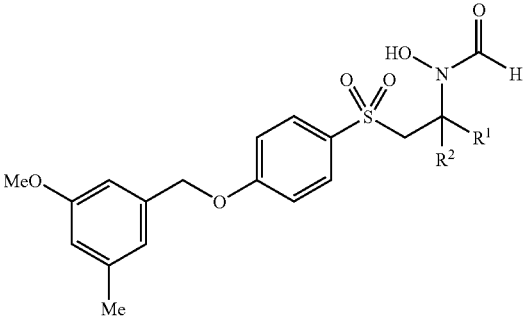
| Compound | R¹ | R² | ¹H-NMR | FABMS (M + 1) |
|---|---|---|---|---|
| I-93 | H | 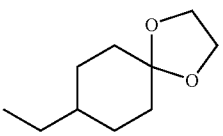 | 1.20-2.00(9H, m), 2.35(3H, s), 3.01-3.25(2H, m), 3.45-3.74(1H, m), 3.80(3H, s), 3.85-4.00(4H, m), 4.25-4.40(1H, m), 4.65-4.80(1H, m), 5.07(2H, s), 6.71(1H, s), 6.76(1H, s), 6.82(1H, s), 7.05-7.15(2H, m), 7.75-7.85(2H, m), 7.89(0.5H, s), 8.44(0.5H, s). (solvent: CDCl3) | 534 |
| I-94 | H | 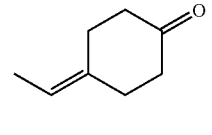 |  | 488 |

TABLE 34-continued

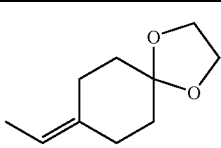

| Compound | R¹ | R² | ¹H-NMR | FABMS (M + 1) |
|---|---|---|---|---|
| I-95 | H | (ethylidene-1,4-dioxaspiro[4.5]decane) | 1.55-1.80(4H, m), 2.05-2.45(4H, m), 2.35(3H, s), 3.10-3.25(2.5H, m), 3.55-3.90(1H, m), 3.80(3H, s), 3.90-4.00(2.5H, m), 5.00-5.15(0.5H, m), 5.08(2H, s), 5.25-5.40(1.5H, m), 6.71(1H, s), 6.76(1H, s), 6.82(1H, s), 7.07-7.13(2H, m), 7.76-7.83(2H, m), 7.96(0.5H, s), 8.37(0.5H, s). (solvent: CDCl3) | 532 |

TABLE 35

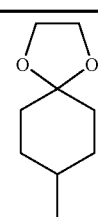

| Compound | R¹ | R² | ¹H-NMR | FABMS (M + 1) |
|---|---|---|---|---|
| I-98 | H | (8-methyl-1,4-dioxaspiro[4.5]decane) | 1.10-1.85(9H, m), 2.36(3H, s), 3.15-3.35(1H, m), 3.55-3.85(3H, m), 3.85-4.00(4H, m), 4.35-4.45(1H, m), 5.07(2H, s), 7.05-7.15(3H, m), 7.16(1H, s), 7.22(1H, s), 7.75-7.85(2.6H, m), 8.46(0.4H, s). (solvent: CDCl3) | 524 |
| I-99 | H | (8-ethyl-1,4-dioxaspiro[4.5]decane) | 1.10-2.05(11H, m), 2.36(3H, s), 3.00-3.25(3H, m), 3.45-3.75(1H, m), 3.85-3.95(2H, m), 4.32(1H, m), 4.70(1H, m), 5.07(2H, s), 7.05-7.15(3H, m), 7.16(1H, s), 7.22(1H, s), 7.75-7.85(2H, m), 7.91(0.6H, s), 8.45(0.4H, s). solvent: CDCl3) | 538 |
| I-100 | H | (4-ethylcyclohexanone oxime) | 1.10-1.55(7H, m), 1.70-2.15(4H, m), 2.36(3H, s), 3.10-3.35(1H, m), 3.55-3.85(1H, m), 4.35(1H, m), 4.75(1H, m), 5.07(2H, s), 7.05-7.15(3H, m), 7.16(1H, s), 7.22(1H, s), 7.75-7.85(2H, m), 7.94(0.6H, s), 8.44(0.4H, s). (solvent: CDCl3) | 509 |

TABLE 35-continued

| Compound | R¹ | R² | ¹H-NMR | FABMS (M + 1) |
|---|---|---|---|---|
| I-101 | H | (4-ethylcyclohexanone) | 1.20-1.50(2H, m), 1.60-1.85(1H, m), 1.90-2.10(4H, m), 2.25-2.40(4H, m), 2.36(3H, s), 3.00-3.25(1H, m), 3.55-3.80(1H, m), 4.39(1H, m), 4.77(1H, m), 5.07(2H, s), 7.05-7.15(3H, m), 7.16(1H, s), 7.21(1H, s), 7.80-7.90(2H, m), 7.97(0.6H, s), 8.48(0.4H, s). (solvent: CDCl3) | 494 |
| I-102 | H | (4-ethylidenecyclohexanone oxime) | 2.36(3H, s), 3.10-3.25(1H, m), 3.65-3.90(1H, m), 5.00-5.20(2.4H, m), 5.30-5.60(1.6H, m), 7.00-7.15(3H, m), 7.16(1H, s), 7.21(1H, s), 7.75-7.90(2H, m), 7.97(0.4H, s), 8.37(0.6H, s), 8.60(1H, s). (solvent: CDCl3) | 507 |
| I-103 | H | (8-ethylidene-1,4-dioxaspiro[4.5]decane) | 1.55-1.80(4H, m), 2.10-2.50(4H, m), 2.36(3H, s), 3.10-3.25(1H, m), 3.60-3.90(1H, m), 3.90-4.00(4H, m), 5.00-5.15(0.5H, m), 5.07(2H, s), 5.20-5.40(1.5H, m), 7.00-7.15(3H, m), 7.16(1H, s), 7.22(1H, s), 7.75-7.90(2H, m), 7.95(0.6H, s), 8.36(0.4H, s). (solvent: CDCl3) | 536 |

TABLE 36

| Compound | R¹ | R² | ¹H-NMR | FABMS (M + 1) |
|---|---|---|---|---|
| I-104 | H | (8-ethylidene-1,4-dioxaspiro[4.5]decane) | 1.55-1.70(4H, m), 2.15-2.35(4H, m), 2.46(3H, s), 3.10-3.20(1H, m), 3.60-3.90(1H, m), 3.92-3.96(7H, m), 5.00-5.10(0.5H, m), 5.07(2H, s), 5.20-5.40(1.5H, m), 6.57(1H, s), 6.75(1H, s), 7.04-7.10(2H, m), 7.76-7.85(2H, m), 7.95(0.5H, s), 8.34(0.5H, s). (solvent: CDCl3) | 533 |

TABLE 36-continued

[Structure: 2,6-dimethylpyridin-4-yl-CH2-O-phenyl-SO2-CH2-C(R1)(R2)-N(OH)-CHO]

| Compound | R¹ | R² | ¹H-NMR | FABMS (M + 1) |
|---|---|---|---|---|
| I-105 | H | 1,1-dimethoxy-4-ethylcyclohexyl (MeO, OMe on ring; ethyl at 4-position) | 1.10-2.05(11H, m), 2.46(3H, s), 2.85-3.25(7H, m), 3.45-3.75(1H, m), 3.92(3H, s), 4.33(1H, m), 4.65-4.75(1H, m), 5.07(2H, s), 6.56(1H, s), 6.75(1H, s), 7.00-7.15(2H, m), 7.75-7.85(2H, m), 7.89(0.6H, s), 8.43(0.4H, s). (solvent: CDCl3) | 537 |
| I-106 | H | 8-ethyl-1,4-dioxaspiro[4.5]decan-2-yl (ethylenedioxy ketal of 4-ethylcyclohexanone) | :0.85-0.95(2H, m), 1.10-1.95(7H, m), 2.46(3H, s), 3.00-3.25(2H, m), 3.49-3.75(1H, m), 3.90-3.92(7H, m), 4.25-4.40(1H, m), 4.65-4.80(1H, m), 5.07(2H, s), 6.57(1H, s), 6.75(1H, s), 7.04-7.10(2H, m), 7.78-7.84(2H, m), 7.89(0.7H, s), 8.43(0.3H, s). (solvent: CDCl3) | 535 |
| I-107 | H | 4-ethylcyclohexylidene-N-OH (oxime) | 1.10-1.30(2H, m), 1.65-2.05(7H, m), 2.46(3H, s), 2.75-2.85(1.7H, m), 3.05-3.35(3.3H, m), 3.65-3.80(1H, m), 3.92(3H, s), 4.30-4.40(1H, m), 4.70-4.80(1H, m), 5.07(2H, s), 6.56(1H, s), 6.74(1H, s), 7.04-7.10(2H, m), 7.77-7.85(2H, m), 7.92(0.7H, s), 8.40(0.3H, s). (solvent: CDCl3) | 506 |
| I-108 | H | 4-ethylidenecyclohexan-1-one | 2.15-2.70(8H, m), 2.46(3H, s), 3.10-3.25(1H, m), 3.60-4.00(2.5H, m), 3.92(3H, s), 5.08(2H, s), 5.20-5.65(1.5H, m), 6.56(1H, s), 6.75(1H, s), 7.00-7.15(2H, m), 7.75-7.90(2H, m), 7.96(0.5H, s), 8.40(0.5H, s). (solvent: CDCl3) | 489 |
| I-109 | H | 4-ethylidenecyclohexylidene-N-OH (oxime) | 2.27-2.45(6H, m), 2.46(3H, s), 2.50-2.70(2H, m), 3.10-3.25(1H, m), 3.60-3.90(1H, m), 3.92(3H, s), 5.05-5.10(2.5H, m), 5.30-5.50(1.5H, m), 6.56(1H, s), 6.75(1H, s), 7.00-7.15(2H, m), 7.75-7.85(2H, m), 7.97(0.5H, s), 8.39(0.5H, s). (solvent: CDCl3) | 504 |

TABLE 36-continued

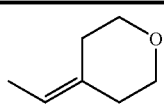

| Compound | R¹ | R² | ¹H-NMR | FABMS (M + 1) |
|---|---|---|---|---|
| I-110 | H | (4-oxanylidene with ethylidene) | 2.10-2.35(4H, m), 2.46(3H, s), 3.10-3.20(1H, m), 3.50-3.90(5H, m), 3.93(3H, s), 5.00-5.15(0.5H, m), 5.08(2H, s), 5.29(1H, m), 5.42(0.5H, d, J=8.9), 6.56(1H, s), 6.75(1H, s), 7.04-7.15(2H, m), 7.75-7.85(2H, m), 7.96(0.5H, s), 8.38(0.5H, s). (solvent: CDCl3) | 477 |

TABLE 37

| Compound | R¹ | R² | ¹H-NMR | FABMS (M + 1) |
|---|---|---|---|---|
| I-111 | H | (cyclohexylidene with =NOH and ethylidene) | 2.00-2.25(4H, m), 2.25-2.55(4H, m), 2.51(6H, m), 3.35-3.55(1H, m), 3.55-3.75(1H, m), 4.75-4.95(0.4H, m), 5.15-5.40(1.6H, m), 5.22(2H, s), 7.09(2H, s), 7.23(2H, m), 7.83(2H, m), 8.14(0.6H, s), 8.32(0.4H, s), 9.63(0.4H, s), 10.02(0.6H, s), 10.31(1H, d, J=3.6). (solvent: DMSO-d6) | 488 |
| I-112 | H | (cyclohexylidene with =NOH and ethyl) | 0.75-1.05(2H, m), 1.20-1.45(2H, m), 1.45-2.00(6H, m), 2.10-2.25(1H, m), 2.43(6H, s), 3.45-3.60(1H, m), 4.00-4.15(1H, m), 4.30-4.70(1H, m), 5.22(2H, s), 7.09(2H, s), 7.24(2H, d, J=8.2), 7.80-7.90(2H, m), 8.11(0.4H, s), 8.14(0.6H, s), 9.45-10.00(1H, m), 10.15(1H, s). (solvent: DMSO-d6) | 490 |
| I-113 | H | (4-oxocyclohexyl with ethyl) | 1.30-1.55(4H, m), 1.60-2.10(3H, m), 2.25-2.40(4H, m), 2.54(6H, s), 3.06(0.6H, dd, J=3.0, 11.2), 3.15-3.22(0.4H, m), 3.54-3.78(1H, m), 4.35-4.45(1H, m), 4.70-4.85(1H, m), 5.09(2H, s), 7.01(2H, s), 7.07-7.12(2H, m), 7.81-7.86(2H, m), 7.98(0.6H, s), 8.47(0.4H, s). (solvent: CDCl3) | 475 |
| I-114 | H | (4-oxocyclohexylidene with ethylidene) | 2.55(6H, s), 3.10-3.25(1H, m), 3.60-3.90(1H, m), 3.95(1H, d, d=7.3), 5.10(2H, s), 5.25-5.65(1H, m), 7.00(2H, s), 7.05-7.15(2H, m), 7.75-7.90(2H, m), 7.96-8.40(1H, m). (solvent: CDCl3) | 473 |

TABLE 37-continued

| Compound | R¹ | R² | ¹H-NMR | FABMS (M + 1) |
|---|---|---|---|---|
| I-115 | H | (4-ethylidene-tetrahydropyran) | 2.05-2.35(4H, m), 2.55(6H, s), 3.10-3.25(1H, m), 3.45-3.90(5H, m), 5.05-5.40(2H, m), 5.10(2H, s), 7.02(2H, s), 7.05-7.15(2H, m), 7.75-7.85(2H, m), 7.95(0.4H, s), 8.33(0.6H, s). (solvent: CDCl3) | 461 |

TABLE 38

| Compound | R¹ | R² | ¹H-NMR | FABMS (M + 1) |
|---|---|---|---|---|
| I-116 | H | (4-ethylidene-tetrahydropyran) | 2.10-2.40(4H, m), 2.57(3H, s), 3.12-3.21(1H, m), 3.45-3.90(4H, m), 3.49(3H, s), 4.57(2H, s), 5.05-5.20(0.6H, m), 5.14(2H, s), 5.25-5.35(1H, m), 5.40-5.45(0.4H, m), 7.05-7.15(4H, m), 7.75-7.85(2H, m), 7.96(0.4H, s), 8.37(0.6H, s). (solvent: CDCl3) | 491 |
| I-117 | H | (2-methylbenzylidene) | 2.18, 2.38(total 3H, each s), 2.56(3H, s), 3.25-3.45(1H, m), 3.49(3H, s), 3.95-4.30(1H, m), 4.56(2H, s), 5.15(2H, s), 5.60-5.80(1H, m), 7.00-7.20(6H, m), 7.30-7.50(2H, m), 7.75-7.90(2H, m), 8.05(0.4H, s), 8.43(0.6H, s). (solvent: CDCl3) | 485 |
| I-118 | H | (8-ethylidene-1,4-dioxaspiro[4.5]decane) | 1.65-1.75(4H, m), 2.10-2.35(4H, m), 2.57(3H, s), 3.10-3.25(1H, m), 3.49(3H, s), 3.55-3.90(2H, m), 3.94-3.96(4H, m), 4.57(2H, s), 5.00-5.40(2H, m), 5.14(2H, s), 7.05-7.15(4H, m), 7.55-7.85(2H, m), 7.96(0.4H, s), 8.37(0.6H, s). (solvent: CDCl3) | 547 |
| I-119 | H | (4-ethylidenecyclohexanone) | 2.57(3H, s), 3.15-3.25(1H, m), 3.49(3H, s), 3.65-3.80(1H, m), 3.90-4.00(1H, m), 4.57(2H, s), 5.17(2H, s), 5.30-5.50(1H, m), 7.00-7.15(4H, m), 7.75-7.90(2H, m), 7.99(0.4H, s), 8.40(0.6H, s). (solvent: CDCl3) | 503 |

TABLE 38-continued
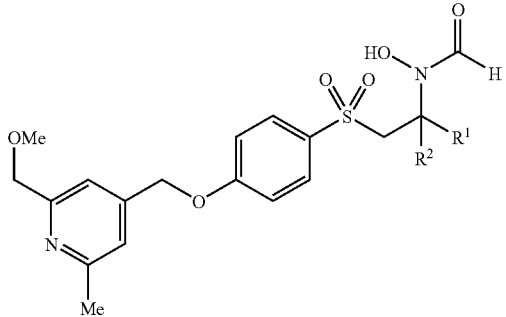
| Compound | R$^1$ | R$^2$ | $^1$H-NMR | FABMS (M + 1) |
|---|---|---|---|---|
| I-120 | H | 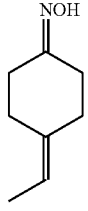 | 2.10-2.50(8H, m), 2.55(3H, s), 3.10-3.25(1H, m), 3.40-3.55(3H, m), 3.65-4.00(1H, m), 4.56(2H, s), 4.95-5.55(2H, m), 5.13(2H, s), 7.00-7.15(4H, m), 7.75-7.90(2H, m), 7.95(0.6H, s), 8.31(0.4H, s). (solvent: CDCl3) | 518 |
| I-121 | H | 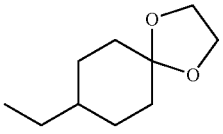 | 1.20-1.80(10H, m), 1.80-1.95(1H, m), 2.57(3H, s), 3.00-3.25(1H, m), 3.49(3H, m), 3.71(1H, dd, J=8.9, 14.5), 3.85-3.95(4H, m), 4.32(1H, m), 4.57(2H, s), 4.65-4.75(1H, m), 5.14(2H, s), 7.05-7.15(4H, m), 7.75-7.85(2H, m), 7.90(0.6H, s), 8.46(0.4H, s). (solvent: CDCl3) | 549 |
| I-122 | H | 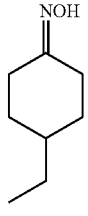 | 1.10-1.30(2H, m), 1.45-2.15(9H, m), 2.57(3H, s), 3.05-3.35(1H, m), 3.45-3.80(1H, m), 3.49(3H, s), 4.35(1H, m), 4.57(2H, s), 4.75(1H, m), 5.14(2H, s), 7.05-7.20(4H, m), 7.75-7.90(2H, m), 7.92(0.6H, s), 8.49(0.4H, s). (solvent: CDCl3) | 520 |
| I-123 | H | 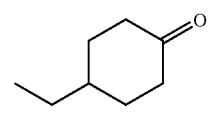 | 1.20-1.50(3H, m), 1.55-1.80(2H, m), 1.80-2.10(2H, m), 2.25-2.40(4H, m), 2.54(3H, s), 3.00-3.25(1H, m), 3.46(3H, m), 3.50-3.80(1H, m), 4.38(1H, m), 4.54(2H, s), 4.70-4.80(1H, m), 5.12(2H, s), 7.00-7.15(4H, m), 7.75-7.90(2H, m), 7.95(0.6H, s), 8.43(0.4H, s). (solvent: CDCl3) | 505 |

TABLE 39

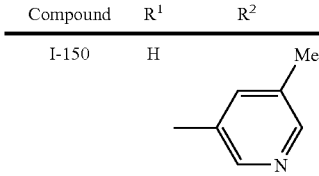

| Compound | R¹ | R² | ¹H-NMR | FABMS (M + 1) |
|---|---|---|---|---|
| I-150 | H | Me | 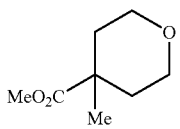 | 510 |

TABLE 40

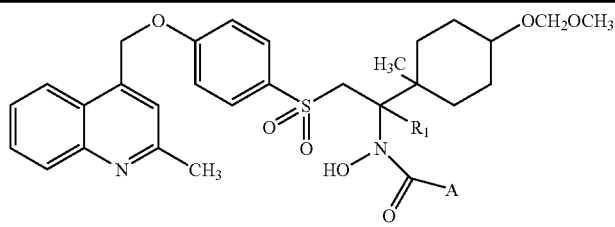

| Compound | R¹ | A | ¹H-NMR | FABMS (M + 1) |
|---|---|---|---|---|
| I-151 | H | Me | 0.89(3H, s), 1.05-1.90(8H, m), 2.07(3H, s), 2.76(3H, s), 3.15-3.75(7H, m), 4.62(2H, s), 5.58(2H, s), 7.18(2H, d, J=8.9), 7.43(1H, s), 7.55(1H, m), 7.62-8.14(6H, m). (solvent: CDCl3) | 571 |

PREPARATION EXAMPLES of novel intermediates used in the present invention are described below.

PREPARATION EXAMPLE 1

Preparation of 4-methyltetrahydropyran-4-carboxylic acid methyl ester (IX-60)

Into a solution of 6.18 g (42.9 mmol) of tetrahydropyran-4-carboxylic acid methyl ester in tetrahydrofuran (140 mL) was dropped, at −78° C. under an atmosphere of argon, 25.7 mL (51.5 mmol) of 2 mol/L lithium diisopropylamide in hexane-heptane-ethylbenzene (available from Aldrich), and stirred for 90 minutes. To this solution, 8.5 g (60.1 mmol) of methyl iodide was added at −78° C. and stirred for 4 hours. Saturated aqueous ammonium chloride solution (30 mL) was added to the reaction mixture and stirred for 10 minutes. Then the reaction mixture was concentrated to about one third of its volume under a reduced pressure and the residue was extracted with ethyl acetate-hexane (3:1). The organic layer was washed with water (twice) and saturated brine successively, and dried over anhydrous magnesium sulfate, and then the solvent was removed. The obtained residue was purified by medium pressure liquid column chromatography on silica gel (developing solvent: hexane:ethyl acetate) to obtain 5.9 g (yield 86.4%) of 4-methyltetrahydropyran-4-carboxylic acid methyl ester (IX-60) as colorless liquid. Its physical property is shown below.

¹H-NMR(CDCl₃) δ value: 1.23(3H, s), 1.50(2H, m), 2.07 (2H, m), 3.47(2H, m), 3.72(3H, s), 3.79 (2H, m).

PREPARATION EXAMPLE 2

Preparation of 4-methoxymethyltetrahydropyran-4-carboxylic acid methyl ester (IX-168)

Into a solution of 3.0 g (20.8 mmol) of tetrahydropyran-4-carboxylic acid methyl ester (IX-49) in tetrahydrofuran (60 mL) was dropped, at −78° C. under an atmosphere of argon, 12.6 mL (25.2 mmol) of 2 mol/L lithium diisopropylamide in hexane-heptane-ethylbenzene (available from Aldrich), and stirred for 90 minutes. To this solution, 1.84 g (22.9 mmol) of chloromethyl methyl ether was added at −78° C., stirred for 30 minutes, and allowed to warm to −10° C. gradually. Saturated aqueous ammonium chloride solution (30 mL) was added to the reaction mixture and stirred for 10 minutes. Then, the reaction mixture was concentrated under a reduced pressure to about one third of its volume, and the residue was extracted with ethyl acetate. The organic layer was washed with water (twice) and saturated brine successively and dried over anhydrous magnesium sulfate, and the solvent was removed. The obtained residue was purified by medium pressure liquid column chromatography on silica gel (developing solvent: hexane-ethyl acetate) to obtain 1.28 g (yield 32.4%) of 4-methoxymethyltetrahydropyran-4-carboxylic acid methyl ester (IX-168) as colorless liquid. Its physical property is shown below.

¹H-NMR(CDCl₃) δ value: 1.58(2H, m), 2.07(2H, m), 3.31 (3H, s), 3.40(2H, s), 3.49(2H, td, J=9.6, 2.7), 3.75(3H, s), 3.82 (2H, dt, J=11.6, 4.0).

PREPARATION EXAMPLE 3

Preparation of 4-methoxymethoxy-1-methylcyclohexanecarbaldehyde (VII-128, -137)

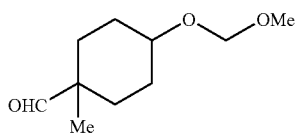

1) To a solution of 3.7 g (20.1 mmol) of 1-methyl-4-oxo-cyclohexanecarboxylic acid methyl ester in mixture of methanol and ethanol (6 mL+15 mL) was added 200 mg (5.29 mmol) of sodium borohydride at 0° C., and stirred for 1 hour at 0° C. After addition of water thereto, the reaction mixture was concentrated under a reduced pressure and the residue was extracted with ethyl acetate. The organic layer was washed with water and saturated brine successively and dried over anhydrous magnesium sulfate. Upon removal of the solvent by evaporation, 3.8 g (yield 100%) of 4-hydroxy-1-methylcyclohexanecarboxylic acid methyl ester was obtained as colorless liquid. Its physical property is shown below.

FAB-MS: Calculated ($M^++1$): 187; Found 187.

2) To a solution of 1.18 g (6.33 mmol) of 4-hydroxy-1-methylcyclohexanecarboxylic acid methyl ester obtained in the above 1) and 2.04 g (15.8 mmol) of diisopropylethylamine in methylene chloride (8.0 mL) was added 1.02 g (12.7 mmol) of chloromethyl methyl ether at room temperature, and stirred for 12 hours. After addition of water, the reaction mixture was stirred for 10 minutes and extracted with ethyl acetate. The organic layer was washed with water and saturated brine successively, and dried over anhydrous magnesium sulfate. The solvent was removed and the residue was purified by medium pressure liquid column chromatography on silica gel (developing solvent: hexane-ethyl acetate) to obtain 620 mg (yield 42.5%) of 4-methoxymethoxy-1-methylcyclohexanecarboxylic acid methyl ester as colorless liquid. Their physical properties are shown below.

Diastereomer A $^1$H-NMR(CDCl$_3$) δ value: 1.10-1.50(10H, m), 1.87(2H, m), 2.13(2H, m), 3.36(3H, s), 3.50(1H, m), 4.15(2H, q, J=6.9), 4.67(2H, s).

FAB-MS: Calculated ($M^++1$): 231; Found 231.

Diastereomer B $^1$H-NMR(CDCl$_3$) δ value: 1.19(3H, s), 1.25(3H, t, J=6.9), 1.52-1.72(6 H, m), 1.86(2H, m), 3.37(3H, s), 3.67(1H, m), 4.13(2H, q, J=6.9), 4. 66(2H, s).

FAB-MS: Calculated ($M^++1$): 231; Found 231.

3) To a solution of 600 g (2.60 mmol) of 4-methoxymethoxy-1-methylcyclohexanecarboxylic acid methyl ester obtained in the above 2) in tetrahydrofuran (8 mL) was added 99 mg (2.60 mmol) of lithium aluminum hydride at 0° C. under an atmosphere of argon, and stirred for 2 hours at 0° C., followed by stirring for 10 hours at room temperature. After dilution of the reaction mixture with ether, excess reagent was carefully quenched with water (3 mL). After the reaction mixture was dried over anhydrous magnesium sulfate, the solvent was evaporated to obtain 603 mg (yield 100%) of (4-methoxymethoxy-1-methylcyclohexyl)methanol as colorless liquid. Its physical property is shown below.

FAB-MS: Calculated ($M^++1$): 189; Found 189.

4) Into a cooled (−78° C.) solution of 1.62 g (12.76 mmol) of oxalyl chloride in methylene chloride (20 mL) was dropped 1.30 g (16.6 mmol) of dimethylsulfoxide under an atmosphere of argon, and stirred for 10 minutes. Into this solution, 600 mg (3.19 mmol) of (4-methoxymethoxy-1-methylcyclohexyl)methanol obtained in the above 3) in methylene chloride (2.5 mL) was dropped at −78° C. and stirred for 15 minutes and then 2.74 g (27.12 mmol) of triethylamine was added. The obtained mixture was stirred for 20 minutes at −78° C. and then for 15 minutes at −20 to −10° C., diluted with ether, and washed with water (three times) and saturated brine successively. The ether layer was dried over anhydrous magnesium sulfate, and the solvent was removed. The obtained residue was purified by medium pressure liquid column chromatography on silica gel (developing solvent: hexane-ethyl acetate) to obtain 600 mg (yield 100%) of 4-methoxymethoxy-1-methylcyclohexanecarbaldehyde (VII-128, -137) as colorless liquid. Its physical property is shown below.

FAB-MS: Calculated ($M^++1$): 187; Found 187.

PREPARATION EXAMPLE 4

Preparation of 2-(tetrahydropyran-4-ylidene)propionaldehyde (VII-15)

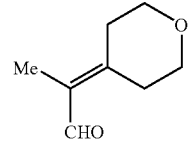

1) To a solution of 12.9 g (54.1 mmol) of 2-phosphonopropionic acid triethyl etser in tetrahydrofuran (60 mL) was added, at 25° C. under an atmosphere of argon, 5.52 g (49.2 mmol) of potassium t-butoxide, and stirred for 10 minutes. Into this solution, 5.42 g (54.1 mmol) of tetrahydropyran-4-one was dropped and stirred for 5 hours at about 70° C. The obtained mixture was cooled to room temperature, poured into water and extracted with ether. The ether extract was washed with water (twice) and saturated brine successively, dried over anhydrous magnesium sulfate, and then, the solvent was removed. The obtained residue was purified by medium pressure liquid column chromatography on silica gel (developing solvent; hexane-ethyl acetate) to obtain 4.2 g (yield 42.1%) of 2-(tetrahydropyran-4-ylidene)propionic acid ethyl ester as colorless liquid. Its physical property is shown below.

$^1$H-NMR(CDCl$_3$) δ value: 1.30(3H, t, J=6.9), 1.88(3H, s), 2.38(2H, t, J=5.3), 2.67(2H, m), 3.72(4H, m), 4.20(2H, q, J=6.9).

2) To a cooled (0° C.) solution of 4.2 g (24.39 mmol) of 2-(tetrahydropyran-4-ylidene)propionic acid ethyl ester obtained in the above 1) in ether (50 mL) was added 1.20 g (31.7 mmol) of lithium aluminum hydride under an atmosphere of argon, and stirred for 1 hour at 0° C., followed by stirring for 2 hours at room temperature. After the reaction mixture was diluted with ether, excess reagent was carefully quenched with ethanol and aqueous ammonium chloride solution. After drying of the reaction mixture with anhydrous magnesium sulfate and subsequent evaporation of the solvent, 4.2 g (yield 100%) of 2-(tetrahydropyran-4-ylidene)propan-1-ol was obtained as colorless liquid. Its physical property is shown below.

$^1$H-NMR(CDCl$_3$) δ value: 1.79(3H, s), 2.25-2.41(4H, m), 3.68(4H, m), 4.14(2H, s).

3) To a suspension of 23 g (0.265 mmol) of activated manganese dioxide in a mixture of hexane-dichloromethane (20 mL+70 mL) was added a solution of 2.0 g (14.07 mmol) of 2-(tetrahydropyran-4-ylidene)propan-1-ol obtained in the above 2) in dichloromethane (4 mL), and stirred for 40 hours at 25° C. Upon filtration of the mixture and subsequent concentration of the filtrate, 2.0 g (yield 100%) of 2-(tetrahydropyran-4-ylidene)propionaldehyde (VII-15) was obtained as colorless liquid. Its physical properties are shown below.

$^1$H-NMR(CDCl$_3$) δ value: 1.79(3H, s), 2.55(2H, t, J=5.3), 2.89(2H, t, J=5.3), 3.82(4H, m), 10.17(1H, s).

FAB-MS: Calculated (M$^+$+1): 141; Found 141.

PREPARATION EXAMPLE 5

Preparation of Fluoro-(tetrahydropyran-4-ylidene)acetic acid ethyl ester (IX-16)

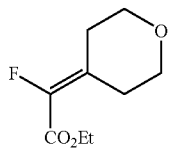

Into a cooled (−10° C.) solution of 5.25 g (21.68 mmol) of 2-fluoro-2-phosphonoacetic acid triethyl ester in tetrahydrofuran (30 mL) under an atmosphere of argon was dropped 13.2 mL (19.87 mmol) of 1.5 mol/L n-butyllithium in hexane (available from KANTO KAGAKU). After stirring for 20 minutes at room temperature, 2.0 g (19.87 mmol) of tetrahydropyran-4-one was dropped thereto and stirred for 2 hours at about 55° C. The obtained mixture was left to cool to room temperature and then poured into water, followed by extraction with ether. The ether extract was washed with water (three times) and saturated brine and dried over anhydrous magnesium sulfate, and the solvent was removed. The obtained residue was purified by medium pressure liquid column chromatography on silica gel (developing solvent: hexane-ethyl acetate) to obtain 3.32 g (yield 88.8%) of fluoro-(tetrahydropyran-4-ylidene)acetic acid ethyl ester (IX-16) as colorless liquid. Its physical property is shown blow.

$^1$H-NMR(CDCl$_3$) δ value: 1.35(3H, t, J=6.9), 2.50(2H, m), 2.90(2H, m), 3.76(4H, m), 4.29(2H, q, J=6.9).

PREPARATION EXAMPLE 6

Preparation of chloro-(tetrahydropyran-4-ylidene)acetic acid ethyl ester (IX-19)

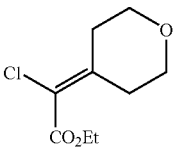

In a manner similar to preparation of fluoro-(tetrahydropyran-4-ylidene)acetic acid ethyl ester (IX-16), 8.2 g (yield 74.02%) of chloro-(tetrahydropyran-4-ylidene)acetic acid ethyl ester (IX-19) was obtained from 5.42 g (54.13 mmol) of tetrahydropyran-4-one, 36.1 mL (54.13 mmol) of 1.5 mol/L n-butyllithium in hexane (available from KANTO KAGAKU) and 15.4 g (59.5 mmol) of 2-chloro-2-phosphonoacetic acid triethyl ester. Its physical property is shown below.

$^1$H-NMR(CDCl$_3$) δ value: 1.35(3H, t, J=6.9), 2.65(2H, t, J=5.6), 2.87(2H, t, J=5.6), 3.73(2H, t, J=5.6), 3.78(2H, t, J=5.6), 4.27(2H, q, J=6.9).

PREPARATION EXAMPLE 7

Preparation of 3-(4-methyltetrahydropyran-4-yl)propenal (VII-143)

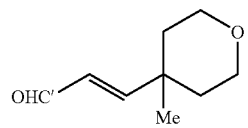

1) To a cooled (0° C.) solution of 3.45 g (21.8 mmol) of 4-methyltetrahydropyran-4-carboxylic acid methyl ester (IX-60) obtained in PREPARATION EXAMPLE 1 in ether (70 mL) was added 830 mg (21.8 mmol) of lithium aluminum hydride under an atmosphere of argon, and stirred for 1 hour at 0° C., and then for another 1 hour at room temperature. After the reaction mixture was cooled again to 0° C., 830 mg (21.8 mmol) of lithium aluminum hydride was added and stirred for 1 hour at 0° C., and subsequently for 1 hour at room temperature. The reaction mixture was diluted with ether, and then excess reagent was carefully quenched with ethanol (8 mL) and saturated brine (10 mL) at 0° C. Upon drying the reaction mixture with anhydrous magnesium sulfate and subsequent evaporation of the solvent, 3.64 g (yield 100%) of (4-methyletetrahydropyran-4-yl)methanol was obtained as colorless liquid. Its physical property is shown below.

$^1$H-NMR(CDCl$_3$) δ value: 1.04(3H, s), 1.29(2H, m), 1.59 (3H, m), 3.40(2H, d, J=5.6), 3.54-3.82(4H, m).

2) Into a cooled (−78° C.) solution of 7.0 g (55.4 mmol) of oxalyl chloride in methylene chloride (90 mL) was dropped 5.6 g (72.0 mmol) of dimethylsulfoxide under an atmosphere of argon, and stirred for 10 minutes. Into this solution, a solution of 3.6 g (27.7 mmol) of (4-methyletetrahydropyran-4-yl)methanol obtained in the above 1) in methylene chloride (5 mL) was dropped at −78° C. and stirred for 15 minutes, followed by adding 14.6 g (144.0 mmol) of triethylamine. The resulting mixture was stirred for 20 minutes at −78° C. and then for 15 minutes at −20 to −10° C., diluted with ether, and washed with water (three times) and saturated brine successively. The ether layer was dried over anhydrous magnesium sulfate and the solvent was removed. The obtained residue was purified by medium pressure liquid column chromatography on silica gel (developing solvent: hexane-ethyl acetate) to obtain 2.75 g (yield 77.5%) of 4-methyltetrahydropyran-4-carbaldeyhde (VII-60) as colorless liquid. Its physical property is shown below.

$^1$H-NMR(CDCl$_3$) δ value: 1.11(3H, s), 1.51(2H, m), 1.94 (2H, m), 3.51(2H, m), 3.78(2H, m), 9.47(1H, s).

3) Into a cooled (0° C.) solution of 1.92 g (8.58 mmol) of diethylphosphonoacetic acid ethyl ester in tetrahydrofuran-methanol (3.5 mL+2.8 mL) was dropped 1.65 mL (8.58 mmol) of 28% sodium methoxide in methanol solution, and stirred for 10 minutes. Into this solution was dropped a solution of 1.0 g (7.80 mmol) of 4-methyltetrahydropyran-4-carbaldeyhde obtained in the above 2) in tetrahydrofuran (1.5 mL), and then stirred for 5 hours at room temperature. After the reaction was completed, the reaction mixture was poured into ice water and extracted with ether. The organic layer was washed with water (three times) and saturated brine successively, dried over anhydrous magnesium sulfate and concentrated under a reduced pressure. The obtained residue was purified by medium pressure liquid column chromatography on silica gel (developing solvent; hexane-ethyl acetate) to obtain 0.93 g (yield 64.7%) of 3-(4-methyltetrahydropyran-4-yl)acrylic acid methyl ester as colorless liquid. Its physical property is shown below.

$^1$H-NMR(CDCl$_3$) δ value: 1.13(3H, s), 1.41-1.76(4H, m), 3.68(4H, m), 3.75(3H, s), 5.79(1H, d, J=16.2), 6.96(1H, d, J=16.2).

4) Into a cooled (−78° C.) solution of 640 mg (3.47 mmol) of 3-(4-methyltetrahydropyran-4-yl)acrylic acid methyl ester obtained in the above 3) in THF was dropped 8.0 mL (8.00 mmol) of 1.0 mol/L diisobutylaluminum hydride in toluene at under an atmosphere of argon, and stirred for 3 hours at −78° C. The reaction mixture was allowed to warm to room temperature, and then an aqueous solution of sodium potassium tartrate was added, followed by a removal of solvent under a reduced pressure. Water was added to the residue and the mixture was extracted with ethyl acetate. The organic layer was washed with saturated brine and dried over anhydrous magnesium sulfate, and the solvent was removed to obtain 543 mg (yield 71%) of crude 3-(4-methyltetrahydropyran-4-yl)prop-2-ene-1-ol. Its physical property is shown below.

$^1$H-NMR(CDCl$_3$) δ value: 1.08(3H, s), 1.40-1.55(2H, m), 1.55-1.70(2H, m), 3.60-3.75(4H, m), 4.15(2H, d, J=5.0), 5.54-5.71(2H, m).

5) To a solution of 543 mg (3.47 mmol) of 3-(4-methyltetrahydropyran-4-yl)prop-2-en-1-ol obtained in the above 4) in a mixture of hexane (30 mL)-chloroform (10 mL) was added 6.0 g of activated manganese dioxide, and vigorously stirred for 18 hours at room temperature. Insoluble materials were filtered off and the solvent was removed under a reduced pressure. The obtained residue was purified by column chromatography (silica gel 25 g, developing solvent: hexane:ethyl acetate=2:1) to obtain 535 mg (yield 100%) of 3-(4-methyltetrahydropyran-4-yl)propenal (VII-143). Its physical property is shown below.

FAB-MS: Calculated (M$^+$+1): 155; Found 155.

PREPARATION EXAMPLE 8

Preparation of 3-(4-methyltetrahydropyran-4-yl)propionic acid methyl Ester (IX-144)

To a solution of 220 g (1.19 mmol) of 3-(4-methyltetrahydropyran-4-yl)acrylic acid methyl ester in methanol (15 mL) was added 40 mg of palladium-carbon, replaced with hydrogen gas, and then stirred for 12 hours at room temperature. After the reaction mixture was filtered through Celite, the solvent was removed under a reduced pressure. The obtained residue was purified by column chromatography (silica gel 20 g, developing solvent: ethyl acetate) to obtain 222 mg (yield 100%) of 3-(4-methyltetrahydropyran-4-yl)propionic acid methyl ester (IX-144). Its physical property is shown below.

$^1$H-NMR(CDCl$_3$) δ value: 0.98(3H, s), 1.20-1.40(2H, m), 1.40-1.55(2H, m), 1.60-1.75(2H, m), 2.25-2.35(2H, m), 3.55-3.80(4H, m), 3.68(3H, s).

PREPARATION EXAMPLE 9

Preparation of 2-methyl-3-(4-methyltetrahydropyran-4-yl)acrylic acid methyl ester (IX-169)

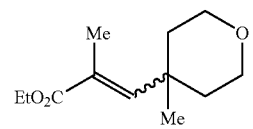

In a manner similar to the synthesis of 2-(tetrahydropyran-4-ylidene)propionic acid ethyl ester in the above PREPARATION EXAMPLE 4, 556 mg (yield 42.0%) of 2-methyl-3-(4-methyltetrahydropyran-4-yl)acrylic acid methyl ester (IX-169) was obtained from 800 mg (6.24 mmol) of 4-methyltetrahydropyran-4-carbaldeyhde (VII-60) obtained in the above PREPARATION EXAMPLE 7, 980 mg (8.74 mmol) of potassium t-butoxide and 2.23 g (9.36 mmol) of 2-phosphonopropionic acid triethyl ester. Its physical property is shown below.

$^1$H-NMR(CDCl$_3$) δ value: 1.18(1.2H, s), 1.21(1.8H, s), 1.30(1.2H, t, J=6.9), 1.31(1.8H, t, J=6.9), 1.42-1.93(4H, m), 1.94(3H, m), 3.42-3.81(4H, m), 4.10-4.22(2H, m), 5.50(0.4H, d, J=1.7), 6.82(0.6H, d, J=1.3).

PREPARATION EXAMPLE 10

Preparation of 2-methyl-3-(4-methyltetrahydropyran-4-yl)propionic acid ethyl ester (IX-170)

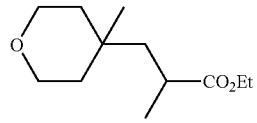

2-Methyl-3-(4-methyltetrahydropyran-4-yl)propionic acid ethyl ester (IX-170) was obtained from 2-methyl-3-(4-methyltetrahydropyran-4-yl)acrylic acid methyl ester (IX-169) in a manner similar to the preparation method in PREPARATION EXAMPLE 8. Its physical property is shown below.

$^1$H-NMR(CDCl$_3$) δ value: 0.97(3H, s), 1.15-1.60(5H, m), 1.17(3H, d, J=7.3), 1.26(3H, t, J=6.9), 1.98(1H, dd, J=14.2, 9.2), 2.53(1H, m), 3.53-3.75(4H, m), 4.12(2H, q, J=6.9).

PREPARATION EXAMPLE 11

Preparation of 2-(tetrahydropyran-4-yl)propionic acid methyl ester (IX-166)

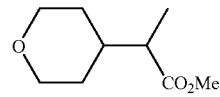

Into a cooled (−78° C.) solution of 1.00 g (6.32 mmol) of (tetrahydropyran-4-yl)acetic acid methyl ester in tetrahydrofuran (20 mL) was dropped, under an atmosphere of argon, a solution of 4.5 mL (9.00 mmol) of 2 mol/L lithium diisopropylamide in hexane-heptane-ethylbenzene (available from Aldrich) and subsequently 0.47 mL (7.55 mmol) of methyl iodide, and then stirred for 30 minutes at −78° C., followed by stirring for 48 hours at room temperature. After 1N hydrochloric acid was added to the reaction mixture, it was concentrated under a reduced pressure and extracted with ethyl acetate. The organic layer was washed with saturated brine and dried over anhydrous magnesium sulfate, and the solvent was removed. The obtained residue was purified by column chromatography (silica gel 30 g, developing solvent: hexane:ethyl acetate=4: 1) to obtain 927 mg (85.1%) of 2-(tetrahydropyran-4-yl)propionic acid methyl ester (IX-166). Its physical property is shown below.

$^1$H-NMR(CDCl$_3$) δ value: 1.14(3H, d, J=6.9), 1.25-1.70 (4H, m), 1.79(1H, m), 2.29(1H, quintet, J=7.3), 3.37(2H, m), 3.68(3H, s), 3.97(2H, m).

PREPARATION EXAMPLE 12

Preparation of 4-(tetrahydropyran-4-ylidene)butanoic acid ethyl ester (IX-127)

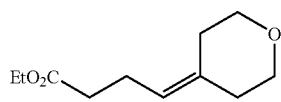

A solution of 11.2 g (24.5 mmol) of [3-(ethoxycarbonyl)propyl]triphenylphosphonium bromide in dimethylformamide (19 mL) was dropped into a cooled (10° C.) suspension of 1.13 g (28.2 mmol) of a 60% sodium hydride in dimethylformamide (2 mL) under an atmosphere of argon, and stirred for 40 minutes. Into this, 2.5 g (24.5 mmol) of tetrahydropyran-4-one was dropped. After dropping, stirring was continued for 1 hour at 10° C. and for 14 hours at room temperature. After the reaction was completed, the reaction mixture was poured into ice water and extracted with ether. The organic layer was washed with water (three times) and saturated brine successively, then dried over anhydrous magnesium sulfate and concentrated under a reduced pressure. The obtained residue was purified by medium pressure liquid column chromatography on silica gel (developing solvent: hexane:etyl acetate) to obtain 320 mg (yield 6.6%) of 4-(tetrahydropyran-4-ylidene)butanoic acid ethyl ester (IX-127) as colorless liquid. Its physical properties are shown below.

$^1$H-NMR(CDCl$_3$) δ value: 1.26(3H, t, J=7.3), 2.19(2H, t, J=5.0), 2.23-2.40(8H, m), 3.65(4H, m), 4.13(1H, q, J=7.3), 5.17(1H, t, J=7.3).

FAB-MS: Calculated (M$^+$+1): 199; Found 199.

PREPARATION EXAMPLE 13

Preparation of 3-(6-methylpyridin-2-yl)proponic acid ethyl ester (IX-129)

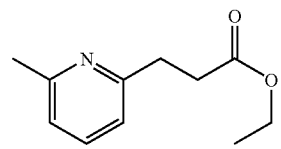

To a solution of 1.39 g (7.85 mmol) of 3-(6-methylpyridin-2-yl)acrylic acid ethyl ester in methanol (50 mL) was added 200 mg of 10% palladium-carbon, and stirred for 4 hours at room temperature under an atmosphere of hydrogen. The solution was filtered through Celite and the obtained filtrate was concentrated under a reduced pressure. The residue was purified by silica gel chromatography (developing solvent; hexane:ethyl acetate=3:1 to 2:1) to obtain 1.09 g (6.09 mmol) of 3-(6-methylpyridin-2-yl)propionic acid ethyl ester (IX-129) as colorless oil. Its physical property is shown below.

$^1$H-NMR(CDCl$_3$) δ value: 1.23(3H, t, J=7.1), 2.52(3H, s), 2.76(2H, t, J=7.7), 3.07(2H, t, J=7.6), 4.13(2H, q, J=7.2), 6.97(2H, d, J=7.6), 7.47(1H, t, J=7.6).

PREPARATION EXAMPLE 14

Preparation of 3-[5-(tert-butyldimethylsilanyloxy)cyclohexy-1-enyl]propionic acid methyl ester (IX-38)

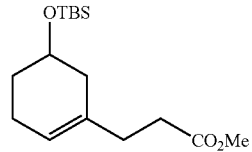

1) Under an atmosphere of argon, 2.18 g (12.09 mmol) of 3-(3-methoxyphenyl)propionic acid was put into a three-neck flask, and tetrahydrofuran (20 mL) and tert-butylalcohol (20 mL) were added thereto. After cooling to −78° C., about 150 mL of liquid ammonia was added thereto, and then sodium was added piece by piece. After the reaction was completed, ethanol was added to stop the reaction, and ammonia was removed at room temperature. After sodium dihydrogen phosphate was added thereto to make the reaction mixture acidic, it was extracted with chloroform, dried over magnesium sulfate and filtered, followed by evaporation of the solvent under a reduced pressure. An aqueous solution of acetic acid (acetic acid:distilled water=4:1) was added to the residue and stirred for 45 minutes, and then the solvent was removed under a reduced pressure. To the obtained residue was added 50 mL of ethanol, followed by 8 mL (16 mmol) of 2M trimethylsilyldiazomethane at 0° C. After stirring for 1 hour, the reaction mixture was concentrated under a reduced pressure and then 50 mL of ethanol was added to the obtained residue. Then, 450 mg (11.9 mmol) of sodium borohydride was added thereto at 0° C., and after the reaction was completed, saturated aqueous ammonium chloride solution was added. The resulting mixture was concentrated under a reduced pressure and extracted with ethyl acetate after the saturated aqueous sodium bicarbonate solution was added. The solvent was removed under a reduced pressure, and then the residue was purified by silica gel column chromatography (developing solvent; hexane:ethyl acetate=7:3 to 1:1) to obtain 793 mg (4.3 mmol) of 3-(5-hydroxycyclohexa-1-enyl)propionic acid methyl ester. Its physical property is shown below.

$^1$H-NMR(CDCl$_3$) δ value: 1.50-1.63(2H, m), 1.79(1H, m), 1.99(1H, m), 2.12(1H, m), 2.24-2.31(3H, m), 2.40-2.45(2H, m), 3.67(3H, s), 3.97(1H, m), 5.41(1H, bs).

2) To a solution of 607 mg (3.29 mmol) of 3-(5-hydroxy-cyclohexa-1-enyl)propionic acid methyl ester obtained in the above 1) in dimethylformamide were added 490 mg (7.24 mmol) of imidazole and 550 mg (3.62 mmol) of tert-butyldimethylchlorosilane, and stirred for 3 hours at room temperature. Water was added to the reaction mixture, and the mixture was extracted with a mixed solvent of ethyl acetate:hexane=3:1, dried over anhydrous magnesium sulfate and filtered, followed by evaporation of the solvent under a reduced pressure. The residue was purified by silica gel column chromatography (developing; hexane:ethyl acetate=5:1) to obtain 678 mg (2.27 mmol) of 3-[5-(tert-butyldimethylsilanyloxy)cyclohexy-1-enyl]propionic acid methyl ester (IX-38). Its physical property is shown below.

¹H-NMR(CDCl₃) δ value: 0.06(6H, s), 0.88(9H, s), 1.46-1.60(2H, m), 1.76(1H, m), 1.96-2.16(2H, m), 2.20-2.31(2H, m), 2.38-2.45(3H, m), 3.66(3H, s), 3.87(1H, m), 5.36(1H, bs).

PREPARATION EXAMPLE 15

Preparation of 4-(2-oxoethylidene)piperidine-1-carboxylic acid t-butyl ester (VII-18, 20, 21, 24, 30, 41, 42, 43, 44, 45)

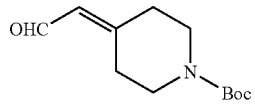

To a solution of 4-(2-hydroxyethylidene)piperidine-1-carboxylic acid t-butyl ester (10.4 g, 46 mmol) in a mixture of hexane (300 mL)-chloroform (100 mL) was added manganese dioxide (100 g), and stirred for 10 hours. After the reaction was completed, insoluble materials were filtered off through Celite and the filtrate was concentrated under a reduced pressure to obtain 9.2 g (yield 89%) of 4-(2-oxoethylidene)piperidine-1-carboxylic acid t-butyl ester (VII-18, 20, 21, 24, 30, 41, 42, 43, 44, 45).

¹H-NMR(CDCl₃) δ value: 7.9(1H, d, J=7.9Hz), 5.9(1H, d, J=7.9Hz), 3.5(4H, m), 2.8(2H, t, J=5.6Hz), 2.4(2H, t, J=5.6Hz), 1.5(9H, s).

PREPARATION EXAMPLE 16

Preparation of (tetrahydrothiopyran-4-ylidene)acetaldehyde (VII-17, 125, 126)

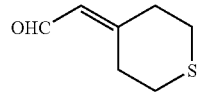

1) Into a cooled (−78° C.) solution of methyl ester of (teterhydrothiopyran-4-ylidene)acetic acid (4.4 g, 25.6 mmol) in tetrahydrofuran (100 mL) was slowly dropped a solution of 1 M diisobutylaluminum hydride in toluene (54.0 mL, 53.8 mmol) under an atmosphere of argon. After dropping, it was stirred for 2 hours at the same temperature. After the reaction was completed, ethanol (10 mL) was added at 0° C. and allowed to warm to room temperature gradually. Then, the reaction mixture was concentrated under a reduced pressure, and an aqueous solution of 20% sodium potassium tartrate (300 mL) was added and stirred for 30 minutes. After stirring, it was extracted with ether and dried over anhydrous sodium sulfate. After drying, it was filtered and the filtrate was concentrated under a reduced pressure. The residue was subjected to silica gel column chromatography (developing solvent, hexane:ethyl acetate=3:1 to 5:2) to obtain 2.7 g (yield 75%) of (tetrahydrothiopyran-4-ylidene)ethanol. Its physical property is shown below.

¹H-NMR(CDCl₃) δ value: 2.45-2.71(8H, m), 4.16(2H, d, J=6.9), 5.46(1H, t, J=6.9).

2) Manganese dioxide (10 g) was added to a solution of (tetrahydrothiopyran-4-ylidene)ethanol (1.0 g, 6.9 mmol) obtained in the above 1) in a mixture of hexane (30 mL)-chloroform (10 mL) and stirred for 10 hours. After the reaction was completed, insoluble materials were filtered off through Celite, and the filtrate was concentrated under a reduced pressure to obtain 0.74 g (yield 76%) of (tetrahydrothiopyran-4-ylidene)acetaldehyde (VII-17, 125, 126). Its physical property is shown below.

¹H-NMR(CDCl₃) δ value: 2.62-2.66(2H, m), 2.81-2.85 (4H, m), 3.07-3.11(2H, m), 5.88(1H, d, J=7.9), 10.05(1H, d, J=7.9).

PREPARATION EXAMPLE 17

Preparation of 4-(2-oxoethylidene)azepane-1-carboxylic acid t-butyl ester (VII-138, 139, 140)

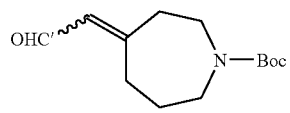

1) To a cooled (0° C.) solution of diethylphosphonoacetic acid ethyl ester (102.5 mL, 0.52 mol) in tetrahydrofuran (760 mL) were added, under an atmosphere of nitrogen, a solution of 28% sodium methoxide in methanol (95.5 mL, 0.65 mol), and then a solution of 4-oxoperhydroazepincarboxylic acid t-butyl ester (100.5 g, 0.47 mol) in tetrahydrofuran (250 mL) and stirred for 3 hours at room temperature. After the reaction was completed, the solvent was removed under a reduced pressure, and water was added to the residue. The mixture was extracted with ether, which was further washed with water and saturated brine and dried over anhydrous sodium sulfate. After drying, it was filtered and the filtrate was concentrated under a reduced pressure. The residue was subjected to silica gel column chromatography (developing solvent; hexane: ethyl acetate=4:1) to obtain 124 g (yield 98%) of 4-methoxycarobonylmethyleneazepane-1-carboxylic acid t-butyl ester. Its physical property is shown below.

¹H-NMR(CDCl₃) δ value: 1.44(9H, s), 1.75-1.82(2H, m), 2.32(1H, m), 2.51(1H, m), 2.81(1H, m), 3.04(1H, m), 3.35-3.51(4H, m), 3.67 and 3.68(3H, s×2), 5.71(1H, m).

2) A solution of 1 M diisobutylaluminum hydride in toluene (800 mL, 0.80 mmol) was slowly dropped into a solution of 68 g (0.25 mol) of 4-methoxycarobonylmethyleneazepane-1-carboxylic acid t-butyl ester obtained in the above 1) in tetrahydrofuran (700 mL) at −78° C. under an atmosphere of argon. After dropping, it was stirred for 2 hours at the same temperature. After the reaction was completed, ethanol (460 mL) was added at 0° C. and allowed to gradually warm to room temperature. The reaction mixture was then concentrated under a reduced pressure, and an aqueous solution of 20% sodium potassium tartrate (1300 mL) was added and stirred for 30 minutes. After stirring, the reaction mixture was extracted with ether and dried over anhydrous sodium sulfate. After drying, it was filtered, and the filtrate was concentrated under a reduced pressure. The residue was subjected to silica gel column chromatography (developing solvent; hexane:ethyl acetate=3:1 to 1:1) to obtain 61.9 g (yield 100%) of 4-(2-hydroxyethylidene)azepane-1-carboxylic acid t-butyl ester. Its physical property is shown below.

¹H-NMR(CDCl₃) δ value: 1.44 and 1.45(9H, s×2), 1.61-1.68(2H, m), 2.19-2.28(3H, m), 2.36-2.61(2H, m), 3.32-3.48 (3H, m), 4.07-4.16(2H, m), 5.60(1H, m).

3) Manganese dioxide (507 g) was added to a solution of 61 g (0.25 mol) of 4-(2-hydroxyethylidene)azepane-1-carboxylic acid t-butyl ester obtained in the above 2) in a mixture of hexane (1865 ml)-chloroform (624 mL) and stirred for 18 hours. After the reaction was completed, insoluble materials were filtered off through Celite and the filtrate was concentrated under a reduced pressure to obtain 33.2 g (yield 55%) of 4-(2-oxoethylidene)azepane-1-carboxylic acid t-butyl ester (VII-17, 125, 126). Its physical property is shown below.

$^1$H-NMR(CDCl$_3$) δ value: 1.44(9H, s), 1.67-1.82(2H, m), 2.44(1H, m), 2.60(1H, m), 2.79(1H m), 3.04(1H, m), 3.38-3.55(4H, m), 5.94(1H, m), 10.0(1H, d, J=7.9).

PREPARATION EXAMPLE 18

Preparation of 3-methyl-4-(2-oxoethylidene)piperidine-1-carboxylic acid t-butyl ester (VII-61, 63, 65, 66)

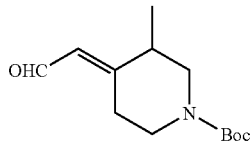

1) To a cooled (0° C.) solution of diethylphosphonoacetic acid ethyl ester (0.46 mL, 2.31 mmol) in tetrahydrofuran (10 mL) under an atmosphere of nitrogen were added a solution of 28% sodium methoxide in methanol (0.43 mL, 2.31 mol), and then a solution of 0.45 g (2.1 mmol) of t-butyl ester of 3-methyl-4-oxopiperidine-1-carbxylic acid in tetrahydrofuran (5 mL) and stirred for 4 hours at room temperature. After the reaction was completed, the solvent was evaporated under a reduced pressure, and water was added to the residue. The mixture was extracted with ether, washed with water and saturated brine and dried over anhydrous sodium sulfate. After drying, the ether extract was filtered and the filtrate was concentrated under a reduced pressure. The residue was subjected to silica gel column chromatography (developing solvent, hexane:ethyl acetate=9:1) to obtain 0.47 g (yield 82.5%) of 4-methoxycarbonylmethylene-3-methylpiperidine-1-carboxylic acid t-butyl ester. Its physical property is shown below.

$^1$H-NMR(CDCl$_3$) δ value: 1.15 and 1.19(3H, d×2, J=6.9), 1.47(9H, s), 1.66(1H, s), 2.05(1H, s), 2.40(1H, m), 2.69(1H, m), 2.91(1H, m), 3.31(1H, m), 3.69 and 3.70(3H, s×2), 5.63 and 5.69(1H, s×2).

2) A solution of 1 M diisobutylaluminum hydride in toluene (13.9 mL, 13.9 mmol) was slowly dropped into a cooled (-78° C.) solution of 4-methoxycarbonylmethylene-3-methylpiperidine-1-carboxylic acid t-butyl ester (1.5 g, 5.6 mmol) obtained in the above 1) in tetrahydrofuran (30 mL) under an atmosphere of argon. After dropping, it was stirred for 2 hours at the same temperature. After the reaction was completed, ethanol (8 mL) was added thereto at 0° C. and allowed to warm to room temperature gradually. The reaction mixture was then concentrated under a reduced pressure, treated with an aqueous solution of 20% sodium potassium tartrate (20 mL), and stirred for 30 minutes. After stirring, the solution was extracted with ether, dried over anhydrous sodium sulfate. After drying, it was filtered, and the filtrate was concentrated under a reduced pressure. The residue was subjected to silica gel column chromatography (developing solvent; hexane:ethyl acetate=2:1) to obtain 1.2 g (yield 89.6%) of 4-(2-hydroxyethylidene)-3-methylpiperidine-1-carboxylic acid t-butyl ester. Its physical property is shown below.

$^1$H-NMR(CDCl$_3$) δ value: 1.05(3H, d, J=6.9), 1.32(1H, m), 1.47(9H, s), 1.63(1H, s), 2.28(1H, m), 2.45(1H, m), 2.83 (1H, m), 3.60(2H, s), 4.20(2d, J=6.9).

3) A solution of 4-(2-hydroxyethylidene)-3-methylpiperidine-1-carboxylic acid t-butyl ester obtained in the above 2) (1.2 g, 5.0 mmol) in a mixture of hexane (30 mL)-chloroform (104 mL) was treated with manganese dioxide (12 g) and stirred for 18 hours. After the reaction was completed, insoluble materials were filtered off through Celite and the filtrate was concentrated under a reduced pressure to obtain 0.86 g (yield 72.3%) of 3-methyl-4-(2-oxoethylidene)piperidine-1-carboxylic t-butyl ester acid (VII-61, 63, 65, 66). Its physical property is shown below.

$^1$H-NMR(CDCl$_3$) δ value: 1.13(3H, d, J=6.6), 1.48(9H, s), 2.45(1H, m), 3.01-3.17(2H, m), 3.61-3.89(4H, m), 5.92(1H, d, J=7.9), 10.05(1H, d, J=7.9).

PREPARATION EXAMPLE 19

Preparation of 4-methoxycarbonylmethyl-3-methylpiperidine-1-carboxylic acid t-butyl ester (IX-64)

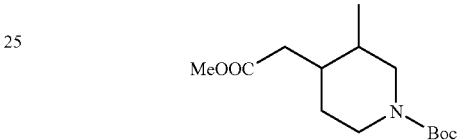

To a solution of 4-methoxycarbonylmethylene-3-methylpiperidine-1-carboxylic acid t-butyl ester (0.47 g. 1.7 mmol) obtained in the above 1) of PREPARATION EXAMPLE 18 in methanol (20 mL) was added 0.03 g of a 10% palladium-carbon under an atmosphere of hydrogen and the reaction was carried out under 3 atm pressure. After the reaction was completed, the catalyst was removed and the filtrate was concentrated under a reduced pressure to obtain 0.44 g (yield 93.6%) of 4-methoxycarbonylmethyl-3-methylpiperidine-1-carboxylic acid t-butyl ester (IX-64). Its physical property is shown below.

$^1$H-NMR(CDCl$_3$) δ value: 0.86(3H, d, J=7.2), 1.45(9H, s), 1.65(2H, s), 1.72(1H, s), 2.11-2.26(3H, m), 2.81(1H, brs), 2.98(1H, m), 3.68(3H, s), 3.76(1H, m), 4.08(1H, brs).

PREPARATION EXAMPLE 20

Preparation of 3,3-dimethyl-4-(2-oxoethylidene)piperidine-1-carboxylic acid t-butyl ester (VII-141, 142)

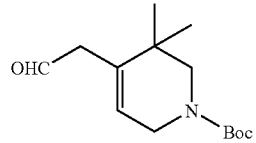

1) To a cooled (0° C.) solution of diethylphosphonoacetic acid ethyl ester (4.4 mL, 24.2 mmol) in tetrahydrofuran (50 mL) under an atmosphere of nitrogen were added a solution of 28% sodium methoxide in methanol (4.6 mL, 26.4 mmol), and then a solution of 3,3-dimethyl-4-oxopiperidine-1-carboxylic acid t-butyl ester (5.0 g, 22.0 mmol) in tetrahydrofuran (10 mL) and stirred for 3 hours at room temperature. After the reaction was completed, the solvent was removed under a reduced pressure and water was added to the residue. The mixture was extracted with ether, washed with water and saturated brine, and dried over anhydrous sodium sulfate.

After drying, the extract was filtered and the filtrate was concentrated under a reduced pressure. The residue was subjected to silica gel column chromatography (developing solvent, hexane:ethyl acetate=6:1) to obtain 1.8 g (yield 32.1%) of 4-methoxycarbonylmethylene-3,3-dimethylpiperidine-1-carbxylic acid t-butyl ester (A) and 3.3 g (yield 58.9%) of 4-methoxycarbonylmethyl-3,3-dimethyl-3,6-dihydro-2H-pyridine-1-carboxylic acid t-butyl ester (B). Each of their physical properties is shown below.

(A) $^1$H-NMR(CDCl$_3$) δ value: 1.11(6H, s), 1.48(9H, s), 3.03-3.08(2H, m), 3.22(2H, s), 3.48-3.53(2H, m), 3.70(3H, s), 5.73(1H, m).

(B) $^1$H-NMR(CDCl$_3$) δ value: 1.00(6H, s), 1.46(9H, s), 3.00(2H, s), 3.24(2H, s), 3.69(3H, s), 3.93(2H, s), 5.46(1H, m).

2) Into a cooled (−78° C.) solution of 4-methoxycarbonylmethylene-3,3-dimethylpiperidine-1-carboxylic acid t-butyl ester (1.8 g, 6.4 mmol) in tetrahydrofuran (50 mL) obtained in the above 1) was slowly dropped, under an atmosphere of argon, 1 M diisobutylaluminum hydride in toluene (15.9 mL, 15.9 mmol). After dropping, the reaction mixture was stirred for 2 hours at the same temperature. After the reaction was completed, ethanol (10 mL) was added at 0° C. and allowed to warm to room temperature gradually. The reaction mixture was then concentrated under a reduced pressure, treated with an aqueous solution of 20% sodium potassium tartrate (50 mL), and stirred for 30 minutes. After stirring, the reaction mixture was extracted with ether, and dried over anhydrous sodium sulfate. After drying, the extract was filtered and filtrate was concentrated under a reduced pressure. The residue was subjected to silica gel column chromatography (developing solvent, hexane:ethyl acetate=2: 1) to obtain 0.95 g (yield 58.6%) of 4-(2-hydroxyethylidene)-3,3-dimethylpiperidine-1-carboxylic acid t-butyl ester. Its physical property is shown below.

$^1$H-NMR(CDCl$_3$) δ value: 1.07(6H, s), 1.47(9H, s), 2.30-2.34(2H, m), 3.15(2H, s), 3.40-3.44(2H, m), 4.20-4.23(2H, m), 5.49(1H, t, J=6.6).

3) Manganese dioxide (10 g) was added to a solution of 4-(2-hydroxyethylidene)-3,3-dimethylpiperidine-1-carboxylic acid t-butyl ester (0.9 g, 3.5 mmol) in a mixture of hexane (30 mL)-chloroform (10 mL) and stirred for 10 hours. After the reaction was completed, insoluble materials were filtered off through Celite, and the filtrate was concentrated under a reduced pressure to obtain 0.63 g (yield 70.8%) of 3,3-dimethyl-4-(2-oxoethylidene)piperidine-1-carboxylic acid t-butyl ester (VII-141, 142). Its physical property is shown below.

$^1$H-NMR(CDCl$_3$) δ value: 1.15(6H, s), 1.49(9H, s), 2.89 (2H, t, J=5.9), 3.27(2H, s), 3.55-3.57(2H, m), 5.96(1H, d, J=7.6), 10.05(1H, d, J=7.9).

PREPARATION EXAMPLE 21

Preparation of 3,3-dimethy-4-(2-oxoethyl)-3,6-dihydro-2H-pyridine-1-carboxylic acid t-butyl ester (VII-152)

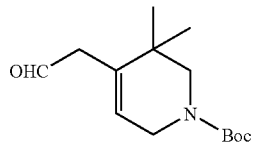

1) A solution of 1 M diisobutylaluminum hydride in toluene (14.0 mL, 14.1 mmol) was slowly dropped into a cooled (−78° C.) solution of 1.6 g (5.7 mmol) of 4-methoxycarbonylmethyl-3,3-dimethyl-3,6-dihydro-2H-pyridine-1-carboxylic acid t-butyl ester obtained in the above 1) of PREPARATION EXAMPLE 20 in tetrahydrofuran (70 mL) under an atmosphere of argon. After dropping, the solution was stirred for 2 hours at the same temperature. After the reaction was completed, ethanol (10 mL) was added at 0° C. and the solution was allowed to warm to room temperature gradually. The reaction mixture was then concentrated under a reduced pressure, treated with an aqueous solution of 20% sodium potassium tartrate (50 mL), and stirred for 30 minutes. After stirring, it was extracted with ether, and dried over anhydrous sodium sulfate. After drying, the extract was filtered and the filtrate was concentrated under a reduced pressure. The residue was subjected to silica gel column chromatography (developing solvent, hexane:ethyl acetate=2:1) to obtain 1.1 g (yield 76.4%) of 4-(2-hydroxylethyl)-3,3-dimethyl-3,6-dihydro-2H-pyridine-1-carboxylic acid t-butyl ester. Its physical property is shown below.

$^1$H-NMR(CDCl$_3$) δ value: 1.02(6H, s), 1.47(9H, s), 2.24-2.31(2H, m), 3.22(2H, s), 3.74-3.79(2H, m), 3.91(2H, s), 5.34(1H, m).

2) A solution of dimethylsulfoxide (1.1 mL, 15 mmol) in dichloromethane (5ml) was added to a cooled (−78° C.) solution of oxalyl chloride (0.67 mL, 7.5 mmol) in dichloromethane (50 mL) under an atmosphere of argon, and stirred for 10 minutes. Then a solution of 4-(2-hydroxyethyl)-3,3-dimethyl-3,6-dihydro-2H-pyridine-1-carboxylic acid t-butyl ester (0.96 g, 3.7 mmol) in dichloromethane (5 mL) was added thereto and stirred for 15 minutes at −78° C. and subsequently for 45 minutes at −40° C. Then triethylamine (3.7 mL, 26.4 mmol) was added thereto and stirred for 30 minutes at room temperature. After the reaction was completed, saturated aqueous ammonium chloride solution was added, followed by extraction with ethyl acetate. The organic layer was washed with water three times and dried over anhydrous magnesium sulfate. After drying, it was filtered and the filtrate was concentrated under a reduced pressure. The residue was subjected to silica gel column chromatography (developing solvent, hexane:ethyl acetate=10:1 to 7:1) to obtain 0.39 g (yield 41.1%) of 3,3-dimethyl-4-(2-oxoethyl)-3,6-dihydro-2H-pyridine-1-carboxylic acid t-butyl ester (VII-152). Its physical property is shown below.

$^1$H-NMR(CDCl$_3$) δ value: 0.99(6H, s), 1.47(9H, s), 3.04 (2H, s), 3.27(2H, s), 3.96(2H, brs), 5.43(1H, m), 9.64(1H, m).

PREPARATION EXAMPLE 22

Preparation of 3-[4-methoxy-2,3-dimethylphenyl]propionic acid methyl ester (IX-145)

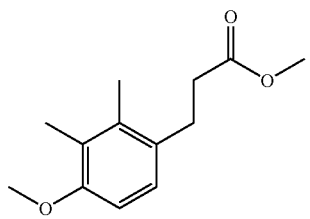

1) In a manner similar to that described in 1) of PREPARATION EXAMPLE 17, 3-(4-methoxy-2,3-dimethylphenyl)acrylic acid methyl ester was obtained from 4-methoxy-2,3-dimethylbenzaldehyde. Its physical property is shown below.

$^1$H-NMR(CDCl$_3$) δ value: 2.18(3H, s), 2.34(3H, s), 3.80 (3H, s), 3.85(3H, s), 6.23(1H, d, J=15.8), 6.74(1H, d, J=8.6), 7.42(1H, d, J=8.6), 8.04(1 H, d, J=15.8).

2) In a manner similar to that described in PREPARATION EXAMPLE 13, 3-[4-methoxy-2,3-dimethylphenyl]propionic acid methyl ester (IX-145) was obtained from 3-(4-methoxy-2,3-dimethylphenyl)acrylic acid methyl ester obtained in the above 1). Its physical property is shown below.

$^1$H-NMR(CDCl$_3$) δ value: 2.18(3H, s), 2.34(3H, s), 3.80 (3H, s), 3.85(3H, s), 6.23(1H, d, J=15.8), 6.74(1H, d, J=8.6), 7.42(1H, d, J=8.6), 8.04(1 H, d, J=15.8).

PREPARATION EXAMPLE 23

Preparation of 4-(2-oxopropylidene)piperidine-1-caroxylic acid tert-butyl ester (VII-163, 164)

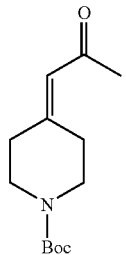

1) An aqueous solution of 1 M sodium hydroxide (15 mL) was added to a solution of 3.02 g (11.8 mmol) of tert-butyl ester of 4-metoxycarbonylmethylenepiperidine-1-carboxylic acid in THF (15 mL) and stirred for 2 hours. Then an aqueous solution of 1 M sodium hydroxide (another 10 mL) was added thereto, and stirred for 18 hours. After the reaction was completed, the reaction mixture was neutralized by addition of 1 M hydrochloric acid and the solvent was removed under a reduced pressure. The residue was extracted with ethyl acetate, and the extract was dried over anhydrous magnesium sulfate. The solvent was removed under a reduced pressure to obtain 2.78 g of tert-butyl ester of 4-carboxymethylenepiperidine-1-carboxylic acid. To a solution of 2.78 g of this 4-carboxymethylenepiperidine-1-carboxylic acid tert-butyl ester in N,N-dimethylformamide (35 mL) was added 3.8 mL (34.6 mmol) of N-methylmolpholine, 2.34 g (17.3 mmol) of 1-hydroxybenzotriazole, 2.65 g (13.8 mmol) of 1-ethyl-3-(3'-dimethylaminopopyl)carbodiimide hydrochloride and 1.35 g (13.8 mmol) of N,O-dimethylhydroxylamine hydrochloride, and stirred for about 20 hours. After the reaction was completed, water was added to the reaction mixture, followed by extraction with ethyl acetate. The extract was washed with saturated brine twice and dried over anhydrous magnesium sulfate, and the solvent was removed under a reduced pressure. Its purification by silica gel column chromatography (developing solvent, hexane:ethyl acetate=3:2 to 1:1) gave 1.99 g (7.00 mmol) of 4-[(methoxymethylcarbamoyl)methylene]piperidine-1-carboxylic acid tert-butyl ester. Its physical property is shown below.

$^1$H-NMR(CDCl$_3$) δ value: 1.47(9H, s), 2.30(2H, m), 2.90 (2H, m), 3.21(3H, s), 3.49(4H, m), 3.69(3H, s), 6.16(1H, s).

2) Into a solution of 1.99 g (7.00 mmol) of 4-[(methoxymethylcarbamoyl)methylene]piperidine-1-carboxylic acid tert-butyl ester obtained in the above 1) in tetrahydrofuran (23 mL) was dropped 3.5 mL (10.5-mmol) of 3M methylmagnesium bromide in ether at −78° C. Another 10.5 mL (31.5 mmol) of methylmagnesium bromide in ether was dropped and stirred for 1 hour. Thereafter, it was stirred for 3 hours at −20° C. and for another 1 hour at 0° C. Saturated brine was added to the solution, followed by extraction with ethyl acetate. The extract was washed with saturated brine, dried over anhydrous magnesium sulfate and filtered, and then, the solvent was removed. The residue was purified by silica gel column chromatography (developing solvent, hexane:ethyl acetate=2:1 to 1:1) to obtain 0.79 g (3.29 mmol) of 4-(2-oxopropylidene)piperidine-1-caroxylic acid tert-butyl ester (VII-163, 164). Its physical property is shown below.

$^1$H-NMR(CDCl$_3$) δ value: 1.47(9H, s), 2.20(3H, s), 2.26 (2H, m), 2.90(2H, m), 3.43-3.54(4H, m), 6.09(1H, s)

PREPARATION EXAMPLE 24

Preparation of 4-chloromethyl-8-fluoro-2-methylquinoline hydrochloride (XII-124)

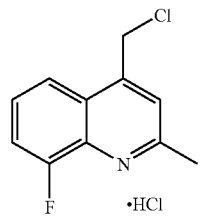

1) Concentrated sulfuric acid (1.2 mL) was added to a solution of 2.70 g (16.8 mmol) of 8-fluoro-2-methylquinoline and 7.70 g (33.7 mmol) of ammonium peroxodisulfate in a mixture of methanol (35 mL)-water (25 mL) and heated under reflux for 15 hours. The reaction mixture was left to cool, followed by a removal of methanol under a reduced pressure. Sodium carbonate was added to the residue to adjust its pH to 10, and then the mixture was extracted with chloroform. The organic layer was washed with saturated brine and dried over anhydrous magnesium sulfate, and the solvent was removed. The obtained residue was washed with ether to obtain 1.03 g (yield 32%) of (8-fluoro-2-methylquinolin-4-yl)methanol. Its physical properties are shown below.

$^1$H-NMR(CDCl$_3$) δ value: 2.50(1H, t, d=1.7), 2.68(3H, s), 4.99(2H, d, J=5.0), 5.61(1H, m), 7.45-7.60(3H, m), 7.75(1H, m).

FAB-MS: Calculated (M$^+$+1): 192; Found 192.

2) At 0° C., 0.75 mL (10.4 mmol) of thionyl chloride was dropped into a solution of 1.00 g (5.23 mmol) of (8-fluoro-2-methylquinolin-4-yl)methanol obtained in the above 1) in chloroform (12 mL) and stirred for 15 hours at room temperature. The reaction mixture was removed under a reduced pressure and then, the residue was washed with ethyl acetate to obtain 1.29 g (yield 100%) of 4-chloromethyl-8-fluoro-2-methylquinoline hydrochloride (XII-124). Its physical property is shown below.

FAB-MS: Calculated (M$^+$+1): 210; Found 210.

TEST EXAMPLE 1

TACE Inhibition Experiment (In Vitro)

The nucleotide sequence of TACE has been reported by Moss et al., (Moss, M. L. et al., Nature 1997, 385, 733-736). Based on this, cDNA of TACE was obtained from THP-1 cells and the like by using an established method and then inserted into an expression vector, followed by transfection of mammalian cells or insect cells with this vector to allow expression of TACE.

TACE inhibition experiments were conducted using TACE obtained as above as an enzyme and by measuring TACE activity in the presence or absence of a test substance using Nma (N-metylanthranilic acid)-Leu-Ala-Gln-Ala-Val-Arg-Ser-Ser-Lys-Dnp(dinitrophenyl)-$_D$-Arg-NH$_2$ being a fluorescent synthetic substrate which contains the sequence of cleavage site of membrane-bound TNF by TACE, as a substrate. The method for the TACE inhibition experiments is described below.

More specifically, 14 units of an enzyme solution (1 unit is defined as the amount of enzyme which degrades 1 pmol of the substrate per minute at 25° C.) which was prepared in 90 μL of assay buffer A (50 mM Tris-HCl buffer (pH 7.5) containing 200 mM sodium chloride, 5 mM calcium chloride, 10 μM zinc sulfate, 0.004% sodium azide and 2 mg/mL bovine serum albumin) and 90 μL of 20 μM fluorescent synthetic substrate prepared in assay buffer B (50 mM Tris-HCl buffer (pH 7.5) containing 200 mM sodium chloride, 5 mM calcium chloride, 10 μM zinc sulfate, 0.004% sodium azide and 0.05% PLURONIC F-68) are mixed and reacted for 2 hours at 37° C. Then, the enzyme activity was determined with a fluorometer (Millipore, Cytoplate 2350) under the conditions of excitation at 360 nm and measurement at 460 nm.

The degree of inhibition was determined from the enzyme activities in the presence and absence of a test compound, and the concentration required for 50% inhibition (IC$_{50}$) was calculated.

TEST EXAMPLE 2

MMP Inhibition Experiment

MMP inhibition experiment may be carried out using a fluorescent synthetic substrate according to, for example, the methods of Bickett et al. (D. Mark Bickett et al., Anal. Biochem., 1993, 212, 58-64) and Nagase et al. (H. Nagase et al., J. Biol. Chem., 1994, 269, 20952-20957). The methods of inhibition experiments carried out for various MMPs are described below.

MMP1 Inhibition Experiment

Human MMP1 (Calbiochem #444208) in amount of 90 μL (100 ng) was activated by mixing with 10 μL of 10 mM p-aminophenylmercuric acetate (APMA), followed by reaction for 1 hour at 37° C. This enzyme solution in amount of 10 μL was diluted to 90 μL with the assay buffer A, which was added to 90 μL of 20 μM fluorescent substrate (Dnp-Pro-Cha (β-cyclohexylalanyl)-Gly-Cys(Me)-His-Ala-Lys(Nma)-NH$_2$) prepared in the assay buffer B, followed by reaction for 5 hours at 37° C. Then, the enzyme activity was determined with the fluorometer (Millipore, Cytoplate 2350) under the conditions of excitation at 360 nm and measurement at 460 nm.

The degree of inhibition was determined from the enzyme activities in the presence and absence of a test compound, and the concentration required for 50% inhibition (IC$_{50}$) was calculated.

MMP2 Inhibition Experiment

Human MMP2 (Calbiochem #444213) in amount of 90 μL (5 ng) was activated by mixing with 10 μL of 10 mM APMA, followed by reaction for 1 hour at 37° C. This enzyme solution in amount of 10 μL was diluted to 90 μL with the assay buffer A, which was added to 90 μL of 20 μM fluorescent substrate (MOCAc((7-methoxycoumarin-4-yl)acetyl)-Pro-Leu-Gly-Leu-A$_2$pr(Dnp)-Ala-Arg-NH$_2$, Peptide Institute, Inc., #3163-v) prepared in the assay buffer B, followed by reaction for 5 hours at 37° C. Then, the enzyme activity was determined with a fluorometer (Labsystems, Fluoroskan Ascent) under the conditions of excitation at 320 nm and measurement at 405 nm.

The degree of inhibition was determined from the enzyme activities in the presence and absence of a test compound, and the concentration required for 50% inhibition (IC$_{50}$) was calculated.

MMP3 Inhibition Experiment

Human MMP3 (Calbiochem #444217) in 90 μL (5 ng) prepared in the assay buffer A was added to 90 μL of 20 μM fluorescent substrate NFF-3(MOCAc-Arg-Pro-Lys-Pro-Val-Glu-Nva-Trp-Arg-Lys(Dnp)-NH$_2$, Peptide Institute, Inc., #3168-v) prepared in the assay buffer B, followed by reaction for 5 hours at 37° C. Then, the enzyme activity was determined with the fluorometers (Millipore, Cytoplate 2350, Excitation at 360 nm, Measurement at 460 nm: or Labsystems, Fluoroskan Ascent, Excitation at 320 nm, Measurement at 405 nm).

The degree of inhibition was determined from the enzyme activities in the presence and absence of a test compound, and the concentration required for 50% inhibition (IC$_{50}$) was calculated.

MMP8 Inhibition Experiment

Human MMP8 (Calbiochem #444229) in amount of 90 μL (30 ng) was activated by mixing with 10 μL of 10 mM APMA, followed by reaction for 1 hour at 37° C. This enzyme solution in amount of 10 μL was diluted to 90 μL with the assay buffer A, which was added to 90 μL of 20 °M fluorescent substrate (MOCAc-Pro-Leu-Gly-Leu-A$_2$pr(Dnp)-Ala-Arg-NH$_2$, Peptide Institute, Inc., #3163-v) prepared in the assay buffer B, followed by reaction for 5 hours at 37° C. Then, the enzyme activity was determined with the fluorometer (Labsystems, Fluoroskan Ascent) under the conditions of excitation at 320 nm and measurement at 405 nm.

The degree of inhibition was determined from the enzyme activities in the presence and absence of a test compound, and the concentration required for 50% inhibition (IC$_{50}$) was calculated.

MMP9 Inhibition Experiment

Human MMP9 (Calbiochem #444231) in amount of 90 μL (80 ng) was activated by mixing with 10 μL of 10 mM p-aminophenylmercuric acetate (APMA) followed by reaction for 2 hour at 37° C. This enzyme solution in amount of 1 μL was diluted to 90 μL with the assay buffer A, which was added to 90 μL of 20 μM fluorescent substrate (Dnp-Pro-Cha-Gly-Cys (Me)-His-Ala-Lys(Nma)-NH$_2$) prepared in the assay buffer B, followed by reaction for 4 hours at 37° C. Then, the enzyme activity was determined with the fluorometer (Millipore, Cytoplate 2350) under the conditions of excitation at 360 nm and measurement at 460 nm.

The degree of inhibition was determined from the enzyme activities in the presence and absence of a test compound, and the concentration required for 50% inhibition (IC$_{50}$) was calculated.

MMP13 Inhibition Experiment

Human MMP13 (Chemicon #CC068) in amount of 90 μL (200 ng) was activated by mixing with 10 μL of 10 mM APMA, followed by reaction for 1 hour at 37° C. This enzyme solution in amount of 0.6 μL was diluted to 90 μL with the assay buffer A, which was added to 90 μL of 20 μM fluorescent substrate (Dnp-Pro-Cha-Gly-Cys(Me)-His-Ala-Lys (Nma)-NH$_2$) prepared in the assay buffer B, followed by reaction for 4 hours at 37° C. Then, the enzyme activity was determined with the fluorometer (Millipore, Cytoplate 2350) under the conditions of excitation at 360 nm and measurement at 460 nm.

The degree of inhibition was determined from the enzyme activities in the presence and absence of a test compound, and the concentration required for 50% inhibition ($IC_{50}$) was calculated.

MMP14 Inhibition Experiment

Human MMP14 (Biogenesis #5980-1461 or Calbiochem #475935) in amount of 90 μL (4 ng) prepared in the assay buffer A was added to 90 μL of 20 μM fluorescent substrate (Dnp-Pro-Cha-Gly-Cys(Me)-His-Ala-Lys(Nma)-$NH_2$) prepared in the assay buffer B, followed by reaction for 5 hours at 37° C. Then, the enzyme activity was determined with the fluorometer (Millipore, Cytoplate 2350) under the conditions of excitation at 360 nm and measurement at 460 nm.

The degree of inhibition was determined from the enzyme activities in the presence and absence of a test compound, and the concentration required for 50% inhibition ($IC_{50}$) was calculated.

MMP17 Inhibition Test

Human MMP17 (Calbiochem #475940) in amount of 90 μL (10 ng) prepared in the assay buffer A was added to 90 μL of 20 μM fluorescent substrate (Dnp-Pro-Cha-Gly-Cys(Me)-His-Ala-Lys(Nma)-$NH_2$) prepared in the assay buffer B, followed by reaction for 5 hours at 25° C. Then, the enzyme activity was determined with the fluorometer (Millipore, Cytoplate 2350) under the conditions of excitation at 360 nm and measurement at 460 nm.

The degree of inhibition was determined from the enzyme activities in the presence and absence of a test compound, and the concentration required for 50% inhibition ($IC_{50}$) was calculated.

Table 41 shows concentrations of the reverse hydroxamic acid derivatives I of the present invention required for 50% inhibition of the enzyme activities. For comparison, concentrations of reference compounds required for 50% inhibition are also shown in Table 41.

TABLE 41

| | $IC_{50}$ value | | | | | | | | |
|---|---|---|---|---|---|---|---|---|---|
| Compound | TACE | MMP-1 | MMP-2 | MMP-3 | MMP-8 | MMP-9 | MMP-13 | MMP-14 | MMP-17 |
| I-1 | 35 | 50000 | — | 6000 | — | 100000< | 7300 | 40000 | 2000 |
| I-2 | 12 | 60000 | — | 1500 | — | 50000 | 6000 | 53000 | 400 |
| I-3 | 3.5 | 100000< | — | 6300 | — | 50000 | 22000 | 43000 | 2500 |
| I-4 | 60 | 100000< | — | 5000 | — | 40000 | 2500 | 43000 | 2000 |
| I-5 | 430 | 33000 | — | 20000 | — | 22000 | 10000 | 25000 | 5000 |
| I-6 | 2.0 | 80000 | — | 5000 | — | 45000 | 15000 | 50000 | 3000 |
| I-7 | 200 | 43000 | — | 20000 | — | 30000 | 10000 | 40000 | 6000 |
| I-8 | 80 | 100000< | — | 2000 | — | 35000 | 2200 | 40000 | 2000 |
| I-9 | 3.5 | 100000< | 60000 | 5500 | 37500 | 53000 | 25000 | 70000 | 3000 |
| I-10 | 60 | 45000 | 6000 | 1200 | — | 12000 | 5000 | 23000 | 1100 |
| I-11 | 20 | 45000 | 30000 | 2000 | — | 28000 | 7000 | 35000 | 600 |
| I-12 | 70 | 45000 | 30000 | 3000 | — | 28000 | 10000 | 35000 | 2000 |
| I-13 | 21 | 60000 | 40000 | 3000 | — | 28000 | 10000 | 40000 | 700 |
| I-14 | 9 | 30000 | 22000 | 1600 | — | 20000 | 7000 | 23000 | 500 |
| I-15 | 5.5 | 100000< | 38000 | 9000 | 60000 | 100000< | 30000 | 70000 | 3500 |
| I-16 | 7 | 100000< | 40000 | 10000 | — | 100000< | 40000 | 100000< | 5500 |
| I-17 | 3 | 43000 | 55000 | 10000 | 100000< | 31000 | 25000 | 50000 | 4000 |
| I-18 | 4 | 65000 | 3300 | 650 | 24500 | 10000 | 3500 | 20000 | 600 |
| I-19 | 6.3 | 100000< | 100000< | 20000 | — | 100000< | 70000 | 100000< | 7000 |
| I-20 | 3 | 42000 | 7000 | 1500 | 55000 | 28000 | 7000 | 30000 | 550 |
| I-21 | 2.2 | 35000 | 630 | 50 | 2650 | 9000 | 600 | 3800 | 45 |
| I-22 | 4.2 | 60000 | 40000 | 7300 | 59500 | 53000 | 21000 | 42000 | 3500 |
| I-23 | 5 | 60000 | 30000 | 3000 | — | 50000 | 15000 | 33000 | 2100 |
| I-24 | 6 | 100000< | 100000< | 10000 | 100000< | 100000< | 40000 | 100000< | 4000 |
| I-25 | 10 | 40000 | 1300 | 110 | 5000 | 8000 | 700 | 20000 | 120 |
| I-26 | 20 | 100000< | 5000 | 1500 | 30000 | 90000 | 4000 | 100000< | 350 |
| I-27 | 3 | 50000 | 8000 | 550 | 8000 | 40000 | 4000 | 30000 | 330 |
| I-28 | 15 | 65000 | 7000 | 280 | 9000 | 40000 | 3300 | 30000 | 220 |
| I-29 | 7.6 | 100000< | 19000 | 1800 | 19000 | 100000< | 18000 | 90000 | 960 |
| I-30 | 12 | 100000< | 83000 | 24000 | 100000< | 100000< | 100000< | 100000< | 8000 |
| I-31 | 2.8 | 100000< | 50000 | 3200 | 62000 | 100000< | 26000 | 90000 | 1800 |
| I-32 | 2.5 | 100000< | 18000 | 2700 | 22000 | 44000 | 9000 | 53000 | 1500 |
| I-33 | 1.9 | 100000< | 28000 | 4200 | 23000 | 100000< | 32000 | 77000 | 2200 |
| I-34 | 33 | 100000< | 100000< | 100000< | 100000< | 100000< | 100000< | 100000< | 40000 |
| I-35 | 32 | 50000 | 4200 | 10000 | 35000 | 37000 | 7800 | 38000 | 6000 |
| I-36 | 170 | 70000 | 6000 | 9700 | 68000 | 43000 | 20000 | 37000 | 20000 |
| I-37 | 170 | 57000 | 2700 | 2000 | 25000 | 22000 | 6000 | 33000 | 1100 |
| I-38 | 12 | 57000 | 12000 | 2000 | 46000 | 54000 | 22000 | 50000 | 2200 |
| I-39 | 210 | 73000 | 30000 | 24000 | 100000< | 36000 | 26000 | 43000 | 25000 |
| I-40 | 270 | — | — | — | — | — | — | — | — |
| I-41 | 3.1 | 100000< | 41000 | 4800 | 50000 | 100000< | 50000 | 100000< | 3700 |
| I-42 | 2.9 | 70000 | 18000 | 2200 | 61000 | 52000 | 20000 | 38000 | 2300 |
| I-43 | 3.1 | 100000< | 50000 | 11000 | 52000 | 100000< | 65000 | 100000< | 4500 |
| I-44 | 7.8 | 100000< | 6500 | 3000 | 42000 | 100000< | 20000 | 60000 | 1100 |
| I-45 | 5 | 85000 | 1000 | 260 | 5000 | 40000 | 2000 | 9000 | 270 |
| I-46 | 22 | 100000< | 20000 | 4400 | 100000 | 100000< | 42000 | 100000< | 650 |
| I-47 | 30 | 100000< | 22000 | 600 | 15000 | 100000< | 18000 | 60000 | 400 |
| I-48 | 19 | 100000< | 70000 | 2800 | 18000 | 100000< | 50000 | 100000< | 1000 |
| I-49 | 13 | 100000< | 24000 | 2000 | 9000 | 100000< | 30000 | 90000 | 610 |
| I-50 | 13 | 60000 | 1400 | 200 | 5800 | 31000 | 3000 | 30000 | 200 |
| I-51 | 10 | 60000 | 3200 | 350 | 7600 | 37000 | 5800 | 40000 | 400 |

TABLE 41-continued

| Compound | TACE | MMP-1 | MMP-2 | MMP-3 | MMP-8 | MMP-9 | MMP-13 | MMP-14 | MMP-17 |
|---|---|---|---|---|---|---|---|---|---|
| I-52 | 12 | 100000< | 22000 | 1000 | 42000 | 100000< | 40000 | 100000< | 1600 |
| I-53 | 10 | 100000< | 13000 | 600 | 25000 | 100000< | 40000 | 100000< | 400 |
| I-54 | 8 | 70000 | 12000 | 1200 | 42000 | 31000 | 23000 | 43000 | 850 |
| I-55 | 13 | 53000 | 1000 | 60 | 2600 | 25000 | 1800 | 22000 | 35 |
| I-56 | 4 | 70000 | 3100 | 1000 | 7200 | 55000 | 6400 | 42000 | 1200 |
| I-57 | 12 | 42000 | 100000< | 6000 | 100000< | 60000 | 33000 | 33000 | 4600 |
| I-58 | 3.1 | 100000< | 21000 | 1900 | 11000 | 100000< | 27000 | 100000< | 580 |
| I-59 | 10 | 54000 | 80000 | 5600 | 58000 | 100000< | 35000 | 60000 | 2600 |
| I-60 | 8.3 | 100000< | 60000 | 2500 | 10000 | 100000< | 56000 | 100000< | 510 |
| I-61 | 3.3 | 80000 | 5000 | 1500 | 24000 | 62000 | 10000 | 54000 | 1800 |
| I-62 | 2 | 60000 | 32000 | 1500 | 73000 | 73000 | 38000 | 74000 | 1200 |
| I-63 | 2 | 64000 | 30000 | 2400 | 60000 | 75000 | 32000 | 65000 | 2200 |
| I-64 | 5.1 | 57000 | 9000 | 700 | 17000 | 58000 | 17000 | 65000 | 580 |
| I-65 | 6.3 | 100000< | 50000 | 17000 | 100000 | 100000< | 100000< | 100000< | 6600 |
| I-66 | 6.1 | 100000< | 73000 | 31000 | 100000< | 100000< | 100000< | 100000< | 10000 |
| I-67 | 3 | 100000< | 20000 | 2700 | 18000 | 100000< | 30000 | 70000 | 1400 |
| I-68 | 23 | 80000 | 1500 | 500 | 8000 | 50000 | 530 | 40000 | 220 |
| I-69 | 5.3 | 100000< | 9000 | 630 | 9800 | 100000< | 13000 | 100000< | 450 |
| I-70 | 11 | 100000< | 11000 | 1300 | 22000 | 100000< | 30000 | 92000 | 1900 |
| I-71 | 20 | 100000< | 780 | 400 | 10000 | 38000 | 1400 | 70000 | 60 |
| I-72 | 24 | 90000 | 2000 | 700 | 10000 | 64000 | 1400 | 48000 | 280 |
| I-73 | 14 | 100000< | 26000 | 1700 | 18000 | 100000< | 50000 | 100000< | 660 |
| I-74 | 5 | 70000 | 41000 | 6000 | 65000 | 50000 | 20000 | 60000 | 10000 |
| I-75 | 4.1 | 65000 | 50000 | 5500 | 90000 | 35000 | 22000 | 40000 | 11000 |
| I-76 | 5 | 40000 | 10000 | 800 | — | 40000 | 6000 | 31000 | 1600 |
| I-77 | 26 | 74000 | 71000 | 3000 | 100000< | 80000 | 28000 | 55000 | 7500 |
| I-78 | 3.1 | 100000< | 36000 | 2800 | 52000 | 100000< | 16000 | 55000 | 3900 |
| I-79 | 15 | 68000 | 58000 | 2900 | 73000 | 70000 | 20000 | 46000 | 6200 |
| I-80 | 4.5 | 100000< | 18000 | 4000 | 27000 | 100000< | 23000 | 100000< | 7000 |
| I-81 | 5.1 | 100000< | 11000 | 2200 | 20000 | 100000< | 17000 | 64000 | 8000 |
| I-82 | 3500 | 92000 | 4200 | 50000 | 100000< | 32000 | 26000 | 38000 | 30000 |
| I-83 | 2500 | 100000< | 7000 | 37000 | 100000< | 53000 | 23000 | 55000 | 36000 |
| I-84 | 550 | 100000< | 6600 | 78000 | 100000< | 100000 | 28000 | 90000 | 42000 |
| I-85 | 360 | 100000< | 4500 | 50000 | 70000 | 56000 | 22000 | 60000 | 31000 |
| I-86 | 420 | 100000< | 5800 | 61000 | 100000< | 70000 | 22000 | 70000 | 31000 |
| I-87 | 5700 | — | — | — | — | — | — | — | — |
| I-88 | 760 | — | — | — | — | — | — | — | — |
| I-89 | 820 | — | — | — | — | — | — | — | — |
| I-90 | 2100 | — | — | — | — | — | — | — | — |
| I-91 | 400 | 100000< | 43000 | 35000 | — | 33000 | 35000 | 40000 | 40000 |
| I-92 | 300 | 100000< | 43000 | 60000 | — | 60000 | 35000 | 100000< | 40000 |
| I-93 | 300 | 60000 | 10000 | 15000 | — | 30000 | 12000 | 33000 | 20000 |
| I-94 | 80 | 90000 | 23000 | 21000 | — | 40000 | 20000 | 40000 | 22000 |
| I-95 | 1500 | 100000< | 100000< | 100000< | — | 100000< | 100000< | 100000< | 100000< |
| I-98 | 80 | 50000 | 2000 | 1200 | — | 20000 | 2000 | 7000 | 1600 |
| I-99 | 1100 | 40000 | 5000 | 6000 | — | 20000 | 18000 | 25000 | 13000 |
| I-100 | 200 | 43000 | 4000 | 7000 | — | 23000 | 6000 | 25000 | 7000 |
| I-101 | 120 | 40000 | 2300 | 7000 | — | 20000 | 3000 | 20000 | 5000 |
| I-102 | 130 | 80000 | 20000 | 25000 | — | 40000 | 16000 | 33000 | 30000 |
| I-103 | 500 | 60000 | 38000 | 30000 | — | 38000 | 25000 | 33000 | 40000 |
| I-104 | 310 | 100000< | 21000 | 23000 | — | 60000 | 15000 | 100000< | 35000 |
| I-105 | 230 | 100000< | 1800 | 2100 | — | 40000 | 2000 | 70000 | 5000 |
| I-106 | 800 | 100000< | 6000 | 6000 | — | 43000 | 7000 | 70000 | 13000 |
| I-107 | 120 | 100000< | 3300 | 8000 | — | 50000 | 3000 | 70000 | 4000 |
| I-108 | 230 | 100000< | 25000 | 40000 | — | 100000< | 15000 | 100000< | 40000 |
| I-109 | 70 | 100000< | 9000 | 33000 | — | 90000 | 7000 | 100000< | 21000 |
| I-110 | 100 | 100000< | 12000 | 43000 | — | 100000< | 8000 | 100000< | 21000 |
| I-111 | 50 | 100000< | 4100 | 30000 | — | 100000< | 8000 | 100000< | 30000 |
| I-112 | 63 | 100000< | 1300 | 4000 | — | 40000 | 2000 | 60000 | 4000 |
| I-113 | 130 | 60000 | 2000 | 8000 | — | 70000 | 2300 | 60000 | 6000 |
| I-114 | 100 | 100000< | 7000 | 23000 | — | 100000< | 10000 | 100000< | 30000 |
| I-115 | 140 | 100000< | 4000 | 40000 | 6000 | 100000< | 8000 | 100000< | 42000 |
| I-116 | 160 | 100000< | 26000 | 70000 | 28000 | 100000< | 39000 | 100000< | 42000 |
| I-117 | 620 | 100000< | 12000 | 20000 | 20000 | 100000< | 28000 | 100000< | 22000 |
| I-118 | 230 | 100000< | 20000 | 30000 | 32000 | 100000< | 31000 | 100000< | 40000 |
| I-119 | 320 | 100000< | 50000 | 100000< | 60000 | 100000< | 60000 | 100000< | 58000 |
| I-120 | 110 | 100000< | 22000 | 68000 | 27000 | 100000< | 62000 | 100000< | 33000 |
| I-121 | 360 | — | — | — | — | — | — | — | — |
| I-122 | 200 | 100000< | 9000 | 21000 | 14000 | 100000< | 12000 | 100000< | 18000 |
| I-123 | 290 | — | — | — | — | — | — | — | — |
| I-124 | 6 | 34000 | 1900 | 4800 | 1900 | 24000 | 5800 | 7000 | 4800 |
| I-125 | 630 | 100000< | 100000< | 100000< | — | 100000< | 100000< | 100000< | 100000< |
| I-126 | 310 | 100000< | 100000< | 12000 | — | 100000< | 70000 | 100000< | 6300 |
| I-127 | 6 | >100000 | 32000 | 3100 | 40000 | >100000 | 16000 | 50000 | 3000 |
| I-128 | 32 | >100000 | 43000 | 1300 | 25000 | >100000 | 22000 | 50000 | 540 |

TABLE 41-continued

| Compound | TACE | MMP-1 | MMP-2 | MMP-3 | MMP-8 | MMP-9 | MMP-13 | MMP-14 | MMP-17 |
|---|---|---|---|---|---|---|---|---|---|
| I-129 | 12 | >100000 | 12000 | 3100 | 33000 | >100000 | 17000 | 50000 | 3400 |
| I-130 | 14 | 50000 | 2600 | 240 | 7000 | 46000 | 2700 | 19000 | 110 |
| I-131 | 20 | 47000 | 4400 | 200 | 4100 | 50000 | 3200 | 22000 | 100 |
| I-132 | 23 | 53000 | 2200 | 210 | 8000 | 40000 | 2200 | 16000 | 85 |
| I-133 | 26 | >100000 | 28000 | 1700 | 18000 | >100000 | 25000 | 100000 | 900 |
| I-134 | 8.1 | 82000 | 100000< | 8000 | 100000< | 100000< | 42000 | 62000 | 4200 |
| I-135 | 4 | — | — | — | — | — | — | — | — |
| I-136 | 6.5 | 48000 | 26000 | 2000 | 13000 | 50000 | 26000 | 50000 | 620 |
| I-137 | 24 | 100000< | 100000< | 3200 | 23000 | 100000< | 50000 | 100000< | 900 |
| I-138 | 2.8 | — | — | — | — | — | — | — | — |
| I-139 | 8.2 | — | — | — | — | — | — | — | — |
| I-140 | 8.2 | — | — | — | — | — | — | — | — |
| I-141 | 3.3 | — | — | — | — | — | — | — | — |
| I-142 | 18 | — | — | — | — | — | — | — | — |
| I-143 | 3.3 | — | — | — | — | — | — | — | — |
| I-144 | 7.2 | — | — | — | — | — | — | — | — |
| I-145 | 210 | — | — | — | — | — | — | — | — |
| I-146 | 9.4 | — | — | — | — | — | — | — | — |
| I-147 | 4.3 | — | — | — | — | — | — | — | — |
| I-148 | 13 | — | — | — | — | — | — | — | — |
| I-149 | 30 | 100000< | 95000 | 26000 | 100000< | 100000< | 35000 | 90000 | 23000 |
| I-150 | 2.5 | 100000< | 34000 | 4000 | 27000 | 100000< | 18000 | 58000 | 2400 |
| I-152 | 13 | — | — | — | — | — | — | — | — |
| I-153 | 33 | — | — | — | — | — | — | — | — |
| I-154 | 31 | — | — | — | — | — | — | — | — |
| I-155 | 62 | — | — | — | — | — | — | — | — |
| I-156 | 33 | — | — | — | — | — | — | — | — |
| I-157 | 13 | — | — | — | — | — | — | — | — |
| I-158 | 26 | — | — | — | — | — | — | — | — |
| I-159 | 48 | — | — | — | — | — | — | — | — |
| I-160 | 50 | — | — | — | — | — | — | — | — |
| I-161 | 44 | — | — | — | — | — | — | — | — |
| I-173 | 5 | — | — | — | — | — | — | — | — |
| I-174 | 15 | — | — | — | — | — | — | — | — |
| I-175 | 11 | — | — | — | — | — | — | — | — |
| Reference Compound 1 | 10 | 20000 | — | 80 | — | 10000 | 200 | 8000 | 20 |
| Reference Compound 2 | 5 | 3000 | — | 40 | — | 20 | 4 | 100 | 21 |
| Reference Compound 3 | 35 | 45 | — | 30 | — | 30 | 10 | 70 | 13 |

Reference compound 1 (a compound described in WO 99/58531)

(S)-4-[[(2,6-dimethyl-4-pyridinyl)methoxy]phenyl]sulfonyl]-N-hydroxy-2,2-dimethyl-3-thiomorp holine-carboxyamide Reference compound 2 (a compound described in WO 00/09492)

(2S,3R,6R)-4-[4-fluorobenzyloxy)benzenesulfonyl]-6-hydroxymethyl-2-methylmorpholine-3-carboxylic acid hydroxyamide Reference compound 3 (a compound described in WO 98/38179)

(2R,3S)-3-(formylhydroxyamino)-2-(2-methyl-1-propyl)-4-methylpentanoic acid [(1S,2S)-2-methyl-1-(pyridin-2-ylcarbamoyl)-1-butyl]amide The above reference compounds 1 to 3 were synthesized according to the methods described in the patent publications in which each compound is described.

TEST EXAMPLE 3

Study for Suppression of TNF-α Production (Release) In Vivo

Male Lewis rats (weight about 250 g, about 8 weeks old, 4 rats per group) were used as a test animal. Lipopolysaccharide (LPS) from *E. coli* (available from SIGMA) was dissolved in physiological saline to prepare a solution of LPS (1 mg/mL). Each of the test compounds (I-2, I-9 and I-24) was dissolved in 5% DMSO-physiological saline to obtain prepared solutions of these test compounds.

The rats received the LPS solution (1 mL/kg) intravenously, and 30 minutes later, the prepared solution of the test compound was administered subcutaneously (5 mL/kg, containing 3 mg of test compound/kg). 90 minutes after administration of LPS, blood was collected from the tail vein and centrifuged for 10 minutes at 3000 rpm at 4° C. to obtain plasma. The plasma TNF-α concentration was determined by an ELISA kit specific for rat TNF-α.

The suppression rate of TNF-α production (release) by the test compound was calculated by the following equation:

Suppression (%)=$(A-B)/A \times 100$

A: Plasma TNF-α concentration in the group not receiving a test compound

B: Plasma TNF-α concentration in the group receiving a test compound

<Results>

Table 42 shows suppression rate of TNF-α production (release) (%) by subcutaneous administration of 3 mg/kg of the test compounds.

TABLE 42

| Test Compound | Suppression rate of TNF-α production (release) (%) |
|---|---|
| I-2 | 42.3 |
| I-9 | 74.8 |
| I-24 | 56.0 |

INDUSTRIAL APPLICABILITY

The reverse hydroxamic acid derivatives I and Ia of the present invention show an excellent selective inhibitory action against TACE, and are useful as a drug for the treatment and prevention of diseases associated with TNF-α.

The invention claimed is:

1. A reverse hydroxamic acid derivative represented by a general formula (Ia):

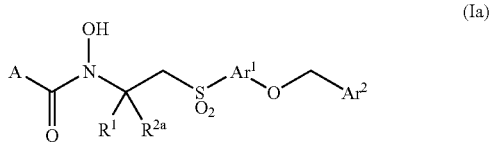

(Ia)

{wherein A is a hydrogen atom, a lower alkyl, a cycloalkyl or —NR$^3$R$^4$ (wherein R$^3$ and R$^4$ are independently a hydrogen atom, a lower alkyl or a cycloalkyl, or form a nitrogen-containing heterocycle together with the nitrogen to which R$^3$ and R$^4$ are attached) Ar$^1$ is phenylene; Ar$^2$ is an optionally substituted quinolinyl; R$^1$ is a hydrogen atom, an optionally substituted lower alkyl, an optionally substituted lower alkenyl or an optionally substituted cycloalkyl; R$^{2a}$ is represented by a general formula (a):

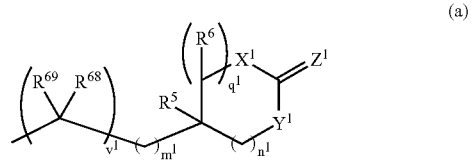

(a)

(wherein R$^5$ and R$^6$ are independently a hydrogen atom, a halogen atom, hydroxyl, cyano, trifluoromethyl, an optionally substituted lower alkyl or an optionally substituted lower alkoxy; R$^{68}$ and R$^{69}$ are independently a hydrogen atom or an optionally substituted lower alkyl; X$^1$ and Y$^1$ are independently a single bond, oxygen, sulfur, —CR$^7$R$^8$— (wherein R$^7$ and R$^8$ are independently the same as R$^5$) or —NR$^9$— (wherein R$^9$ is a hydrogen atom or an optionally substituted lower alkyl, an optionally substituted aryl or an optionally substituted heteroaryl); Z$^1$ is oxygen, sulfur, =CR$^{10}$R$^{11}$ (wherein R$^{10}$ and R$^{11}$ are independently a hydrogen atom, a halogen atom, cyano, trifluoromethyl, an optionally substituted lower alkyl, carboxyl, —CONR$^{12}$R$^{13}$ (wherein R$^{12}$ and R$^{13}$ are independently a hydrogen atom, a lower alkyl or a cycloalkyl, or form a nitrogen-containing heterocycle together with the nitrogen to which R$^{12}$ and R$^{13}$ are attached), —COR$^{14}$ (wherein R$^{14}$ is a hydrogen atom, an optionally substituted lower alkyl, an optionally substituted lower alkoxy, an optionally substituted aryl, an optionally substituted aralkyl, an optionally substituted heteroaryl or an optionally substituted heteroarylalkyl)), =NR$^{15}$ (wherein R$^{15}$ is a hydrogen atom, hydroxyl, an optionally substituted lower alkyl, an optionally substituted lower alkoxy or an optionally substituted acyl), —O(CH$_2$)$_{p1}$O— (wherein p$^1$ is an integer from 2 to 4), —S(CH$_2$)$_{r1}$S— (wherein r$^1$ is an integer from 2 to 4) or —O(CH$_2$)$_{t1}$S— (wherein t$^1$ is an integer from 2 to 4); m$^1$ is an integer from 0 to 6; n$^1$ and q$^1$ are independently an integer from 0 to 3; and v$^1$ is 0 or 1), by a general formula (b):

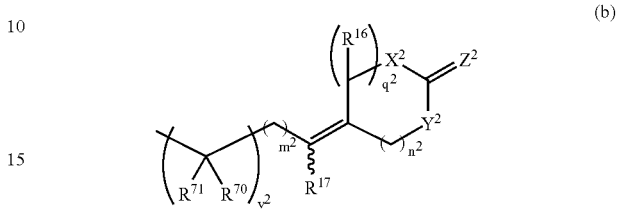

(b)

(wherein R$^{16}$ is a hydrogen atom, a halogen atom, hydroxyl, cyano, trifluoromethyl, an optionally substituted lower alkyl or an optionally substituted lower alkoxy; R$^{17}$ is a hydrogen atom, a halogen atom, or an optionally substituted lower alkyl; R$^{70}$ and R$^{71}$ are independently a hydrogen atom or an optionally substituted lower alkyl; X$^2$ and Y$^2$ are independently a single bond, oxygen, sulfur, —CR$^{18}$R$^{19}$— (wherein R$^{18}$ is a hydrogen atom, a halogen atom, an optionally substituted lower alkyl or an optionally substituted lower alkoxy, and R$^{19}$ is a hydrogen atom, a halogen atom, hydroxyl, cyano, trifluoromethyl, an optionally substituted lower alkyl, an optionally substituted lower alkoxy, an optionally substituted acyl, carboxyl, —CONR$^{20}$R$^{21}$ (wherein R$^{20}$ and R$^{21}$ are independently a hydrogen atom, a lower alkyl or a cycloallcyl, or form a nitrogen-containing heterocycle together with the nitrogen to which R$^{20}$ and R$^{21}$ are attached), —SO$_2$R$^{22}$ (wherein R$^{22}$ is a lower alkyl, a cycloalkyl, an optionally substituted aryl or an optionally substituted heteroaryl), —NR$^{23}$R$^{24}$ (wherein R$^{23}$ and R$^{24}$ are independently a hydrogen atom, an optionally substituted lower alkyl, formyl, an optionally substituted acyl, a lower alkylsulfonyl, an optionally substituted arylsulfonyl, an optionally substituted heteroarylsulfonyl, —CONR$^{25}$R$^{26}$ (wherein R$^{25}$ and R$^{26}$ are independently a hydrogen atom, an optionally substituted lower alkyl, an optionally substituted aryl or an optionally substituted heteroaryl, or form a nitrogen-containing heterocycle together with the nitrogen to which R$^{25}$ and R$^{26}$ are attached), or a cycloalkyl, or form a nitrogen-containing heterocycle together with the nitrogen to which R$^{23}$ and R$^{24}$ are attached), or —OCOR$^{27}$ (wherein R$^{27}$ is an optionally substituted lower alkyl, an optionally substituted aryl, an optionally substituted heteroaryl or —NR$^{28}$R$^{29}$ (wherein R$^{28}$ and R$^{29}$ are independently a hydrogen atom, an optionally substituted lower alkyl, an optionally substituted aryl or an optionally substituted heteroaryl, or form a nitrogen-containing heterocycle together with the nitrogen to which R$^{28}$ and R$^{29}$ we attached))), or —NR$^{30}$— (wherein R$^{30}$ is a hydrogen atom, an optionally substituted lower alkyl, an optionally substituted aryl, an optionally substituted heteroaryl, —COR$^{31}$ (wherein R$^{31}$ is a hydrogen atom, an optionally substituted lower alkyl or an optionally substituted lower alkoxy) or —CONR$^{32}$R$^{33}$ (wherein R$^{32}$ and R$^{33}$ are independently a hydrogen atom, a lower alkyl or a cycloalkyl, or form a nitrogen-containing heterocycle together with the nitrogen to which R$^{32}$ and R$^{33}$ are attached)); Z$^2$ is two hydrogen atoms, oxygen, sulfur, =CR$^{34}$R$^{35}$ (wherein R$^{34}$ and R$^{35}$ are independently a hydrogen atom, a halogen atom, cyano, trifluoromethyl or an optionally substituted lower alkyl, an optionally substituted acyl, carboxyl, —CONR$^{36}$R$^{37}$ (wherein R$^{36}$ and R$^{37}$ are independently a hydrogen atom, a lower alkyl or a cycloalkyl, or form a nitrogen-containing heterocycle together with the nitrogen to which 1($^{36}$ and 1($^{37}$ are attached)), =NR$^{38}$ (wherein R$^{38}$ is a hydrogen atom, hydroxyl, an optionally substituted lower alkyl, an optionally substituted lower alkoxy or an optionally substituted acyl), —O(CH$_2$)$_{p2}$O— (wherein p$^2$ is an integer from 2 to 4), —S(CH$_2$)$_{p2}$S— (wherein r$^2$ is an integer from 2 to 4) or —O(CH$_2$)$_{r2}$S— (wherein t$^2$ is an integer from 2 to 4); m$^2$ is an integer from 0 to 6; n$^2$ and q$^2$ are independently an integer from 0 to 3, and v$^2$ is 0 or 1), by a general formula (c):

(c)

(wherein G$^1$ is an unsaturated four to seven membered ring optionally substituted with 1 to 4 of independent R$^{39}$ at an optional position; R$^{39}$ is hydroxyl, a halogen atom, cyano, trifluoromethyl, an optionally substituted lower alkyl, an optionally substituted lower alkoxy, an optionally substituted acyl, carboxyl, —CONR$^{40}$R$^{41}$ (wherein R$^{40}$ and R$^{41}$ are independently a hydrogen atom, a lower alkyl or a cycloalkyl, or form a nitrogen-containing heterocycle together with the nitrogen to which R$^{40}$ and R$^{41}$ are attached), —SO$_2$R$^{42}$ (wherein R$^{42}$ is a lower alkyl, a cycloalkyl, an optionally substituted aryl or an optionally substituted heteroaryl), —NR$^{43}$R$^{44}$ (wherein R$^{43}$ and R$^{44}$ are independently a hydrogen atom, an optionally substituted lower alkyl, formyl, an optionally substituted acyl, a lower alkylsulfonyl, an optionally substituted arylsulfonyl, an optionally substituted heteroarylsufonyl, —CONR$^{45}$R$^{46}$ (wherein R$^{45}$ and R$^{46}$ are independently a hydrogen atom, an optionally substituted lower alkyl, an optionally substituted aryl or an optionally substituted heteroaryl, or form a nitrogen-containing heterocycle together with the nitrogen to which R$^{45}$ and R$^{46}$ are attached) or a cycloalkyl, or form a nitrogen-containing heterocycle together with the nitrogen to which R$^{43}$ and R$^{44}$ are attached), or —OCOR$^{47}$ (wherein R$^{47}$ is an optionally substituted lower alkyl, an optionally substituted aryl, an optionally substituted heteroaryl or —NR$^{48}$R$^{49}$ (wherein R$^{48}$ and R$^{49}$ are independently a hydrogen atom, an optionally substituted lower alkyl, an optionally substituted aryl or an optionally substituted heteroaryl, or form a nitrogen-containing heterocycle together with the nitrogen to which R$^{48}$ and R$^{49}$ are attached)); and m$^3$ is an integer from 0 to 6), by a general formula (da):

(da)

(wherein G$^{2a}$ is an optionally substituted aryl, an optionally substituted heteroaryl, an optionally substituted cycloalkyl or an optionally substituted heterocycloalkyl each of which are substituted with R$^{50}$ at an optional position (R$^{50}$ is an optionally substituted lower alkyl or an optionally substituted lower alkenyl); and m$^4$ is an integer from 0 to 6), by a general formula (e):

(e)

(wherein R$^{51}$ is —CR$^{72}$=CR$^{73}$—, —C≡C— or —CR$^{74}$R$^{75}$—CR$^{76}$R$^{77}$— (wherein R$^{72}$, R$^{73}$, R$^{74}$, R$^{75}$, R$^{76}$ and R$^{77}$ are independently a hydrogen atom or an optionally substituted lower alkyl); R$^{52}$ is an optionally substituted aryl, an optionally substituted aralkyl, an optionally substituted heteroaryl, an optionally substituted heteroarylalkyl, an optionally substituted cycloalkyl, an optionally substituted cycloalkylalkyl, an optionally substituted heterocycloalkyl, an optionally substituted heterocycloalkenyl, an optionally substituted heterocycloalkylalkyl or an optionally substituted heterocycloalkenylalkyl; and m$^5$ is an integer from 0 to 6), or by a general formula (f):

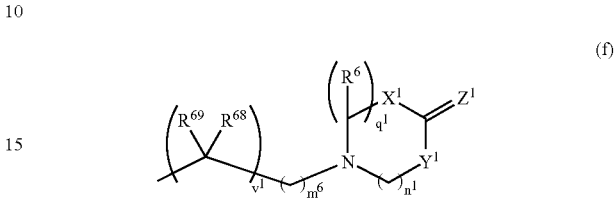

(f)

(wherein R$^6$, R$^{68}$, R$^{69}$, X$^1$, Y$^1$, Z$^1$, n$^1$, q$^1$ and v$^1$ are the same as defined above; and m$^6$ is an integer from 1 to 6)}
or a salt thereof.

2. A medicament comprising the reverse hydroxamic acid derivative or salt thereof according to claim 1 as an active component.

3. A TNF-α converting enzyme inhibitor comprising a reverse hydroxamic acid derivative represented by a general formula (I):

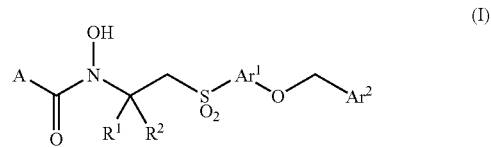

(I)

{wherein A is a nyorogen atom, a lower alkyl, a cycloalkyl or —NR$^3$R$^4$ (wherein R$^3$ and R$^4$ are independently a hydrogen atom, a lower alkyl or a cycloalkyl, or form a nitrogen-containing heterocycle together with the nitrogen to which R$^3$ and R$^4$ are attached); Ar$^1$ phenylene; Ar$^2$ is an optionally substituted quinolinyl; R$^1$ is a hydrogen atom, an optionally substituted lower alkyl, an optionally substituted lower alkenyl or an optionally substituted cycloalkyl; R$^2$ is a hydrogen atom, an optionally substituted lower alkyl, or R$^2$ is represented by a general formula (a):

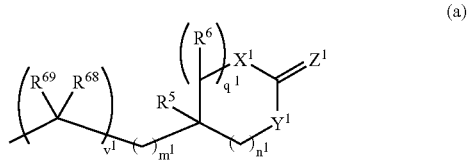

(a)

(wherein R$^5$ and R$^6$ are independently a hydrogen atom, a halogen atom, hydroxyl, cyano, trifluoromethyl, an optionally substituted lower alkyl or an optionally substituted lower alkoxy; R$^{68}$ and R$^{69}$ are independently a hydrogen atom or an optionally substituted lower alkyl; X$^1$ and Y$^1$ are independently a single bond, oxygen, sulfur, —CR$^7$R$^8$— (wherein R$^7$ and R$^8$ are independently the same as R$^5$) or —NR$^9$— (wherein R$^9$ is a hydrogen atom or an optionally substituted lower alkyl, an optionally substituted aryl or an optionally substituted heteroaryl); Z$^1$ is oxygen, sulfur, =CR$^{10}$R$^{11}$ (wherein R$^{10}$ and R$^{11}$ are independently a hydrogen atom, a halogen atom, cyano, trifluoromethyl, an optionally substituted lower alkyl, carboxyl, —CONR$^{12}$R$^{13}$ (wherein R$^{12}$ and R$^{13}$ are independently a hydrogen atom, a lower alkyl or a cycloalkyl, or form a nitrogen-containing heterocycle together with the nitrogen to which $R^{12}$ and $R^{13}$ are attached), —COR$^{14}$ (wherein $R^{14}$ is a hydrogen atom, an optionally substituted lower alkyl, an optionally substituted lower alkoxy, an optionally substituted aryl, an optionally substituted aralkyl, an optionally substituted heteroaryl or an optionally substituted heteroarylalkyl)), =NR$^{15}$ (wherein $R^{15}$ is a hydrogen atom, hydroxyl, an optionally substituted lower alkyl, an optionally substituted lower alkoxy or an optionally substituted acyl), —O(CH$_2$)$_{p1}$O— (wherein $p^1$ is an integer from 2 to 4), —S(CH$_2$)$_{r1}$S— (wherein $r^1$ is an integer from 2 to 4) or —O(CH$_2$)$_{t1}$S— (wherein $t^1$ is an integer from 2 to 4); $m^1$ is an integer from 0 to 6; $n^1$ and $q^1$ are independently an integer from 0 to 3; and $v^1$ is 0 or 1), by a general formula (b):

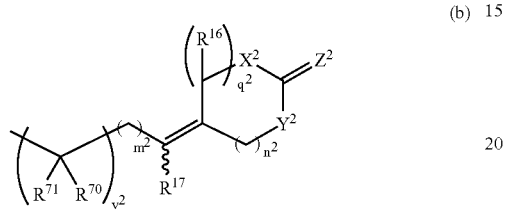

(b)

(wherein $R^{16}$ is a hydrogen atom, a halogen atom, hydroxyl, cyano, trifluoromethyl, an optionally substituted lower alkyl or an optionally substituted lower alkoxy; $R^{17}$ is a hydrogen atom, a halogen atom, or an optionally substituted lower alkyl; $R^{70}$ and $R^{71}$ are independently a hydrogen atom or an optionally substituted lower alkyl; $X^2$ and $Y^2$ are independently a single bond, oxygen, sulfur, —CR$^{18}$R$^{19}$— (wherein $R^{18}$ is a hydrogen atom, a halogen atom, an optionally substituted lower alkyl or an optionally substituted lower alkoxy, and $R^{19}$ is a hydrogen atom, a halogen atom, hydroxyl, cyano, trifluoromethyl, an optionally substituted lower alkyl, an optionally substituted lower alkoxy, an optionally substituted acyl, carboxyl, —CONR$^{20}$R$^{21}$ (wherein $R^{20}$ and $R^{21}$ are independently a hydrogen atom, a lower alkyl or a cycloalkyl, or form a nitrogen-containing heterocycle together with the nitrogen to which $R^{20}$ and $R^{21}$ are attached), —SO$_2$R$^{22}$ (wherein $R^{22}$ is a lower alkyl, a cycloalkyl, an optionally substituted aryl or an optionally substituted heteroaryl), —NR$^{23}$R$^{24}$ (wherein $R^{23}$ and $R^{24}$ are independently a hydrogen atom, an optionally substituted lower alkyl, formyl, an optionally substituted acyl, a lower alkylsulfonyl, an optionally substituted arylsulfonyl, an optionally substituted heteroarylsulfonyl, —CONR$^{25}$R$^{26}$ (wherein $R^{25}$ and $R^{26}$ are independently a hydrogen atom, an optionally substituted lower alkyl, an optionally substituted aryl or an optionally substituted heteroaryl, or form a nitrogen-containing heterocycle together with the nitrogen to which $R^{25}$ and $R^{26}$ are attached), or a cycloalkyl, or form a nitrogen-containing heterocycle together with the nitrogen to which $R^{23}$ and $R^{24}$ are attached), or —OCOR$^{27}$ (wherein $R^{27}$ is an optionally substituted lower alkyl, an optionally substituted aryl, an optionally substituted heteroaryl or —NR$^{28}$R$^{29}$ (wherein $R^{28}$ and $R^{29}$ are independently a hydrogen atom, an optionally substituted lower alkyl, an optionally substituted aryl or an optionally substituted heteroaryl, or form a nitrogen-containing heterocycle together with the nitrogen to which $R^{28}$ and $R^{29}$ are attached))), or —NR$^{30}$— (wherein $R^{30}$ is a hydrogen atom, an optionally substituted lower alkyl, an optionally substituted aryl, an optionally substituted heteroaryl, —COR$^{31}$ (wherein $R^{31}$ is a hydrogen atom, an optionally substituted lower alkyl or an optionally substituted lower alkoxy) or —CONR$^{32}$R$^{33}$ (wherein $R^{32}$ and $R^{33}$ are independently a hydrogen atom, a lower alkyl or a cycloalkyl, or form a nitrogen-containing heterocycle together with the nitrogen to which $R^{32}$ and $R^{33}$ are attached)); $Z^2$ is two hydrogen atoms, oxygen, sulfur, =CR$^{34}$R$^{35}$ (wherein $R^{34}$ and $R^{35}$ are independently a hydrogen atom, a halogen atom, cyano, trifluoromethyl or an optionally substituted lower alkyl, an optionally substituted acyl, carboxyl, —CONR$^{36}$R$^{37}$ (wherein $R^{36}$ and $R^{37}$ are independently a hydrogen atom, a lower alkyl or a cycloalkyl, or form a nitrogen-containing heterocycle together with the nitrogen to which $R^{36}$ and $R^{37}$ are attached)), =NR$^{38}$ (wherein $R^{38}$ is a hydrogen atom, hydroxyl, an optionally substituted lower alkyl, an optionally substituted lower alkoxy or an optionally substituted acyl), —O(CH$_2$)$_{p2}$O— (wherein $p^2$ is an integer from 2 to 4), —S(CH$_2$)$_{r2}$S— (wherein $r^2$ is an integer from 2 to 4) or —O(CH$_2$)$_{t2}$S— (wherein $t^2$ is an integer from 2 to 4); $m^2$ is an integer from 0 to 6; $n^2$ $q^2$ are independently an integer from 0 to 3, and $v^2$ is 0 or 1), by a general formula (c):

(c)

(wherein $G^1$ is an unsaturated four to seven membered ring optionally substituted with 1 to 4 of independent $R^{39}$ at an optional position; $R^{39}$ is hydroxyl, a halogen atom, cyano, trifluoromethyl, an optionally substituted lower alkyl, an optionally substituted lower alkoxy, an optionally substituted acyl, carboxyl, —CONR$^{40}$R$^{41}$ (wherein $R^{40}$ and $R^{41}$ are independently a hydrogen atom, a lower alkyl or a cycloalkyl, or form a nitrogen-containing heterocycle together with the nitrogen to which $R^{40}$ and $R^{41}$ are attached), —SO$_2$R$^{42}$ (wherein $R^{42}$ is a lower alkyl, a cycloalkyl, an optionally substituted aryl or an optionally substituted heteroaryl), —NR$^{43}$R$^{44}$ (wherein $R^{43}$ and $R^{44}$ are independently a hydrogen atom, an optionally substituted lower alkyl, formyl, an optionally substituted acyl, a lower alkylsulfonyl, an optionally substituted arylsulfonyl, an optionally substituted heteroarylsufonyl, —CONR$^{45}$R$^{44}$ (wherein $R^{45}$ and $R^{46}$ are independently a hydrogen atom, an optionally substituted lower alkyl, an optionally substituted aryl or an optionally substituted heteroaryl, or form a nitrogen-containing heterocycle together with the nitrogen to which $R^{45}$ and $R^{46}$ are attached) or a cycloalkyl, or form a nitrogen-containing heterocycle together with the nitrogen to which $R^{43}$ and $R^{44}$ are attached), or —OCOR$^{47}$ (wherein $R^{47}$ is an optionally substituted lower alkyl, an optionally substituted aryl, an optionally substituted heteroaryl or —NR$^{48}$R$^{49}$ (wherein $R^{48}$ and $R^{49}$ are independently a hydrogen atom, an optionally substituted lower alkyl, an optionally substituted aryl or an optionally substituted heteroaryl, or form a nitrogen-containing heterocycle together with the nitrogen to which $R^{48}$ and $R^{49}$ are attached)); and $m^3$ is an integer from 0 to 6), by a general formula (d):

(d)

(wherein $G^{50}$ is an optionally substituted aryl, an optionally substituted heteroaryl, an optionally substituted cycloalkyl or an optionally substituted heterocycloalkyl each of which are optionally substituted with $R^{50}$ ($R^{50}$ is an optionally substituted lower alkyl or an optionally substituted lower alkenyl); $m^4$ is an integer from 0 to 6), by a general formula (e):

(e)

(wherein $R^{51}$ is —CR$^{72}$=CR$^{73}$—, —C≡C— or —CR$^{74}$R$^{75}$—CR$^{76}$R$^{77}$— (wherein $R^{72}$, $R^{73}$, $R^{74}$, $R^{75}$, $R^{76}$ and $R^{77}$ are independently a hydrogen atom or an optionally substituted lower alkyl); $R^{52}$ is an optionally substituted aryl, an optionally substituted aralkyl, an optionally substituted heteroaryl, an optionally substituted heteroarylalkyl, an optionally substituted cycloalkyl, an optionally substituted cycloalkyalkyl, an optionally substituted heterocycloalkyl, an optionally substituted heterocycloalkenyl, an optionally substituted heterocycloalkylalkyl or an optionally substituted heterocycloalkenylalkyl; and $m^5$ is an integer from 0 to 6), or by a general formula (f):

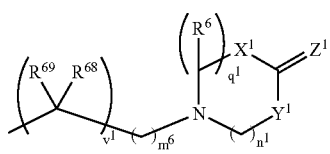

(f)

(wherein $R^6$, $R^{68}$, $R^{69}$, $X^1$, $Y^1$, $Z^1$, $n^1$, $q^1$ and $v^1$ are the same as defined above; and $m^6$ is an integer from 1 to 6)} or a salt thereof as an active component.

4. A medicament comprising the reverse hydroxamic acid derivative or salt thereof according to claim 3 as an active component.

5. A reverse hydroxamic acid derivative according to claim 1, wherein substituent $R^{2a}$ is represented by general formula (da).

6. A reverse hydroxamic acid derivative according to claim 5, wherein substituent $G^{2a}$ is an optionally substituted heterocycloalkyl which is substituted with $R^{50}$ which is an optionally substituted lower alkyl.

7. A reverse hydroxamic acid derivative according to claim 3, substituent $R^2$ is represented by general formula (d).

8. A reverse hydroxamic acid derivative according to claim 5, wherein $Ar^2$ is substituted with lower alkyl.

9. A reverse hydroxamic acid derivative according to claim 7, wherein $Ar^2$ is substituted with lower alkyl.

* * * * *